US011008398B2

(12) United States Patent
Agatsuma et al.

(10) Patent No.: US 11,008,398 B2
(45) Date of Patent: May 18, 2021

(54) ANTI-TROP2 ANTIBODY-DRUG CONJUGATE

(71) Applicants: DAIICHI SANKYO COMPANY, LIMITED, Tokyo (JP); SAPPORO MEDICAL UNIVERSITY, Sapporo (JP)

(72) Inventors: Toshinori Agatsuma, Tokyo (JP); Shu Takahashi, Tokyo (JP); Jun Hasegawa, Tokyo (JP); Daisuke Okajima, Tokyo (JP); Hirofumi Hamada, Sapporo (JP); Miki Yamaguchi, Sapporo (JP)

(73) Assignees: DAIICHI SANKYO COMPANY, LIMITED, Tokyo (JP); SAPPORO MEDICAL UNIVERSITY, Sapporo (JP)

( * ) Notice: Subject to any disclaimer, the term of this patent is extended or adjusted under 35 U.S.C. 154(b) by 7 days.

(21) Appl. No.: 16/256,715

(22) Filed: Jan. 24, 2019

(65) Prior Publication Data

US 2019/0144559 A1 May 16, 2019

Related U.S. Application Data

(63) Continuation of application No. 15/821,662, filed on Nov. 22, 2017, now Pat. No. 10,227,417, which is a continuation of application No. 15/187,179, filed on Jun. 20, 2016, now Pat. No. 9,850,312, which is a continuation of application No. PCT/JP2014/006421, filed on Dec. 24, 2014.

(51) Int. Cl.
*C07K 16/30* (2006.01)
*A61K 31/4745* (2006.01)
*A61K 47/68* (2017.01)

(52) U.S. Cl.
CPC .......... *C07K 16/30* (2013.01); *A61K 31/4745* (2013.01); *A61K 47/6803* (2017.08); *A61K 47/6851* (2017.08); *A61K 47/6857* (2017.08); *A61K 47/6859* (2017.08); *A61K 47/6863* (2017.08); *A61K 47/6865* (2017.08); *A61K 47/6869* (2017.08); *A61K 47/6889* (2017.08); *C07K 16/303* (2013.01); *C07K 16/3023* (2013.01); *C07K 16/3046* (2013.01); *C07K 16/3053* (2013.01); *C07K 16/3069* (2013.01); *C07K 2317/24* (2013.01); *C07K 2317/77* (2013.01); *C07K 2317/92* (2013.01)

(58) Field of Classification Search
CPC ..................................................... C07K 16/30
USPC ..................................................... 424/181.1
See application file for complete search history.

(56) References Cited

U.S. PATENT DOCUMENTS

| 5,677,171 | A | 10/1997 | Hudziak et al. |
| 5,821,337 | A | 10/1998 | Carter et al. |
| 5,834,476 | A | 11/1998 | Terasawa et al. |
| 5,837,673 | A | 11/1998 | Tsujihara et al. |
| 5,892,043 | A | 4/1999 | Tsujihara et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,041,818 | B2 | 5/2006 | Susaki et al. |
| 7,449,184 | B2 | 11/2008 | Allison et al. |
| 7,585,491 | B2 | 9/2009 | Govindan |
| 7,837,980 | B2 | 11/2010 | Alley et al. |
| 7,999,083 | B2 | 8/2011 | Govindan et al. |
| 8,802,820 | B2 | 8/2014 | Chamberlain et al. |
| 9,808,537 | B2 * | 11/2017 | Masuda ............. A61K 47/6803 |
| 9,850,312 | B2 * | 12/2017 | Agatsuma .......... A61K 47/6865 |
| 9,872,924 | B2 * | 1/2018 | Naito ................. A61K 47/6803 |
| 10,195,288 | B2 * | 2/2019 | Masuda ............. C07K 16/2803 |
| 10,227,417 | B2 * | 3/2019 | Agatsuma .............. C07K 16/30 |
| 10,383,878 | B2 * | 8/2019 | Hettmann .......... A61K 47/6863 |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0271671 | A1 | 12/2005 | Griffiths |

(Continued)

FOREIGN PATENT DOCUMENTS

| CA | 2927832 A1 | 11/2011 |
| CA | 2859255 A1 | 6/2013 |

(Continued)

OTHER PUBLICATIONS

Alley et al., "Antibody-drug conjugates: targeted drug delivery for cancer," Current Opinion in Chemical Biology 14:529-537 (2010).

(Continued)

*Primary Examiner* — Sean E Aeder

(74) *Attorney, Agent, or Firm* — Foley & Lardner LLP

(57) ABSTRACT

It is intended to provide an antitumor drug having an excellent therapeutic effect, which is excellent in terms of antitumor effect and safety. There is provided an antibody-drug conjugate in which an antitumor compound represented by the following formula is conjugated to an anti-TROP2 antibody via a linker having a structure represented by the following formula: $-L^1-L^2-L^P-NH-(CH_2)n^1-L^a-(CH_2)n^2-C(=O)-$ wherein the anti-TROP2 antibody is connected to the terminal of $L^1$, and the antitumor compound is connected to the carbonyl group of the $-(CH_2)n^2-C(=O)-$ moiety with the nitrogen atom of the amino group at position 1 as a connecting position.

8 Claims, 27 Drawing Sheets

Specification includes a Sequence Listing.

(56) References Cited

U.S. PATENT DOCUMENTS

| | | |
|---|---|---|
| 2005/0276812 A1 | 12/2005 | Ebens et al. |
| 2006/0018899 A1 | 1/2006 | Kao et al. |
| 2006/0193865 A1 | 8/2006 | Govindan |
| 2007/0071764 A1 | 3/2007 | Sullivan et al. |
| 2008/0050310 A1 | 2/2008 | Ebens, Jr. et al. |
| 2008/0131363 A1 | 6/2008 | Govindan et al. |
| 2008/0161245 A1 | 7/2008 | Kratz et al. |
| 2008/0305044 A1 | 12/2008 | McDonagh et al. |
| 2009/0274713 A1 | 11/2009 | Chari et al. |
| 2009/0286258 A1 | 11/2009 | Kauer et al. |
| 2011/0059076 A1 | 3/2011 | McDonagh et al. |
| 2011/0070248 A1 | 3/2011 | Ichikawa et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2013/0089872 A1 | 4/2013 | Nakamura et al. |
| 2013/0123178 A1 | 5/2013 | Dimarchi et al. |
| 2015/0297748 A1 | 10/2015 | Masuda et al. |
| 2015/0352224 A1 | 12/2015 | Naito et al. |
| 2016/0279259 A1 | 9/2016 | Masuda et al. |
| 2016/0287722 A1 | 10/2016 | Govindan et al. |
| 2016/0297890 A1 | 10/2016 | Agatsuma et al. |

FOREIGN PATENT DOCUMENTS

| | | |
|---|---|---|
| CN | 1764478 A | 4/2006 |
| CN | 101023100 A | 8/2007 |
| CN | 101490087 A | 7/2009 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 5/2015 |
| EP | 2 910 573 A | 8/2015 |
| JP | H05-059061 A | 3/1993 |
| JP | H08-337584 A | 12/1996 |
| JP | H10-095802 A | 4/1998 |
| JP | H1171280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2008-521828 A | 6/2008 |
| JP | 2009-538629 A | 11/2009 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| KR | 1020010052385 A | 6/2001 |
| KR | 1020110044808 A | 4/2011 |
| RU | 2404810 C2 | 7/2008 |
| TW | 1232930 B | 5/2005 |
| TW | 200817434 A | 4/2008 |
| WO | WO-97/46260 A1 | 12/1997 |
| WO | WO-00/25825 A1 | 5/2000 |
| WO | WO-01/00244 A2 | 1/2001 |
| WO | WO-02/00734 A1 | 1/2002 |
| WO | WO-2003/043583 A2 | 5/2003 |
| WO | WO-03/74566 A2 | 9/2003 |
| WO | WO-2005/112919 A2 | 12/2005 |
| WO | WO-2006/065533 A2 | 6/2006 |
| WO | WO-2006/092230 A2 | 9/2006 |
| WO | WO-2008/144891 A1 | 12/2008 |
| WO | WO-2011-011474 A1 | 1/2011 |
| WO | WO-2011/022474 A1 | 1/2011 |
| WO | WO-2011/068845 A1 | 6/2011 |
| WO | WO-2011/145744 A1 | 11/2011 |
| WO | WO-2011/155579 A1 | 12/2011 |
| WO | WO-2013/068946 A2 | 5/2013 |
| WO | WO-2013/077458 A1 | 5/2013 |
| WO | WO-2013/163229 A1 | 10/2013 |
| WO | WO-2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |

OTHER PUBLICATIONS

Barginear et al., "Trastuzumab-DM1: A Review of the Novel Immuno-Conjugate for HER2-Overexpressing Breast Cancer," The Open Breast Cancer Journal 1:25-30 (2009).

Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).

Beck, Alain, "The Next Generation of Antibody-drug Conjugates Comes of Age," Discovery Medicine 10(53):329-339 (Oct. 16, 2010).

Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).

Damle, Nitin K., "Tumour-targeted chemotherapy with immunoconjugates of calicheamicin," Expert Opin. Biol. Ther. 4(9):1445-1452 (2004).

De Jager et al., "DX-8951f: Summary of Phase I Clinical Trials," Ann. N.Y. Acad. Sci. 922:260-273 (2000).

Ducry et al., "Antibody—Drug Conjugates: Linking Cytotoxic Payloads to Monoclonal Antibodies," Bioconjugate Chem. 21:5-13 (2010).

El Sewedy et al., "Cloning of the Murine Trop2 Gene: Conservation of a $PIP_2$-Binding Sequence in the Cytoplasmic Domain of Trop-2," Int. J. Cancer 75(2):324-330 (1998).

Faulk et al., "Antigens of human trophoblasts: A working hypothesis for their role in normal and abnormal pregnancies," Proc. Natl. Acad. Sci. USA 75(4):1947-1951 (1978).

Fong et al., "High expression of TROP2 correlates with poor prognosis in pancreatic cancer," Br. J. Cancer 99(8):1290-1295 (2008).

Fong et al., "TROP2: a novel prognostic marker in squamous cell carcinoma of the oral cavity," Mod. Pathol. 21(2):186-191 (2008).

Fornaro et al., "Cloning of the Gene Encoding Trop-2, a Cell-Surface Glycoprotein Expressed by Human Carcinomas," Int. J. Cancer 62(5):610-618 (1995).

Inoue et al., "CM-Dextran-Polyalcohol-Camptothecin Conjugate: DE-310 with a Novel Carrier System and its Preclinical Data," Polymer Drugs in the Clinical Stage, 145-153 (2003).

Joto et al., "DX-8951 F, A Water-Soluble Camptothecin Analog, Exhibits Potent Antitumor Activity Against a Human Lung Cancer Cell Line and its SN-38-Resistant Variant," Int. J. Cancer 72:680-686 (1997).

Kumazawa et al., "Antitumor activity of DX-8951f: a new camptothecin derivative," Exp. Opin. Invest. Drugs 7(4):625-632 (1998).

Kumazawa et al., "Potent and broad antitumor effects of DX-8951f, a water-soluble camptothecin derivative, against various human tumors xenografted in nude mice," Cancer Chemother. Pharmacol. 42:210-220 (1998).

Kumazawa et al., "DE-310, a novel macromolecular carrier system for the camptothecin analog DX-8951f: Potent antitumor activities in various murine tumor models," Cancer Sci. 95(2):168-175 (Feb. 2004).

Linnenbach et al., "Sequence investigation of the major gastrointestinal tumor-associated antigen gene family, GA733," Proc. Natl. Acad. Sci. 86(1):27-31 (Jan. 1989).

Lipinski et al., "Human trophoblast cell-surface antigens defined by monoclonal antibodies," Proc. Natl. Acad. Sci. 78(8):5147-5150 (Aug. 1981).

Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995).

Mühlmann et al., "TROP2 expression as prognostic marker for gastric carcinoma," J. Clin. Pathol. 62(2):152-158 (2009).

(56) References Cited

OTHER PUBLICATIONS

Nakada et al., "Novel antibody drug conjugates containing exatecan derivative-based cytotoxic payloads," Bioorganic & Medical Chemistry Letters 26(6):1542-1545 (2016).
Ning et al., "TROP2 expression and its correlation with tumor proliferation and angiogenesis in human gliomas," Neurol. Sci. 34(10):1745-1750 (2013).
Ohmachi et al., "Clinical Significance of TROP2 Expression in Colorectal Cancer," Clin. Cancer Res. 12(10):3057-3063 (May 15, 2006).
Ripani et al., "Human Trop-2 is a Tumor-Associated Calcium Signal Transducer," Int. J. Cancer 76(5):671-676 (1998).
Senter et al., "The discovery and development of brentuximab vedotin for use in relapsed Hodgkin lymphoma and systemic anaplastic large cell lymphoma," Nature Biotechnology 30(7):631-637 (Jul. 2012).
Soepenberg et al., "Phase I and Pharmacokinetic Study of DE-310 in Patients with Advanced Solid Tumors," Clin. Cancer Res. 11:703-711 (Jan. 15, 2005).
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-1-inhibitor exatecan (DX-8951), in patients with operable solid tumors," Investigational New Drugs 23:339-347 (2005).
International Search Report for PCT/JP2014/006421 dated Mar. 17, 2015.
Non-Final Office Action issued in U.S. Appl. No. 14/436,458 dated Jul. 19, 2016.
Non-Final Office Action issued in U.S. Appl. No. 14/435,114 dated Jul. 21, 2016.
Non-Final Office Action issued in U.S. Appl. No. 15/180,203 dated Jul. 25, 2016.
Decision to Grant issued in Japanese Patent Application No. 2016-166850 dated Oct. 18, 2016.
Office Action issued in Chinese Patent Application No. 201380053256.2 dated Nov. 1, 2016.
Office Action issued in Japanese Patent Application No. 2016-540705 dated Dec. 6, 2016.
Canadian Examiner's Interview Summary issued in Canadian Patent Application No. 2,885,800 dated Mar. 28, 2017.
Extended European Search Report issued in European Patent Application No. 14 874 745.4 dated May 10, 2017.
N. Masubuchi, "Pharmacokinetics of DE-310, a novel macromolecular carrier system for the camptothecin analog DX-8951f, in tumor-bearing mice," Pharmazie 59: 374-377 (2004).
Ochi et al, "A possible mechanism for the long-lasting antitumor effect of the macromolecular conjugate DE-310: mediation by cellular uptake and drug release of its active camptothecin analog DX-8951," Cancer Chemotherapy and Pharmacology 55(4): 323-332 (2005).
Office Action issued in Colombian Application No. NC2016/0000187 and English translation dated May 9, 2017.
Soepenberg et al., "Liquid chromatographic assays for DE-310, a novel camptothecin analog, and two major enzymatic products in human matrices," Journal of Chromatography B, 799, 15-22 (2004).
Shiose et al, "Systematic Research of Peptide Spacers Controlling Drug Release from Macromolecular Prodrug System, Carboxymethyldextran Polyalcohol-Peptide-Drug Conjugates," Bioconjugate Chem. 20(1): 60-70 (2009).
Taiwanese Office Action issued in Taiwanese Patent Application No. 102136742 dated May 15, 2017.
Cardillo et al., "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Extended European Search Report issued in European Patent Application No. 15743738.5 dated Aug. 9, 2017.
Extended European Search Report issued in European Patent Application No. 15776810.2 dated Aug. 11, 2017.
Burke P J et al. (2009), "Design, Synthesis, and Biological Evaluation of Antibody-Drug Conjugates Comprised of Potent Camptothecin Analogues", Bioconjugate Chemistry, vol. 20, No. 6, Jun. 17, 2009, pp. 1242-1250.
Non-Final Office Action issued in U.S. Appl. No. 15/187,179 dated Oct. 21, 2016.
Notice of Allowance issued in U.S. Appl. No. 15/187,179 dated May 18, 2017.
Notice of Allowance issued in U.S. Appl. No. 15/187,179 dated Aug. 25, 2017.
Behrens et al, Methods for site-specific drug conjugation to antibodies, mAbs, 2014, vol. 6, No. 1. pp. 46-53.
Korean Office Action dated May 1, 2018 in corresponding application No. 10-2016-7015961.
Shen et al, Conjugation site modulates the in vivo stability and therapeutic activity of antibody-drug conjugates, Nature Biotechnology, 2012, vol. 30, pp. 184-189.
Taiwanese Office Action dated Jul. 30, 2018 in corresponding application No. 104111534.
Canadian Office Action dated Apr. 13, 2018 in corresponding application No. 2,939,802.
Russian Office Action dated Oct. 11, 2018 in corresponding application No. 2016123597.
Barok et al, Trastuzumab-DM1 is highly effective in preclinical models of HER2-positive gastric cancer, Cancer Letters, 2011, vol. 306, No. 2, pp. 172-179.
Oguma et al, Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26.
U.S. Patent and Trademark Office, "Non-Final Office Action," issued in connection with U.S. Appl. No. 15/821,662, dated Jan. 17, 2018.
U.S. Patent and Trademark Office, "Notice of Allowance," issued in connection with U.S. Appl. No. 15/821,662, dated Nov. 2, 2018.
Adams et al., "Humanization of a recombinant monoclonal antibody to produce a therapeutic HER dimerization inhibitor, pertuzumab," Cancer Immunol. Immunother. 55:717-727 (2006).
Allowance issued in connection with Taiwanese Patent Application No. 104103127,dated Apr. 11, 2018.
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3):737-744 (Mar. 1996).
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," J. Clin. Oncol. 29(4):398-405 (Feb. 2011).
Coussens et al., "Tyrosine Kinase Receptor with Extensive Homology to EGF Receptor Shares Chromosomal Location with neu Oncogene," Science 230(4730):1132-1139 (Dec. 1985).
Di Fiore et al., "erbB-2 is a Potent Oncogene When Overexpressed in NIH/3T3 Cells," Science 237:178-182 (Jul. 1987).
Esteva et al., A Phase II Study of Intravenous Exatecan Mesylate (DX-8951f) Administered Daily for 5 Days Every 3 Weeks to Patients with Metastatic Breast Carcinoma, American Cancer Society,2003,900-907.
European Search Report in corresponding application No. 15776810.2 dated Aug. 11, 2017.
European Search Report issued in corresponding application No. 14874745 dated May 10, 2017.
European Search Report issued in corresponding application No. 15743738.5 dated Aug. 9, 2017.
Fendly et al., "Characterization of Murine Monoclonal Antibodies Reactive to Either the Human Epidermal Growth Factor Receptor or HER2/neu Gene Product," Cancer Research 50:1550-1558 (1990).

(56) References Cited

OTHER PUBLICATIONS

Fukushige et al., "Localization of a Novel v-erbB-Related Gene, c-erbB-2, on Human Chromosome 17 and its Amplification in a Gastric Cancer Cell Line," Mol. Cell. Biol. 6(3):955-958 (1986).
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Hardwick et al., "Immunohistochemical detection of p53 and c-erbB-2 in oesophageal carcinoma; no correlation with prognosis," Eur. J. Surg. Oncol. 23:30-35 (1997).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
Indian Office Action issued in the corresponding Indian Patent Application Ser. No. 201647013640, dated Jul. 19, 2019.
International Search Report issued in International Patent Application No. PCT/JP2015/000355 dated Apr. 21, 2015.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Korkaya et al., "HER2 regulates the mammary stem/progenitor cell population driving tumorigenesis and invasion," Oncogene 27:6120-6130 (2008).
Office Action dated Nov. 21, 2017 in corresponding application No. PCT/JP2017/036215.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12: 60-70 (Aug. 1999).
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Yano et al., "Comparison of HER2 gene amplification assessed by fluorescence in situ hybridization and HER2 protein expression assessed by immunohistochemistry in gastric cancer," Oncol. Rep. 15:65-71 (2006).
Chinese Office Action issued to corresponding App. No. 201480071134.0-DTD Aug. 20, 2019 (5 pages).
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Australian Intellectual Property Office, "Examination Report No. 2 for Standard Patent Application," Australian Patent Application No. 2014371934, dated Sep. 13, 2019.
Barok et al, Trastuzumab-DM1 is highly effective in preclinical models of HER2-positive gastric cancer, Cancer Letters, 2011, vol. 306, No. 2, pp. 171-179.
Acchione et al, Impact of linker and conjugation chemistry on antigen binding, Fc receptor binding and thermal stability of model antibody-drug conjugates, mABs, 2012, vol. 4, No. 3, pp. 362-372.
Colombian Reconsideration Petition in application No. NC2016/0000187.
Rowinsky, Eric K., Preclinical and Clinical Development of Exatecan (DX-8951f), Camptothecins in Cancer Therapy, 2005, pp. 317-318.
Russian Office Action dated Mar. 5, 2019 in corresponding application No. 2016143351.
Sievers et al, Antibody-Drug Conjugates in Cancer Therapy, Annual Review of Medicine, 2013, vol. 64, No. 1, pp. 15-29.
United States Office Action dated Apr. 5, 2019 in U.S. Appl. No. 15/821,697.
Blok et al., "Cytoplasmic Overexpression of HER2: a Key Factor in Colorectal Cancer", Clinical Insights: Oncology, vol. 7, 2013 pp. 41-51.
Chinese Search Report dated Jun. 24, 2020 for corresponding Application No. 108114649.
Moghaddas et al., "Whether HER2-positive non-breast cancers are candidates for treatment with Ado-trastuzumab emtansine?", J. Res Parm Pract, vol. 5(4), 2016 pp. 227-233.

\* cited by examiner

FIG.1

SEQ ID NO: 7: Nucleotide sequence of cTINA1 antibody heavy chain atgaaacacctgtggttcttcctcctgctggtggcagctcccagatgggtgctgagccagatccag
ttggtgcagtctggacctgagctgaagaagcctggagagacagtcaggatctcctgcaaggcttct
gggtataccttcacaactgctggaatgcagtgggtgcaaaagatgccaggaaagggtttgaagtgg
attggctggataaacacccactctggagtgccaaaatatgcagaagacttcaagggacggtttgcc
ttctctttggaaacctctgccagcactgcatatttacagataagcaacctcaaaaatgaggacacg
actacgtatttctgtgcgagatcggggttcggtagtagctactggtacttcgatgtctggggcgca
gggaccgcggtcaccgtcagctcagcctccaccaagggcccaagcgtcttccccctggcaccctcc
tccaagagcacctctggcggcacagccgccctgggctgcctggtcaaggactacttccccgaaccc
gtgaccgtgagctggaactcaggcgccctgaccagcggcgtgcacaccttccccgctgtcctgcag
tcctcaggactctactccctcagcagcgtggtgaccgtgccctccagcagcttgggcacccagacc
tacatctgcaacgtgaatcacaagcccagcaacaccaaggtggacaagagagttgagcccaaatct
tgtgacaaaactcacacatgcccaccctgcccagcacctgaactcctggggggaccctcagtcttc
ctcttccccccaaaacccaaggacaccctcatgatctcccggacccctgaggtcacatgcgtggtg
gtggacgtgagccacgaagaccctgaggtcaagttcaactggtacgtggacggcgtggaggtgcat
aatgccaagacaaagccccgggaggagcagtacaacagcacgtaccgggtggtcagcgtcctcacc
gtcctgcaccaggactggctgaatggcaaggagtacaagtgcaaggtctccaacaaagccctccca
gcccccatcgagaaaaccatctccaaagccaaaggccagccccgggaaccacaggtgtacaccctg
cccccatcccgggaggagatgaccaagaaccaggtcagcctgacctgcctggtcaaaggcttctat
cccagcgacatcgccgtggagtgggagagcaatggccagccggagaacaactacaagaccacccct
cccgtgctggactccgacggctccttcttcctctacagcaagctcaccgtggacaagagcaggtgg
cagcagggcaacgtcttctcatgctccgtgatgcatgaggctctgcacaaccactacacccagaag
agcctctccctgtctccgggtaaa Signal sequence (1-57), variable region (58-420), constant region (421-1410)

SEQ ID NO: 8: Amino acid sequence of cTINA1 antibody heavy chain

MKHLWFFLLLVAAPRWVLSQIQLVQSGPELKKPGETVRISCKASGYTFTTAGMQWVQKMPGKGLKWIGWINT
HSGVPKYAEDFKGRFAFSLETSASTAYLQISNLKNEDTTTYFCARSGFGSSYWYFDVWGAGTAVTVSSASTK
GPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Signal sequence (1-19), variable region (20-140), constant region (141-470)

FIG.2

SEQ ID NO: 9: Nucleotide sequence of cTINA1 antibody light chain
atggtgctgcagacccaggtgttcatctccctgctgctgtggatctccggcgcgtacggcgacatt
gtgatgacccagtctcacaaattcatgtccacatcagtaggagacagggtcagcatcacctgcaag
gccagtcaggatgtgagtactgctgtagcctggtatcaacagaaaccaggacaatctcctaaactg
ctgatttactcggcatcctaccgctacactggagtccctgatcgcttcactggcagtggatctggg
acggctttcactttcaccatcagcagtgtgcaggctgaagacctggcagtttattactgtcagcaa
cattatattactccgctcacgttcggtgctgggaccaagctggagctgaaacgggctgtggccgcc
ccctccgtgttcatcttccccccctccgacgagcagctgaagtccggcaccgcctccgtggtgtgc
ctgctgaataacttctacccagagaggccaaggtgcagtggaaggtggacaacgccctgcagtcc
gggaactcccaggagagcgtgaccgagcaggacagcaaggacagcacctacagcctgagcagcacc
ctgaccctgagcaaagccgactacgagaagcacaaggtgtacgcctgcgaggtgacccaccagggc
ctgagctccccgtcaccaagagcttcaacagggggagtgt Signal sequence (1-60), variable region (61-387), constant region (388-702)

SEQ ID NO: 10: Amino acid sequence of cTINA1 antibody light chain
MVLQTQVFISLLLWISGAYGDIVMTQSHKFMSTSVGDRVSITCKASQDVSTAVAWYQQKPGQSPKLLIYSAS
YRYTGVPDRFTGSGSGTAFTFTISSVQAEDLAVYYCQQHYITPLTFGAGTKLELKRAVAAPSVFIFPPSDEQ
LKSGTASVVCLLNNFYPREAKVQWKVDNALQSGNSQESVTEQDSKDSTYSLSSTLTLSKADYEKHKVYACEV
THQGLSSPVTKSFNRGEC Signal sequence (1-20), variable region (21-129), constant region (130-234)

FIG.3

SEQ ID NO: 11: Nucleotide sequence of hTINA1-H1 atgaaacacctgtggttcttcctcctgctggtggcagctcccagatgggtgctgagccaggtgcagctggtg
cagtctggcgccgaagtgaagaaaccaggcgccagcgtgaaggtgtcctgcaaggccagcggctacacctttt
accaccgccggcatgcagtgggtgcgccaggctcctggacagggcctggaatggatgggctggatcaacacc
cacagcggcgtgcccaaatacgccgaggacttcaagggcagagtgaccatcagcgccgacaccagcacctcc
acagcctacctgcagctgagcagcctgaagtccgaggacaccgccgtgtactactgcgccagaagcggcttc
ggcagcagctactggtacttcgacgtgtggggccagggcaccctcgtgaccgtcagctcagcctccaccaag
ggcccaagcgtcttccccctggcaccctcctccaagagcacctctggcggcacagccgccctgggctgcctg
gtcaaggactacttccccgaacccgtgaccgtgagctggaactcaggcgccctgaccagcggcgtgcacacc
ttccccgctgtcctgcagtcctcaggactctactccctcagcagcgtggtgaccgtgcctccagcagcttg
ggcacccagacctacatctgcaacgtgaatcacaagcccagcaacaccaaggtggacaagagagttgagccc
aaatcttgtgacaaaactcacacatgcccaccctgcccagcacctgaactcctggggggaccctcagtcttc
ctcttccccccaaaacccaaggacaccctcatgatctcccggacccctgaggtcacatgcgtggtggtggac
gtgagccacgaagaccctgaggtcaagttcaactggtacgtggacggcgtggaggtgcataatgccaagaca
aagccccgggaggagcagtacaacagcacgtaccgggtggtcagcgtcctcaccgtcctgcaccaggactgg
ctgaatggcaaggagtacaagtgcaaggtctccaacaaagccctcccagcccccatcgagaaaaccatctcc
aaagccaaaggccagccccgggaaccacaggtgtacaccctgcccccatcccgggaggagatgaccaagaac
caggtcagcctgacctgcctggtcaaaggcttctatcccagcgacatcgccgtggagtgggagagcaatggc
cagccggagaacaactacaagaccaccctcccgtgctggactccgacggctccttcttcctctacagcaag
ctcaccgtggacaagagcaggtggcagcagggcaacgtcttctcatgctccgtgatgcatgaggctctgcac
aaccactacacccagaagagcctctccctgtctccggcaaa Signal sequence (1-57), variable region (58-420), constant region (421-1410)

SEQ ID NO: 12: Amino acid sequence of hTINA1-H1

MKHLWFFLLLVAAPRWVLSQVQLVQSGAEVKKPGASVKVSCKASGYTFTTAGMQWVRQAPGQGLEWMGWINT
HSGVPKYAEDFKGRVTISADTSTSTAYLQLSSLKSEDTAVYYCARSGFGSSYWYFDVWGQGTLVTVSSASTK
GPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Signal sequence (1-19), variable region (20-140), constant region (141-470)

FIG.4

SEQ ID NO: 13: Nucleotide sequence of hTINA1-H2

```
atgaaacacctgtggttcttcctcctgctggtggcagctcccagatgggtgctgagccaggtgcagctggtg
cagtctggcgccgaagtgaagaaaccaggcgccagcgtgaaggtgtcctgcaaggccagcggctacacctt t
accaccgccggcatgcagtgggtgcgccaggctcctggacagggcctggaatggatgggctggatcaacacc
cacagcggcgtgcccaaatacgccgaggacttcaagggcagagtgaccatcagcctggacaccagcacctcc
accgcctacctgcagctgagcagcctgaagtccgaggacaccgccgtgtactactgcgccagaagcggcttc
ggcagcagctactggtacttcgacgtgtggggccagggcaccctcgtgaccgtcagctcagcctccaccaag
ggcccaagcgtcttccccctggcaccctcctccaagagcacctctggcggcacagccgccctgggctgcctg
gtcaaggactacttccccgaacccgtgaccgtgagctggaactcaggcgccctgaccagcggcgtgcacacc
ttccccgctgtcctgcagtcctcaggactctactccctcagcagcgtggtgaccgtgcctccagcagcttg
ggcacccagacctacatctgcaacgtgaatcacaagcccagcaacaccaaggtggacaagagagttgagccc
aaatcttgtgacaaaactcacacatgcccaccctgcccagcacctgaactcctggggggaccctcagtcttc
ctcttccccccaaaacccaaggacaccctcatgatctcccggacccctgaggtcacatgcgtggtggtggac
gtgagccacgaagaccctgaggtcaagttcaactggtacgtggacggcgtggaggtgcataatgccaagaca
aagccccgggaggagcagtacaacagcacgtaccgggtggtcagcgtcctcaccgtcctgcaccaggactgg
ctgaatggcaaggagtacaagtgcaaggtctccaacaaagccctcccagcccccatcgagaaaaccatctcc
aaagccaaaggccagccccgggaaccacaggtgtacaccctgcccccatcccgggaggagatgaccaagaac
caggtcagcctgacctgcctggtcaaaggcttctatcccagcgacatcgccgtggagtgggagagcaatggc
cagccggagaacaactacaagaccaccctcccgtgctggactccgacggctccttcttcctctacagcaag
ctcaccgtggacaagagcaggtggcagcagggcaacgtcttctcatgctccgtgatgcatgaggctctgcac
aaccactacacccagaagagcctctccctgtctccgggcaaa
```
Signal sequence (1-57), variable region (58-420), constant region (421-1410)

SEQ ID NO: 14: Amino acid sequence of hTINA1-H2

MKHLWFFLLLVAAPRWVLSQVQLVQSGAEVKKPGASVKVSCKASGYTFTTAGMQWVRQAPGQGLEWMGWINT
HSGVPKYAEDFKGRVTISLDTSTSTAYLQLSSLKSEDTAVYYCARSGFGSSYWYFDVWGQGTLVTVSSASTK
GPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Signal sequence (1-19), variable region (20-140), constant region (141-470)

FIG.5

SEQ ID NO: 15: Nucleotide sequence of hTINA1-H3 atgaaacacctgtggttcttcctcctgctggtggcagctcccagatgggtgctgagccagatccagctggtg
cagtctggcgccgaagtgaagaaacccggcgagagcgtgaaggtgtcctgcaaggccagcggctacacctttt
accaccgccggcatgcagtgggtgcagcagatgcctggcaagggcctggaatggatgggctggatcaacacc
cacagcggcgtgcccaaatacgccgaggacttcaagggcagagtgaccttcagcctggacaccagcacctcc
accgcctacctgcagctgagcagcctgaagtccgaggacaccgccgtgtactactgcgccagaagcggcttc
ggcagcagctactggtacttcgacgtgtggggccagggcaccctcgtgaccgtcagctcagcctccaccaag
ggcccaagcgtcttccccctggcaccctcctccaagagcacctctggcggcacagccgccctgggctgcctg
gtcaaggactacttccccgaaccgtgaccgtgagctggaactcaggcgccctgaccagcggcgtgcacacc
ttccccgctgtcctgcagtcctcaggactctactccctcagcagcgtggtgaccgtgcctccagcagcttg
ggcacccagacctacatctgcaacgtgaatcacaagcccagcaacaccaaggtggacaagagagttgagccc
aaatcttgtgacaaaactcacacatgcccaccctgcccagcacctgaactcctggggggaccctcagtcttc
ctcttccccccaaaacccaaggacacccctcatgatctcccggacccctgaggtcacatgcgtggtggtggac
gtgagccacgaagaccctgaggtcaagttcaactggtacgtggacggcgtggaggtgcataatgccaagaca
aagccccgggaggagcagtacaacagcacgtaccgggtggtcagcgtcctcaccgtcctgcaccaggactgg
ctgaatggcaaggagtacaagtgcaaggtctccaacaaagccctcccagcccccatcgagaaaaccatctcc
aaagccaaaggccagccccgggaaccacaggtgtacaccctgcccccatcccgggaggagatgaccaagaac
caggtcagcctgacctgcctggtcaaaggcttctatcccagcgacatcgccgtggagtgggagagcaatggc
cagcccgagaacaactacaagaccacccctcccgtgctggactccgacggctccttcttcctctacagcaag
ctcaccgtggacaagagcaggtggcagcagggcaacgtcttctcatgctccgtgatgcatgaggctctgcac
aaccactacacccagaagagcctctccctgtctccggcaaa Signal sequence (1-57), variable region (58-420), constant region (421-1410)

SEQ ID NO: 16: Amino acid sequence of hTINA1-H3

MKHLWFFLLLVAAPRWVLSQIQLVQSGAEVKKPGESVKVSCKASGYTFTTAGMQWVQQMPGKGLEWMGWINT
HSGVPKYAEDFKGRVTFSLDTSTSTAYLQLSSLKSEDTAVYYCARSGFGSSYWYFDVWGQGTLVTVSSASTK
GPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Signal sequence (1-19), variable region (20-140), constant region (141-470)

FIG.6

SEQ ID NO: 17: Nucleotide sequence of hTINA1-L1 atggtgctgcagacccaggtgttcatctccctgctgctgtggatctccggcgcgtacggcgacatccagatg
acccagagccctagcagcctgagcgccagcgtgggcgacagagtgaccatcacatgcaaggccagccaggac
gtgtccacagccgtggcctggtatcagcagaagcctggcaaggcccccaagctgctgatctacagcgccagc
taccggtacaccggcgtgcccagcagatttctggcagcggctccggcaccgacttcaccctgacaatcagc
agcctgcagcccgaggacttcgccgtgtactactgccagcagcactacatcacccccctgacctttggccag
ggcaccaagctggaaatcaagcgtacggtggccgcccctccgtgttcatcttcccccctccgacgagcag
ctgaagtccggcaccgcctccgtggtgtgcctgctgaataacttctaccccagagaggccaaggtgcagtgg
aaggtggacaacgccctgcagtccggggaactcccaggagagcgtgaccgagcaggacagcaaggacagcacc
tacagcctgagcagcaccctgaccctgagcaaagccgactacgagaagcacaaggtgtacgcctgcgaggtg
acccaccagggcctgagctcccccgtcaccaagagcttcaacaggggggagtgt Signal sequence (1-60), variable region (61-387), constant region (388-702)

SEQ ID NO: 18: Amino acid sequence of hTINA1-L1

MVLQTQVFISLLLWISGAYGDIQMTQSPSSLSASVGDRVTITCKASQDVSTAVAWYQQKPGKAPKLLIYSAS
YRYTGVPSRFSGSGSGTDFTLTISSLQPEDFAVYYCQQHYITPLTFGQGTKLEIKRTVAAPSVFIFPPSDEQ
LKSGTASVVCLLNNFYPREAKVQWKVDNALQSGNSQESVTEQDSKDSTYSLSSTLTLSKADYEKHKVYACEV
THQGLSSPVTKSFNRGEC

Signal sequence (1-20), variable region (21-129), constant region (130-234)

FIG.7

SEQ ID NO: 19: Nucleotide sequence of hTINA1-L2 atggtgctgcagacccaggtgttcatctccctgctgctgtggatctccggcgcgtacggcgacatcgtgatg
acccagagccctagcagcctgagcgccagcgtgggcgacagagtgaccatcacatgcaaggccagccaggac
gtgtccacagccgtggcctggtatcagcagaagcctggcaaggcccccaagctgctgatctacagcgccagc
taccggtacaccggcgtgcccagcagatttctggcagcggctccggcaccgacttcaccctgacaatcagc
agcctgcagcccgaggacttcgccgtgtactactgccagcagcactacatcacccccctgacctttggccag
ggcaccaagctggaaatcaagcgtacggtggccgcccctccgtgttcatcttcccccctccgacgagcag
ctgaagtccggcaccgcctccgtggtgtgcctgctgaataacttctaccccagagaggccaaggtgcagtgg
aaggtggacaacgccctgcagtccgggaactcccaggagagcgtgaccgagcaggacagcaaggacagcacc
tacagcctgagcagcaccctgaccctgagcaaagccgactacgagaagcacaaggtgtacgcctgcgaggtg
acccaccagggcctgagctcccccgtcaccaagagcttcaacaggggggagtgt Signal sequence (1-60), variable region (61-387), constant region (388-702)

SEQ ID NO: 20: Amino acid sequence of hTINA1-L2

MVLQTQVFISLLLWISGAYGDIVMTQSPSSLSASVGDRVTITCKASQDVSTAVAWYQQKPGKAPKLLIYSAS
YRYTGVPSRFSGSGSGTDFTLTISSLQPEDFAVYYCQQHYITPLTFGQGTKLEIKRTVAAPSVFIFPPSDEQ
LKSGTASVVCLLNNFYPREAKVQWKVDNALQSGNSQESVTEQDSKDSTYSLSSTLTLSKADYEKHKVYACEV
THQGLSSPVTKSFNRGEC

Signal sequence (1-20), variable region (21-129), constant region (130-234)

FIG.8

SEQ ID NO: 21: Nucleotide sequence of hTINA1-L3 atggtgctgcagacccaggtgttcatctccctgctgctgtggatctccggcgcgtacggcgacatcgtgatg
acccagagccctagcagcctgagcgccagcgtgggcgacagagtgaccatcacatgcaaggccagccaggac
gtgtccacagccgtggcctggtatcagcagaagcccggcaagcagcccaagctgctgatctacagcgccagc
taccggtacaccggcgtgcccagcagatttctggcagcggctccggcaccgacttcaccctgacaatcagc
agcctgcagcccgaggacttcgccgtgtactactgccagcagcactacatcacccccctgacctttggccag
ggcaccaagctggaaatcaagcgtacggtggccgccccctccgtgttcatcttccccccctccgacgagcag
ctgaagtccggcaccgcctccgtggtgtgcctgctgaataacttctacccagagaggccaaggtgcagtgg
aaggtggacaacgccctgcagtccgggaactcccaggagagcgtgaccgagcaggacagcaaggacagcacc
tacagcctgagcagcaccctgaccctgagcaaagccgactacgagaagcacaaggtgtacgcctgcgaggtg
acccaccagggcctgagctcccccgtcaccaagagcttcaacagggggagtgt Signal sequence (1-60), variable region (61-387), constant region (388-702)

SEQ ID NO: 22: Amino acid sequence of hTINA1-L3

MVLQTQVFISLLLWISGAYGDIVMTQSPSSLSASVGDRVTITCKASQDVSTAVAWYQQKPGKQPKLLIYSAS
YRYTGVPSRFSGSGSGTDFTLTISSLQPEDFAVYYCQQHYITPLTFGQGTKLEIKRTVAAPSVFIFPPSDEQ
LKSGTASVVCLLNNFYPREAKVQWKVDNALQSGNSQESVTEQDSKDSTYSLSSTLTLSKADYEKHKVYACEV
THQGLSSPVTKSFNRGEC

Signal sequence (1-20), variable region (21-129), constant region (130-234)

FIG.9

SEQ ID NO: 23: Amino acid sequence of CDRH1 of TINA1 antibody

TAGMQ

SEQ ID NO: 24: Amino acid sequence of CDRH2 of TINA1 antibody

WINTHSGVPKYAEDFKG

SEQ ID NO: 25: Amino acid sequence of CDRH3 of TINA1 antibody

SGFGSSYWYFDV

SEQ ID NO: 26: Amino acid sequence of CDRL1 of TINA1 antibody

KASQDVSTAVA

SEQ ID NO: 27: Amino acid sequence of CDRL2 of TINA1 antibody

SASYRYT

SEQ ID NO: 28: Amino acid sequence of CDRL3 of TINA1 antibody

QQHYITPLT

ANTI-TROP2 ANTIBODY-DRUG CONJUGATE

CROSS-REFERENCE TO RELATED APPLICATIONS

The present application is a Continuation of U.S. patent application Ser. No. 15/821,662, filed on Nov. 22, 2017, which is a Continuation of U.S. patent application Ser. No. 15/187,179, filed Jun. 20, 2016 (issued as U.S. Pat. No. 9,850,312 on Dec. 26, 2017), which is a Bypass Continuation of International Patent Application No. PCT/JP2014/006421, filed on Dec. 24, 2014, which claims the benefit of priority to Japanese Patent Application No. 2013-267548, filed on Dec. 25, 2013. The entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy is named 111119-0108_Sequence Listing.txt and is 56,415 bytes in size.

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are DAIICHI SANKYO COMPANY, LIMITED and SAPPORO MEDICAL UNIVERSITY.

Technical Field

The present invention relates to an antibody-drug conjugate having an antitumor drug conjugated to an anti-TROP2 antibody via a linker structure moiety, the conjugate being useful as an antitumor drug.

Background Art

An antibody-drug conjugate (ADC) having a drug with cytotoxicity conjugated to an antibody, whose antigen is expressed on a surface of cancer cells and which also binds to an antigen capable of cellular internalization, and therefore can deliver the drug selectively to cancer cells and is thus expected to cause accumulation of the drug within cancer cells and to kill the cancer cells (see, Non Patent Literatures 1 to 3). As an ADC, Mylotarg (Gemtuzumab ozogamicin (registered trademark)) in which calicheamicin is conjugated to an anti-CD33 antibody is approved as a therapeutic agent for acute myeloid leukemia. Further, Adcetris (Brentuximab vedotin (registered trademark)), in which auristatin E is conjugated to an anti-CD30 antibody, has recently been approved as a therapeutic agent for Hodgkin's lymphoma and anaplastic large cell lymphoma (see, Non Patent Literature 4). The drugs contained in ADCs which have been approved until now target DNA or tubulin.

With regard to an antitumor, low-molecular-weight compounds, camptothecin derivatives, compounds that inhibit topoisomerase I to exhibit an antitumor effect, are known. Among them, an antitumor compound represented by the formula below

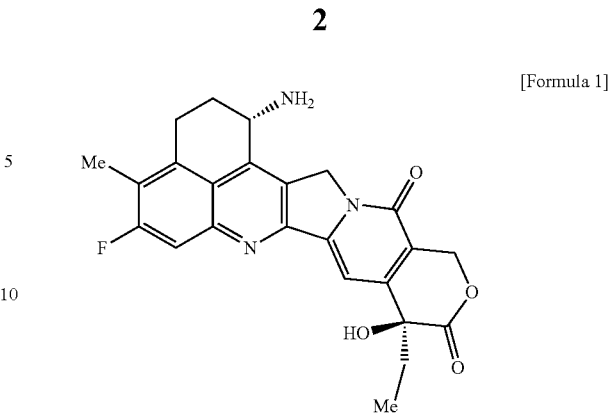

[Formula 1]

(exatecan, chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione) is a water soluble derivative of camptothecin (Patent Literature 1 and 2). Unlike irinotecan currently used in clinical settings, this compound does not require an activation by an enzyme for exerting an antitumor effect. Further, the inhibitory activity on topoisomerase I is higher than SN-38 which is a main pharmaceutically active substance of irinotecan and topotecan also used in clinical settings, and higher in vitro cytocidal activity is obtained for against various cancer cells. In particular, it exhibits the effect against cancer cells which have resistance to SN-38 or the like due to expression of P-glycoprotein. Further, in a human tumor subcutaneously transplanted mouse model, it exhibited a potent antitumor effect, and thus has undergone the clinical studies, but has not been put on the market yet (see, Non Patent Literatures 5 to 10). It remains unclear whether or not exatecan acts effectively as an ADC.

DE-310 is a complex in which exatecan is conjugated to a biodegradable carboxymethyldextran polyalcohol polymer via a GGFG peptide spacer (Patent Literature 3). By converting exatecan into a form of a polymer prodrug, a high blood retention property can be maintained and also a high targetable property to a tumor area is passively increased by utilizing the increased permeability of newly formed blood vessels within tumor and retention property in tumor tissues. With DE-310, through a cleavage of the peptide spacer by enzyme, exatecan and exatecan with glycine connected to an amino group are continuously released as a main active substance. As a result, the pharmacokinetics are improved. DE-310 was found to have higher effectiveness than exatecan administered alone even though the total amount of exatecan contained therein is lower than the case of administration of exatecan alone according to various tumor evaluation models in non-clinical studies. A clinical study was conducted for DE-310, and also effective cases were confirmed, in which a report suggesting that the main active substance accumulates in a tumor than in normal tissues was present, however, there is also a report indicating that the accumulation of DE-310 and the main active substance in a tumor is not much different from the accumulation in normal tissues in humans, and thus no passive targeting is observed in humans (see, Non Patent Literatures 11 to 14). As a result, DE-310 was not also commercialized, and it remains unclear whether or not exatecan effectively acts as a drug directed to such targeting.

As a compound relating to DE-310, a complex in which a structure moiety represented by —NH—(CH$_2$)$_4$—C(=O)— is inserted between -GGFG-spacer and exatecan to form -GGFG-NH—(CH$_2$)$_4$—C(=O)— used as a spacer structure is also known (Patent Literature 4). However, the antitumor effect of said complex is not known at all.

Human TROP2 (TACSTD2: tumor-associated calcium signal transducer 2, GA733-1, EGP-1, M1S1; hereinafter, referred to as hTROP2) is a single-pass transmembrane type 1 cell membrane protein consisting of 323 amino acid residues. While the presence of a cell membrane protein involved in immune resistance, which is common to human trophoblasts and cancer cells (Non Patent Literature 15), has previously been suggested, an antigen molecule recognized by a monoclonal antibody (162-25.3 or 162-46.2) against a cell membrane protein in a human choriocarcinoma cell line was identified and designated as TROP2 as one of the molecules expressed in human trophoblasts (Non Patent Literature 16). This molecule was also found later by other researchers and also designated as a tumor antigen GA733-1 recognized by a mouse monoclonal antibody GA733 (Non Patent Literature 17) obtained by immunization with a gastric cancer cell line or an epithelial glycoprotein (EGP-1; Non Patent Literature 18) recognized by a mouse monoclonal antibody RS7-3G11 obtained by immunization with non-small cell lung cancer cells. In 1995, however, the TROP2 gene was cloned, and all of these molecules were confirmed to be identical molecules (Non Patent Literature 19). The DNA sequence and amino acid sequence of hTROP2 are available on a public database and can be referred to, for example, under Accession Nos. NM_002353 and NP_002344 (NCBI).

The hTROP2 gene constitutes the TACSTD gene family, together with human TROP-1 (EpCAM, EGP-2, TACSTD1) gene having about 50% homology (Non Patent Literature 21). The hTROP2 protein is constituted by a signal sequence consisting of N-terminal 26 amino acid residues, an extracellular domain consisting of 248 amino acid residues, a transmembrane domain consisting of 23 amino acid residues, and an intracellular domain consisting of 26 amino acid residues. The extracellular domain has four N-linked glycosylation sites and is known to have an apparent molecular weight of about 10 kD plus the theoretical calculated value 35 kD (Non Patent Literature 19).

Neither has a physiological ligand of hTROP2 been identified, nor its molecular functions has been revealed so far. hTROP2 was found to transduce calcium signals in tumor cells (Non Patent Literature 20). In addition, hTROP2 is phosphorylated at an intracellular residue serine 303 by protein kinase C, which is a $Ca^{2+}$-dependent kinase (Non Patent Literature 18), and has a $PIP_2$-binding sequence in the intracellular domain, suggesting signaling functions in tumor cells (Non Patent Literature 22).

In immunohistochemical analysis using clinical samples, hTROP2 was found to be overexpressed in various epithelial cell carcinomas and to be expressed in epithelial cells in limited types of normal tissues at a low expression level as compared with tumor tissues (Non Patent Literatures 23 to 27). Also, the expression of hTROP2 was reported to correlate with the poor prognosis of colorectal cancer (Non Patent Literature 23), gastric cancer (Non Patent Literature 24), pancreatic cancer (Non Patent Literature 25), oral cancer (Non Patent Literature 26), and glioma (Non Patent Literature 27).

From models using colorectal cancer cells, it was further reported that the expression of hTROP2 is involved in scaffold-independent cell growth of tumor cells and tumorigenesis in immunodeficient mice (Non Patent Literature 28).

In response to such information suggesting the association with cancer, a plurality of anti-hTROP2 antibodies have been established so far and studied for their antitumor effects. Among these antibodies, there is disclosed, for example, an unconjugated antibody that exhibits in itself antitumor activity in nude mouse xenograft models (Patent Literatures 5 to 8) as well as an antibody that exhibits antitumor activity as ADC with a cytotoxic drug (Patent Literatures 9 to 12). However, the strength or coverage of their activity is still insufficient, and there are unsatisfied medical needs for hTROP2 as a therapeutic target.

CITATION LIST

Patent Literature

Patent Literature 1: Japanese Patent Laid-Open No. 5-59061
Patent Literature 2: Japanese Patent Laid-Open No. 8-337584
Patent Literature 3: International Publication No. WO 1997/46260
Patent Literature 4: International Publication No. WO 2000/25825
Patent Literature 5: International Publication No. WO 2008/144891
Patent Literature 6: International Publication No. WO 2011/145744
Patent Literature 7: International Publication No. WO 2011/155579
Patent Literature 8: International Publication No. WO 2013/077458
Patent Literature 9: International Publication No. WO 2003/074566
Patent Literature 10: International Publication No. WO 2011/068845
Patent Literature 11: International Publication No. WO 2013/068946
Patent Literature 12: U.S. Pat. No. 7,999,083

Non Patent Literature

Non Patent Literature 1: Ducry, L., et al., Bioconjugate Chem. (2010) 21, 5-13.
Non Patent Literature 2: Alley, S. C., et al., Current Opinion in Chemical Biology (2010) 14, 529-537.
Non Patent Literature 3: Damle N. K., Expert Opin. Biol. Ther. (2004) 4, 1445-1452.
Non Patent Literature 4: Senter P. D., et al., Nature Biotechnology (2012) 30, 631-637.
Non Patent Literature 5: Kumazawa, E., Tohgo, A., Exp. Opin. Invest. Drugs (1998) 7, 625-632.
Non Patent Literature 6: Mitsui, I., et al., Jpn J. Cancer Res. (1995) 86, 776-782.
Non Patent Literature 7: Takiguchi, S., et al., Jpn J. Cancer Res. (1997) 88, 760-769.
Non Patent Literature 8: Joto, N. et al., Int J Cancer (1997) 72, 680-686.
Non Patent Literature 9: Kumazawa, E. et al., Cancer Chemother. Pharmacol. (1998) 42, 210-220.
Non Patent Literature 10: De Jager, R., et al., Ann N Y Acad Sci (2000) 922, 260-273.
Non Patent Literature 11: Inoue, K. et al., Polymer Drugs in the Clinical Stage, Edited by Maeda et al. (2003), 145-153.
Non Patent Literature 12: Kumazawa, E. et al., Cancer Sci (2004) 95, 168-175.
Non Patent Literature 13: Soepenberg, O. et al., Clinical Cancer Research, (2005) 11, 703-711.
Non Patent Literature 14: Wente M. N. et al., Investigational New Drugs (2005) 23, 339-347.

Non Patent Literature 15: Faulk W P, et al., Proc. Natl. Acad. Sci.75(4), 1947-1951 (1978).
Non Patent Literature 16: Lipinski M, et al., Proc. Natl. Acad. Sci. 78(8), 5147-5150 (1981).
Non Patent Literature 17: Linnenbach A J, et al., Proc. Natl. Acad. Sci. 86(1), 27-31 (1989).
Non Patent Literature 18: Basu A, et al., Int. J. Cancer, 62(4), 472-479 (1995).
Non Patent Literature 19: Fornaro M, et al., Int. J. Cancer, 62 (5), 610-618 (1995).
Non Patent Literature 20: Ripani E, et al., Int. J. Cancer, 76(5), 671-676 (1998).
Non Patent Literature 21: Calabrese G, et al., Cytogenet. Cell Genet., 92(1-2), 164-165 (2001).
Non Patent Literature 22: El Sewedy T, et al., Int. J. Cancer, 75(2), 324-330 (1998).
Non Patent Literature 23: Ohmachi T, et al., Clin. Cancer Res., 12(10), 3057-3063 (2006).
Non Patent Literature 24: Muhlmann G, et al., J. Clin. Pathol., 62(2), 152-158 (2009).
Non Patent Literature 25: Fong D, et al., Br. J. Cancer, 99(8), 1290-1295 (2008).
Non Patent Literature 26: Fong D, et al., Mod. Pathol., 21(2), 186-191 (2008).
Non Patent Literature 27: Ning S, et al., Neurol. Sci., 34(10), 1745-1750 (2013).
Non Patent Literature 28: Wang J, et al., Mol. Cancer Ther., 7 (2), 280-285 (2008).

SUMMARY OF INVENTION

Technical Problem

With regard to the treatment of tumor by an antibody, an insufficient antitumor effect may be observed even when the antibody recognizes an antigen to bind to tumor cells, and there is a case in which a more effective antitumor antibody is needed. Further, many antitumor low-molecular-weight compounds have a problem in safety like side effect and toxicity even the compounds have an excellent antitumor effect, it remains as a subject to achieve a superior therapeutic effect by further enhancing the safety. Thus, an object of the present invention is to obtain to provide an antitumor drug having an excellent therapeutic effect, which is excellent in terms of antitumor effect and safety.

The inventors thought that, when an antitumor compound exatecan is converted into an antibody-drug conjugate, via a linker structure moiety, by conjugation to the anti-TROP2 antibody, which is capable of targeting tumor cells, that is having a property capable of recognizing tumor cells, a property capable of binding to tumor cells, a property of internalizing within tumor cells, or the like, the cytocidal activity based on the antibody can be acquired, the antitumor compound can be more surely delivered to tumor cells to specifically exhibit the antitumor effect of the compound in tumor cells, and thus the antitumor effect can be surely exhibited, and a dose of the antitumor compound can be reduced compared to a case of administering the compound alone, and thus an influence of the antitumor compound on normal cells can be alleviated so that higher safety can be achieved.

In this connection, the inventors created a linker with a specific structure and succeeded in obtaining an antibody-drug conjugate in which the anti-TROP2 antibody and exatecan are conjugated to each other via the linker, and confirmed an excellent antitumor effect exhibited by the conjugate to thereby complete the present invention.

Specifically, the present invention relates to the followings.
[1] An antibody-drug conjugate wherein an antitumor compound represented by the following formula:

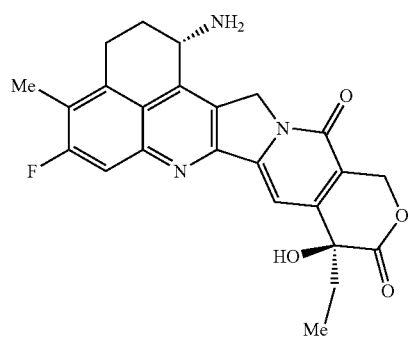

[Formula 2]

is conjugated to an anti-TROP2 antibody by a thioether bond which is formed at a disulfide bond moiety present in a hinge part of the anti-TROP2 antibody via a linker having a structure represented by the following formula:

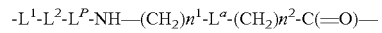

-L$^1$-L$^2$-L$^P$-NH—(CH$_2$)n$^1$-L$^a$-(CH$_2$)n$^2$-C(=O)—

Here, the anti-TROP2 antibody is connected to the terminal of L$^1$, the antitumor compound is connected to the carbonyl group of the —(CH$_2$)n$^2$-C(=O)— moiety with the nitrogen atom of the amino group at position 1 as the connecting position,
wherein
n$^1$ represents an integer of 0 to 6,
n$^2$ represents an integer of 0 to 5,
L$^1$ represents -(Succinimid-3-yl-N)—(CH$_2$)n$^3$-C(=O)—, wherein n$^3$ represents an integer of 2 to 8,
L$^2$ represents —NH—(CH$_2$CH$_2$—O)n$^4$-CH$_2$CH$_2$—C (=O)— or a single bond, wherein n$^4$ represents an integer of 1 to 6,
L$^P$ represents a peptide residue consisting of 2 to 7 amino acids,
L$^a$ represents —O— or a single bond, and
-(Succinimid-3-yl-N)— has a structure represented by the following formula:

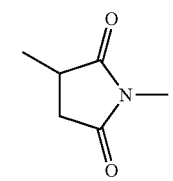

[Formula 3]

which is connected to the anti-TROP2 antibody at position 3 thereof and is connected to a methylene group in the linker structure containing this structure on the nitrogen atom at position 1.

The present invention further relates to each of the followings.
[2] The antibody-drug conjugate according to [1], wherein the peptide residue of L$^P$ is a peptide residue comprising an amino acid selected from phenylalanine, glycine, valine, lysine, citrulline, serine, glutamic acid, and aspartic acid.

[3] The antibody-drug conjugate according to [1] or [2], wherein $L^P$ is a peptide residue selected from the following group:
-GGF-,
-DGGF-,
-(D-)D-GGF-,
-EGGF-,
-GGFG-,
-SGGF-,
-KGGF-,
-DGGFG-,
-GGFGG-,
-DDGGFG-,
-KDGGFG-, and
-GGFGGGF-;
wherein "(D-)D" represents D-aspartic acid.

[4] The antibody-drug conjugate according to [1] or [2], wherein $L^P$ is a peptide residue consisting of 4 amino acids.

[5] The antibody-drug conjugate according to any one of [1] to [4], wherein $L^P$ is a tetrapeptide residue of -GGFG-.

[6] The antibody-drug conjugate according to any one of [1] to [5], wherein $n^3$ is an integer of 2 to 5, and $L^2$ is a single bond.

[7] The antibody-drug conjugate according to any one of [1] to [5], wherein $n^3$ is an integer of 2 to 5, $L^2$ is —NH—(CH$_2$CH$_2$—O)n$^4$-CH$_2$CH$_2$—C(=O)—, and $n^4$ is 2 or 4.

[8] The antibody-drug conjugate according to any one of [1] to [7], wherein —NH—(CH$_2$)n$^1$-L$^a$-(CH$_2$)n$^2$-C(=O)— is a partial structure having a chain length of 4 to 7 atoms.

[9] The antibody-drug conjugate according to any one of [1] to [7], wherein —NH—(CH$_2$)n$^1$-L$^a$-(CH$_2$)n$^2$-C(=O)— is a partial structure having a chain length of 5 or 6 atoms.

[10] The antibody-drug conjugate according to any one of [1] to [9], wherein —NH—(CH$_2$)n$^1$-L$^a$-(CH$_2$)n$^2$-C(=O)— is
—NH—CH$_2$CH$_2$—C(=O)—,
—NH—CH$_2$CH$_2$CH$_2$—C(=O)—,
—NH—CH$_2$CH$_2$CH$_2$CH$_2$—C(=O)—,
—NH—CH$_2$CH$_2$CH$_2$CH$_2$CH$_2$—C(=O)—,
—NH—CH$_2$—O—CH$_2$—C(=O)—, or
—NH—CH$_2$CH$_2$—O—CH$_2$—C(=O)—.

[11] The antibody-drug conjugate according to any one of [1] to [9], wherein —NH—(CH$_2$)n$^1$-L$^a$-(CH$_2$)n$^2$-C(=O)— is
—NH—CH$_2$CH$_2$CH$_2$—C(=O)—,
—NH—CH$_2$—O—CH$_2$—C(=O)—, or
—NH—CH$_2$CH$_2$—O—CH$_2$—C(=O)—.

[12] The antibody-drug conjugate according to any one of [1] to [9], wherein the drug-linker structure moiety having a drug connected to -L$^1$-L$^2$-L$^P$-NH—(CH$_2$)n$^1$-L$^a$-(CH$_2$)n$^2$-C(=O)— is one drug-linker structure selected from the following group:
-(Succinimid-3-yl-N)—CH$_2$CH$_2$—C(=O)-GGFG-NH—CH$_2$CH$_2$—C(=O)—(NH-DX),
-(Succinimid-3-yl-N)—CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$CH$_2$CH$_2$—C(=O)—(NH-DX).

Wherein -(Succinimid-3-yl-N)— has a structure represented by the following formula:

[Formula 4]

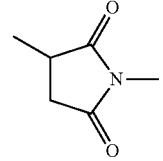

which is connected to the anti-TROP2 antibody at position 3 thereof and is connected to a methylene group in the linker structure containing this structure on the nitrogen atom at position 1,
—(NH-DX) represents a group represented by the following formula:

[Formula 5]

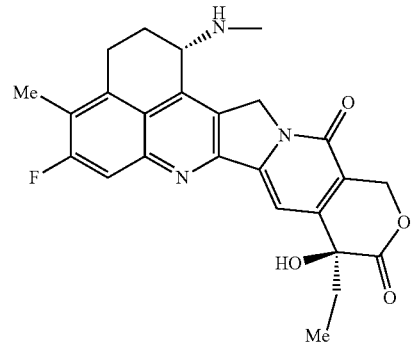

wherein the nitrogen atom of the amino group at position 1 is a connecting position, and
-GGFG- represents a tetrapeptide residue of -Gly-Gly-Phe-Gly-.

[13] The antibody-drug conjugate according to any one of [1] to [9], wherein the drug-linker structure moiety having a drug connected to -L$^1$-L$^2$-L$^P$-NH—(CH$_2$)n$^1$-L$^a$-(CH$_2$)n$^2$-C(=O)— is one drug-linker structure selected from the following group:
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX).

Here, -(Succinimid-3-yl-N)—, —(NH-DX), and -GGFG- are as defined above.

[14] An antibody-drug conjugate wherein an antitumor compound represented by the following formula:

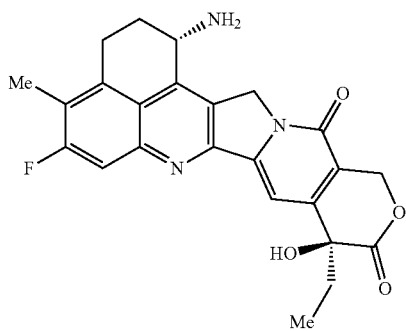

[Formula 6]

is conjugated to an anti-TROP2 antibody by a thioether bond which is formed at a disulfide bond moiety present in a hinge part of the anti-TROP2 antibody via a linker having a structure represented by the following formula:

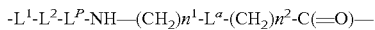

-$L^1$-$L^2$-$L^P$-NH—(CH$_2$)$n^1$-$L^a$-(CH$_2$)$n^2$-C(=O)— wherein the anti-TROP2 antibody is connected to the terminal of $L^1$, the antitumor compound is connected to the carbonyl group of the —(CH$_2$)$n^2$-C(=O)— moiety, wherein
$n^1$ represents an integer of 0 to 6,
$n^2$ represents an integer of 0 to 5,
$L^1$ represents -(Succinimid-3-yl-N)—(CH$_2$)$n^3$-C(=O)—, wherein $n^3$ represents an integer of 2 to 8,
$L^2$ represents —NH—(CH$_2$CH$_2$—O)$n^4$-CH$_2$CH$_2$—C(=O)— or a single bond,
wherein $n^4$ represents an integer of 1 to 6,
$L^P$ represents a tetrapeptide residue of -GGFG-,
$L^a$ represents —O— or a single bond, and
-(Succinimid-3-yl-N)— has a structure represented by the following formula:

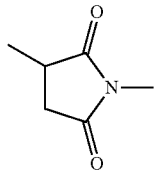

[Formula 7]

which is connected to the anti-TROP2 antibody at position 3 thereof and is connected to a methylene group in the linker structure containing this structure on the nitrogen atom at position 1.

[15] The antibody-drug conjugate according to [14], wherein
$n^1$ is 3, $n^2$ is 0, $n^3$ is 2, $L^2$ is —NH—(CH$_2$CH$_2$—O)$n^4$-CH$_2$CH$_2$—C(=O)—, $n^4$ is 2, and $L^a$ is a single bond,
$n^1$ is 1, $n^2$ is 1, $n^3$ is 5, $L^2$ is a single bond, and $L^a$ is —O—, or
$n^1$ is 2, $n^2$ is 1, $n^3$ is 5, $L^2$ is a single bond, and $L^a$ is —O—.

[16] The antibody-drug conjugate according to [14] or [15], wherein $n^3$ is 2 or 5, and $L^2$ is a single bond.

[17] The antibody-drug conjugate according to [14] or [15], wherein $n^3$ is 2 or 5, $L^2$ is —NH—(CH$_2$CH$_2$—O)$n^4$-CH$_2$CH$_2$—C(=O)—, and $n^4$ is 2 or 4.

[18] The antibody-drug conjugate according to any one of [14] to [17], wherein —NH—(CH$_2$)$n^1$-$L^a$-(CH$_2$)$n^2$-C(=O)— is
—NH—CH$_2$CH$_2$CH$_2$—C(=O)—,
—NH—CH$_2$—O—CH$_2$—C(=O)—, or
—NH—CH$_2$CH$_2$—O—CH$_2$—C(=O)—.

[19] The antibody-drug conjugate according to any one of [14] to [18], wherein the drug-linker structure moiety having a drug connected to -$L^1$-$L^2$-$L^P$-NH—(CH$_2$)$n^1$-$L^a$-(CH$_2$)$n^2$-C(=O)— is one drug-linker structure selected from the following group:
-(Succinimid-3-yl-N)—CH$_2$CH$_2$—C(=O)-GGFG-NH—CH$_2$CH$_2$—C(=O)—(NH-DX),
-(Succinimid-3-yl-N)—CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$CH$_2$CH$_2$—C(=O)—(NH-DX);
wherein -(Succinimid-3-yl-N)— has a structure represented by the following formula:

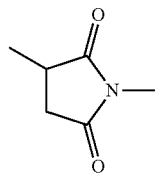

[Formula 8]

which is connected to the anti-TROP2 antibody at position 3 thereof and is connected to a methylene group in the linker structure containing this structure on the nitrogen atom at position 1,
—(NH-DX) represents a group represented by the following formula:

[Formula 9]

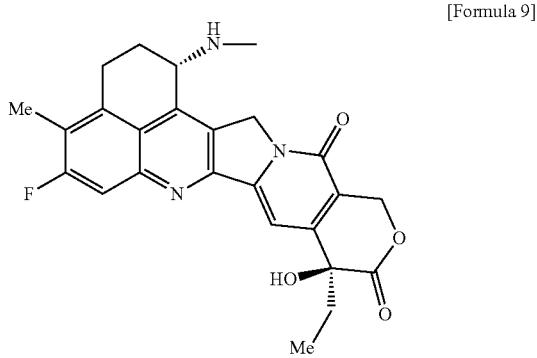 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is a connecting position, and
-GGFG- represents a tetrapeptide residue of -Gly-Gly-Phe-Gly-.

[20] The antibody-drug conjugate according to any one of [14] to [18], wherein the drug-linker structure moiety having a drug connected to -L$^1$-L$^2$-L$^P$-NH—(CH$_2$)n$^1$-L$^a$-(CH$_2$)n$^2$-C(=O)— is one drug-linker structure selected from the following group:
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX).
Here, -(Succinimid-3-yl-N)—, —(NH-DX) and -GGFG- are as defined above.

[21] The antibody-drug conjugate according to any one of [1] to [20], wherein an average number of units of the selected one drug-linker structure conjugated per antibody is in a range of from 1 to 10.

[22] The antibody-drug conjugate according to any one of [1] to [20], wherein an average number of units of the selected one drug-linker structure conjugated per antibody is in a range of from 2 to 8.

[23] The antibody-drug conjugate according to any one of [1] to [20], wherein an average number of units of the selected one drug-linker structure conjugated per antibody is in a range of from 3 to 8.

[24] A drug containing the antibody-drug conjugate according to any one of [1] to [23], a salt thereof or a hydrate thereof.

[25] An antitumor drug and/or anticancer drug containing the antibody-drug conjugate according to any one of [1] to [23], a salt thereof or a hydrate thereof.

[26] The antitumor drug and/or anticancer drug according to [25], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, cervical cancer, head and neck cancer, or esophageal cancer.

[27] A pharmaceutical composition containing the antibody-drug conjugate according to any one of [1] to [23], a salt thereof or a hydrate thereof as an active component, and a pharmaceutically acceptable formulation component.

[28] The pharmaceutical composition according to [27], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, cervical cancer, head and neck cancer, or esophageal cancer.

[29] A method for treating tumor and/or cancer comprising administering the antibody-drug conjugate according to any one of [1] to [23], a salt thereof or a hydrate thereof.

[30] A method for producing an antibody-drug conjugate comprising reacting a compound represented by the following formula:

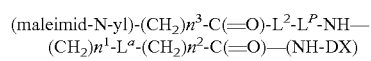

with an anti-TROP2 antibody or a reactive derivative thereof and conjugating a drug-linker moiety to the antibody by a method for forming a thioether bond at a disulfide bond site present in a hinge part of the antibody.

In the formula, n$^3$ represents an integer of 2 to 8,
L$^2$ represents —NH—(CH$_2$CH$_2$—O)n$^4$-CH$_2$CH$_2$—C(=O)— or a single bond, wherein n$^4$ represents an integer of 1 to 6,
L$^P$ represents a peptide residue consisting of 2 to 7 amino acids selected from phenylalanine, glycine, valine, lysine, citrulline, serine, glutamic acid, and aspartic acid,
n$^1$ represents an integer of 0 to 6,
n$^2$ represents an integer of 0 to 5,
L$^a$ represents —O— or a single bond,
(maleimid-N-yl)- is a group represented by the following formula:

[Formula 10]

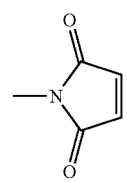

wherein the nitrogen atom is a connecting position.
—(NH-DX) is a group represented by the following formula:

[Formula 11]

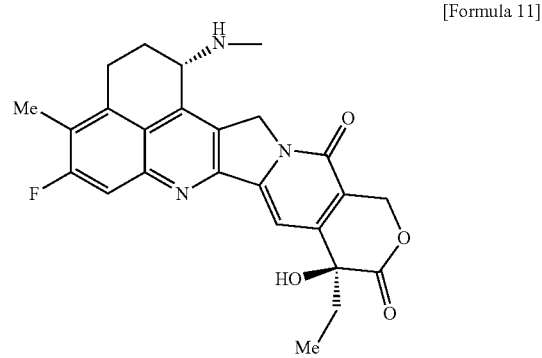 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is a connecting position.

[31] The production method according to [30], wherein the method for conjugating a drug-linker moiety to an anti-TROP2 antibody is a method of reducing the antibody to convert the antibody to a reactive derivative.

[32] The production method according to [30] or [31], wherein an average number of units of the selected one drug-linker structure conjugated per antibody is in a range of from 1 to 10.

[33] The production method according to [30] or [31], wherein an average number of units of the selected one drug-linker structure conjugated per antibody is in a range of from 2 to 8.

[34] The production method according to [30] or [31], wherein an average number of units of the selected one drug-linker structure conjugated per antibody is in a range of from 3 to 8.

[35] An antibody-drug conjugate obtained by the production method according to any of [30] to [34].

[36] An antibody-drug conjugate obtained by forming a thioether bond at a sulfide bond site in a hinge part of an anti-TROP2 antibody, wherein the anti-TROP2 antibody is treated in a reducing condition and thereafter reacted with a compound selected from the following group:

(maleimid-N-yl)-CH$_2$CH$_2$—C(=O)-GGFG-NH—CH$_2$CH$_2$—C(=O)—(NH-DX), (maleimid-N-yl)-CH$_2$CH$_2$CH$_2$—C(=O)-GGFG-NH—CH$_2$CH$_2$—C(=O)—(NH-DX), (maleimid-N-yl)-CH$_2$CH$_2$CH$_2$CH$_2$—C(=O)-GGFG-NH—CH$_2$CH$_2$—C(=O)—(NH-DX), (maleimid-N-yl)-CH$_2$CH$_2$CH$_2$CH$_2$CH$_2$—C(=O)-GGFG-NH—CH$_2$CH$_2$—C(=O)—(NH-DX), (maleimid-N-yl)-CH$_2$CH$_2$—C(=O)-GGFG-NH—CH$_2$CH$_2$CH$_2$—C(=O)—(NH-DX), (maleimid-N-yl)-CH$_2$CH$_2$CH$_2$—C(=O)-GGFG-NH—CH$_2$CH$_2$CH$_2$—C(=O)—(NH-DX), (maleimid-N-yl)-CH$_2$CH$_2$CH$_2$CH$_2$—C(=O)-GGFG-NH—CH$_2$CH$_2$CH$_2$—C(=O)—(NH-DX), (maleimid-N-yl)-CH$_2$CH$_2$CH$_2$CH$_2$CH$_2$—C(=O)-GGFG-NH—CH$_2$CH$_2$CH$_2$—C(=O)—(NH-DX), (maleimid-N-yl)-CH$_2$CH$_2$—C(=O)-GGFG-NH—CH$_2$CH$_2$CH$_2$CH$_2$CH$_2$—C(=O)—(NH-DX), (maleimid-N-yl)-CH$_2$CH$_2$CH$_2$—C(=O)-GGFG-NH—CH$_2$CH$_2$CH$_2$CH$_2$CH$_2$—C(=O)—(NH-DX), (maleimid-N-yl)-CH$_2$CH$_2$CH$_2$CH$_2$—C(=O)-GGFG-NH—CH$_2$CH$_2$CH$_2$CH$_2$CH$_2$—C(=O)—(NH-DX), (maleimid-N-yl)-CH$_2$CH$_2$CH$_2$CH$_2$CH$_2$—C(=O)-GGFG-NH—CH$_2$CH$_2$CH$_2$CH$_2$CH$_2$—C(=O)—(NH-DX), (maleimid-N-yl)-CH$_2$CH$_2$—C(=O)-GGFG-NH—CH$_2$—O—CH$_2$—C(=O)—(NH-DX), (maleimid-N-yl)-CH$_2$CH$_2$CH$_2$—C(=O)-GGFG-NH—CH$_2$—O—CH$_2$—C(=O)—(NH-DX), (maleimid-N-yl)-CH$_2$CH$_2$CH$_2$CH$_2$—C(=O)-GGFG-NH—CH$_2$—O—CH$_2$—C(=O)—(NH-DX), (maleimid-N-yl)-CH$_2$CH$_2$CH$_2$CH$_2$CH$_2$—C(=O)-GGFG-NH—CH$_2$—O—CH$_2$—C(=O)—(NH-DX), (maleimid-N-yl)-CH$_2$CH$_2$—C(=O)-GGFG-NH—CH$_2$CH$_2$—O—CH$_2$—C(=O)—(NH-DX), (maleimid-N-yl)-CH$_2$CH$_2$CH$_2$—C(=O)-GGFG-NH—CH$_2$CH$_2$—O—CH$_2$—C(=O)—(NH-DX), (maleimid-N-yl)-CH$_2$CH$_2$CH$_2$CH$_2$—C(=O)-GGFG-NH—CH$_2$CH$_2$—O—CH$_2$—C(=O)—(NH-DX), (maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)—(NH-DX), (maleimid-N-yl)-CH$_2$CH$_2$—C(=O)—NH—CH$_2$CH$_2$—O—CH$_2$CH$_2$—C(=O)-GGFG-NH—CH$_2$CH$_2$CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX), (maleimid-N-yl)-CH$_2$CH$_2$—C(=O)—NH—CH$_2$CH$_2$—O—CH$_2$CH$_2$—C(=O)-GGFG-NH—CH$_2$—O—CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$—O—CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$—O—CH$_2$—C(=O)—(NH-DX), (maleimid-N-yl)-CH$_2$CH$_2$—C(=O)—NH—CH$_2$CH$_2$—O—CH$_2$CH$_2$—C(=O)-GGFG-NH—CH$_2$CH$_2$—O—CH$_2$—C(=O)—(NH-DX), (maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—O—CH$_2$—C(=O)—(NH-DX), and (maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$CH$_2$—O—CH$_2$—C(=O)—(NH-DX).

In the above, (maleimid-N-yl)- is a group represented by the following formula:

[Formula 12]

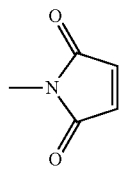

wherein the nitrogen atom is a connecting position.

—(NH-DX) is a group represented by the following formula:

[Formula 13]

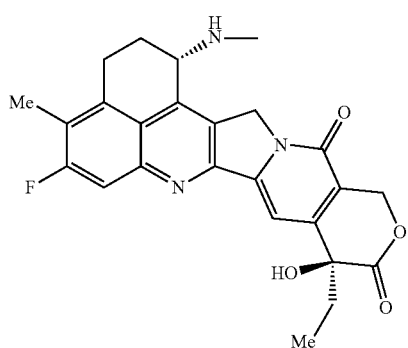

wherein the nitrogen atom of the amino group at position 1 is a connecting position.

-GGFG- represents a tetrapeptide residue of -Gly-Gly-Phe-Gly-.

[37] An antibody-drug conjugate obtained by forming a thioether bond at a sulfide bond site present in a hinge part of an anti-TROP2 antibody, wherein the anti-TROP2 antibody is treated in a reducing condition and thereafter reacted with a compound selected from the following group:

(maleimid-N-yl)-$CH_2CH_2$—C(=O)—NH—$CH_2CH_2$—O—$CH_2CH_2$—O—$CH_2CH_2$—C(=O)-GGFG-NH—$CH_2CH_2CH_2$—C(=O)—(NH-DX), (maleimid-N-yl)-$CH_2CH_2CH_2CH_2CH_2$—C(=O)-GGFG-NH—$CH_2$—O—$CH_2$—C(=O)—(NH-DX), and (maleimid-N-yl)-$CH_2CH_2CH_2CH_2CH_2$—C(=O)-GGFG-NH—$CH_2CH_2$—O—$CH_2$—C(=O)—(NH-DX).

Here, (maleimid-N-yl)-, —(NH-DX), and -GGFG- are as defined above.

[38] The antibody-drug conjugate according to [36] or [37], wherein an average number of units of the selected one drug-linker structure conjugated per antibody is in a range of from 1 to 10.

[39] The antibody-drug conjugate according to [36] or [37], wherein an average number of units of the selected one drug-linker structure conjugated per antibody is in a range of from 2 to 8.

[40] The antibody-drug conjugate according to [36] or [37], wherein an average number of units of the selected one drug-linker structure conjugated per antibody is in a range of from 3 to 8.

Advantageous Effects of Invention

With an anti-TROP2 antibody-drug conjugate having an antitumor compound exatecan conjugated via a linker with a specific structure, an excellent antitumor effect and safety can be achieved.

BRIEF DESCRIPTION OF DRAWINGS

FIG. 1 shows a nucleotide sequence (SEQ ID NO: 7) and an amino acid sequence (SEQ ID NO: 8) of a cTINA1 antibody heavy chain.

FIG. 2 shows a nucleotide sequence (SEQ ID NO: 9) and an amino acid sequence (SEQ ID NO: 10) of a cTINA1 antibody light chain.

FIG. 3 shows a nucleotide sequence (SEQ ID NO: 11) and an amino acid sequence (SEQ ID NO: 12) of an hTINA1-H1 heavy chain.

FIG. 4 shows a nucleotide sequence (SEQ ID NO: 13) and an amino acid sequence (SEQ ID NO: 14) of an hTINA1-H2 heavy chain.

FIG. 5 shows a nucleotide sequence (SEQ ID NO: 15) and an amino acid sequence (SEQ ID NO: 16) of an hTINA1-H3 heavy chain.

FIG. 6 shows a nucleotide sequence (SEQ ID NO: 17) and an amino acid sequence (SEQ ID NO: 18) of an hTINA1-L1 light chain.

FIG. 7 shows a nucleotide sequence (SEQ ID NO: 19) and an amino acid sequence (SEQ ID NO: 20) of an hTINA1-L2 light chain.

FIG. 8 shows a nucleotide sequence (SEQ ID NO: 21) and an amino acid sequence (SEQ ID NO: 22) of an hTINA1-L3 light chain.

FIG. 9 shows an amino acid sequence (SEQ ID NO: 23) of CDRH1 of a TINA1 antibody, an amino acid sequence (SEQ ID NO: 24) of CDRH2 thereof, an amino acid sequence (SEQ ID NO: 25) of CDRH3 thereof, an amino acid sequence (SEQ ID NO: 26) of CDRL1 thereof, an amino acid sequence (SEQ ID NO: 27) of CDRL2 thereof, and an amino acid sequence (SEQ ID NO: 28) of CDRL3 thereof.

DESCRIPTION OF EMBODIMENTS

Figure 10:
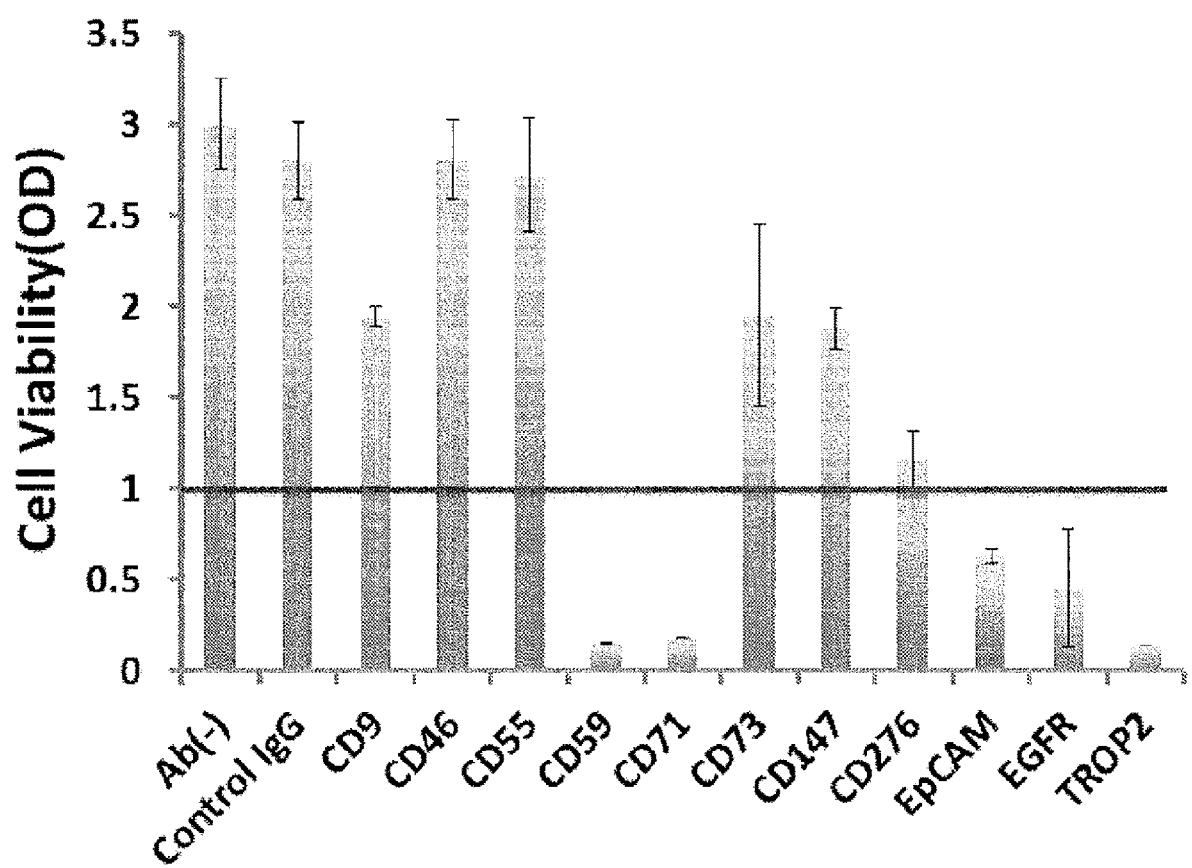
FIG. 10 shows the cell internalization ability of an anti-CD9 antibody, an anti-CD46 antibody, an anti-CD55 antibody, an anti-CD59 antibody, an anti-CD71 antibody, an anti-CD73 antibody, an anti-CD147 antibody, an anti-CD276 antibody, an anti-EpCAM antibody, an anti-EGFR antibody, and an anti-TROP2 antibody (TINA1 antibody).

Hereinafter, preferred modes for carrying out the present invention will be described with reference to the drawings. The embodiments described below are given as typical examples of the embodiments of the present invention and are not intended to limit the scope of the present invention.

The anti-TROP2 antibody-drug conjugate of the present invention is an antitumor drug in which an anti-TROP2 antibody is conjugated to an antitumor compound via a linker structure moiety and explained in detail hereinbelow.

[Antibody]

The anti-TROP2 antibody used in the anti-TROP2 antibody-drug conjugate of the present invention may be derived from any species, and preferred examples of the species can include humans, rats, mice, and rabbits. In case when derived from other than human species, it is preferably chimerized or humanized using a well known technique. The antibody of the present invention may be a polyclonal antibody or a monoclonal antibody and is preferably a monoclonal antibody.

The anti-TROP2 antibody is capable of targeting tumor cells, that is, has a property capable of recognizing a tumor cell, a property capable of binding to a tumor cell, a property of internalizing in a tumor cell, or the like, and can be converted into an antibody-drug conjugate by conjugation to a compound having antitumor activity via a linker.

The binding activity of the antibody against tumor cells can be confirmed using flow cytometry. Examples of the method for confirming the internalization of the antibody into tumor cells can include (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). A recombinant complex protein of a catalytic region of diphtheria toxin and protein G may be used as the immunotoxin.

Since the drug conjugated in the antibody-drug conjugate exerts an antitumor effect, it is preferred but not essential that the antibody itself should have an antitumor effect. For the purpose of specifically and selectively exerting the cytocidal activity of the antitumor compound on tumor cells, it is important and also preferred that the antibody should have the property of internalizing to migrate into tumor cells.

The anti-TROP2 antibody can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can be also obtained using a method of immunizing animals with the above-described genetically engineered antigen-expressing cells or a cell line expressing the antigen.

The anti-TROP2 antibody can obtained by a procedure known in the art.

The anti-TROP2 antibody that can be used in the present invention is not particularly limited, and, for example, those specified by the amino acid sequences shown in the Sequence Listing of the present application can be preferably used. The anti-TROP2 antibody used in the present invention preferably has properties as described below.

(1) An antibody having the following properties:
   (a) specifically binding to TROP2, and
   (b) having an activity of internalizing in TROP2-expressing cells by binding to TROP2.

(2) The antibody according to (1), wherein TROP2 is human TROP2.

(3) The antibody according to (1) or (2), wherein the antibody has CDRH1 comprising the amino acid sequence represented by SEQ ID NO: 23, CDRH2 comprising the amino acid sequence represented by SEQ ID NO: 24, and CDRH3 comprising the amino acid sequence represented by SEQ ID NO: 25 as heavy chain complementarity determining regions, and CDRL1 comprising the amino acid sequence represented by SEQ ID NO: 26, CDRL2 comprising the amino acid sequence represented by SEQ ID NO: 27, and CDRL3 comprising the amino acid sequence represented by SEQ ID NO: 28 as light chain complementarity determining regions.

(4) The antibody according to any of (1) to (3), wherein the constant region thereof is a human-derived constant region.

(5) The antibody according to any of (1) to (4), wherein the antibody is a humanized antibody.

(6) The antibody according to (5), wherein the antibody has a heavy chain variable region comprising an amino acid sequence selected from the group consisting of (a) an amino acid sequence described in amino acid positions 20 to 140 in SEQ ID NO: 12, (b) an amino acid sequence described in amino acid positions 20 to 140 in SEQ ID NO: 14, (c) an amino acid sequence described in amino acid positions 20 to 140 in SEQ ID NO: 16, (d) an amino acid sequence having at least 95% or higher homology to any of the sequences (a) to (c), and (e) an amino acid sequence derived from any of the sequences (a) to (c) by the deletions, replacements, or additions of at least one amino acid, and a light chain variable region comprising an amino acid sequence selected from the group consisting of (f) an amino acid sequence described in amino acid positions 21 to 129 in SEQ ID NO: 18, (g) an amino acid sequence described in amino acid positions 21 to 129 in SEQ ID NO: 20, (h) an amino acid sequence described in amino acid positions 21 to 129 in SEQ ID NO: 22, (i) an amino acid sequence having at least 95% or higher homology to any of the sequences (f) to (h), and (j) an amino acid sequence derived from any of the sequences (f) to (h) by the deletions, replacements, or additions of at least one amino acid.

(7) The antibody according to (6), wherein the antibody has a heavy chain variable region and a light chain variable region selected from the group consisting of a heavy chain variable region comprising an amino acid sequence described in amino acid positions 20 to 140 in SEQ ID NO: 12 and a light chain variable region comprising an amino acid sequence described in amino acid positions 21 to 129 in SEQ ID NO: 18, a heavy chain variable region comprising an amino acid sequence described in amino acid positions 20 to 140 in SEQ ID NO: 12 and a light chain variable region comprising an amino acid sequence described in amino acid positions 21 to 129 in SEQ ID NO: 20, a heavy chain variable region comprising an amino acid sequence described in amino acid positions 20 to 140 in SEQ ID NO: 12 and a light chain variable region comprising an amino acid sequence described in amino acid positions 21 to 129 in SEQ ID NO: 22, a heavy chain variable region comprising an amino acid sequence described in amino acid positions 20 to 140 in SEQ ID NO: 14 and a light chain variable region comprising an amino acid sequence described in amino acid positions 21 to 129 in SEQ ID NO: 18, a heavy chain variable region comprising an amino acid sequence described in amino acid positions 20 to 140 in SEQ ID NO: 14 and a light chain variable region comprising an amino acid sequence described in amino acid positions 21 to 129 in SEQ ID NO: 20, a heavy chain variable region comprising an amino acid sequence described in amino acid positions 20 to 140 in SEQ ID NO: 14 and a light chain variable region comprising an amino acid sequence described in amino acid positions 21 to 129 in SEQ ID NO: 22, a heavy chain variable region comprising an amino acid sequence described in amino acid positions 20 to 140 in SEQ ID NO: 16 and a light chain variable region comprising an amino acid sequence described in amino acid positions 21 to 129 in SEQ ID NO: 18, a heavy chain variable region comprising an amino acid sequence described in amino acid positions 20 to 140 in SEQ ID NO: 16 and a light chain variable region comprising an amino acid sequence described in amino acid positions 21 to 129 in SEQ ID NO: 20, and a heavy chain variable region comprising an amino acid sequence described in amino acid positions 20 to 140 in SEQ ID NO: 16 and a light chain variable region comprising an amino acid sequence described in amino acid positions 21 to 129 in SEQ ID NO: 22.

(8) The antibody according to (7), wherein the antibody has a heavy chain variable region and a light chain variable region selected from the group consisting of a heavy chain variable region comprising an amino acid sequence described in amino acid positions 20 to 140 in SEQ ID NO: 12 and a light chain variable region comprising an amino acid sequence described in amino acid positions 21 to 129 in SEQ ID NO: 18, a heavy chain variable region comprising an amino acid sequence described in amino acid positions 20 to 140 in SEQ ID NO: 14 and a light chain variable region comprising an amino acid sequence described in amino acid positions 21 to 129 in SEQ ID NO: 18, a heavy chain variable region comprising an amino acid sequence described in amino acid positions 20 to 140 in SEQ ID NO: 14 and a light chain variable region comprising an amino acid sequence described in amino acid positions 21 to 129 in SEQ ID NO: 20, and a heavy chain variable region comprising an amino acid sequence described in amino acid positions 20 to 140 in SEQ ID NO: 16 and a light chain variable region comprising an amino acid sequence described in amino acid positions 21 to 129 in SEQ ID NO: 22.

(9) The antibody according to (6) or (7), wherein the antibody comprises a heavy chain and a light chain selected from the group consisting of a heavy chain comprising an amino acid sequence described in amino acid positions 20 to 470 in SEQ ID NO: 12 and a light chain comprising an amino acid sequence described in amino acid positions 21 to 234 in SEQ ID NO: 18, a heavy chain comprising an amino acid sequence described in amino acid positions 20 to 470 in SEQ ID NO: 12 and a light chain comprising an amino acid sequence described in amino acid positions 21 to 234 in SEQ ID NO: 20, a heavy chain comprising an amino acid sequence described in amino acid positions 20 to 470 in SEQ ID NO: 12 and a light chain comprising an amino acid sequence described in amino acid positions 21 to 234 in SEQ ID NO: 22, a heavy chain comprising an amino acid sequence described in amino acid positions 20 to 470 in SEQ ID NO: 14 and a light chain comprising an amino acid sequence described in amino acid positions 21 to 234 in SEQ ID NO: 18, a heavy chain comprising an amino acid sequence described in amino acid positions 20 to 470 in SEQ ID NO: 14 and a light chain comprising an amino acid sequence described in amino acid positions 21 to 234 in SEQ ID NO: 20, a heavy chain comprising an amino acid sequence described in amino acid positions 20 to 470 in SEQ ID NO: 14 and a light chain comprising an amino acid sequence described in amino acid positions 21 to 234 in SEQ ID NO: 22, a heavy chain comprising an amino acid sequence described in amino acid positions 20 to 470 in SEQ ID NO: 16 and a light chain comprising an amino acid sequence described in amino acid positions 21 to 234 in SEQ ID NO: 18, a heavy chain comprising an amino acid sequence described in amino acid positions 20 to 470 in SEQ ID NO: 16 and a light chain comprising an amino acid sequence described in amino acid positions 21 to 234 in SEQ ID NO: 20, and a heavy chain comprising an amino acid sequence described in amino acid positions 20 to 470 in SEQ ID NO: 16 and a light chain comprising an amino acid sequence described in amino acid positions 21 to 234 in SEQ ID NO: 22.

(10) The antibody according to (6) or (7), wherein the antibody comprises a heavy chain and a light chain selected from the group consisting of a heavy chain comprising the amino acid sequence represented by SEQ ID NO: 12 and a light chain comprising the amino acid sequence represented by SEQ ID NO: 18, a heavy chain comprising the amino acid sequence represented by SEQ ID NO: 12 and a light chain comprising the amino acid sequence represented by SEQ ID NO: 20, a heavy chain comprising the amino acid sequence represented by SEQ ID NO: 12 and a light chain comprising the amino acid sequence represented by SEQ ID NO: 22, a heavy chain comprising the amino acid sequence represented by SEQ ID NO: 14 and a light chain comprising the amino acid sequence represented by SEQ ID NO: 18, a heavy chain comprising the amino acid sequence represented by SEQ ID NO: 14 and a light chain comprising the amino acid sequence represented by SEQ ID NO: 20, a heavy chain comprising the amino acid sequence represented by SEQ ID NO: 14 and a light chain comprising the amino acid sequence represented by SEQ ID NO: 22, a heavy chain comprising the amino acid sequence represented by SEQ ID NO: 16 and a light chain comprising the amino acid sequence represented by SEQ ID NO: 18, a heavy chain comprising the amino acid sequence represented by SEQ ID NO: 16 and a light chain comprising the amino acid sequence represented by SEQ ID NO: 20, and a heavy chain comprising the amino acid sequence represented by SEQ ID NO: 16 and a light chain comprising the amino acid sequence represented by SEQ ID NO: 22.

(11) The antibody according to (8), wherein the antibody comprises a heavy chain and a light chain selected from the group consisting of a heavy chain comprising an amino acid sequence described in amino acid positions 20 to 470 in SEQ ID NO: 12 and a light chain comprising an amino acid sequence described in amino acid positions 21 to 234 in SEQ ID NO: 18, a heavy chain comprising an amino acid sequence described in amino acid positions 20 to 470 in SEQ ID NO: 14 and a light chain comprising an amino acid sequence described in amino acid positions 21 to 234 in SEQ ID NO: 18, a heavy chain comprising an amino acid sequence described in amino acid positions 20 to 470 in SEQ ID NO: 14 and a light chain comprising an amino acid sequence described in amino acid positions 21 to 234 in SEQ ID NO: 20, and a heavy chain comprising an amino acid sequence described in amino acid positions 20 to 470 in SEQ ID NO: 16 and a light chain comprising an amino acid sequence described in amino acid positions 21 to 234 in SEQ ID NO: 22.

(12) The antibody according to any of (1) to (11), wherein the antibody lacks a lysine residue at the carboxyl terminus of the heavy chain.

(13) An antibody obtained by a method for producing the antibody according to any of (1) to (12), the method comprising the steps of: culturing a host cell transformed with an expression vector containing a polynucleotide encoding the antibody; and collecting the antibody of interest from the cultures obtained in the preceding step.

Hereinafter, the anti-TROP2 antibody used in the invention is described.

The terms "cancer" and "tumor" as used herein are used with the same meaning.

The term "gene" as used herein includes not only DNA, but also mRNA thereof, cDNA thereof, and cRNA thereof.

The term "polynucleotide" as used herein is used with the same meaning as a nucleic acid and also includes DNA, RNA, probes, oligonucleotides, and primers.

The terms "polypeptide" and "protein" as used herein are used without distinction.

The term "cell" as used herein also includes cells in an animal individual and cultured cells.

The term "TROP2" as used herein is used in the same meaning as TROP2 protein.

The term "CDR" as used herein refers to a complementarity determining region (CDR). It is known that each heavy and light chain of an antibody molecule has three complementarity determining regions (CDRs). The CDR is also called the hypervariable domain, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. TROP2

TROP2 is a member of the TACSTD family expressed in human trophoblasts and is a single-pass transmembrane type 1 cell membrane protein involved in immune resistance, which is common to human trophoblasts and cancer cells.

As for TROP2 protein to be used in the invention, TROP2 protein can be directly purified from the TROP2-expressing cells of a human or a non-human mammal (such as a rat or a mouse) and used, or a cell membrane fraction of the above-described cells can be prepared and used. Further, TROP2 can be obtained by in vitro synthesis thereof or production thereof in a host cell through genetic engineering. In the genetic engineering, specifically, after TROP2 cDNA is integrated into a vector capable of expressing TROP2 cDNA, the TROP2 protein can be obtained by synthesizing it in a solution containing an enzyme, a substrate and an energy substance required for transcription and translation, or by expressing TROP2 in another prokaryotic or eucaryotic transformed host cell. Alternatively, the above-described genetically engineered TROP2-expressing cells or a cell line expressing TROP2 may be used as the TROP2 protein.

The DNA sequence and amino acid sequence of TROP2 are available on a public database and can be referred to, for example, under Accession Nos. NM_002353 and NP_002344 (NCBI).

Further, a protein which consists of an amino acid sequence wherein one or several amino acids are substituted, deleted and/or added in any of the above-described amino acid sequences of TROP2 and also has a biological activity equivalent to that of the protein is also included in TROP2.

The human TROP2 protein is constituted by a signal sequence consisting of N-terminal 26 amino acid residues, an extracellular domain consisting of 248 amino acid residues, a transmembrane domain consisting of 23 amino acid residues, and an intracellular domain consisting of 26 amino acid residues.

2. Production of Anti-TROP2 Antibody

The antibody against TROP2 of the invention can be obtained using a method usually carried out in the art, which involves immunizing an animal with TROP2 or an arbitrary polypeptide selected from the amino acid sequence of TROP2, and collecting and purifying the antibody produced in vivo. The biological species of TROP2 to be used as an antigen is not limited to being human, and an animal can be immunized with TROP2 derived from an animal other than humans such as a mouse or a rat. In this case, by examining the cross-reactivity between an antibody binding to the obtained heterologous TROP2 and human TROP2, an antibody applicable to a human disease can be selected.

Further, a monoclonal antibody can be obtained from a hybridoma established by fusing antibody-producing cells which produce an antibody against TROP2 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

TROP2 to be used as an antigen can be obtained by expressing TROP2 gene in a host cell using genetic engineering.

Specifically, a vector capable of expressing TROP2 gene is produced, and the resulting vector is transfected into a host cell to express the gene, and then, the expressed TROP2 is purified.

Alternatively, the above-described genetically engineered TROP2-expressing cells or a cell line expressing TROP2 may be used as the TROP2 protein. Hereinafter, a method of obtaining an antibody against TROP2 is specifically described.

(1) Preparation of Antigen

Examples of the antigen to be used for producing the anti-TROP2 antibody include TROP2, or a polypeptide consisting of a partial amino acid sequence comprising at least 6 consecutive amino acids of TROP2, or a derivative obtained by adding a given amino acid sequence or carrier thereto.

TROP2 can be purified directly from human tumor tissues or tumor cells and used. Further, TROP2 can be obtained by synthesizing it in vitro or by producing it in a host cell by genetic engineering.

With respect to the genetic engineering, specifically, after TROP2 cDNA is integrated into a vector capable of expressing TROP2 cDNA, the antigen can be obtained by synthesizing it in a solution containing an enzyme, a substrate and an energy substance required for transcription and translation, or by expressing TROP2 in another prokaryotic or eucaryotic transformed host cell.

Further, the antigen can also be obtained as a secretory protein by expressing a fusion protein obtained by ligating the extracellular domain of TROP2, which is a membrane protein, to the constant region of an antibody in an appropriate host-vector system.

TROP2 cDNA can be obtained by, for example, a so-called PCR method in which a polymerase chain reaction (hereinafter referred to as "PCR"; see Saiki, R. K., et al., Science, (1988) 239, pp. 487-489) is performed using a cDNA library expressing TROP2 cDNA as a template and primers which specifically amplify TROP2 cDNA.

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650; ATCC: American Type Culture Collection), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a method usually carried out in the art, and by the culturing of the transformant, a target polypeptide is produced intracellularly or extracellularly.

A suitable medium to be used for the culturing can be selected by those skilled in the art from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

The above-described transformant itself can be also used as the antigen. Alternatively, a cell line expressing TROP2 may be used as the antigen. Examples of such a cell line can include human lung cancer lines NCI-H322, PC14, NCIH-H2122, and LCAM1, a human prostate cancer line PC3, human pancreatic cancer lines BxPC-3, Capan-1, and PK-1, a human ovarian cancer line SKOV3, and a human colorectal cancer line COLO205, though the cell line according to the present invention is not limited to these cell lines as long as expressing TROP2.

(2) Production of Anti-TROP2 Monoclonal Antibody

Examples of the antibody specifically bind to TROP2 include a monoclonal antibody specifically bind to TROP2, and a method of obtaining such antibody is as described below.

The production of a monoclonal antibody generally requires the following operational steps of:

(a) purifying a biopolymer to be used as an antigen, or preparing antigen-expressing cells;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, TROP2 prepared by the method as described above or a partial peptide thereof can be used.

Further, a membrane fraction prepared from recombinant cells expressing TROP2 or the recombinant cells expressing TROP2 themselves, and also a partial peptide of the protein of the invention chemically synthesized by a method known to those skilled in the art can also be used as the antigen.

Further, a cell line expressing TROP2 can be also used as the antigen.

(b) Preparation of Antibody-Producing Cells

The antigen obtained in the step (a) is mixed with an adjuvant such as Freund's complete or incomplete adjuvant or auxiliary agent such as aluminum potassium sulfate and the resulting mixture is used as an immunogen to immunize an experimental animal. In an alternative method, the experimental animal is immunized with antigen-expressing cells as an immunogen. As the experimental animal, any animal used in a known hybridoma production method can be used without hindrance. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats can be obtained from breeders/distributors of experimental animals, for example, CLEA Japan, Inc. and Charles River Laboratories Japan, Inc.

In consideration of compatibility of fusing with myeloma cells described below, in the case of a mouse, BALB/c strain, and in the case of a rat, Wistar and Low strains are particularly preferred as the animal to be immunized.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with TROP2 or a recombinant thereof, for example, a known method described in detail in, for example, Weir, D. M., Handbook of Experimental Immunology Vol. I. II. III., Blackwell Scientific Publications, Oxford (1987); Kabat, E. A. and Mayer, M. M., Experimental Immunochemistry, Charles C Thomas Publisher Springfield, Ill. (1964) or the like can be used.

Among these immunization methods, a preferred specific method in the present invention is, for example, as follows.

That is, first, a membrane protein fraction serving as the antigen or cells caused to express the antigen is/are intradermally or intraperitoneally administrated to an animal. However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 1 to 4 weeks, more preferably 1 to 3 weeks after the administration of the antigen as described above. When the immunogen is cells, $1\times10^6$ to $1\times10^7$ cells are employed.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg. When the immunogen is cells, $1\times10^6$ to $1\times10^7$ cells are employed.

Spleen cells or lymphocytes including antibody-producing cells are aseptically removed from the immunized animal after 1 to 10 days, preferably 2 to 5 days, more preferably 2 to 3 days from the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto. For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (BSA). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to obtain the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Ag14(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500·GTG-A12 (GM1500), UC729-6, LICR-LOW-HMy2(HMy2) and 8226AR/NIP4-1(NP41) derived from humans. These HGPRT-deficient strains are available from, for example, ATCC or the like.

These cell strains are subcultured in an appropriate medium such as an 8-azaguanine medium (a medium obtained by adding 8-azaguanine to an RPMI 1640 medium supplemented with glutamine, 2-mercaptoethanol, gentamicin, and fetal calf serum (hereinafter referred to as "FBS")), Iscove's Modified Dulbecco's Medium (IMDM), or Dulbecco's Modified Eagle Medium (DMEM). In this case, 3 to 4 days before performing cell fusion, the cells are subcultured in a normal medium (for example, an ASF104 medium (manufactured by Ajinomoto Co., Ltd.) containing 10% FCS) to ensure not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987); Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin. That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, Inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a TROP2 monoclonal antibody-producing hybridoma strain.

Examples of the thus established hybridoma strain include TROP2 hybridoma TINA1. In this specification, an antibody produced by the TROP2 hybridoma TINA1 is referred to as "TINA1 antibody" or simply "TINA1".

The heavy chain variable region of the TINA1 antibody has an amino acid sequence represented by SEQ ID NO: 2 in the Sequence Listing. Further, the light chain variable region of the TINA1 antibody has an amino acid sequence represented by SEQ ID NO: 4 in the Sequence Listing.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administrated in the abdominal cavity, if a mineral oil such as 2,6,10,14-tetramethyl pentadecane (pristane) is administrated 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for TROP2.

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm (1.4 (OD 280)=Immunoglobulin 1 mg/ml).

Further, even when the monoclonal antibody is separately and independently obtained by performing again the steps of (a) to (h) in (2), it is possible to obtain an antibody having a cytotoxic activity equivalent to that of the TINA1 antibody. As one example of such an antibody, an antibody which binds to the same epitope as the TINA1 antibody can be exemplified. If a newly produced monoclonal antibody binds to a partial peptide or a partial tertiary structure to which the TINA1 antibody binds, it can be determined that the monoclonal antibody binds to the same epitope as the TINA1 antibody. Further, by confirming that the monoclonal antibody competes with the TINA1 antibody for the binding to TROP2 (that is, the monoclonal antibody inhibits the binding between the TINA1 antibody and TROP2), it can be determined that the monoclonal antibody binds to the same epitope as the anti-TROP2 antibody even if the specific epitope sequence or structure has not been determined. When it is confirmed that the monoclonal antibody binds to the same epitope as the anti-TROP2 antibody, the monoclonal antibody is strongly expected to have the antigen-binding affinity and a biological activity equivalent to that of the TINA1 antibody.

(3) Other Antibodies

The antibody of the invention includes not only the above-described monoclonal antibody against TROP2 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (see Proc. Natl. Acad. Sci. USA, 81, 6851-6855, (1984)).

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (International Publication No. WO 90/07861) can be exemplified.

However, the humanized antibody derived from the TINA1 antibody is not limited to a specific humanized antibody as long as the humanized antibody has all 6 types of CDR sequences of the TINA1 antibody. The heavy chain variable region of the TINA1 antibody has CDRH1 (TAGMQ) consisting of an amino acid sequence represented by SEQ ID NO: 23 in the Sequence Listing, CDRH2 (WINTHSGVPKYAEDFKG) consisting of an amino acid sequence represented by SEQ ID NO: 24 in the Sequence Listing, and CDRH3 (SGFGSSYWYFDV) consisting of an amino acid sequence represented by SEQ ID NO: 25 in the Sequence Listing. Further, the light chain variable region of the TINA1 antibody has CDRL1 (KASQDVSTAVA) consisting of an amino acid sequence represented by SEQ ID NO: 26 in the Sequence Listing, CDRL2 (SASYRYT) consisting of an amino acid sequence represented by SEQ ID NO: 27 in the Sequence Listing, and CDRL3 (QQHYITPLT) consisting of an amino acid sequence represented by SEQ ID NO: 28 in the Sequence Listing.

As an example of the humanized antibody of a mouse antibody TINA1, an arbitrary combination of a heavy chain comprising a heavy chain variable region consisting of any one of (1) an amino acid sequence consisting of amino acid residues 20 to 140 of SEQ ID NO: 12, 14, or 16 in the Sequence Listing, (2) an amino acid sequence having a homology of at least 95% or more with the amino acid sequence (1) described above, and (3) an amino acid sequence wherein one or several amino acids in the amino acid sequence (1) described above are deleted, substituted or added and a light chain comprising a light chain variable region consisting of any one of (4) an amino acid sequence consisting of amino acid residues 21 to 129 of SEQ ID NO: 18, 20, or 22 in the Sequence Listing, (5) an amino acid sequence having a homology of at least 95% or more with the amino acid sequence (4) described above, and (6) an amino acid sequence wherein one or several amino acids in the amino acid sequence (4) described above are deleted, substituted or added can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

As an antibody which has a preferred combination of a heavy chain and a light chain described above, an antibody consisting of a heavy chain comprising a variable region consisting of an amino acid sequence consisting of amino acid positions 20 to 140 of SEQ ID NO: 12 and a light chain comprising a variable region consisting of an amino acid sequence consisting of amino acid positions 21 to 129 of SEQ ID NO: 18; an antibody consisting of a heavy chain comprising a variable region consisting of an amino acid sequence consisting of amino acid positions 20 to 140 of SEQ ID NO: 12 and a light chain comprising a variable region consisting of an amino acid sequence consisting of amino acid positions 21 to 129 of SEQ ID NO: 20; an antibody consisting of a heavy chain comprising a variable region consisting of an amino acid sequence consisting of amino acid positions 20 to 140 of SEQ ID NO: 12 and a light chain comprising a variable region consisting of an amino acid sequence consisting of amino acid positions 21 to 129 of SEQ ID NO: 22; an antibody consisting of a heavy chain comprising a variable region consisting of an amino acid sequence consisting of amino acid positions 20 to 140 of SEQ ID NO: 14 and a light chain comprising a variable region consisting of an amino acid sequence consisting of amino acid positions 21 to 129 of SEQ ID NO: 18; an antibody consisting of a heavy chain comprising a variable region consisting of an amino acid sequence consisting of amino acid positions 20 to 140 of SEQ ID NO: 14 and a light chain comprising a variable region consisting of an amino acid sequence consisting of amino acid positions 21 to 129 of SEQ ID NO: 20; an antibody consisting of a heavy chain comprising a variable region consisting of an amino acid sequence consisting of amino acid positions 20 to 140 of SEQ ID NO: 14 and a light chain comprising a variable region consisting of an amino acid sequence consisting of amino acid positions 21 to 129 of SEQ ID NO: 22; an antibody consisting of a heavy chain comprising a variable region consisting of an amino acid sequence consisting of amino acid positions 20 to 140 of SEQ ID NO: 16 and a light chain comprising a variable region consisting of an amino acid sequence consisting of amino acid positions 21 to 129 of SEQ ID NO: 18; an antibody consisting of a heavy chain comprising a variable region consisting of an amino acid sequence consisting of amino acid positions 20 to 140 of SEQ ID NO: 16 and a light chain comprising a variable region consisting of an amino acid sequence consisting of amino acid positions 21 to 129 of SEQ ID NO: 20; and an antibody consisting of a heavy chain comprising a variable region consisting of an amino acid sequence consisting of amino acid positions 20 to 140 of SEQ ID NO: 16 and a light chain comprising a variable region consisting of an amino acid sequence consisting of amino acid positions 21 to 129 of SEQ ID NO: 22 can be exemplified.

Further, as an antibody which has a more preferred combination of a heavy chain and a light chain described above, an antibody consisting of a heavy chain consisting of an amino acid sequence consisting of amino acid positions 20 to 470 of SEQ ID NO: 12 and a light chain consisting of an amino acid sequence consisting of amino acid positions 21 to 234 of SEQ ID NO: 18; an antibody consisting of a heavy chain consisting of an amino acid sequence consisting of amino acid positions 20 to 470 of SEQ ID NO: 12 and a light chain consisting of an amino acid sequence consisting of amino acid positions 21 to 234 of SEQ ID NO: 20; an antibody consisting of a heavy chain consisting of an amino acid sequence consisting of amino acid positions 20 to 470 of SEQ ID NO: 12 and a light chain consisting of an amino acid sequence consisting of amino acid positions 21 to 234 of SEQ ID NO: 22; an antibody consisting of a heavy chain consisting of an amino acid sequence consisting of amino acid positions 20 to 470 of SEQ ID NO: 14 and a light chain consisting of an amino acid sequence consisting of amino acid positions 21 to 234 of SEQ ID NO: 18; an antibody consisting of a heavy chain consisting of an amino acid sequence consisting of amino acid positions 20 to 470 of SEQ ID NO: 14 and a light chain consisting of an amino acid sequence consisting of amino acid positions 21 to 234 of SEQ ID NO: 20; an antibody consisting of a heavy chain consisting of an amino acid sequence consisting of amino acid positions 20 to 470 of SEQ ID NO: 14 and a light chain consisting of an amino acid sequence consisting of amino acid positions 21 to 234 of SEQ ID NO: 22; an antibody consisting of a heavy chain consisting of an amino acid sequence consisting of amino acid positions 20 to 470 of SEQ ID NO: 16 and a light chain consisting of an amino acid sequence consisting of amino acid positions 21 to 234 of SEQ ID NO: 18; an antibody consisting of a heavy chain consisting of an amino acid sequence consisting of amino acid positions 20 to 470 of SEQ ID NO: 16 and a light chain consisting of an amino acid sequence consisting of amino acid positions 21 to 234 of SEQ ID NO: 20; and an antibody consisting of a heavy chain consisting of an amino acid sequence consisting of amino acid positions 20 to 470 of SEQ ID NO: 16 and a light chain consisting of an amino acid sequence consisting of amino acid positions 21 to 234 of SEQ ID NO: 22 can be exemplified.

As an antibody which has a superior preferred combination of a heavy chain and a light chain described above, an antibody consisting of a heavy chain comprising a variable region consisting of an amino acid sequence consisting of amino acid residues 20 to 140 of SEQ ID NO: 12 and a light chain comprising a variable region consisting of an amino acid sequence consisting of amino acid residues 21 to 129 of SEQ ID NO: 18; an antibody consisting of a heavy chain comprising a variable region consisting of an amino acid sequence consisting of amino acid residues 20 to 140 of SEQ ID NO: 14 and a light chain comprising a variable region consisting of an amino acid sequence consisting of amino acid residues 21 to 129 of SEQ ID NO: 18; an antibody consisting of a heavy chain comprising a variable region consisting of an amino acid sequence consisting of amino acid residues 20 to 140 of SEQ ID NO: 14 and a light chain comprising a variable region consisting of an amino acid sequence consisting of amino acid residues 21 to 129 of SEQ ID NO: 20; and an antibody consisting of a heavy chain comprising a variable region consisting of an amino acid sequence consisting of amino acid residues 20 to 140 of SEQ ID NO: 16 and a light chain comprising a variable region consisting of an amino acid sequence consisting of amino acid residues 21 to 129 of SEQ ID NO: 22 can be exemplified.

Furthermore, as an antibody which has another more preferred combination of a heavy chain and a light chain described above, an antibody consisting of a heavy chain consisting of an amino acid sequence of SEQ ID NO: 12 and a light chain consisting of an amino acid sequence of SEQ ID NO: 18; an antibody consisting of a heavy chain consisting of an amino acid sequence of SEQ ID NO: 12 and a light chain consisting of an amino acid sequence of SEQ ID NO: 20; an antibody consisting of a heavy chain consisting of an amino acid sequence of SEQ ID NO: 12 and a light chain consisting of an amino acid sequence of SEQ ID NO: 22; an antibody consisting of a heavy chain consisting of an amino acid sequence of SEQ ID NO: 14 and a light chain consisting of an amino acid sequence of SEQ ID NO: 18; an antibody consisting of a heavy chain consisting of an amino acid sequence of SEQ ID NO: 14 and a light chain consisting of an amino acid sequence of SEQ ID NO: 20; an antibody consisting of a heavy chain consisting of an amino acid sequence of SEQ ID NO: 14 and a light chain consisting of an amino acid sequence of SEQ ID NO: 22; an antibody consisting of a heavy chain consisting of an amino acid sequence of SEQ ID NO: 16 and a light chain consisting of an amino acid sequence of SEQ ID NO: 18; an antibody consisting of a heavy chain consisting of an amino acid sequence of SEQ ID NO: 16 and a light chain consisting of an amino acid sequence of SEQ ID NO: 20; and an antibody consisting of a heavy chain consisting of an amino acid sequence of SEQ ID NO: 16 and a light chain consisting of an amino acid sequence of SEQ ID NO: 22 can be exemplified.

As an antibody which has a superior preferred combination of a heavy chain and a light chain described above, an antibody consisting of a heavy chain consisting of an amino acid sequence consisting of amino acid positions 20 to 470 of SEQ ID NO: 12 and a light chain consisting of an amino acid sequence consisting of amino acid positions 21 to 234 of SEQ ID NO: 18; an antibody consisting of a heavy chain consisting of an amino acid sequence consisting of amino acid positions 20 to 470 of SEQ ID NO: 14 and a light chain consisting of an amino acid sequence consisting of amino acid positions 21 to 234 of SEQ ID NO: 18; an antibody consisting of a heavy chain consisting of an amino acid sequence consisting of amino acid positions 20 to 470 of SEQ ID NO: 14 and a light chain consisting of an amino acid sequence consisting of amino acid positions 21 to 234 of SEQ ID NO: 20; and an antibody consisting of a heavy chain consisting of an amino acid sequence consisting of amino acid positions 20 to 470 of SEQ ID NO: 16 and a light chain consisting of an amino acid sequence consisting of amino acid positions 21 to 234 of SEQ ID NO: 22 can be exemplified.

Further, as an antibody which has a more superior preferred combination of a heavy chain and a light chain described above, an antibody consisting of a heavy chain consisting of an amino acid sequence consisting of amino acid positions 20 to 469 of SEQ ID NO: 12 and a light chain consisting of an amino acid sequence consisting of amino acid positions 21 to 234 of SEQ ID NO: 18; an antibody consisting of a heavy chain consisting of an amino acid sequence consisting of amino acid positions 20 to 469 of SEQ ID NO: 14 and a light chain consisting of an amino acid sequence consisting of amino acid positions 21 to 234 of SEQ ID NO: 18; an antibody consisting of a heavy chain consisting of an amino acid sequence consisting of amino acid positions 20 to 469 of SEQ ID NO: 14 and a light chain consisting of an amino acid sequence consisting of amino acid positions 21 to 234 of SEQ ID NO: 20; and an antibody consisting of a heavy chain consisting of an amino acid sequence consisting of amino acid positions 20 to 469 of SEQ ID NO: 16 and a light chain consisting of an amino acid sequence consisting of amino acid positions 21 to 234 of SEQ ID NO: 22 can be exemplified.

By combining a sequence having a high homology with the above-described heavy chain amino acid sequence with a sequence having a high homology with the above-described light chain amino acid sequence, it is possible to select an antibody having a biological activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a biological activity equivalent to that of each of the above-described antibodies.

The homology between two amino acid sequences can be determined using default parameters of Blast algorithm version 2.2.2 (Altschul, Stephen F., Thomas L. Madden, Alejandro A. Schaeffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site www.ncbi.nlm.nih.gov/blast.

In the heavy chain amino acid sequence represented by SEQ ID NO: 12, 14 or 16 in the Sequence Listing, an amino acid sequence consisting of amino acid residues 1 to 19 is a signal sequence, an amino acid sequence consisting of amino acid residues 20 to 140 is a variable region, and an amino acid sequence consisting of amino acid residues 141 to 470 is a constant region. The sequence of SEQ ID NO: 12, 14 and 16 are shown in FIGS. 3, 4 and 5 respectively.

Further, in the light chain amino acid sequence represented by SEQ ID NO: 18, 20 or 22 in the Sequence Listing, an amino acid sequence consisting of amino acid residues 1 to 20 is a signal sequence, an amino acid sequence consisting of amino acid residues 21 to 129 is a variable region, and an amino acid sequence consisting of amino acid residues 130 to 234 is a constant region. The sequence of SEQ ID NO: 18, 20 and 22 are shown in FIGS. 6, 7 and 8 respectively.

Further, the antibody of the invention includes a human antibody which binds to TROP2. An anti-TROP2 human antibody refers to a human antibody having only a sequence of an antibody derived from a human chromosome. The anti-TROP2 human antibody can be obtained by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

Further, a method of obtaining a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (International Publication No. WO 92/01047, WO 92/20791, WO 93/06213, WO 93/11236, WO 93/19172, WO 95/01438, WO 95/15388; Annu. Rev. Immunol. (1994) 12, pp. 433-455; Nature Biotechnology (2005) 23 (9), pp. 1105-1116).

If a newly produced human antibody binds to a partial peptide or a partial tertiary structure to which the TINA1 antibody binds, it can be determined that the human antibody binds to the same epitope as the TINA1 antibody. Further, by confirming that the human antibody competes with the TINA1 antibody for the binding to TROP2 (that is, the human antibody inhibits the binding between the TINA1 antibody and TROP2), it can be determined that the human antibody binds to the same epitope as the TINA1 antibody even if the specific epitope sequence or structure has not been determined. When it is confirmed that the human antibody binds to the same epitope as the TINA1 antibody, the human antibody is strongly expected to have a biological activity equivalent to that of the TINA1 antibody.

The chimeric antibodies, humanized antibodies, or human antibodies obtained by the above-described method are evaluated for the binding property to an antigen by a known method or the like, and a preferred antibody can be selected.

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

In the present invention, a modified variant of the antibody is also included. The modified variant refers to a variant obtained by subjecting the antibody of the present invention to chemical or biological modification. Examples of the chemically modified variant include variants chemically modified by linking a chemical moiety to an amino acid skeleton, variants chemically modified with an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell.

Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody of the invention is useful for improving the stability and blood retention of the antibody, reducing the antigenicity thereof, detecting or isolating an antibody or an antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, International Publication No. WO 1999/54342, WO 2000/61739, WO 2002/31140, etc. are known. However, the technique is not limited thereto. In the antibody of the present invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the present invention, an antibody obtained by a method of producing an antibody, characterized by including a step of culturing the transformed host cell and a step of collecting a desired antibody from a cultured product obtained in the culturing step is also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the antibody according to the present invention, an antibody subjected to such modification and a functional fragment of the antibody are also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like are also encompassed. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified.

As isotype of the antibody of the invention, for example, IgG (IgG1, IgG2, IgG3, IgG4) can be exemplified, and IgG1 or IgG2 can be exemplified preferably.

As the biological activity of the antibody, generally an antigen-binding activity, an activity of internalizing in cells expressing an antigen by binding to the antigen, an activity of neutralizing the activity of an antigen, an activity of enhancing the activity of an antigen, an antibody-dependent cellular cytotoxicity (ADCC) activity, a complement-dependent cytotoxicity (CDC) activity, and an antibody-dependent cell-mediated phagocytosis (ADCP) activity can be exemplified. The function of the antibody of the present invention is a binding activity to TROP2, preferably an activity of internalizing in TROP2-expressing cells by binding to TROP2. Further, the antibody of the present invention may have an ADCC activity, a CDC activity, and/or an ADCP activity in addition to a cell internalization activity.

The obtained antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia) and the like can be exemplified.

Further, by using a carrier having an antigen immobilized thereon, the antibody can also be purified utilizing the binding property of the antibody to the antigen.

[Antitumor Compound]

The antitumor compound to be conjugated to the anti-TROP2 antibody-drug conjugate of the present invention is explained. The antitumor compound used in the present invention is not particularly limited if it is a compound having an antitumor effect and a substituent group or a partial structure allowing connecting to a linker structure. When a part or whole linker is cleaved in tumor cells, the antitumor compound moiety is released to exhibit the antitumor effect of the antitumor compound. As the linker is cleaved at a connecting position to drug, the antitumor compound is released in its unmodified structure to exhibit its intrinsic antitumor effect.

As the antitumor compound used in the present invention, exatecan (((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione; shown in the following formula), one of the camptothecin derivatives, can be preferably used.

[Formula 14]

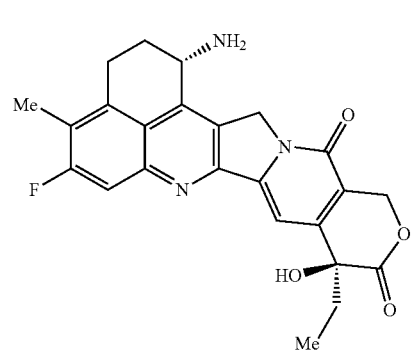

Although having an excellent antitumor effect, exatecan has not been commercialized as an antitumor drug. The compound can be easily obtained by a known method and the amino group at position 1 can be preferably used as a connecting position to the linker structure. Further, although exatecan can be also released in tumor cells while part of the linker is still attached thereto, it is an excellent compound exhibiting an excellent antitumor effect even in such structure.

Because exatecan has a camptothecin structure, it is known that the equilibrium shifts to a structure with a closed lactone ring (closed ring) in an aqueous acidic medium (for example, pH 3 or so) but it shifts to a structure with an open lactone ring (open ring) in an aqueous basic medium (for example, pH 10 or so). A drug conjugate being introduced with an exatecan residue corresponding to the closed ring structure and the open ring structure is also expected to have the same antitumor effect and it is needless to say that any of these states is within the scope of the present invention.

Other examples of the antitumor compound can include doxorubicin, daunorubicin, mitomycin C, bleomycin, cyclocytidine, vincristine, vinblastine, methotrexate, platinum-based antitumor agent (cisplatin or derivatives thereof), taxol or derivatives thereof, and camptothecin or derivatives thereof (antitumor agent described in Japanese Patent Laid-Open No. 6-87746).

With regard to the antibody-drug conjugate, the number of conjugated drug molecules per antibody molecule is a key factor having an influence on the efficacy and safety. Production of the antibody-drug conjugate is performed by defining the reaction condition including the amounts of use of raw materials and reagents for reaction so as to have a constant number of conjugated drug molecules, and the antibody-drug conjugate is generally obtained as a mixture containing different numbers of conjugated drug molecules, unlike the chemical reaction of a low-molecular-weight compound. The number of drugs conjugated in an antibody molecule is expressed or specified by the average value, that is, the average number of conjugated drug molecules. Unless specifically described otherwise as a principle, the number of conjugated drug molecules means an average value except in a case in which it represents an antibody-drug conjugate having a specific number of conjugated drug molecules that is included in an antibody-drug conjugate mixture having different number of conjugated drug molecules. The number of exatecan molecules conjugated to an antibody molecule is controllable, and as an average number of conjugated drug molecules per antibody, about 1 to 10 exatecans can be connected. Preferably, it is 2 to 8, and more preferably 3 to 8. Meanwhile, a person skilled in the art can design a reaction for conjugating a required number of drug molecules to an antibody molecule based on the description of the Examples of the present application and can obtain an antibody-drug conjugate with a controlled number of exatecan molecules.

[Linker Structure]

With regard to the anti-TROP2 antibody-drug conjugate of the present invention, the linker structure for conjugating an antitumor compound to the anti-TROP2 antibody is explained. The linker has a structure of the following formula:

-L$^1$-L$^2$-L$^P$-NH—(CH$_2$)n$^1$-L$^a$-(CH$_2$)n$^2$-C(=O)—

The antibody is connected to the terminal of L$^1$ (terminal opposite to the connection to L$^2$), and the antitumor compound is connected to the carbonyl group of the -L$^a$-(CH$_2$)n$^2$-C(=O)— moiety.

n$^1$ represents an integer of 0 to 6 and is preferably an integer of 1 to 5, and more preferably 1 to 3.

1. L$^1$

L$^1$ is represented by the structure of -(Succinimid-3-yl-N)—(CH$_2$)n$^3$-C(=O)—.

In the above, n$^3$ is an integer of 2 to 8, and "-(Succinimid-3-yl-N)—" has a structure represented by the following formula:

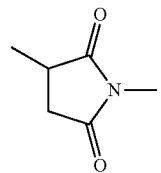

[Formula 15]

Position 3 of the above partial structure is a connecting position to the anti-TROP2 antibody. The bond to the anti-TROP2 antibody at position 3 is characterized by bonding with thioether formation. The nitrogen atom at position 1 of the structure moiety is connected to the carbon atom of methylene which is present within the linker including the structure. Specifically, -(Succinimid-3-yl-N)—(CH$_2$)n$^3$-C(=O)-L$^2$- is a structure represented by the following formula (herein, "antibody-S—" originates from an antibody).

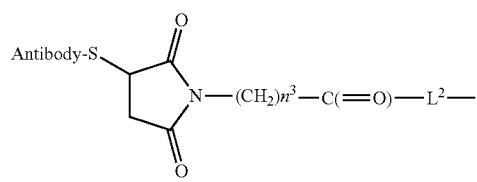

[Formula 16]

In the formula, n$^3$ is an integer of 2 to 8, and preferably 2 to 5.

Specific examples of L$^1$ can include
-(Succinimid-3-yl-N)—CH$_2$CH$_2$—C(=O)—,
-(Succinimid-3-yl-N)—CH$_2$CH$_2$CH$_2$—C(=O)—,
-(Succinimid-3-yl-N)—CH$_2$CH$_2$CH$_2$CH$_2$—C(=O)—,
-(Succinimid-3-yl-N)—CH$_2$CH$_2$CH$_2$CH$_2$CH$_2$—C(=O)—.

2. L$^2$

L$^2$ is a linker represented by the following structure:
—NH—(CH$_2$CH$_2$—O)n$^4$-CH$_2$CH$_2$—C(=O)—,
L$^2$ may not be present, and in such a case, L$^2$ is a single bond. In the above, n$^4$ is an integer of 1 to 6, and preferably 2 to 4. L$^2$ is connected to L$^1$ at its terminal amino group and is connected to L$^P$ at its carbonyl group at the other terminal.

Specific examples of L$^2$ can include
—NH—CH$_2$CH$_2$—O—CH$_2$CH$_2$—C(=O)—,
—NH—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)—.

3. L$^P$

L$^P$ is a peptide residue consisting of 2 to 7 amino acids. Specifically, it consists of an oligopeptide residue in which 2 to 7 amino acids are linked by a peptide bonding. L$^P$ is connected to L$^2$ at its N terminal and is connected to the amino group of —NH—(CH$_2$)n$^1$-L$^a$-(CH$_2$)n$^2$-C(=O)— moiety of the linker at its C terminal.

The amino acid constituting $L^P$ in the linker is not particularly limited, however, examples thereof include an L- or a D-amino acid, preferably an L-amino acid. And, it can be an amino acid having a structure such as β-alanine, ε-aminocaproic acid, or γ-aminobutyric acid in addition to an α-amino acid, further, it can be a non-natural type amino acid such as N-methylated amino acid.

The amino acid sequence of $L^P$ is not particularly limited, but examples of the constituting amino acid include phenylalanine (Phe; F), tyrosine (Tyr; Y), leucine (Leu; L), glycine (Gly; G), alanine (Ala; A), valine (Val; V), lysine (Lys; K), citrulline (Cit), serine (Ser; S), glutamic acid (Glu; E), and aspartic acid (Asp; D).

Among them, preferred examples include phenylalanine, glycine, valine, lysine, citrulline, serine, glutamic acid, and aspartic acid. Depending on the type of the amino acid, drug release pattern can be controlled. The number of the amino acid can be between 2 to 7.

Specific examples of $L^P$ can include
-GGF-,
-DGGF-,
-(D-)D-GGF-,
-EGGF-,
-GGFG-,
-SGGF-,
-KGGF-,
-DGGFG-,
-GGFGG-,
-DDGGFG-,
-KDGGFG-,
-GGFGGGF-.

In the above, "(D-)D" represents a D-aspartic acid. Particularly preferred examples of $L^P$ for the antibody-drug conjugate of the present invention can include a tetrapeptide residue of -GGFG-.

4. $L^a$-(CH$_2$)n$^2$-C(=O)—

$L^a$ in $L^a$-(CH$_2$)n$^2$-C(=O)— is a structure of —O— or a single bond. $n^2$ is an integer of 0 to 5, more preferably 0 to 3, more preferably 0 or 1.

Examples of $L^a$-(CH$_2$)n$^2$-C(=O)— can include those having the following structures:
—O—CH$_2$—C(=O)—,
—O—CH$_2$CH$_2$—C(=O)—,
—O—CH$_2$CH$_2$CH$_2$—C(=O)—,
—O—CH$_2$CH$_2$CH$_2$CH$_2$—C(=O)—,
—O—CH$_2$CH$_2$CH$_2$CH$_2$CH$_2$—C(=O)—,
—CH$_2$—C(=O)—,
—CH$_2$CH$_2$—C(=O)—,
—CH$_2$CH$_2$CH$_2$—C(=O)—,
—CH$_2$CH$_2$CH$_2$CH$_2$—C(=O)—,
—CH$_2$CH$_2$CH$_2$CH$_2$CH$_2$—C(=O)—.

Of them,
—O—CH$_2$—C(=O)—,
—O—CH$_2$CH$_2$—C(=O)—, or
a case in which $L^a$ is a single bond, and $n^2$ is 0 is preferred.

Specific examples of the structure represented by —NH—(CH$_2$)n$^1$-$L^a$-(CH$_2$)n$^2$-C(=O)— in the linker can include
—NH—CH$_2$—C(=O)—,
—NH—CH$_2$CH$_2$—C(=O)—,
—NH—CH$_2$—O—CH$_2$—C(=O)—,
—NH—CH$_2$CH$_2$—O—C(=O)—,
—NH—CH$_2$CH$_2$—O—CH$_2$—C(=O)—,
—NH—CH$_2$CH$_2$CH$_2$—C(=O)—,
—NH—CH$_2$CH$_2$CH$_2$CH$_2$—C(=O)—,
—NH—CH$_2$CH$_2$CH$_2$CH$_2$CH$_2$—C(=O)—.
—NH—CH$_2$CH$_2$CH$_2$—C(=O)—,
—NH—CH$_2$—O—CH$_2$—C(=O)—, or
—NH—CH$_2$CH$_2$—O—C(=O)—
is more preferred.

In the linker, the chain length of —NH—(CH$_2$)n$^1$-$L^a$-(CH$_2$)n$^2$-C(=O)— is preferably a chain length of 4 to 7 atoms, and more preferably a chain length of 5 or 6 atoms.

With regard to the anti-TROP2 antibody-drug conjugate of the present invention, it is considered that when the anti-TROP2 antibody-drug conjugate is transferred to the inside of tumor cells, the linker moiety is cleaved and the drug derivative having a structure represented by NH$_2$—(CH$_2$)n$^1$-$L^a$-(CH$_2$)n$^2$-C(=O)—(NH-DX) is released to express an antitumor action. Examples of the antitumor derivative exhibiting an antitumor effect by releasing from the antibody-drug conjugate of the present invention include an antitumor derivative having a structure moiety in which the structure represented by —NH—(CH$_2$)n$^1$-$L^a$-(CH$_2$)n$^2$-C(=O)— of the linker has a terminal amino group, and the particularly preferred include the followings.

NH$_2$—CH$_2$CH$_2$—C(=O)—(NH-DX),
NH$_2$—CH$_2$CH$_2$CH$_2$—C(=O)—(NH-DX),
NH$_2$—CH$_2$—O—CH$_2$—C(=O)—(NH-DX),
NH$_2$—CHCH$_2$—O—CH$_2$—C(=O)—(NH-DX).

Meanwhile, in case of NH$_2$—CH$_2$—O—CH$_2$—C(=O)—(NH-DX), it was confirmed that, as the aminal structure in the molecule is unstable, it again undergoes a self-degradation to release the following HO—CH$_2$—C(=O)—(NH-DX). Those compounds can be also preferably used as a production intermediate of the antibody-drug conjugate of the present invention.

For the antibody-drug conjugate of the present invention in which exatecan is used as a drug, it is preferable that the drug-linker structure moiety [-$L^1$-$L^2$-$L^P$-NH—(CH$_2$)n$^1$-$L^a$-(CH$_2$)n$^2$-C(=O)—(NH-DX)] having the following structure is connected to an antibody. The average conjugated number of said drug-linker structure moiety per antibody can be 1 to 10. Preferably, it is 2 to 8, and more preferably 3 to 8.

-(Succinimid-3-yl-N)—CH$_2$CH$_2$—C(=O)-GGFG-NH—CH$_2$CH$_2$—C(=O)—(NH-DX),
-(Succinimid-3-yl-N)—CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$CH$_2$CH$_2$—C(=O)—(NH-DX).

Among them, the more preferred are the followings.
-(Succinimid-3-yl-N)—CH$_2$CH$_2$—C(=O)-GGFG-NH—CH$_2$CH$_2$CH$_2$—C(=O)—(NH-DX), -(Succinimid-3-yl-N)—$CH_2CH_2CH_2CH_2CH_2$—C(=O)-GGFG-NH—$CH_2CH_2CH_2$—C(=O)—(NH-DX),
-(Succinimid-3-yl-N)—$CH_2CH_2CH_2CH_2CH_2$—C(=O)-GGFG-NH—$CH_2$—O—$CH_2$—C(=O)—(NH-DX),
-(Succinimid-3-yl-N)—$CH_2CH_2CH_2CH_2CH_2$—C(=O)-GGFG-NH—$CH_2CH_2$—O—$CH_2$—C(=O)—(NH-DX),
-(Succinimid-3-yl-N)—$CH_2CH_2$—C(=O)—NH—$CH_2CH_2$—O—$CH_2CH_2$—O—$CH_2CH_2$—C(=O)-GGFG-NH—$CH_2CH_2CH_2$—C(=O)—(NH-DX),
-(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-GGFG-NH—$CH_2CH_2CH_2$—C(=O)—(NH-DX).

The particularly preferred are the followings.
-(Succinimid-3-yl-N)—$CH_2CH_2CH_2CH_2CH_2$—C(=O)-GGFG-NH—$CH_2$—O—$CH_2$—C(=O)—(NH-DX),
-(Succinimid-3-yl-N)—$CH_2CH_2CH_2CH_2CH_2$—C(=O)-GGFG-NH—$CH_2CH_2$—O—$CH_2$—C(=O)—(NH-DX),
-(Succinimid-3-yl-N)—$CH_2CH_2$—C(=O)—NH—$CH_2CH_2$—O—$CH_2CH_2$—O—$CH_2CH_2$—C(=O)-GGFG-NH—$CH_2CH_2CH_2$—C(=O)—(NH-DX).

With regard to the linker structure for conjugating the anti-TROP2 antibody and a drug in the antibody-drug conjugate of the present invention, the preferred linker can be constructed by connecting preferred structures shown for each part of the linker explained above. As for the linker structure, those with the following structure can be preferably used. Meanwhile, the left terminal of the structure is a connecting position with the antibody and the right terminal is a connecting position with the drug.
-(Succinimid-3-yl-N)—$CH_2CH_2$—C(=O)-GGFG-NH—$CH_2CH_2$—C(=O)—,
-(Succinimid-3-yl-N)—$CH_2CH_2$—C(=O)-GGFG-NH—$CH_2CH_2CH_2$—C(=O)—,
-(Succinimid-3-yl-N)—$CH_2CH_2CH_2CH_2CH_2$—C(=O)-GGFG-NH—$CH_2CH_2$—C(=O)—,
-(Succinimid-3-yl-N)—$CH_2CH_2CH_2CH_2CH_2$—C(=O)-GGFG-NH—$CH_2CH_2CH_2$—C(=O)—,
-(Succinimid-3-yl-N)—$CH_2CH_2CH_2CH_2CH_2$—C(=O)-GGFG-NH—$CH_2CH_2CH_2CH_2$—C(=O)—,
-(Succinimid-3-yl-N)—$CH_2CH_2CH_2CH_2CH_2$—C(=O)-GGFG-NH—$CH_2$—O—$CH_2$—C(=O)—,
-(Succinimid-3-yl-N)—$CH_2CH_2CH_2CH_2CH_2$—C(=O)-GGFG-NH—$CH_2CH_2$—O—$CH_2$—C(=O)—,
-(Succinimid-3-yl-N)—$CH_2CH_2$—C(=O)—NH—$CH_2CH_2$—O—$CH_2CH_2$—O—$CH_2CH_2$—C(=O)-GGFG-NH—$CH_2CH_2$—C(=O)—,
-(Succinimid-3-yl-N)—$CH_2CH_2$—C(=O)—NH—$CH_2CH_2$—O—$CH_2CH_2$—O—$CH_2CH_2$—C(=O)-GGFG-NH—$CH_2CH_2CH_2$—C(=O)—,
-(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-GGFG-NH—$CH_2CH_2$—C(=O)—,
-(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-GGFG-NH—$CH_2CH_2CH_2$—C(=O)—.

Among them, the more preferred are the followings.
-(Succinimid-3-yl-N)—$CH_2CH_2$—C(=O)-GGFG-NH—$CH_2CH_2CH_2$—C(=O)—,
-(Succinimid-3-yl-N)—$CH_2CH_2CH_2CH_2CH_2$—C(=O)-GGFG-NH—$CH_2CH_2$—C(=O)—,
-(Succinimid-3-yl-N)—$CH_2CH_2CH_2CH_2CH_2$—C(=O)-GGFG-NH—$CH_2$—O—$CH_2$—C(=O)—,
-(Succinimid-3-yl-N)—$CH_2CH_2CH_2CH_2CH_2$—C(=O)-GGFG-NH—$CH_2CH_2$—O—$CH_2$—C(=O)—,
-(Succinimid-3-yl-N)—$CH_2CH_2$—C(=O)—NH—$CH_2CH_2$—O—$CH_2CH_2$—O—$CH_2CH_2$—C(=O)-GGFG-NH—$CH_2CH_2CH_2$—C(=O)—,
-(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-GGFG-NH—$CH_2CH_2CH_2$—C(=O)—.

The particularly preferred include the followings.
-(Succinimid-3-yl-N)—$CH_2CH_2CH_2CH_2CH_2$—C(=O)-GGFG-NH—$CH_2$—O—$CH_2$—C(=O)—,
-(Succinimid-3-yl-N)—$CH_2CH_2CH_2CH_2CH_2$—C(=O)-GGFG-NH—$CH_2CH_2$—O—$CH_2$—C(=O)—,
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

[Production Method]

Next, explanations are given for the representative method for producing the antibody-drug conjugate of the present invention or a production intermediate thereof. Meanwhile, the compounds are hereinbelow described with the compound number shown in each reaction formula. Specifically, they are referred to as a "compound of the formula (1)", a "compound (1)", or the like. The compounds with numbers other than those are also described similarly.

1. Production Method 1

The antibody-drug conjugate represented by the formula (1) which is connected to the drug-linker structure via thioether can be produced by the following method, for example.

[Formula 17]

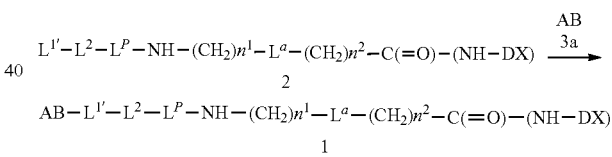

[In the formula, AB represents an antibody having a sulfhydryl group, and $L^{1'}$ represents $L^1$ linker structure in which the linker terminal is a maleimidyl group (formula shown below)

[Formula 18]

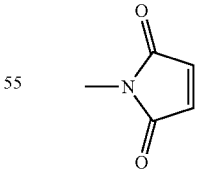

(in the formula, the nitrogen atom is the connecting position), and specifically represents a group in which the -(Succinimid-3-yl-N)— moiety in -(Succinimid-3-yl-N)—$(CH_2)n^3$-C(=O)— of $L^1$ is a maleimidyl group. Further, the —(NH-DX) represents a structure represented by the following formula:

[Formula 19]

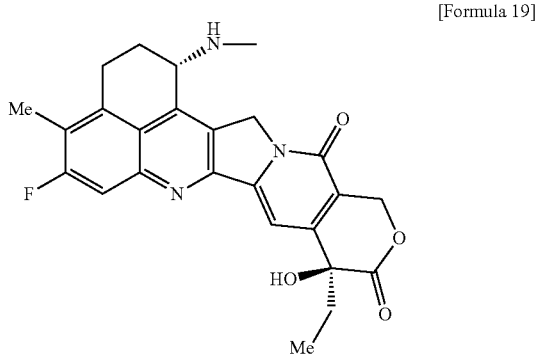 [SMILES: CC[C@@]1(O)C(=O)OCc2c1cc1n(c2=O)Cc2c-1nc1cc(F)c(C)c3c1c2[C@@H](NC)CC3]

and it represents a group that is derived by removing one hydrogen atom of the amino group at position 1 of exatecan.]

Further, the compound of the formula (1) in the above reaction formula is interpreted as a structure in which one structure moiety corresponding from drug to the linker terminal connects to one antibody. However, it is only the description given for the sake of convenience, and there are actually many cases in which a plurality of the structure moieties are connected to one antibody molecule. The same applies to the explanation of the production method described below.

The antibody-drug conjugate (1) can be produced by reacting the compound (2), which is obtainable by the method described below, with the antibody (3a) having a sulfhydryl group.

The antibody (3a) having a sulfhydryl group can be obtained by a method well known in the art (Hermanson, G. T, Bioconjugate Techniques, pp. 56-136, pp. 456-493, Academic Press (1996)). Examples include: Traut's reagent is reacted with the amino group of the antibody; N-succinimidyl S-acetylthioalkanoates are reacted with the amino group of the antibody followed by reaction with hydroxylamine; after reacting with N-succinimidyl 3-(pyridyldithio)propionate, the antibody is reacted with a reducing agent; the antibody is reacted with a reducing agent such as dithiothreitol, 2-mercaptoethanol, and tris(2-carboxyethyl)phosphine hydrochloride (TCEP) to reduce the disulfide bond in a hinge part in the antibody to form a sulfhydryl group, but it is not limited thereto.

Specifically, using 0.3 to 3 molar equivalents of TCEP as a reducing agent per disulfide in hinge part in the antibody and reacting with the antibody in a buffer solution containing a chelating agent, the antibody with partially or completely reduced disulfide in hinge part in the antibody can be obtained. Examples of the chelating agent include ethylenediamine tetraacetic acid (EDTA) and diethylenetriamine pentaacetic acid (DTPA). It can be used at concentration of 1 mM to 20 mM. Examples of the buffer solution which may be used include a solution of sodium phosphate, sodium borate, or sodium acetate. Specifically, by reacting the antibody with TCEP at 4° C. to 37° C. for 1 to 4 hours, the antibody (3a) having partially or completely reduced sulfhydryl group can be obtained.

Meanwhile, by conducting the reaction for adding a sulfhydryl group to a drug-linker moiety, the drug-linker moiety can be conjugated by a thioether bond.

Using 2 to 20 molar equivalents of the compound (2) per the antibody (3a) having a sulfhydryl group, the antibody-drug conjugate (1) in which 2 to 8 drug molecules are conjugated per antibody can be produced. Specifically, it is sufficient that the solution containing the compound (2) dissolved therein is added to a buffer solution containing the antibody (3a) having a sulfhydryl group for the reaction. Herein, examples of the buffer solution which may be used include sodium acetate solution, sodium phosphate, and sodium borate. pH for the reaction is 5 to 9, and more preferably the reaction is performed near pH 7. Examples of the solvent for dissolving the compound (2) include an organic solvent such as dimethyl sulfoxide (DMSO), dimethylformamide (DMF), dimethyl acetamide (DMA), and N-methyl-2-pyridone (NMP).

It is sufficient that the organic solvent solution containing the compound (2) dissolved therein is added at 1 to 20% v/v to a buffer solution containing the antibody (3a) having a sulfhydryl group for the reaction. The reaction temperature is 0 to 37° C., more preferably 10 to 25° C., and the reaction time is 0.5 to 2 hours. The reaction can be terminated by deactivating the reactivity of unreacted compound (2) with a thiol-containing reagent. Examples of the thiol-containing reagent include cysteine and N-acetyl-L-cysteine (NAC). More specifically, 1 to 2 molar equivalents of NAC are added to the compound (2) used and, by incubating at room temperature for 10 to 30 minutes, the reaction can be terminated.

The produced antibody-drug conjugate (1) can be subjected to, after concentration, buffer exchange, purification, and measurement of antibody concentration and average number of conjugated drug molecules per antibody molecule according to common procedures described below, identification of the antibody-drug conjugate (1).

Common Procedure A: Concentration of Aqueous Solution of Antibody or Antibody-Drug Conjugate To a Amicon Ultra (50,000 MWCO, Millipore Corporation) container, a solution of antibody or antibody-drug conjugate was added and the solution of the antibody or antibody-drug conjugate was concentrated by centrifugation (centrifuge for 5 to 20 minutes at 2000 G to 3800 G) using a centrifuge (Allegra X-15R, Beckman Coulter, Inc.).

Common Procedure B: Measurement of Antibody Concentration

Using a UV detector (Nanodrop 1000, Thermo Fisher Scientific Inc.), measurement of the antibody concentration was performed according to the method defined by the manufacturer. At that time, 280 nm absorption coefficient different for each antibody was used (1.3 mLmg$^{-1}$cm$^{-1}$ to 1.8 mLmg$^{-1}$cm$^{-1}$).

Common Procedure C-1: Buffer Exchange for Antibody

NAP-25 column (Cat. No. 17-0852-02, GE Healthcare Japan Corporation) using Sephadex G-25 carrier was equilibrated with phosphate buffer (10 mM, pH 6.0; it is referred to as PBS6.0/EDTA in the specification) containing sodium chloride (137 mM) and ethylene diamine tetraacetic acid (EDTA, 5 mM) according to the method defined by the manufacturer. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure C-2: Buffer Exchange for Antibody

NAP-25 column (Cat. No. 17-0852-02, GE Healthcare Japan Corporation) using Sephadex G-25 carrier was equilibrated with phosphate buffer (50 mM, pH 6.5; it is referred to as PBS6.5/EDTA in the specification) containing sodium chloride (50 mM) and EDTA (2 mM) according to the method defined by the manufacturer. Aqueous solution of the antibody was applied in an amount of 2.5 mL to single NAP-25 column, and then the fraction (3.5 mL) eluted with 3.5 mL of PBS6.5/EDTA was collected. The resulting fraction was concentrated by the Common procedure A. After measuring the concentration of the antibody using the Common procedure B, the antibody concentration was adjusted to 20 mg/mL using PBS6.5/EDTA.

Common Procedure D: Purification of Antibody-Drug Conjugate

NAP-25 column was equilibrated with any buffer selected from commercially available phosphate buffer (PBS7.4, Cat. No. 10010-023, Invitrogen), sodium phosphate buffer (10 mM, pH 6.0; it is referred to as PBS6.0) containing sodium chloride (137 mM), and acetate buffer containing sorbitol (5%) (10 mM, pH 5.5; it is referred to as ABS in the specification). Aqueous solution of the antibody-drug conjugate reaction was applied in an amount of about 1.5 mL to the NAP-25 column, and then eluted with the buffer in an amount defined by the manufacturer to collect the antibody fraction. The collected fraction was again applied to the NAP-25 column and, by repeating 2 to 3 times in total the gel filtration purification process for eluting with buffer, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide) was obtained.

Common Procedure E: Measurement of Antibody Concentration in Antibody-Drug Conjugate and Average Number of Conjugated Drug Molecules per Antibody Molecule (1).

The conjugated drug concentration in the antibody-drug conjugate can be calculated by measuring UV absorbance of an aqueous solution of the antibody-drug conjugate at two wavelengths of 280 nm and 370 nm, followed by performing the calculation shown below.

Because the total absorbance at any wavelength is equal to the sum of the absorbance of every light-absorbing chemical species that are present in a system (additivity of absorbance), when the molar absorption coefficients of the antibody and the drug remain the same before and after conjugation between the antibody and the drug, the antibody concentration and the drug concentration in the antibody-drug conjugate are expressed with the following equations.

$$A_{280} = A_{D,280} + A_{A,280} = \varepsilon_{D,280} C_D + \varepsilon_{A,280} C_A \quad \text{Equation (I)}$$

$$A_{370} = A_{D,370} + A_{A,370} = \varepsilon_{D,370} C_D + \varepsilon_{A,370} C_A \quad \text{Equation (II)}$$

In the above, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of an antibody at 280 nm, $\varepsilon_{A,370}$ represents the molar absorption coefficient of an antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in an antibody-drug conjugate, and $C_D$ represent the drug concentration in an antibody-drug conjugate.

As for $\varepsilon_{A,280}$, $\varepsilon_{A,370}$, $\varepsilon_{D,280}$, and $\varepsilon_{D,370}$ in the above, previously prepared values (estimated value based on calculation or measurement value obtained by UV measurement of the compound) are used. For example, $\varepsilon_{A,280}$ can be estimated from the amino acid sequence of an antibody using a known calculation method (Protein Science, 1995, vol. 4, 2411-2423). $\varepsilon_{A,370}$ is generally zero. $\varepsilon_{D,280}$ and $\varepsilon_{D,370}$ can be obtained based on Lambert-Beer's law (Absorbance=molar concentration×molar absorption coefficient×cell path length) by measuring the absorbance of a solution in which the conjugate precursor to be used is dissolved at a certain molar concentration. By measuring $A_{280}$ and $A_{370}$ of an aqueous solution of the antibody-drug conjugate and solving the simultaneous equations (I) and (II) using the values, $C_A$ and $C_D$ can be obtained. Further, by diving $C_D$ by $C_A$, the average number of conjugated drug per antibody can be obtained.

Common Procedure F: Measurement of Average Number of Conjugated Drug Molecules per Antibody Molecule in Antibody-Drug Conjugate-(2).

The average number of conjugated drug molecules per antibody molecule in the antibody-drug conjugate can be also determined by high-performance liquid chromatography (HPLC) analysis using a method described below, in addition to the above-mentioned Common procedure E.

[F-1. Preparation of Sample for HPLC Analysis (Reduction of Antibody-Drug Conjugate)]

An antibody-drug conjugate solution (about 1 mg/mL, 60 μL) is mixed with an aqueous dithiothreitol (DTT) solution (100 mM, 15 μL). The mixture is incubated at 37° C. for 30 minutes to cleave the disulfide bond between the L chain and the H chain of the antibody-drug conjugate. The resulting sample is used in HPLC analysis.

[F-2. HPLC Analysis]

The HPLC analysis is conducted under the following measurement conditions:

HPLC system: Agilent 1290 HPLC system (Agilent Technologies, Inc.)

Detector: UV absorption spectrometer (measurement wavelength: 280 nm)

Column: PLRP-S (2.1×50 mm, 8 μm, 1000 angstroms; Agilent Technologies, Inc., P/N PL1912-1802)

Column temperature: 80° C.

Mobile phase A: 0.04% aqueous trifluoroacetic acid (TFA) solution

Mobile phase B: acetonitrile solution containing 0.04% TFA

Gradient program: 29%-36% (0 min-12.5 min), 36%-42% (12.5-15 min), 42%-29% (15 min-15.1 min), 29%-29% (15.1 min-25 min)

Sample injection volume: 15 μL

[F-3. Data Analysis]

[F-3-1] Compared with an L chain ($L_0$) and an H chain ($H_0$) of a non-conjugated antibody, a drug-conjugated L chain (L chain connected to one drug molecule: $L_1$) and H chains (H chain connected to one drug molecule: $H_1$, H chain connected to two drug molecule: $H_2$, H chain connected to three drug molecules: $H_3$) exhibit higher hydrophobicity in proportion to the number of conjugated drug molecules and thus have a larger retention time. These chains are therefore eluted in the order of $L_0$ and $L_1$ or $H_0$, $H_1$, $H_2$, and $H_3$. Detection peaks can be assigned to any of $L_0$, $L_1$, $H_0$, $H_1$, $H_2$, and $H_3$ by the comparison of retention times with $L_0$ and $H_0$.

[F-3-2] Since the drug linker has UV absorption, peak area values are corrected in response to the number of conjugated drug linker molecules according to the following expression using the molar absorption coefficients of the L chain, the H chain, and the drug linker.

Corrected value of peak area of the L chain ($L_i$) = Peak area × $\dfrac{\text{Molar extinction coefficient of the } L \text{ chain}}{\text{Molar extiction coefficient of the } L \text{ chain} + \text{The number of conjugated drug molecules} \times \text{Molar extinction coefficient of the drug linker}}$ [Expression 1]

Corrected value of peak area of the H chain ($H_i$) = Peak area × $\dfrac{\text{Molar extinction coefficient of the } H \text{ chain}}{\text{Molar extiction coefficient of the } H \text{ chain} + \text{The number of conjugated drug molecules} \times \text{Molar extinction coefficient of the drug linker}}$ [Expression 2]

Here, as for the molar extinction coefficient (280 nm) of the L chain or the H chain of each antibody, a value estimated from the amino acid sequence of the L chain or the H chain of each antibody by a known calculation method (Protein Science, 1995, vol. 4, 2411-2423) can be used. In the case of hTINA, a molar extinctio coefficient of 34690 and a molar extinctio coefficient of 95000 were used as estimated values for the L chain and the H chain, respectively, according to its amino acid sequence. As for the molar extinctio coefficient (280 nm) of the drug linker, the measured molar extinctio coefficient (280 nm) of a compound in which the maleimide group was converted to succinimide thioether by the reaction of each drug linker with mercaptoethanol or N-acetylcysteine was used.

[F-3-3] The peak area ratio (%) of each chain is calculated for the total of the corrected values of peak areas according to the following expression.

Peak area ratio of the L chain = $\dfrac{A_{Li}}{A_{L0} + A_{L1}} \times 100$ [Expression 3]

Peak area ratio of the H chain =

$$\dfrac{A_{Hi}}{A_{H0} + A_{H1} + A_{H2} + A_{H3}} \times 100$$

$A_{Li}$, $A_{Hi}$: Corrected values of respective peak areas of $L_i$ and $H_i$

[F-3-4] The average number of conjugated drug molecules per antibody molecule in the antibody-drug conjugate is calculated according to the following expression.

Average number of conjugated drug molecules=($L_0$ peak area ratio×0+$L_0$ peak area ratio×1+$H_0$ peak area ratio×0+$H_1$ peak area ratio×1+$H_2$ peak area ratio×2+$H_3$ peak area ratio×3)/100×2

The compound represented by the formula (2) in Production method 1 is a compound represented by the following formula:

(maleimid-N-yl)-(CH$_2$)$n^3$-C(=O)-L$^2$-L$^P$-NH—(CH$_2$)$n^1$-L$^a$-(CH$_2$)$n^2$-C(=O)—(NH-DX)

In the formula,
$n^3$ represents an integer of 2 to 8,
L$^2$ represents —NH—(CH$_2$CH$_2$—O)$n^4$-CH$_2$CH$_2$—C(=O)— or a single bond, wherein $n^4$ represents an integer of 1 to 6,
L$^P$ represents a peptide residue consisting of 2 to 7 amino acids selected from phenylalanine, glycine, valine, lysine, citrulline, serine, glutamic acid, and aspartic acid
$n^1$ represents an integer of 0 to 6,
$n^2$ represents an integer of 0 to 5,
L$^a$ represents —O— or a single bond,
(maleimid-N-yl)- is a maleimidyl group (2,5-dioxo-2,5-dihydro-1H-pyrrol-1-yl group) represented by the following formula:

[Formula 20]

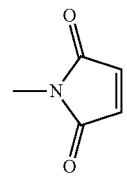

wherein the nitrogen atom is a connecting position, —(NH-DX) is a group represented by the following formula:

[Formula 21]

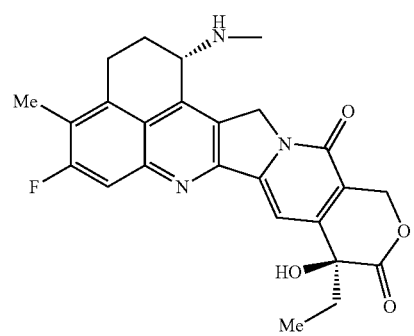

wherein the nitrogen atom of the amino group at position 1 is a connecting position.

When L$^2$ is a single bond or —NH—(CH$_2$CH$_2$—O)$n^4$-CH$_2$CH$_2$—C(=O)—, a compound in which $n^4$ is an integer of 2 to 4 is preferred as a production intermediate.

As for the peptide residue of L$^P$, a compound having a peptide residue comprising an amino acid selected from phenylalanine, glycine, valine, lysine, citrulline, serine, glutamic acid, and aspartic acid is preferred as a production intermediate. Among those peptide residues, a compound in which L$^P$ is a peptide residue consisting of 4 amino acids is preferred as a production intermediate. More specifically, a compound in which L$^P$ is a tetrapeptide residue of -GGFG- is preferred as a production intermediate.

Further, as for the —NH—(CH$_2$)$n^1$-L$^a$-(CH$_2$)$n^2$-, a compound having —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound having —NH—CH$_2$CH$_2$CH$_2$—, —NH—CH$_2$—O—CH$_2$—, or —NH—CH$_2$CH$_2$—O—CH$_2$ is more preferred.

Further, in the compound represented by the formula (2), a compound in which $n^3$ is an integer of 2 to 5, L$^2$ is a single bond, and —NH—(CH$_2$)$n^1$-L$^a$-(CH$_2$)$n^2$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which —NH—(CH$_2$)$n^1$-L$^a$-(CH$_2$)$n^2$- is —NH—CH$_2$CH$_2$—, —NH—CH$_2$CH$_2$CH$_2$—, —NH—CH$_2$—O—CH$_2$—, or —NH—CH$_2$CH$_2$—O—CH$_2$— is more preferred. A compound in which $n^3$ is an integer of 2 or 5 is further preferred.

Further, in the compound represented by the formula (2), a compound in which $n^3$ is an integer of 2 to 5, $L^2$ is —NH—(CH$_2$CH$_2$—O)n$^4$-CH$_2$CH$_2$—C(=O)—, $n^4$ is an integer of 2 to 4, and —NH—(CH$_2$)n$^1$-L$^a$-(CH$_2$)n$^2$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which $n^4$ is an integer of 2 or 4 is more preferred. A compound in which —NH—(CH$_2$)n$^1$-L$^a$-(CH$_2$)n$^2$- is —NH—CH$_2$CH$_2$CH$_2$—, —NH—CH$_2$—O—CH$_2$—, or —NH—CH$_2$CH$_2$—O—CH$_2$— is further preferred.

As such preferred intermediates useful in the production of the compound of the present invention, the followings can be exemplified.

(maleimid-N-yl)-CH$_2$CH$_2$—C(=O)-GGFG-NH—CH$_2$CH$_2$—C(=O)—(NH-DX),
(maleimid-N-yl)-CH$_2$CH$_2$CH$_2$—C(=O)-GGFG-NH—CH$_2$CH$_2$—C(=O)—(NH-DX),
(maleimid-N-yl)-CH$_2$CH$_2$CH$_2$CH$_2$—C(=O)-GGFG-NH—CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$—C(=O)—(NH-DX),
(maleimid-N-yl)-CH$_2$CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$CH$_2$—C(=O)—(NH-DX),
(maleimid-N-yl)-CH$_2$CH$_2$—C(=O)-GGFG-NH—CH$_2$CH$_2$CH$_2$CH$_2$—C(=O)—(NH-DX),
(maleimid-N-yl)-CH$_2$CH$_2$CH$_2$—C(=O)-GGFG-NH—CH$_2$CH$_2$CH$_2$CH$_2$—C(=O)—(NH-DX),
(maleimid-N-yl)-CH$_2$CH$_2$CH$_2$CH$_2$—C(=O)-GGFG-NH—CH$_2$CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$CH$_2$CH$_2$—C(=O)—(NH-DX),
(maleimid-N-yl)-CH$_2$CH$_2$—C(=O)-GGFG-NH—CH$_2$CH$_2$CH$_2$CH$_2$CH$_2$—C(=O)—(NH-DX),
(maleimid-N-yl)-CH$_2$CH$_2$CH$_2$—C(=O)-GGFG-NH—CH$_2$CH$_2$CH$_2$CH$_2$CH$_2$—C(=O)—(NH-DX),
(maleimid-N-yl)-CH$_2$CH$_2$CH$_2$CH$_2$—C(=O)-GGFG-NH—CH$_2$CH$_2$CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$CH$_2$CH$_2$CH$_2$—C(=O)—(NH-DX),
(maleimid-N-yl)-CH$_2$CH$_2$—C(=O)-GGFG-NH—CH$_2$—O—CH$_2$—C(=O)—(NH-DX),
(maleimid-N-yl)-CH$_2$CH$_2$CH$_2$—C(=O)-GGFG-NH—CH$_2$—O—CH$_2$—C(=O)—(NH-DX),
(maleimid-N-yl)-CH$_2$CH$_2$CH$_2$CH$_2$—C(=O)-GGFG-NH—CH$_2$—O—CH$_2$—C(=O)—(NH-DX),
(maleimid-N-yl)-CH$_2$CH$_2$CH$_2$CH$_2$CH$_2$—C(=O)-GGFG-NH—CH$_2$—O—CH$_2$—C(=O)—(NH-DX),
(maleimid-N-yl)-CH$_2$CH$_2$—C(=O)-GGFG-NH—CH$_2$CH$_2$—O—CH$_2$—C(=O)—(NH-DX),
(maleimid-N-yl)-CH$_2$CH$_2$CH$_2$—C(=O)-GGFG-NH—CH$_2$CH$_2$—O—CH$_2$—C(=O)—(NH-DX),
(maleimid-N-yl)-CH$_2$CH$_2$CH$_2$CH$_2$—C(=O)-GGFG-NH—CH$_2$CH$_2$—O—CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$CH$_2$CH$_2$—C(=O)—(NH-DX).

The anti-TROP2 antibody-drug conjugate of the present invention can be produced by reacting a drug-linker compound selected from the above-described group of production intermediate compounds with an anti-TROP2 antibody or a reactive derivative thereof and forming a thioether bond at a disulfide bond site present in a hinge part of the anti-TROP2 antibody. In this case, a reactive derivative of the anti-TROP2 antibody is preferably used. Particularly, a reactive derivative obtained by reducing the anti-TROP2 antibody is preferred.

The followings are compounds more preferred as production intermediates.

(maleimid-N-yl)-CH$_2$CH$_2$—C(=O)-GGFG-NH—CH$_2$CH$_2$—C(=O)—(NH-DX),
(maleimid-N-yl)-CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$—O—CH$_2$—C(=O)—(NH-DX),
(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
(maleimid-N-yl)-CH$_2$CH$_2$—C(=O)—NH—CH$_2$CH$_2$—O—CH$_2$CH$_2$—C(=O)-GGFG-NH—CH$_2$CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG-NH—CH$_2$CH$_2$CH$_2$—C(=O)—(NH-DX).

Among the above-described group of intermediate compounds, a compound represented by the following formula:
(maleimid-N-yl)-CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$—O—CH$_2$—C(=O)—(NH-DX), or
(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX),
is a further preferred compound.

In order to secure the amount of the conjugate, a plurality of conjugates obtained under similar production conditions to have an equivalent number of drugs (e.g., about ±1) can be mixed to prepare new lots. In this case, the average number of drugs falls between the average numbers of drugs in the conjugates before the mixing.

2. Production Method 2

The compound represented by the formula (2) as an intermediate used in the previous production method and a pharmacologically acceptable salt thereof can be produced by the following method, for example.

[Formula 22]

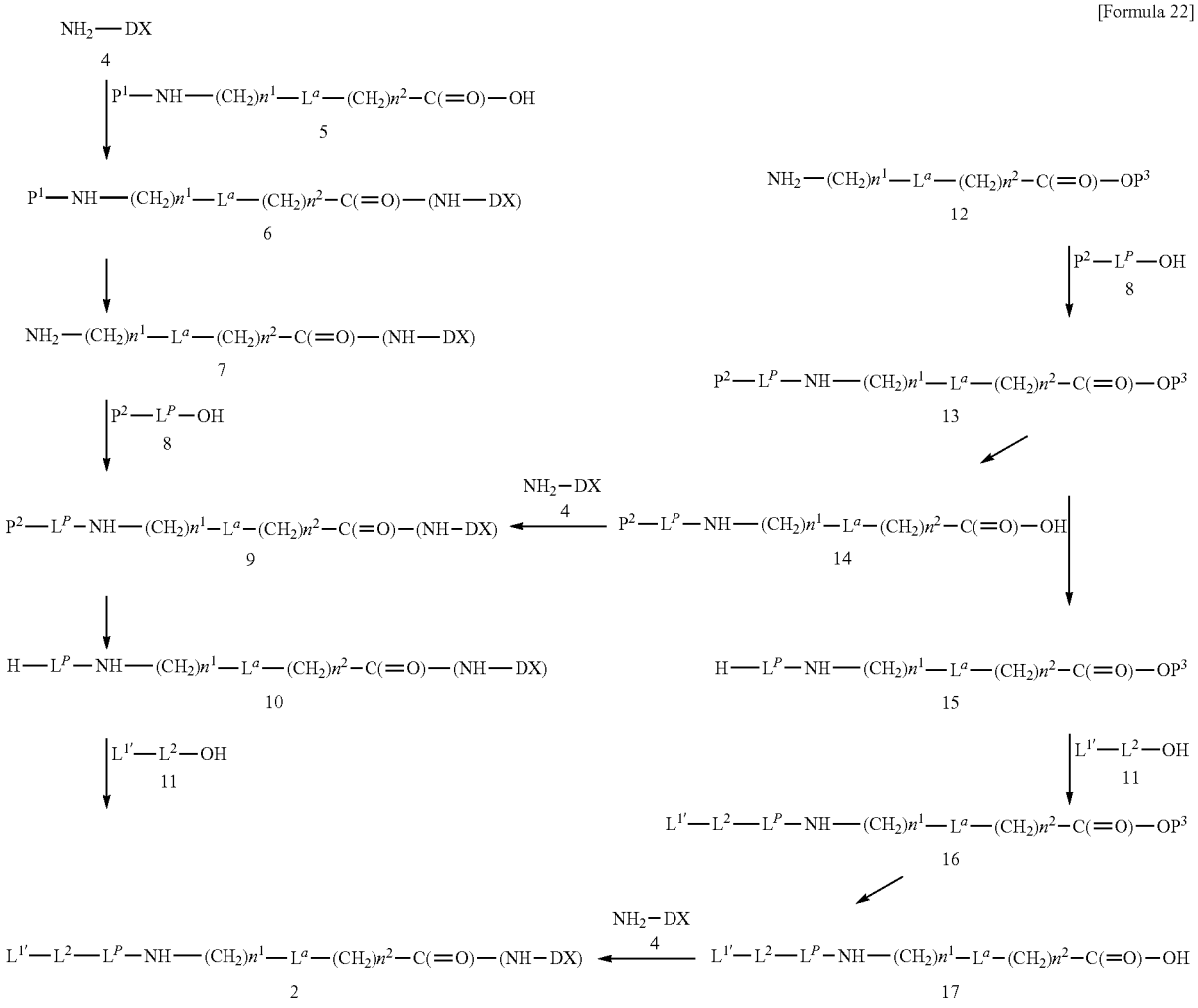

In the formula, $L^{1'}$ represents a maleimidyl group, and $P^1$, $P^2$, and $P^3$ each represents a protecting group.

The compound (6) can be produced by derivatizing the carboxylic acid (5) into an active ester, mixed acid anhydride, acid halide, or the like and reacting it with $NH_2$-DX (4) or a pharmacologically acceptable salt thereof in the presence of a base. $NH_2$-DX (4) represents exatecan (chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione).

Reaction reagents and conditions that are commonly used for peptide synthesis can be employed for the reaction. There are various kinds of active ester. For example, it can be produced by reacting phenols such as p-nitrophenol, N-hydroxy benzotriazole, N-hydroxy succinimide, or the like, with the carboxylic acid (5) using a condensing agent such as N,N'-dicyclohexylcarbodiimide or 1-ethyl-3-(3-dimethylaminopropyl)carbodiimide hydrochloride. Further, the active ester can be also produced by a reaction of the carboxylic acid (5) with pentafluorophenyl trifluoroacetate or the like; a reaction of the carboxylic acid (5) with 1-benzotriazolyl oxytripyrrolidinophosphonium hexafluorophosphite; a reaction of the carboxylic acid (5) with diethyl cyanophosphonate (salting-in method); a reaction of the carboxylic acid (5) with triphenylphosphine and 2,2'-dipyridyl disulfide (Mukaiyama's method); a reaction of the carboxylic acid (5) with a triazine derivative such as 4-(4, 6-dimethoxy-1,3,5-triazin-2-yl)-4-methylmorpholinium chloride (DMTMM); or the like. Further, the reaction can be also performed by, e.g., an acid halide method by which the carboxylic acid (5) is treated with acid halide such as thionyl chloride and oxalyl chloride in the presence of a base.

By reacting the active ester, mixed acid anhydride, or acid halide of the carboxylic acid (5) obtained as above with the compound (4) in the presence of a suitable base in an inert solvent at a reaction temperature of −78° C. to 150° C., the compound (6) can be produced. Meanwhile, "inert solvent" indicates a solvent which does not inhibit a target reaction for which the solvent is used.

Specific examples of the base used for each step described above can include carbonate, alkoxide, hydroxide, or hydride of an alkali metal or an alkali earth metal including sodium carbonate, potassium carbonate, sodium ethoxide, potassium butoxide, sodium hydroxide, potassium hydroxide, sodium hydride, and potassium hydride, organometallic base represented by an alkyl lithium including n-butyl lithium, dialkylamino lithium including lithium diisopropylamide; organometallic base of bissilylamine including lithium bis(trimethylsilyl)amide; and organic base including tertiary amine or nitrogen-containing heterocyclic compound such as pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the inert solvent which is used for the reaction of the present invention include a halogenated hydrocarbon solvent such as dichloromethane, chloroform, and carbon tetrachloride; an ether solvent such as tetrahydrofuran, 1,2-dimethoxyethane, and dioxane; an aromatic hydrocarbon solvent such as benzene and toluene; and an amide solvent such as N,N-dimethylformamide, N,N-dimethylacetamide, and N-methylpyrrolidin-2-one. In addition to them, a sulfoxide solvent such as dimethyl sulfoxide and sulfolane; a ketone solvent such as acetone and methyl ethyl ketone; and an alcohol solvent such as methanol and ethanol may be used in some case. Further, these solvents may be mixed for use.

As for the protecting group $P^1$ for the terminal amino group of the compound (6), a protecting group for an amino group which is generally used for peptide synthesis, for example, tert-butyloxy carbonyl group, 9-fluorenylmethyloxy carbonyl group, and benzyloxy carbonyl group, can be used. Examples of the other protecting group for an amino group can include an alkanoyl group such as acetyl group; an alkoxycarbonyl group such as methoxycarbonyl group and ethoxycarbonyl group; an arylmethoxy carbonyl group such as paramethoxybenzyloxy carbonyl group, and para (or ortho)nitroybenzyloxy carbonyl group; an arylmethyl group such as benzyl group and triphenyl methyl group; an aroyl group such as benzoyl group; and an aryl sulfonyl group such as 2,4-dinitrobenzene sulfonyl group and orthonitrobenzene sulfonyl group. The protecting group $P^1$ can be selected depending on, e.g., properties of a compound having an amino group to be protected.

By deprotecting the protecting group $P^1$ for the terminal amino group of the compound (6) obtained, the compound (7) can be produced. For this deprotection, reagents and conditions can be selected depending on the protecting group.

The compound (9) can be produced by derivatizing the peptide carboxylic acid (8) having the N terminal protected with $P^2$ into an active ester, mixed acid anhydride, or the like and reacting it with the compound (7) obtained. The reaction conditions, reagents, base, and inert solvent used for forming a peptide bond between the peptide carboxylic acid (8) and the compound (7) can be suitably selected and used from those described for the synthesis of the compound (6). The protecting group $P^2$ can be suitably selected and used from those described for the protecting group of the compound (6), and the selection can be made based on, e.g., the properties of the compound having an amino group to be protected. As it is generally used for peptide synthesis, by repeating sequentially the reaction and deprotection of the amino acid or peptide constituting the peptide carboxylic acid (8) for elongation, the compound (9) can be also produced.

By deprotecting the protecting group $P^2$ for the amino group of the compound (9) obtained, the compound (10) can be produced. For this deprotection, reagents and conditions can be selected depending on the protecting group.

It is possible to produce the compound (2) by derivatizing the carboxylic acid (11) into an active ester, mixed acid anhydride, acid halide, or the like and reacting it with the compound (10) obtained. The reaction conditions, reagents, base, and inert solvent used for forming a peptide bond between the carboxylic acid (11) and the compound (10) can be suitably selected and used from those described for the synthesis of the compound (6).

The compound (9) can be also produced by the following method, for example.

The compound (13) can be produced by derivatizing the peptide carboxylic acid (8) having the N terminal protected with $P^2$ into active ester, mixed acid anhydride, or the like and reacting it in the presence of a base with the amine compound (12) having the carboxy group protected with $P^3$. The reaction conditions, reagents, base, and inert solvent used for forming a peptide bond between the peptide carboxylic acid (8) and the compound (12) can be suitably selected and used from those described for the synthesis of the compound (6).

The protecting group $P^2$ for the amino group of the compound (13) may be protected with a protecting group which is commonly used.

Specifically, examples of the protecting group for a hydroxyl group include an alkoxymethyl group such as methoxymethyl group; an arylmethyl group such as benzyl group, 4-methoxybenzyl group, and triphenylmethyl group; an alkanoyl group such as acetyl group; an aroyl group such as benzoyl group; and a silyl group such as tert-butyl diphenylsilyl group. Carboxy group can be protected, e.g., as an ester with an alkyl group such as methyl group, ethyl group, and tert-butyl group, an allyl group, or an arylmethyl group such as benzyl group. Examples of the protecting group for an amino group include, for example, an alkyloxy carbonyl group such as tert-butyloxy carbonyl group, methoxycarbonyl group, and ethoxycarbonyl group; allyloxycarbonyl group, or an arylmethoxy carbonyl group such as 9-fluorenylmethyloxy carbonyl group, benzyloxy carbonyl group, paramethoxybenzyloxy carbonyl group, and para (or ortho)nitroybenzyloxy carbonyl group; an alkanoyl group such as acetyl group; an arylmethyl group such as benzyl group and triphenyl methyl group; an aroyl group such as benzoyl group; and an aryl sulfonyl group such as 2,4-dinitrobenzene sulfonyl group or orthonitrobenzene sulfonyl group.

As for the protecting group $P^3$ for a carboxy group, a protecting group commonly used as a protecting group for a carboxy group in organic synthetic chemistry, in particular, peptide synthesis can be used. Specific examples include esters with an alkyl group such as a methyl group, an ethyl group, or a tert-butyl, allyl esters, and benzyl esters, and the protective group can be suitably selected from the above-described protective groups. In such case, it is preferred that the protecting group for an amino group and the protecting group for a carboxy group can be those preferably removed by a different method or different conditions. For example, a representative example includes a combination in which $P^2$ is a tert-butyloxy carbonyl group and $P^3$ is a benzyl group. The protecting groups can be selected from the aforementioned ones depending on, e.g., the properties of a compound having an amino group and a carboxy group to be protected. For removal of the protecting groups, reagents and conditions can be selected depending on the protecting group.

By deprotecting the protecting group $P^3$ for the carboxy group of the compound (13) obtained, the compound (14) can be produced. For this deprotection, reagents and conditions are selected depending on the protecting group.

The compound (9) can be produced by derivatizing the compound (14) obtained into active ester, mixed acid anhydride, acid halide, or the like and reacting with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

The compound (2) can be also produced by the following method, for example.

By deprotecting the protecting group $P^2$ for the amino group of the compound (13), the compound (15) can be produced. For this deprotection, reagents and conditions can be selected depending on the protecting group.

The compound (16) can be produced by derivatizing the carboxylic acid derivative (11) into active ester, mixed acid anhydride, acid halide, or the like and reacting it with the compound (15) obtained in the presence of a base. The reaction conditions, reagents, base, and inert solvent used for forming an amide bond between the peptide carboxylic acid (11) and the compound (15) can be suitably selected from those described for the synthesis of the compound (6).

By deprotecting the protecting group for the carboxy group of the compound (16) obtained, the compound (17) can be produced. This deprotection can be carried out similarly to the deprotection at carboxy group for producing the compound (14).

The compound (2) can be produced by derivatizing the compound (17) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

3. Production Method 3

The compound represented by the formula (2) of an intermediate can be also produced by the following method.

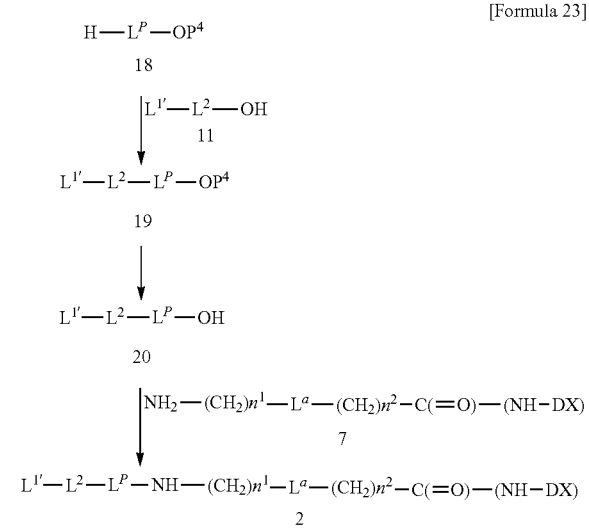

[Formula 23]

In the formula, $L^{1'}$ corresponds to $L^1$ having a structure in which the terminal is converted to a maleimidyl group, and $P^4$ represents a protecting group.

The compound (19) can be produced by derivatizing the compound (11) into active ester, mixed acid anhydride, or the like and reacting it in the presence of a base with the peptide carboxylic acid (18) having the C terminal protected with $P^4$. The reaction conditions, reagents, base, and inert solvent used for forming a peptide bond between the peptide carboxylic acid (18) and the compound (11) can be suitably selected from those described for the synthesis of the compound (6). The protecting group $P^4$ for the carboxy group of the compound (18) can be suitably selected from the protecting group described above.

By deprotecting the protecting group for the carboxy group of the compound (19) obtained, the compound (20) can be produced. This deprotection can be performed similar to the deprotection of the carboxy group for producing the compound (14).

The compound (2) can be produced by derivatizing the compound (20) obtained into active ester, mixed acid anhydride, or the like and reacting it with the compound (7). For the reaction, reaction reagents and conditions that are generally used for peptide synthesis can be also used, and the reaction conditions, reagents, base, and inert solvent used for the reaction can be suitably selected from those described for the synthesis of the compound (6).

4. Production Method 4

Hereinbelow, the method for producing the compound (10b) having $n^1=1$, $L^a=0$ in the production intermediate (10) described in Production method 2 is described in detail. The compound represented by the formula (10b), a salt or a solvate thereof can be produced according to the following method, for example.

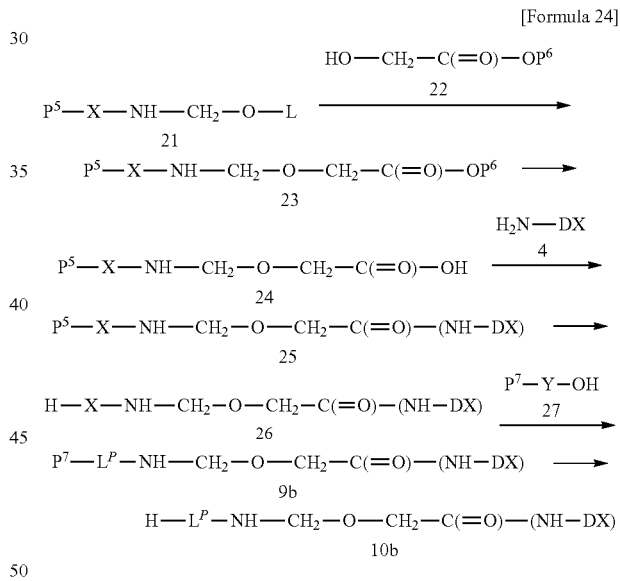

[Formula 24]

In the formula, $L^P$ is as defined above, L represents an acyl group which is an alkanoyl group such as an acetyl group or an alloy group such as a benzoyl group, a hydrogen atom, or the like, X and Y each represent an oligopeptide consisting of 1 to 3 amino acids, $P^5$ and $P^7$ each represent a protecting group for an amino group, and $P^6$ represents a protecting group for a carboxy group.

A compound represented by the formula (21) can be produced by using or applying the method described in Japanese Patent Laid-Open No. 2002-60351 or the literature (J. Org. Chem., Vol. 51, page 3196, 1986), and, by conducting removal of the protecting groups or modification of the functional groups, if necessary. Alternatively, it can be also obtained by treating an amino acid with a protected terminal amino group or acid amide of oligopeptide with protected amino group with aldehyde or ketone.

By reacting the compound (21) with the compound (22) having a hydroxyl group at a temperature ranging from under temperature conditions of cooling to room temperature in an inert solvent in the presence of an acid or a base, the compound (23) can be produced.

Examples of the acid which may be used here can include inorganic acid such as hydrofluoric acid, hydrogen chloride, sulfuric acid, nitric acid, phosphoric acid, and boric acid; an organic acid such as acetic acid, citric acid, paratoluene sulfonic acid, and methanesulfonic acid; and a Lewis acid such as tetrafluoroborate, zinc chloride, tin chloride, aluminum chloride, and iron chloride. Among them, sulfonic acids, particularly, paratoluene sulfonic acid is preferable. As for the base, any one of the aforementioned base can be suitably selected and used. Preferred examples thereof include an alkali metal alkoxide such as potassium tert-butoxide; an alkali metal hydroxide such as sodium hydroxide and potassium hydroxide; alkali metal hydride such as sodium hydride and potassium hydride; organometallic base represented by dialkylamino lithium such as lithium diisopropylamide; and organometallic base of bissilylamine such as lithium bis(trimethylsilyl)amide. Examples of the solvent to be used for the reaction include an ether solvent such as tetrahydrofuran and 1,4-dioxane; and an aromatic hydrocarbon solvent such as benzene and toluene. Those solvents can be prepared as a mixture with water. Further, the protecting group for an amino group as exemplified by $P^5$ is not particularly limited if it is a group commonly used for protection of an amino group. Representative examples include the protecting groups for an amino group that are described in Production method 2. However, in the present reaction, there may be a case in which the protecting group for an amino group as exemplified by $P^5$ is cleaved off. In such case, it is necessary to perform a reaction with a suitable reagent for protecting an amino group as it may be required to introduce the protecting group again.

The compound (24) can be produced by removing the protecting group $P^6$ of the compound (23). Herein, the representative examples of the protecting group for a carboxy group as exemplified by $P^6$ are described in Production method 2, and a suitable one can be selected from them. In the compound (23), it is desirable that the protecting group $P^5$ for an amino group and the protecting group $P^6$ for a carboxy group are the protecting groups that can be removed by a different method or different conditions. For example, a representative example includes a combination in which $P^5$ is a 9-fluorenylmethyloxy carbonyl group and $P^6$ is a benzyl group. The protecting groups can be selected depending on, e.g., the properties of a compound having an amino group and a carboxy group to be protected. For removal of the protecting groups, reagents and conditions are selected depending on the protecting group.

The compound (26) can be produced by derivatizing the carboxylic acid (24) into active ester, mixed acid anhydride, acid halide, or the like and reacting it with the compound (4) or a pharmacologically acceptable salt thereof to produce the compound (25) followed by removing the protecting group $P^5$ of the compound (25) obtained. For the reaction between the compound (4) and the carboxylic acid (24) and the reaction for removing the protecting group $P^6$, the same reagents and reaction conditions as those described for Production method 2 can be used.

The compound (10b) can be produced by reacting the compound (26) with an amino acid having protected terminal amino group or the oligopeptide (27) having protected amino group to produce the compound (9b) and removing the protecting group $P^7$ of the compound (9b) obtained. The protecting group for an amino group as represented by $P^7$ is not particularly limited if it is generally used for protection of an amino group. Representative examples thereof include the protecting groups for an amino group that are described in Production method 2. For removing the protecting group, reagents and conditions are selected depending on the protecting group. For the reaction between the compound (26) and the compound (27), reaction reagents and conditions that are commonly used for peptide synthesis can be employed. The compound (10b) produced by the aforementioned method can be derivatized into the compound (1) of the present invention according to the method described above.

The anti-TROP2 antibody-drug conjugate of the present invention, when it is left in air or recrystallized, for example, for purification, may absorb moisture to have adsorption water or turn into a hydrate, and such a compound and a salt containing water are also included in the present invention.

A compound labeled with various radioactive or non-radioactive isotopes is also included in the present invention. One or more atoms constituting the antibody-drug conjugate of the present invention may contain an atomic isotope at non-natural ratio. Examples of the atomic isotope include deuterium ($^2$H), tritium ($^3$H), iodine-125 ($^{125}$I), and carbon-14 ($^{14}$C). Further, the compound of the present invention may be radioactive-labeled with a radioactive isotope such as tritium ($^3$H), iodine-125 ($^{125}$I), carbon-14 ($^{14}$C), copper-64 ($^{64}$Cu), zirconium-89 ($^{89}$Zr), iodine-124 ($^{124}$I), fluorine-18 ($^{18}$F), indium-111 ($^{111}$In), carbon-11 ($^{11}$C) and iodine-131 ($^{131}$I). The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate of the present invention is within the scope of the present invention.

[Drugs]

The anti-TROP2 antibody-drug conjugate of the present invention exhibits a cytotoxic activity against cancer cells, and thus, it can be used as a drug, particularly as a therapeutic agent and/or prophylactic agent for cancer.

That is, the anti-TROP2 antibody-drug conjugate of the present invention can be selectively used as a drug for chemotherapy, which is a main method for treating cancer, and as a result, can delay development of cancer cells, inhibit growth thereof, and further kill the cancer cells. This can allow cancer patients to be free from symptoms caused by cancer or achieve improvement in QOL of cancer patients and attains a therapeutic effect by sustaining the lives of the cancer patients. Even if the anti-TROP2 antibody-drug conjugate of the present invention does not accomplish killing cancer cells, it can achieve higher QOL of cancer patients while achieving their longer-term survival, by inhibiting or controlling the growth of cancer cells.

In such drug therapy, it can be used as a drug alone as well as a drug in combination with an additional therapy in adjuvant therapy and can be combined with surgical operation, radiotherapy, hormone therapy, or the like. Furthermore, it can also be used as a drug for drug therapy in neoadjuvant therapy.

In addition to the therapeutic use as described above, an effect of suppressing the growth of minute metastatic cancer cells and further killing them by binding to these cancer cells can also be expected by virtue of the binding property of the antibody to the antigen. Particularly, when the expression of TROP2 is confirmed in primary cancer cells, inhibition of cancer metastasis or a prophylactic effect can be expected by administering the anti-TROP2 antibody-drug conjugate of the present invention. For example, an effect of inhibiting and killing cancer cells in a body fluid in the course of metastasis or an effect of, for example, inhibiting and killing minute cancer cells immediately after implantation in any tissue can be expected. Further, inhibition of cancer metastasis or a prophylactic effect can be expected, particularly, after surgical removal of cancer. Accordingly, an effect of inhibiting cancer metastasis can be expected.

The anti-TROP2 antibody-drug conjugate of the present invention can be expected to exert a therapeutic effect by administration as systemic therapy to patients, and additionally, by local administration to cancer tissues.

Examples of the cancer type to which the anti-TROP2 antibody-drug conjugate of the present invention is applied include lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, cervical cancer, head and neck cancer, or esophageal cancer, however, it is not limited to them as long as it is a cancer cell expressing, in a cancer cell as a treatment subject, a protein which the antibody within the antibody-drug conjugate can recognize.

The anti-TROP2 antibody-drug conjugate of the present invention can be preferably administered to a mammal, but it is more preferably administered to a human.

Substances used in a pharmaceutical composition containing anti-TROP2 antibody-drug conjugate of the present invention can be suitably selected and applied from formulation additives or the like that are generally used in the art, in view of the dosage or administration concentration.

The anti-TROP2 antibody-drug conjugate of the present invention can be administered as a pharmaceutical composition containing at least one pharmaceutically suitable ingredient. For example, the pharmaceutical composition above typically contains at least one pharmaceutical carrier (for example, sterilized liquid). Herein, the liquid includes, for example, water and oil (petroleum oil and oil of animal origin, plant origin, or synthetic origin). The oil may be, for example, peanut oil, soybean oil, mineral oil, or sesame oil. Water is a more typical carrier when the pharmaceutical composition above is intravenously administered. Saline solution, an aqueous dextrose solution, and an aqueous glycerol solution can be also used as a liquid carrier, in particular, for an injection solution. A suitable pharmaceutical vehicle is known in the art. If desired, the composition above may also contain a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the anti-TROP2 antibody-drug conjugate of the present invention. Examples of the administration route include intradermal, intramuscular, intraperitoneal, intravenous, and subcutaneous routes, but not limited thereto. The administration can be made by injection or bolus injection, for example. According to a specific preferred embodiment, the administration of the antibody-drug conjugate is performed by injection. Parenteral administration is a preferred administration route.

According to a representative embodiment, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the drug may contain a solubilizing agent and local anesthetics to alleviate pain at injection site (for example, lignocaine). Generally, the ingredient above is provided individually as any one of lyophilized powder or an anhydrous concentrate contained in a container which is obtained by sealing in an ampoule or a sachet having an amount of the active agent or as a mixture in a unit dosage form. When the drug is in the form of administration by injection, it may be administered from an injection bottle containing water or saline of sterile pharmaceutical grade. When the drug is administered by injection, an ampoule of sterile water or saline for injection may be provided such that the aforementioned ingredients are admixed with each other before administration.

The pharmaceutical composition of the present invention may be a pharmaceutical composition containing only the anti-TROP2 antibody-drug conjugate of the present application or a pharmaceutical composition containing the anti-TROP2 antibody-drug conjugate and at least one cancer treating agent other than the conjugate. The anti-TROP2 antibody-drug conjugate of the present invention can be administered with other cancer treating agent. The anticancer effect may be enhanced accordingly. Another anticancer agent used for such purpose may be administered to an individual simultaneously with, separately from, or subsequently to the antibody-drug conjugate, and it may be administered while varying the administration interval for each. Examples of the cancer treating agent include abraxane, paclitaxel, cisplatin, gemcitabine, irinotecan (CPT-11), paclitaxel, pemetrexed, sorafenib, vinorelbine, drugs described in International Publication No. WO 2003/038043, LH-RH analogues (leuprorelin, goserelin, or the like), estramustine phosphate, estrogen antagonist (tamoxifen, raloxifene, or the like), and an aromatase inhibitor (anastrozole, letrozole, exemestane, or the like), but it is not limited as long as it is a drug having an antitumor activity.

The pharmaceutical composition can be formulated into a lyophilization formulation or a liquid formulation as a formulation having desired composition and required purity. When formulated as a lyophilization formulation, it may be a formulation containing suitable formulation additives that are used in the art. Also for a liquid formulation, it can be formulated as a liquid formulation containing various formulation additives that are used in the art.

Composition and concentration of the pharmaceutical composition may vary depending on administration method. However, the anti-TROP2 antibody-drug conjugate contained in the pharmaceutical composition of the present invention can exhibit the pharmaceutical effect even at a small dosage when the antibody-drug conjugate has higher affinity for an antigen, that is, higher affinity (=lower Kd value) in terms of the dissociation constant (that is, Kd value) for the antigen. Thus, for determining dosage of the antibody-drug conjugate, the dosage can be determined in view of a situation relating to the affinity between the antibody-drug conjugate and antigen. When the antibody-drug conjugate of the present invention is administered to a human, for example, about 0.001 to 100 mg/kg can be administered once or administered several times with an interval of one time for 1 to 180 days.

EXAMPLES

The present invention is specifically described in view of the examples shown below. However, the present invention is not limited to them. Further, it is by no means interpreted in a limited way. Further, unless specifically described

Example 1

Immunization of Mouse and Obtainment of Hybridoma 1-1) Preparation of Cell to be Used in Mouse Immunization $5×10^6$ NCI-H322 cells (human non-small cell lung cancer cell line, ATCC CRL-5806; ATCC: American Type Culture Collection) were cultured in an RPMI-1640 (Roswell Park Memorial Institute-1640) medium (10 ml) for 5 days, then recovered, washed with PBS (phosphate-buffered saline) twice, and resuspended in PBS (500 µl).

1-2) Immunization of Mouse

For the first immunization, each BALB/c mouse (6 weeks old) was intraperitoneally immunized with NCI-H322 cells (1 x $10^7$ cells). For the second to fifth immunizations, the mouse was intraperitoneally immunized with $1×10^6$ NCI-H322 cells at 1-week intervals. For the sixth (final) immunization, the mouse was immunized through the tail vein and intraperitoneally with the NCI-H322 cells at $1×10^6$ cells/200 µl PBS for each route. Spleen cells were excised 3 days after the final immunization.

1-3) Preparation of Spleen Cell of Immunized Mouse

The spleen of the immunized mouse was excised, then ground, and suspended in an RPMI 1640 10% FBS (fetal bovine serum) (+) medium. The cell suspension was passed through a cell strainer (100 µm, BD Falcon) and then centrifuged at 1500 rpm at room temperature for 5 minutes, and the supernatant was discarded. A Tris-$NH_4$Cl solution (20 mM Tris-HCl pH 7.5, 0.83% $NH_4$Cl; 10 mL) was added to the residue, followed by treatment at room temperature for 5 minutes. An RPMI 1640 FBS(+) medium (10 ml) was added to the cell suspension, and the mixture was passed through a cell strainer and then centrifuged at 1500 rpm at room temperature for 5 minutes. The supernatant was discarded, and the spleen cells were resuspended in an RPMI 1640 FBS(−) medium (10 ml).

1-4) Preparation of Myeloma Cell

P3U1 cells (mouse myeloma cell line) were recovered and centrifuged at 1500 rpm at room temperature for 5 minutes. An EDTA (0.02%) solution (10 ml) was added to the P3U1 cells, followed by treatment at 37° C. for 5 minutes. The P3U1 cell suspension was centrifuged at 1500 rpm at room temperature for 5 minutes. The supernatant was discarded and resuspended in an RPMI 1640 FBS(−) medium (10 ml).

1-5) Cell Fusion

The spleen cells and the myeloma cells were mixed at a ratio of 5:1 and centrifuged (1200 rpm, 5 minutes). The obtained cells in the precipitated fraction was well loosened, and polyethylene glycol-4000 (PEG-4000; 1 mL) was then gradually added thereto over about 1 minute with stirring. Then, an RPMI medium (1 mL) was added to the fluid containing the cell several times with inerval of 1 minute, and an RPMI medium was then added thereto to adjust the total amount to 50 mL. The cell suspension was centrifuged (900 rpm, 5 minutes), and the obtained cells in the precipitated fraction were mildly loosened and then gently suspended in a HAT medium (PRMI 1640 medium supplemented with 10% fetal bovine serum and HAT Media Supplement; 100 mL). The suspension was dispensed at 200 µL/well to a 96-well plate for culture and cultured until 50% confluency in a 5% $CO_2$ incubator of 37° C.

1-6) Screening of Hybridoma Using Variant Adenovirus FZ33

The NCI-H322 cells were seeded at $5×10^3$ cells/well to a 96-well plate and cultured at 37° C. for 48 hours. The cells were washed with 150 µl/well of PBS twice, and each hybridoma culture supernatant (50 µl) was added to each well and reacted at 4° C. for 1 hour. The cells were washed with 150 µl/well of PBS twice. An adenovirus Ax3CAZ3-FZ33 (β-galactosidase-expressing adenovirus modified with Z33 fiber so as to bind to an antibody (see U.S. Patent Application Publication No. 2012/0237518)) was diluted with an RPMI1640(−) medium to a concentration of $3×10^6$ vp/100 µl ($1×10^3$ vp/cell), and this diluted solution was added thereto at 100 µl/well. After reaction at 4° C. for 1 hour, the cells were washed with 150 µl/well of PBS twice. An RPMI1640 FBS(+) medium was added thereto at 100 µl/well, and the cells were cultured at 37° C. for 24 hours. The NCI-H322 cells treated with β-Gal reporter gene assay using Galacto-Light Plus Reporter Gene Assay System (Applied Biosystems, Inc.) were washed with 200 µl/well of PBS. Lysis Solution was added thereto at 50 µl/well, and the mixture was left at room temperature for 10 minutes. This cell lysate (10 µL) was diluted 100-fold with Galacton-Plus Galacto Reaction Buffer Diluent, then added to a White microwell SH 96 well plate (Nunc/Thermo Fisher Scientific, Inc.), and reacted at room temperature for 1 hour. Accelerator II was added thereto at 150 µl/well. Chemiluminescence was measured for 5 seconds using a multi-label counter Wallac 1420 ARVOsx (PerkinElmer, Inc.), and the infective dose of the virus in the NCI-H322 cells was indicated with the average value per second as RLU (amount of luminescence). In the screening of the hybridoma group thus performed, a clone whose measurement value (RLU) was 5000 RLU or higher was selected from the whole group (minimum: 1383 RLU, average: 10914 RLU, maximum: 78746 RLU). First, as primary screening, 81 positive wells were selected from 960 hybridoma wells obtained by one cell fusion. As validation screening, assay was further conducted in duplicate by the same approach as in the primary screening. When a well that exhibited a measurement value of 5000 RLU or higher in both the tests was regarded as positive, 52 positive wells were selected from the 81 wells obtained in the primary screening. The selected clones were subcloned 2 to 4 times to establish 44 monoclonal hybridoma cell lines.

Example 2

Purification of Antibody from Hybridoma

Pristane (2,6,10,14-tetramethylpentadecane; 0.5 ml) was intraperitoneally administered in advance to each 8- to 10-week old mouse or nude mouse, which was then raised for 2 weeks. Each monoclonal antibody-producing hybridoma obtained in Example 1 was intraperitoneally injected to the mouse. After 10 to 21 days, the hybridoma was allowed to cause ascitic canceration, and the ascites was then collected. The obtained ascites was centrifuged to remove solid matter. Then, antibodies were purified by salting out with 40 to 50% ammonium sulfate, a caprylic acid precipitation method, a DEAE-Sepharose column, and a protein G column, and IgG or IgM fractions were collected and used as purified monoclonal antibodies.

Example 3

Identification of Antigen to which Antibody Produced by Hybridoma Binds

An antigen was identified for TINA1, an antibody produced by the hybridoma prepared in Example 2.

3-1) Immunoprecipitation of Biotin-Labeled Cell Surface Protein Using TINA1 Antibody 5×10⁶ NCI-H322 cells were recovered and washed with PBS three times. EZ-Link Sulfo-NHS-Biotin (Pierce/Thermo Fisher Scientific, Inc.) was suspended in PBS at a concentration of 0.1 mg/ml. The NCI-H322 cells were rotated at room temperature for 30 minutes in biotin/PBS solution, then washed with 100 mM glycine/PBS solution (25 ml) twice, and then washed with PBS (25 ml) three times. The cells thus washed were resuspended in a lysis buffer (150 mM NaCl, 50 mM Tris-HCl pH 7.6, 1% NP-40+ Protease inhibitor, 1 tablet/50 ml of Complete EDTA free (Hoffmann-La Roche Ltd.); 2 ml) and treated at 4° C. for 30 minutes. Protein G Sepharose/lysis buffer (50% slurry; 30 µl) obtained by replacing a buffer of Protein G Sepharose (Protein G Sepharose 4 Fast Flow (GE Healthcare Japan Corporation)) with a lysis buffer was added to the cell lysate, and the mixture was rotated at 4° C. for 1 hour and then centrifuged at 4° C. for 5 minutes to recover a supernatant. The TINA1 antibody (3 µg) was added to the supernatant, and the mixture was rotated at 4° C. for 1 hour. Then, Protein G Sepharose/lysis buffer (50% slurry; 60 µl) was added thereto, and the mixture was rotated at 4° C. for 2 hours. Protein G Sepharose was washed with a lysis buffer (1 ml) six times and then resuspended in 1×SDS sample buffer/5% 2-ME (2-mercaptoethanol) buffer (62.5 mM Tris-HCl (pH 6.8 at 25° C.), 2% (w/v) SDS, 10% glycerol, and 0.01% (w/v) phenol red). The suspension was treated at 100° C. for 5 minutes, and the solution was then recovered and used as a sample for SDS-PAGE (polyacrylamide gel electrophoresis).

3-2) SDS-PAGE and Western Blotting

The SDS-PAGE sample prepared in 3-1) was electrophoresed at 20 mA using Ready Gels J 5-20% (Bio-Rad Laboratories, Inc.) and then blotted at 0.1 mA/cm² from the gel to the membrane. The membrane was washed with PBS-T (PBS(−)-0.05% Tween 20) for 5 minutes and then blocked for 1 hour. The membrane was washed with PBS-T for 5 minutes tree times and then reacted with Streptavidin-horseradish peroxidase conjugate (Amersham Biosciences Corp.; diluted 2000-fold with PBS-T for use) for 1 hour. The membrane was washed with PBS-T for 10 minutes four times, and a target band was then detected using ECL western blotting detection reagents (Amersham Biosciences Corp.) and Hyperfilm ECL (Amersham Biosciences Corp.). The NCI-H322 cells biotin-labeled by the procedures of Example 3-1) were subjected to immunoprecipitation with a KCI7A3 antibody whose antigen was already found to be TROP2 by mass spectrometry, or the TINA1 antibody, and the obtained immunoprecipitated products were analyzed by SDS-PAGE and Western blotting in the presence or absence of DTT. In either case of using the KCI7A3 antibody or the TINA1 antibody, a band was detected at a molecular weight of 46 kDa in the absence of DTT, and a band was detected at a molecular weight of 37 kDa in the samples supplemented with DTT.

3-3) FACS Analysis

Because the antigen of the TINA1 antibody was predicted to be TROP2 from the band pattern, overexpression analysis by gene transfer of cDNA was conducted without mass spectrometry. As a result of FACS analysis, the TINA1 antibody exhibited a strong positive response in CHOK1 cells expressing human TROP2, indicating the antigen of the TINA1 antibody is TROP2. Similar FACS analysis was conducted using a lung cancer cell line PC14, a lung cancer cell line NCI-H322, a lung cancer cell line NCI-H2122, a lung cancer cell line LCAM1, a lung cancer cell line LC2/ad, a pancreatic cancer cell line MIAPaCa2, a pancreatic cancer cell line PK-1, a prostate cancer cell line PC3, a colorectal cancer cell line HCT116, a melanoma cell line A375, an ovarian cancer cell line SKOV3, a hematopoietic tumor cell line RPMI8226, a hematopoietic tumor cell line K562, PBMC (human peripheral blood mononuclear cells), and human platelet. All of the examined lung cancer cell lines were TROP2-positive, and PC3, PK1, and SKOV3 were positive as the cell lines except for the lung cancer ones. On the other hand, all of the normal blood cells were negative.

Example 4

Measurement of Antibody Internalization Activity 4-1) Antibody Internalization Activity Evaluation System A recombinant fusion protein DT3C was produced for the purpose of measuring internalization activity and immunotoxin activity of an antibody. This DT3C is a protein having a catalytic domain of diphtheria toxin (DT) and three antibody-binding regions of protein G. DT3C specifically binds to an Fc moiety of an antibody, is stable, and induces cell death by inhibiting protein synthesis when taken up into cells. By use of this system, the internalization effect of antibody and the cytocidal effect thereof by immunotoxin can be observed at the same time (Yamaguchi, M., Hamada, H., et al., Biochemical and Biophysical Research Communications 454 (2014) 600-603).

4-2) Evaluation of Internalization Activity and Immunotoxin Activity Using DT3C

4 µg/mL of DT3C was added at 25 µL/well to a 96-well plate, further the culture supernatants of 11 hybridomas obtained by the method of Example 1 or a method equivalent thereto were each added at 25 µL/well to the plate, and the plate was incubated at room temperature for 30 minutes. The antigens recognized by antibodies produced by the hybridomas other than the TINA1 antibody-producing hybridoma were confirmed in advance to be CD9, CD46, CD55, CD59, CD71, CD73, CD147, CD276, EpCAM, or EGFR. 2×10⁴ cells/mL (RPMI1640 medium supplemented with 20% Low IgG FBS) of NCI-H322 cells were seeded thereto at 50 µL/well. After incubation at room temperature for 30 minutes, the cells were cultured for 3 days in a CO₂ incubator of 37° C. After the culture, the supernatant was removed, and 10% WST-10% FBS-RPMI1640 was added at 100 µL/well to the plate. After incubation for 1 hour in a CO₂ incubator of 37° C., the number of live cells was measured using a microplate reader (OD₄₅₀ to OD₆₄₀, infinite 200, Tecan Trading AG). Among the culture supernatants of the evaluated hybridoma cells, the antibodies against CD59, CD71, EGFR, EpCAM, or TROP2 were confirmed to have strong internalization activity and immunotoxin activity (FIG. 10).

4-3) Difference in Internalization Activity and Immunotoxin Activity Among Antibodies Against CD59, CD71, EGFR, EpCAM, or TROP2

Figure 11:
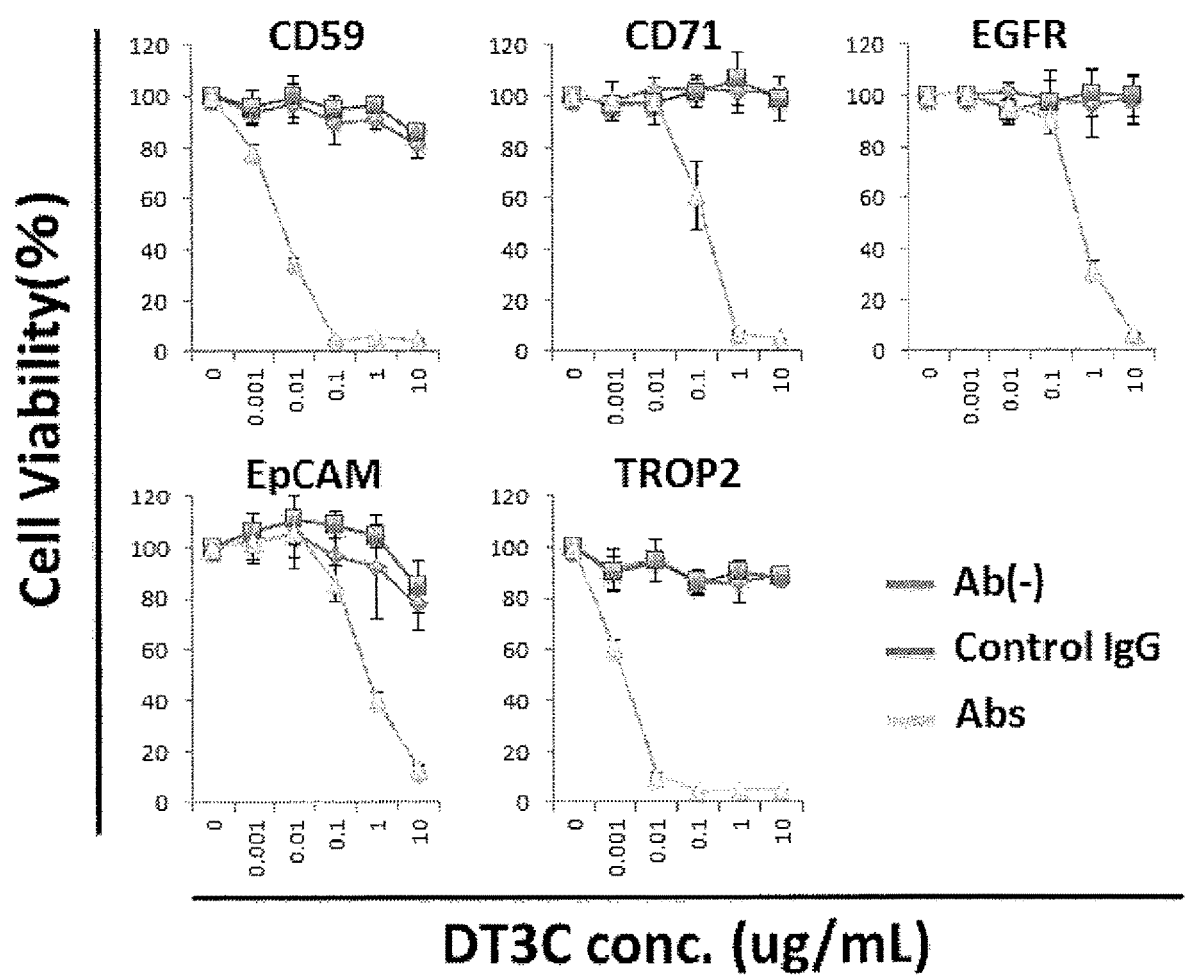
FIG. 11 shows the cell internalization ability of an anti-CD59 antibody, an anti-CD71 antibody, an anti-EGFR antibody, an anti-EpCAM antibody, and an anti-TROP2 antibody (TINA1 antibody).

Each diluted solution of DT3C (0, 0.004, 0.04, 0.4, 4, or 40 µg/mL) was added at 25 µL/well to a 96-well plate, then each antibody (40 µg/mL) was added at 25 µL/well to the plate, and the plate was incubated at room temperature for 30 minutes. Further, 2×10⁴ cells/mL (RPMI1640 medium supplemented with 20% Low IgG FBS) of NCI-H322 cells were seeded thereto at 50 µL/well. After incubation at room temperature for 30 minutes, the cells were cultured for 3 days in a CO₂ incubator of 37° C. After the culture, the supernatant was removed, and 10% WST-1-10% FBS-RPMI1640 was added at 100 µL/well to the plate. After incubation for 1 hour in a CO₂ incubator of 37° C., the number of live cells was measured using a plate reader ($GD_{450}$ to $GD_{640}$). Among the evaluated antibodies, TINA1, an antibody against TROP2, had the strongest internalization activity and immunotoxin activity (FIG. 11).

Figure 12:
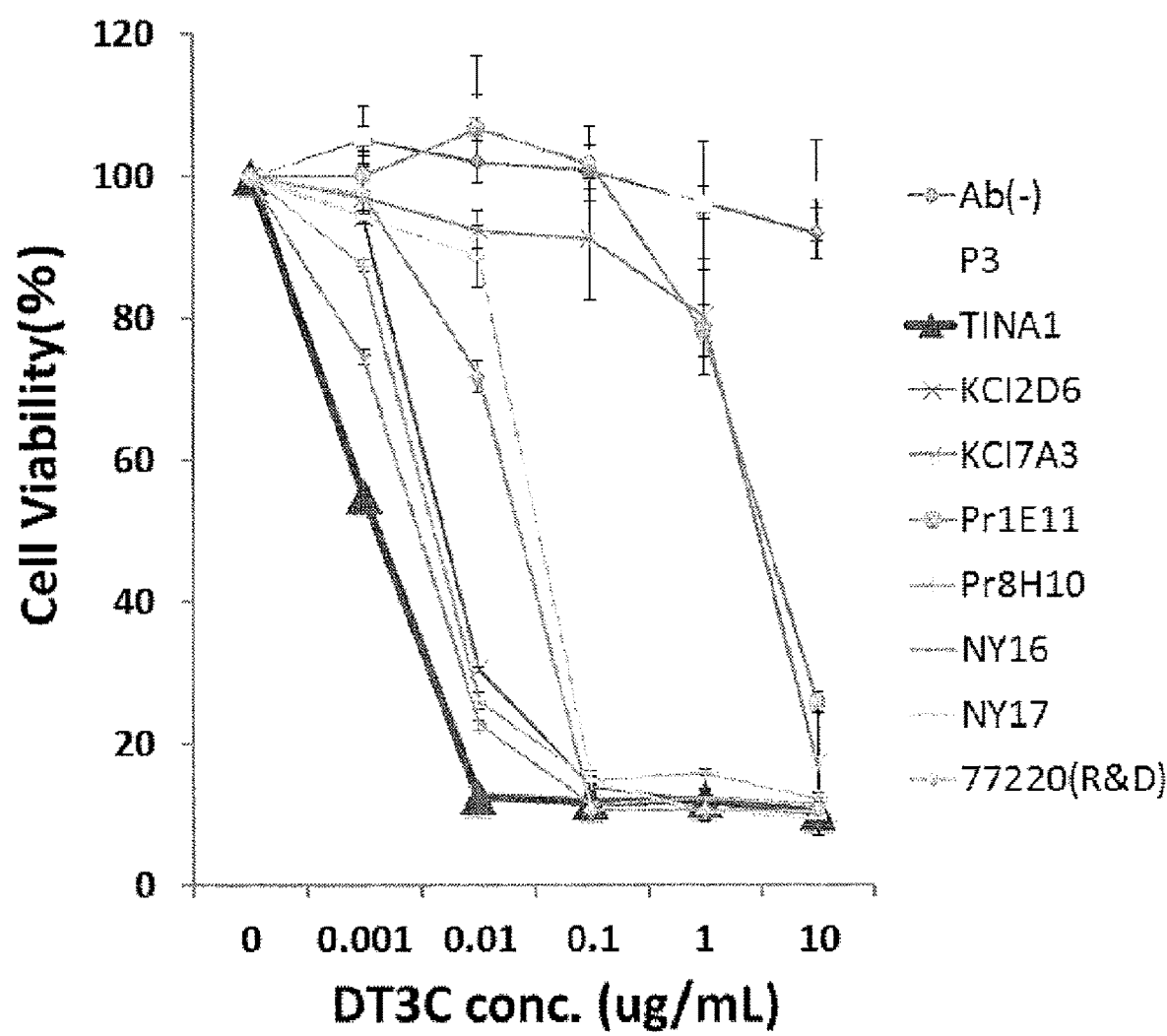
FIG. 12 shows the cell internalization ability of various anti-TROP2 antibodies.

4-4) Difference in Internalization Activity and Immunotoxin Activity Among Clones of Anti-TROP2 Antibody Anti-TROP2 antibodies TINA1 (immunogen: lung cancer line NCI-H322), KCL7A3 and KCL2D6 (immunogen: pancreatic cancer cell line KCL-MOH1), Pr1E11 and Pr8H10 (immunogen: prostate cancer cell line Pc-1), and NY16 and NY17 (immunogen: pancreatic cancer cell line PK-1) obtained by the method of Example 1 or a method equivalent thereto, and commercially available 77220 (R&D Systems Inc.) were evaluated for their internalization activity and immunotoxin activity in the same manner as in Example 4-3). As a result, among the 8 anti-TROP2 antibodies, the TINA1 antibody had the strongest activity (FIG. 12).

Example 5

Determination of Nucleotide Sequence of Variable Region-Encoding cDNA of TINA1 Antibody Gene and Production of Chimeric TINA1 (Hereinafter, Referred to as cTINA1) Antibody 5-1) Determination of Nucleotide Sequence of Variable Region-Encoding cDNA of TINA1 Antibody Gene
5-1-1) Preparation of mRNA from TINA1 Antibody-Producing Hybridoma In order to amplify cDNAs encoding the variable regions of the TINA1 antibody, mRNA was prepared from the TINA1 antibody-producing hybridoma using mRNA Isolation kit (Roche Applied Science).
5-1-2) Synthesis of cDNA (5'-RACE-Ready cDNA)

cDNA (5'-RACE-Ready cDNA) was synthesized using the mRNA (100 ng) prepared in 5-1-1), and SMARTer RACE cDNA Amplification Kit (Clontech Laboratories, Inc.).
5-1-3) Amplification of cDNA Encoding Heavy Chain Variable Region of TINA1 Antibody by 5'-RACE PCR, and Determination of Sequence UPM (Universal Primer A Mix: included in SMARTer RACE cDNA Amplification Kit) and an oligonucleotide having a sequence of 5'-AGAGTTCCAGGTCAAGGT-CACTGGCTCAGG-3' (SEQ ID NO: 33: primer mG2aVR2) were used as primers for amplifying the variable region cDNA of the heavy chain gene by PCR. UPM included in SMARTer RACE cDNA Amplification Kit (Clontech Laboratories, Inc.) was used, and mG2aVR2 was designed from the sequence of a mouse heavy chain (IgG2a) constant region on a database.

cDNA encoding the heavy chain variable region of the TINA1 antibody was amplified by 5'-RACE PCR using this primer set and the cDNA (5'-RACE-Ready cDNA) synthesized in Example 5-1-2) as a template. This PCR was carried out according to the manual of SMARTer RACE cDNA Amplification Kit (Clontech Laboratories, Inc.) on the touchdown PCR program using KOD-plus (Toyobo Co., Ltd.) as polymerase.

The heavy chain variable region-encoding cDNA amplified by 5'-RACE PCR was purified using MinElute PCR Purification Kit (QIAGEN N.V.) and then cloned using Zero Blunt TOPO PCR Cloning Kit (Invitrogen Corp.). The nucleotide sequence of the cloned heavy chain variable region-encoding cDNA was analyzed by sequencing. The sequencing primers used were the above-described primer mG2aVR2 designed from the sequence of a mouse heavy chain constant region on a database, and NUP (Nested Universal Primer A: included in SMARTer RACE cDNA Amplification Kit).

The sequencing analysis was carried out using a gene sequence analysis apparatus ("ABI PRISM 3700 DNA Analyzer" or "Applied Biosystems 3730x1 Analyzer", Applied Biosystems, Inc.), and the sequencing reaction employed Gene Amp 9700 (Applied Biosystems, Inc.).

The determined nucleotide sequence of the cDNA encoding the heavy chain variable region of the TINA1 antibody is shown in SEQ ID NO: 1 of the Sequence Listing, and the amino acid sequence encoded thereby is shown in SEQ ID NO: 2.
5-1-4) Amplification of cDNA encoding light chain variable region of TINA1 antibody by 5'-RACE PCR, and determination of sequence UPM (Universal Primer A Mix: included in SMARTer RACE cDNA Amplification Kit) and an oligonucleotide having a sequence of 5'-AGTCCAACTGTTCAGGACGC-CATTTTGTCG-3' (SEQ ID NO: 34: primer mKVR2) were used as primers for amplifying the variable region cDNA of the light chain gene of the TINA1 antibody by PCR. UPM included in SMARTer RACE cDNA Amplification Kit (Clontech Laboratories, Inc.) was used, and mKVR2 was designed from the sequence of a mouse light chain constant region on a database.

cDNA encoding the light chain variable region of the TINA1 antibody was amplified by 5'-RACE PCR using this primer set and the cDNA (5'-RACE-Ready cDNA) synthesized in Example 5-1-2) as a template. This PCR was carried out according to the manual of SMARTer RACE cDNA Amplification Kit (Clontech Laboratories, Inc.) on the touchdown PCR program using KOD-plus- (Toyobo Co., Ltd.) as polymerase.

The light chain variable region-encoding cDNA amplified by 5'-RACE PCR was purified using MinElute PCR Purification Kit (QIAGEN N.V.) and then cloned using Zero Blunt TOPO PCR Cloning Kit (Invitrogen Corp.). The nucleotide sequence of the cloned light chain variable region-encoding cDNA was analyzed by sequencing.

The sequencing primers used were the above-described primer mKVR2 designed from the sequence of a mouse light chain constant region on a database, and NUP.

The sequencing analysis and the sequencing reaction employed the above-described apparatus.

The determined nucleotide sequence of the cDNA encoding the light chain variable region of the TINA1 antibody is shown in SEQ ID NO: 3 of the Sequence Listing, and the amino acid sequence encoded thereby is shown in SEQ ID NO: 4.
5-2) Production of cTINA1 Antibody
5-2-1) Construction of Chimeric and Humanized Antibody Light Chain Expression Vector pCMA-LK A fragment of about 5.4 kb obtained by digesting a plasmid pcDNA3.3-TOPO/LacZ (Invitrogen Corp.) with restriction enzymes XbaI and PmeI, and a DNA fragment containing a DNA sequence encoding a human κ chain secretion signal and a human κ chain constant region shown in SEQ ID NO: 5 were ligated using In-Fusion Advantage PCR cloning kit (Clontech Laboratories, Inc.) to produce pcDNA3.3/LK.

pcDNA3.3/LK was used as a template in PCR using a primer set described below. The obtained fragment of about 3.8 kb was phosphorylated and then self-ligated to construct a chimeric and humanized antibody light chain expression vector pCMA-LK having a signal sequence, a cloning site, and the human κ chain constant region gene downstream of CMV promoter.
Primer Set

```
5'-tataccgtcgacctctagctagagcttggc-3'
(SEQ ID NO: 35: primer 3.3-F1)

5'-gctatggcagggcctgccgccccgacgttg-3'
(SEQ ID NO: 36: primer 3.3-R1)
```

5-2-2) Construction of Chimeric and Humanized Antibody IgG1-Type Heavy Chain Expression Vector pCMA-G1

A DNA fragment of pCMA-LK lacking the DNA sequence encoding a human κ chain secretion signal and a human κ chain constant region by digestion with XbaI and PmeI, and a DNA fragment containing a DNA sequence encoding amino acids of a human heavy chain signal sequence and a human IgG1 constant region shown in SEQ ID NO: 6 were ligated using In-Fusion Advantage PCR cloning kit (Clontech Laboratories, Inc.) to construct a chimeric and humanized antibody IgG1-type heavy chain expression vector pCMA-G1 having a signal sequence, a cloning site, and the human IgG1 heavy chain constant region gene downstream of CMV promoter.

5-2-3) Construction of cTINA1 Antibody Heavy Chain Expression Vector

A DNA fragment containing the cDNA encoding the heavy chain variable region of the TINA1 antibody was amplified using the heavy chain variable region-encoding cDNA obtained in Example 5-1-3) as a template, KOD-Plus- (Toyobo Co., Ltd.), and a primer set described below, and inserted to a restriction enzyme BlpI-cleaved site of the chimeric and humanized IgG1-type heavy chain expression vector pCMA-G1 using In-Fusion HD PCR cloning kit (Clontech Laboratories, Inc.) to construct a cTINA1 antibody heavy chain expression vector. The obtained expression vector was designated as "pCMA-G1/cTINA1". The nucleotide sequence of the cTINA1 antibody heavy chain is shown in SEQ ID NO: 7 and the amino acid sequence encoded thereby is shown in SEQ ID NO: 8. The nucleotide sequence of SEQ ID NO: 7 and the amino acid sequence of SEQ ID NO: 8 are also described in FIG. 1. Primer set for cTINA1 antibody heavy chain

```
5'-CCAGATGGGTGCTGAGCCAGATCCAGTTGGTGCAGTCTGGACCTGA
G-3'
(SEQ ID NO: 37: primer TINA1H-F)

5'-CTTGGTGGAGGCTGAGCTGACGGTGACCGCGGTCCCTGCGCCCCAG
AC-3'
(SEQ ID NO: 38: primer TINA1H-R)
```

5-2-4) Construction of cTINA1 Antibody Light Chain Expression Vector

A DNA fragment containing the cDNA encoding the light chain variable region of the TINA1 antibody was amplified using the light chain variable region-encoding cDNA obtained in Example 5-1-4) as a template, KOD-Plus- (Toyobo Co., Ltd.), and a primer set described below, and inserted to a restriction enzyme BsiWI-cleaved site of the chimeric and humanized antibody light chain expression general-purpose vector pCMA-LK using In-Fusion HD PCR cloning kit (Clontech Laboratories, Inc.) to construct a cTINA1 antibody light chain expression vector. The obtained expression vector was designated as "pCMA-LK/cTINA1". The nucleotide sequence of the cTINA1 antibody light chain is shown in SEQ ID NO: 9, and the amino acid sequence encoded thereby is shown in SEQ ID NO: 10. The nucleotide sequence of SEQ ID NO: 9 and the amino acid sequence of SEQ ID NO: 10 are also described in FIG. 2.
Primer Set for cTINA1 Antibody Light Chain

```
5'-ATCTCCGGCGCGTACGGCGACATTGTGATGACCCAGTCTCACAAAT
TC-3'
(SEQ ID NO: 39: primer TINA1L-F)

5'-GGAGGGGCGGCCACAGCCCGTTTCAGCTCCAGCTTGGTCCCAGC-
3'
(SEQ ID NO: 40: primer TINA1L-R)
```

5-2-5) Small-Scale Production of cTINA1 Antibody

FreeStyle 293F cells (Invitrogen Corp.) were subcultured and cultured according to the manual.

$1 \times 10^7$ FreeStyle 293F cells (Invitrogen Corp.) in the logarithmic growth phase were diluted with a FreeStyle 293 expression medium (Invitrogen Corp.) to 9.6 mL, then seeded in a 30 mL Square Storage Bottle (Nalgene/Thermo Fisher Scientific, Inc.), and then shake-cultured at 90 rpm for 1 hour in an 8% $CO_2$ incubator of 37° C. Polyethyleneimine (Polyscience #24765; 30 µg) was dissolved in Opti-Pro SFM (Invitrogen Corp.; 200 µL). Then, the light chain expression vector (6 µg) and the heavy chain expression vector (4 µg) prepared using PureLink HiPure Plasmid kit (Invitrogen Corp.) were added to Opti-Pro SFM (Invitrogen Corp.; 200 µL). The expression vector/Opti-Pro SFM mixed solution (200 µL) was added to the polyethyleneimine/Opti-Pro SFM mixed solution (200 µL), and the mixture was gently stirred, further left for 5 minutes, and then added to the FreeStyle 293F cells. A culture supernatant obtained by shake culture at 90 rpm for 7 days in an 8% $CO_2$ incubator of 37° C. was filtered through Minisart-Plus filter (Sartorius AG) and used as a sample for evaluation.

The human chimeric TINA1 antibody obtained by the combination of pCMA-G1/cTINA1 and pCMA-LK/cTINA1 was designated as a "cTINA1 antibody".

Example 6

Design of Humanized Antibody of Mouse Anti-TROP2 Monoclonal Antibody 6-1) Design of Humanized Version of TINA1

6-1-1) Molecular Modeling of Variable Region of TINA1

The molecular modeling of the variable regions of TINA1 was carried out by a method known in the art as homology modeling (Methods in Enzymology, 203, 121-153 (1991)). The variable regions of TINA1 determined above were compared with the primary sequences (three-dimensional structures derived from X-ray crystal structures are available) of human immunoglobulin variable regions registered in Protein Data Bank (Nuc. Acid Res. 35, D301-D303 (2007)). As a result, 1ZEA was selected as one having the highest sequence homology to the heavy chain variable region of TINA1 among antibodies similarly having a deletion in their frameworks. Also, 3IU4 was selected as one having the highest sequence homology to the light chain variable region of TINA1. The three-dimensional structures of framework regions were prepared as a "framework model" by combining the coordinates of 1ZEA and 3IU4 corresponding to the heavy chain and the light chain of TINA1. Subsequently, the typical conformation of each CDR was incorporated into the framework model.

Finally, energy calculation for excluding disadvantageous interatomic contact was conducted in order to obtain possible molecular models of the TINA1 variable regions in terms of energy. These procedures were performed using a commercially available protein three-dimensional structure prediction program Discovery Studio (Accelrys, Inc.).

6-1-2) Design of Amino Acid Sequence for Humanized TINA1

The humanized TINA1 antibody was constructed by a method known in the art as CDR grafting (Proc. Natl. Acad. Sci. USA 86, 10029-10033 (1989)). An acceptor antibody was selected on the basis of the homology of amino acids in framework regions. The sequences of the framework regions of TINA1 were compared with the sequences of all human frameworks registered in the Kabat database (Nuc. Acid Res., 29, 205-206 (2001)) of antibody amino acid sequences. As a result, a HuPR1A3 antibody was selected as an acceptor due to its 74% sequence homology as to framework regions. The amino acid residues of the framework regions in HuPR1A3 were aligned with the amino acid residues of the framework regions of TINA1 to identify the positions of amino acids that did not match therebetween. The positions of these residues were analyzed using the three-dimensional model of TINA1 constructed above. Then, the donor residues to be grafted onto the acceptor were selected according to the criteria provided by Queen et al. (Proc. Natl. Acad. Sci. USA 86, 10029-10033 (1989)). Some donor residues thus selected were transferred to the acceptor antibody to construct the humanized TINA1 sequence as described in Examples below.

6-2) Humanization of TINA1 Heavy Chain 6-2-1) hTINA1-H1-Type Heavy Chain:

A humanized TINA1 heavy chain designed by involving the replacement of amino acid position 21 (isoleucine) with valine, amino acid position 28 (proline) with alanine, amino acid position 30 (leucine) with valine, amino acid position 35 (glutamic acid) with alanine, amino acid position 36 (threonine) with serine, amino acid position 38 (arginine) with lysine, amino acid position 39 (isoleucine) with valine, amino acid position 57 (glutamine) with arginine, amino acid position 58 (lysine) with glutamine, amino acid position 59 (methionine) with alanine, amino acid position 62 (lysine) with glutamine, amino acid position 65 (lysine) with glutamic acid, amino acid position 67 (isoleucine) with methionine, amino acid position 87 (phenylalanine) with valine, amino acid position 88 (alanine) with threonine, amino acid position 89 (phenylalanine) with isoleucine, amino acid position 91 (leucine) with alanine, amino acid position 92 (glutamic acid) with aspartic acid, amino acid position 95 (alanine) with threonine, amino acid position 102 (isoleucine) with leucine, amino acid position 104 (asparagine) with serine, amino acid position 107 (asparagine) with serine, amino acid position 111 (threonine) with alanine, amino acid position 112 (threonine) with valine, amino acid position 114 (phenylalanine) with tyrosine, amino acid position 132 (alanine) with glutamine, and amino acid position 135 (alanine) with leucine as to the TINA1 heavy chain shown in SEQ ID NO: 8 of the Sequence Listing was designated as a "hTINA1-H1-type heavy chain".

The amino acid sequence of the hTINA1-H1-type heavy chain is described in SEQ ID NO: 12 of the Sequence Listing. A sequence consisting of amino acid residues 1 to 19, a sequence consisting of amino acid residues 20 to 140, and a sequence consisting of amino acid residues 141 to 470 in the amino acid sequence of SEQ ID NO: 12 correspond to the signal sequence, the heavy chain variable region, and the heavy chain constant region, respectively. The nucleotide sequence encoding the amino acid sequence of SEQ ID NO: 12 is described in SEQ ID NO: 11 of the Sequence Listing. A sequence consisting of nucleotides 1 to 57, a sequence consisting of nucleotides 58 to 420, and a sequence consisting of nucleotides 421 to 1410 in the nucleotide sequence of SEQ ID NO: 11 encode the signal sequence, the heavy chain variable region sequence, and the heavy chain constant region sequence, respectively. The nucleotide sequence of SEQ ID NO: 11 and the amino acid sequence of SEQ ID NO: 12 are also described in FIG. 3.

6-2-2) hTINA1-H2-Type Heavy Chain:

A humanized TINA1 heavy chain designed by involving the replacement of amino acid position 21 (isoleucine) with valine, amino acid position 28 (proline) with alanine, amino acid position 30 (leucine) with valine, amino acid position 35 (glutamic acid) with alanine, amino acid position 36 (threonine) with serine, amino acid position 38 (arginine) with lysine, amino acid position 39 (isoleucine) with valine, amino acid position 57 (glutamine) with arginine, amino acid position 58 (lysine) with glutamine, amino acid position 59 (methionine) with alanine, amino acid position 62 (lysine) with glutamine, amino acid position 65 (lysine) with glutamic acid, amino acid position 67 (isoleucine) with methionine, amino acid position 87 (phenylalanine) with valine, amino acid position 88 (alanine) with threonine, amino acid position 89 (phenylalanine) with isoleucine, amino acid position 92 (glutamic acid) with aspartic acid, amino acid position 95 (alanine) with threonine, amino acid position 102 (isoleucine) with leucine, amino acid position 104 (asparagine) with serine, amino acid position 107 (asparagine) with serine, amino acid position 111 (threonine) with alanine, amino acid position 112 (threonine) with valine, amino acid position 114 (phenylalanine) with tyrosine, amino acid position 132 (alanine) with glutamine, and amino acid position 135 (alanine) with leucine as to the TINA1 heavy chain shown in SEQ ID NO: 8 of the Sequence Listing was designated as a "hTINA1-H2-type heavy chain".

The amino acid sequence of the hTINA1-H2-type heavy chain is described in SEQ ID NO: 14 of the Sequence Listing. A sequence consisting of amino acid residues 1 to 19, a sequence consisting of amino acid residues 20 to 140, and a sequence consisting of amino acid residues 141 to 470 in the amino acid sequence of SEQ ID NO: 14 correspond to the signal sequence, the heavy chain variable region, and the heavy chain constant region, respectively. The nucleotide sequence encoding the amino acid sequence of SEQ ID NO: 14 is described in SEQ ID NO: 13 of the Sequence Listing. A sequence consisting of nucleotides 1 to 57, a sequence consisting of nucleotides 58 to 420, and a sequence consisting of nucleotides 421 to 1410 in the nucleotide sequence of SEQ ID NO: 13 encode the signal sequence, the heavy chain variable region sequence, and the heavy chain constant region sequence, respectively. The nucleotide sequence of SEQ ID NO: 13 and the amino acid sequence of SEQ ID NO: 14 are also described in FIG. 4.

6-2-3) hTINA1-H3-Type Heavy Chain:

A humanized TINA1 heavy chain designed by involving the replacement of amino acid position 28 (proline) with alanine, amino acid position 30 (leucine) with valine, amino acid position 36 (threonine) with serine, amino acid position 38 (arginine) with lysine, amino acid position 39 (isoleucine) with valine, amino acid position 58 (lysine) with glutamine, amino acid position 65 (lysine) with glutamic acid, amino acid position 67 (isoleucine) with methionine, amino acid position 87 (phenylalanine) with valine, amino acid position 88 (alanine) with threonine, amino acid position 92 (glutamic acid) with aspartic acid, amino acid position 95 (alanine) with threonine, amino acid position 102 (isoleucine) with leucine, amino acid position 104 (asparagine) with serine, amino acid position 107 (asparagine) with serine, amino acid position 111 (threonine) with alanine, amino acid position 112 (threonine) with valine, amino acid position 114 (phenylalanine) with tyrosine, amino acid position 132 (alanine) with glutamine, and amino acid position 135 (alanine) with leucine as to the TINA1 heavy chain shown in SEQ ID NO: 8 of the Sequence Listing was designated as a "hTINA1-H3-type heavy chain".

The amino acid sequence of the hTINA1-H3-type heavy chain is described in SEQ ID NO: 16 of the Sequence Listing. A sequence consisting of amino acid residues 1 to 19, a sequence consisting of amino acid residues 20 to 140, and a sequence consisting of amino acid residues 141 to 470 in the amino acid sequence of SEQ ID NO: 16 correspond to the signal sequence, the heavy chain variable region, and the heavy chain constant region, respectively. The nucleotide sequence encoding the amino acid sequence of SEQ ID NO: 16 is described in SEQ ID NO: 15 of the Sequence Listing. A sequence consisting of nucleotides 1 to 57, a sequence consisting of nucleotides 58 to 420, and a sequence consisting of nucleotides 421 to 1410 in the nucleotide sequence of SEQ ID NO: 15 encode the signal sequence, the heavy chain variable region sequence, and the heavy chain constant region sequence, respectively. The nucleotide sequence of SEQ ID NO: 15 and the amino acid sequence of SEQ ID NO: 16 are also described in FIGS. 5.

6-3) Humanization of TINA1 Light Chain
6-3-1) hTINA1-L1-Type Light Chain:

A humanized TINA1 light chain designed by involving the replacement of amino acid position 23 (valine) with glutamine, amino acid position 28 (histidine) with proline, amino acid position 29 (lysine) with serine, amino acid position 30 (phenylalanine) with serine, amino acid position 31 (methionine) with leucine, amino acid position 33 (threonine) with alanine, amino acid position 40 (serine) with threonine, amino acid position 62 (glutamine) with lysine, amino acid position 63 (serine) with alanine, amino acid position 80 (aspartic acid) with serine, amino acid position 83 (threonine) with serine, amino acid position 90 (alanine) with aspartic acid, amino acid position 93 (phenylalanine) with leucine, amino acid position 98 (valine) with leucine, amino acid position 100 (alanine) with proline, amino acid position 103 (leucine) with phenylalanine, amino acid position 120 (alanine) with glutamine, amino acid position 126 (leucine) with isoleucine, and amino acid position 129 (alanine) with threonine as to the TINA1 light chain shown in SEQ ID NO: 10 of the Sequence Listing was designated as a "hTINA1-L1-type light chain".

The amino acid sequence of the hTINA1-L1-type light chain is described in SEQ ID NO: 18 of the Sequence Listing. A sequence consisting of amino acid residues 1 to 20, a sequence consisting of amino acid residues 21 to 129, and a sequence consisting of amino acid residues 130 to 234 in the amino acid sequence of SEQ ID NO: 18 correspond to the signal sequence, the light chain variable region, and the light chain constant region, respectively. The nucleotide sequence encoding the amino acid sequence of SEQ ID NO: 18 is described in SEQ ID NO: 17 of the Sequence Listing. A sequence consisting of nucleotides 1 to 60, a sequence consisting of nucleotides 61 to 387, and a sequence consisting of nucleotides 388 to 702 in the nucleotide sequence of SEQ ID NO: 17 encode the signal sequence, the light chain variable region sequence, and the light chain constant region sequence, respectively. The nucleotide sequence of SEQ ID NO: 17 and the amino acid sequence of SEQ ID NO: 18 are also described in FIG. 6.

6-3-2) hTINA1-L2-Type Light Chain:

A humanized TINA1 light chain designed by involving the replacement of amino acid position 28 (histidine) with proline, amino acid position 29 (lysine) with serine, amino acid position 30 (phenylalanine) with serine, amino acid position 31 (methionine) with leucine, amino acid position 33 (threonine) with alanine, amino acid position 40 (serine) with threonine, amino acid position 62 (glutamine) with lysine, amino acid position 63 (serine) with alanine, amino acid position 80 (aspartic acid) with serine, amino acid position 83 (threonine) with serine, amino acid position 90 (alanine) with aspartic acid, amino acid position 93 (phenylalanine) with leucine, amino acid position 98 (valine) with leucine, amino acid position 100 (alanine) with proline, amino acid position 103 (leucine) with phenylalanine, amino acid position 120 (alanine) with glutamine, amino acid position 126 (leucine) with isoleucine, and amino acid position 129 (alanine) with threonine as to the TINA1 light chain shown in SEQ ID NO: 10 of the Sequence Listing was designated as a "hTINA1-L2-type light chain".

The amino acid sequence of the hTINA1-L2-type light chain is described in SEQ ID NO: 20 of the Sequence Listing. A sequence consisting of amino acid residues 1 to 20, a sequence consisting of amino acid residues 21 to 129, and a sequence consisting of amino acid residues 130 to 234 in the amino acid sequence of SEQ ID NO: 20 correspond to the signal sequence, the light chain variable region, and the light chain constant region, respectively. The nucleotide sequence encoding the amino acid sequence of SEQ ID NO: 20 is described in SEQ ID NO: 19 of the Sequence Listing. A sequence consisting of nucleotides 1 to 60, a sequence consisting of nucleotides 61 to 387, and a sequence consisting of nucleotides 388 to 702 in the nucleotide sequence of SEQ ID NO: 19 encode the signal sequence, the light chain variable region sequence, and the light chain constant region sequence, respectively. The nucleotide sequence of SEQ ID NO: 19 and the amino acid sequence of SEQ ID NO: 20 are also described in FIG. 7.

6-3-3) hTINA1-L3-Type Light Chain:

A humanized TINA1 light chain designed by involving the replacement of amino acid position 28 (histidine) with proline, amino acid position 29 (lysine) with serine, amino acid position 30 (phenylalanine) with serine, amino acid position 31 (methionine) with leucine, amino acid position 33 (threonine) with alanine, amino acid position 40 (serine) with threonine, amino acid position 62 (glutamine) with lysine, amino acid position 63 (serine) with glutamine, amino acid position 80 (aspartic acid) with serine, amino acid position 83 (threonine) with serine, amino acid position 90 (alanine) with aspartic acid, amino acid position 93 (phenylalanine) with leucine, amino acid position 98 (valine) with leucine, amino acid position 100 (alanine) with proline, amino acid position 103 (leucine) with phenylalanine, amino acid position 120 (alanine) with glutamine, amino acid position 126 (leucine) with isoleucine, and amino acid position 129 (alanine) with threonine as to the TINA1 light chain shown in SEQ ID NO: 10 of the Sequence Listing was designated as a "hTINA1-L3-type light chain".

The amino acid sequence of the hTINA1-L3-type light chain is described in SEQ ID NO: 22 of the Sequence Listing. A sequence consisting of amino acid residues 1 to 20, a sequence consisting of amino acid residues 21 to 129, and a sequence consisting of amino acid residues 130 to 234 in the amino acid sequence of SEQ ID NO: 22 correspond to the signal sequence, the light chain variable region, and the light chain constant region, respectively. The nucleotide sequence encoding the amino acid sequence of SEQ ID NO: 22 is described in SEQ ID NO: 21 of the Sequence Listing. A sequence consisting of nucleotides 1 to 60, a sequence consisting of nucleotides 61 to 387, and a sequence consisting of nucleotides 388 to 702 in the nucleotide sequence of SEQ ID NO: 21 encode the signal sequence, the light chain variable region sequence, and the light chain constant region sequence, respectively. The nucleotide sequence of SEQ ID NO: 21 and the amino acid sequence of SEQ ID NO: 22 are also described in FIG. 8.

Example 7

Construction of hTINA1 Antibody Expression Vector and Production of Antibody 7-1) Construction of hTINA1 Heavy Chain Expression Vector 7-1-1) Construction of hTINA1-H1 Expression Vector A DNA fragment containing a hTINA1-H1 variable region-encoding DNA sequence shown in nucleotide positions 36 to 437 of the nucleotide sequence of hTINA1-H1 represented by SEQ ID NO: 11 of the Sequence Listing was synthesized (GeneArt Artificial Gene Synthesis service). A DNA fragment containing the DNA sequence encoding the variable region of hTINA1-H1 was amplified using the synthesized DNA fragment as a template, KOD-Plus- (Toyobo Co., Ltd.), and a primer set described below, and inserted to a restriction enzyme BlpI-cleaved site of the chimeric and humanized IgG1-type heavy chain expression vector pCMA-G1 using In-Fusion HD PCR cloning kit (Clontech Laboratories, Inc.) to construct a hTINA1-H1 expression vector. The obtained expression vector was designated as "pCMA-G1/hTINA1-H1".

Primer Set

```
5'-agctcccagatgggtgctgagc-3'
(SEQ ID NO: 41: primer EG-Inf-F)

5'-gggcccttggtggaggctgagc-3'
(SEQ ID NO: 42: primer EG1-Inf-R)
```

7-1-2) Construction of hTINA1-H2 Expression Vector

A DNA fragment containing a hTINA1-H2 variable region-encoding DNA sequence shown in nucleotide positions 36 to 437 of the nucleotide sequence of hTINA1-H2 represented by SEQ ID NO: 13 of the Sequence Listing was synthesized (GeneArt Artificial Gene Synthesis service), and a hTINA1-H2 expression vector was constructed in the same manner as in Example 7-1-1). The obtained expression vector was designated as "pCMA-G1/hTINA1-H2".

7-1-3) Construction of hTINA1-H3 Expression Vector

A DNA fragment containing a hTINA1-H3 variable region-encoding DNA sequence shown in nucleotide positions 36 to 437 of the nucleotide sequence of hTINA1-H3 represented by SEQ ID NO: 15 of the Sequence Listing was synthesized (GeneArt Artificial Gene Synthesis service), and a hTINA1-H3 expression vector was constructed in the same manner as in Example 7-1-1). The obtained expression vector was designated as "pCMA-G1/hTINA1-H3".

7-2) Construction of hTINA1 Light Chain Expression Vector 7-2-1) Construction of hTINA1-L1 Expression Vector A DNA fragment containing a hTINA1-L1 variable region-encoding DNA sequence shown in nucleotide positions 38 to 402 of the nucleotide sequence of hTINA1-L1 represented by SEQ ID NO: 17 of the Sequence Listing was synthesized (GeneArt Artificial Gene Synthesis service). A DNA fragment containing the DNA sequence encoding the variable region of hTINA1-L1 was amplified using the synthesized DNA fragment as a template, KOD-Plus- (Toyobo Co., Ltd.), and a primer set described below, and inserted to a restriction enzyme BsiWI-cleaved site of the chimeric and humanized antibody light chain expression vector pCMA-LK using In-Fusion HD PCR cloning kit (Clontech Laboratories, Inc.) to construct a hTINA1-L1 expression vector. The obtained expression vector was designated as "pCMA-LK/hTINA1-L1".

Primer Set

```
5'-ctgtggatctccggcgcgtacggc-3'
(SEQ ID NO: 43: primer CM-LKF)

5'-ggaggggcggccaccgtacg-3'
(SEQ ID NO: 44: primer KCL-Inf-R)
```

7-2-2) Construction of hTINA1-L2 Expression Vector

A DNA fragment containing a hTINA1-L2 variable region-encoding DNA sequence shown in nucleotide positions 38 to 402 of the nucleotide sequence of hTINA1-L2 represented by SEQ ID NO: 19 of the Sequence Listing was synthesized (GeneArt Artificial Gene Synthesis service), and a hTINA1-L2 expression vector was constructed in the same manner as in Example 7-2-1). The obtained expression vector was designated as "pCMA-LK/hTINA1-L2".

7-2-3) Construction of hTINA1-L3 Expression Vector

A DNA fragment containing a hTINA1-L3 variable region-encoding DNA sequence shown in nucleotide positions 38 to 402 of the nucleotide sequence of hTINA1-L3 represented by SEQ ID NO: 21 of the Sequence Listing was synthesized (GeneArt Artificial Gene Synthesis service), and a hTINA1-L3 expression vector was constructed in the same manner as in Example 7-2-1). The obtained expression vector was designated as "pCMA-LK/hTINA1-L3".

7-3) Production and Purification of hTINA1 Antibody 7-3-1) Small-Scale Production of hTINA1 Antibody Each antibody was produced in the same manner as in Example 5-2-5).

The hTINA1 antibody obtained by the combination of pCMA-G1/hTINA1-H1 and pCMA-LK/hTINA1-L1 was designated as "hTINA1-H1L1"; the hTINA1 antibody obtained by the combination of pCMA-G1/hTINA1-H2 and pCMA-LK/hTINA1-L1 was designated as "hTINA1-H2L1"; the hTINA1 antibody obtained by the combination of pCMA-G1/hTINA1-H2 and pCMA-LK/hTINA1-L2 was designated as "hTINA1-H2L2"; and the hTINA1 antibody obtained by the combination of pCMA-G1/hTINA1-H3 and pCMA-LK/hTINA1-L3 was designated as "hTINA1-H3L3".

7-3-2) Production of hTINA1 Antibody hTINA1-H1L1, hTINA1-H2L1, hTINA1-H2L2, and hTINA1-H3L3 were produced by the following method.

FreeStyle 293F cells (Invitrogen Corp.) were subcultured and cultured according to the manual. $1.2 \times 10^9$ FreeStyle 293F cells (Invitrogen Corp.) in the logarithmic growth phase were seeded in 3 L Fernbach Erlenmeyer Flask (Corning Inc.), then diluted with a FreeStyle 293 expression medium (Invitrogen Corp.) to $1.0 \times 10^6$ cells/ml, and then shake-cultured at 90 rpm for 1 hour in an 8% $CO_2$ incubator of 37° C. Polyethyleneimine (Polyscience #24765; 3.6 mg)

was dissolved in Opti-Pro SFM (Invitrogen Corp.; 20 ml). Then, the light chain expression vector (0.8 mg) and the heavy chain expression vector (0.4 mg) prepared using PureLink HiPure Plasmid kit (Invitrogen Corp.) were added to Opti-Pro SFM (Invitrogen Corp.; 20 ml). The expression vector/Opti-Pro SFM mixed solution (20 ml) was added to the polyethyleneimine/Opti-Pro SFM mixed solution (20 ml), and the mixture was gently stirred, further left for 5 minutes, and then added to the FreeStyle 293F cells. A culture supernatant obtained by shake culture at 90 rpm for 7 days in an 8% $CO_2$ incubator of 37° C. was filtered through Disposable Capsule Filter (ADVANTEC #CCS-045-E1H).

7-3-3) Purification of hTINA1 Antibody

Each antibody was purified from the culture supernatant obtained in 7-3-2) above by two steps using rProtein A affinity chromatography (4 to 6° C.) and ceramic hydroxyapatite (room temperature). Buffer replacement steps after the rProtein A affinity chromatography purification and after the ceramic hydroxyapatite purification were carried out at 4 to 6° C. First, the culture supernatant was applied to MabSelect SuRe (manufactured by GE Healthcare Japan Corporation, HiTrap column) equilibrated with PBS. After entry of the whole culture supernatant in the column, the column was washed with PBS in an amount at least twice the column volume. Next, antibody-containing fractions were collected by elution with 2 M arginine hydrochloride solution (pH 4.0). The fractions were buffer-replaced with PBS by dialysis (Thermo Fisher Scientific, Inc., Slide-A-Lyzer Dialysis Cassette) and then diluted 5-fold with a buffer of 5 mM sodium phosphate and 50 mM MES (pH 7.0). The resulting antibody solution was applied to a ceramic hydroxyapatite column (Bio-Rad Laboratories, Inc., Bio-Scale CHT Type-I Hydroxyapatite Column) equilibrated with a buffer of 5 mM NaPi, 50 mM MES, and 30 mM NaCl (pH 7.0). Antibody-containing fractions were collected by linear concentration gradient elution using sodium chloride. The fractions were buffer-replaced with HBSor (25 mM histidine/5% sorbitol, pH 6.0) by dialysis (Thermo Fisher Scientific, Inc., Slide-A-Lyzer Dialysis Cassette). Finally, the fractions were concentrated and adjusted to an IgG concentration of 20 mg/ml or higher using Centrifugal UF Filter Device VIVASPIN 20 (molecular weight cutoff: UF10K, Sartorius AG, 4° C.), and used as a purified sample.

Reference Example 1

Production of hRS7 Antibody Expression Vector and Production of Antibody

The hRS7 antibody was produced on the basis of the amino acid sequences of a light chain and a heavy chain described in International Publication No. WO 2003/074566.

1-1) Construction of hRS7 Antibody Heavy Chain Expression Vector

A DNA fragment containing an hRS7 antibody heavy chain variable region-encoding DNA sequence shown in nucleotide positions 36 to 437 of the nucleotide sequence of the hRS7 antibody heavy chain represented by SEQ ID NO: 29 of the Sequence Listing was synthesized (GeneArt Artificial Gene Synthesis service), and a hRS7 antibody heavy chain expression vector was constructed in the same manner as in Example 7-1-1). The obtained expression vector was designated as "pCMA-G1/hRS7". The amino acid sequence of the hRS7 antibody heavy chain is shown in SEQ ID NO: 30 of the Sequence Listing.

1-2) Construction of hRS7 Antibody Light Chain Expression Vector

A DNA fragment containing an hRS7 antibody light chain variable region-encoding DNA sequence shown in nucleotide positions 38 to 402 of the nucleotide sequence of the hRS7 antibody light chain represented by SEQ ID NO: 31 of the Sequence Listing was synthesized (GeneArt Artificial Gene Synthesis service), and an hRS7 antibody light chain expression vector was constructed in the same manner as in Example 7-2-1). The obtained expression vector was designated as "pCMA-LK/hRS7". The amino acid sequence of the hRS7 antibody heavy chain is shown in SEQ ID NO: 32 of the Sequence Listing.

1-3) Production and Purification of hRS7 Antibody 1-3-1) Production of hRS7 Antibody The hRS7 antibody was produced in the same manner as in Example 7-3-2) by the combination of pCMA-G1/hRS7 and pCMA-LK/hRS7.

1-3-2) Purification of hRS7 Antibody

The antibody was purified from the culture supernatant obtained in 1-3-1) in the same manner as in Example 7-3-3).

Example 8

Measurement of Antigen-Binding Affinity of hTINA1 Antibody and hRS7 Antibody 8-1) Measurement of Antigen-Binding Affinity Using Antibody (Culture Supernatant) Produced at Small Scale Each antibody was assayed for its dissociation constant for an antigen (Recombinant Human TROP-2 Fc chimera) using Biacore 3000 (GE Healthcare Japan Corporation) by the capture method of capturing the antibody as a ligand onto an immobilized anti-human IgG (Fab) antibody and assaying the antigen as an analyte. About 2000 RU of the anti-human IgG (Fab) antibody (Human Fab capture kit, GE Healthcare Japan Corporation) was covalently bonded to a sensor chip CM5 (BIAcore, Inc.) by the amine coupling method. Similarly, this antibody was immobilized onto a reference flow cell. The running buffer used was HBS-EP+ (10 mM HEPES pH 7.4, 0.15 M NaCl, 3 mM EDTA, 0.05% Surfactant P20). The culture supernatant containing the antibody was added for 80 seconds onto the anti-human IgG (Fab) antibody-immobilized chip, and then, serial dilutions (1 to 1000 nM) of the antigen were each added thereto at a flow rate of 30 µL/min for 300 seconds. Subsequently, the dissociation phase was monitored for 600 seconds. 10 mM Gly-HCl (pH 1.5) containing 20% DMSO was added thereto as a regenerating solution at a flow rate of 10 µl/min for 60 seconds. The data was analyzed using the Bivalent binding model of analytical software (BIAevaluation software, version 4.1) to calculate an association rate constant kon, a dissociation rate constant koff, and a dissociation constant (KD; KD=koff/kon).

TABLE 1

|   | Name | KD (M) |
|---|------|--------|
| 1 | hTINA1-H1L1 | 6.3E−08 |
| 2 | hTINA1-H2L1 | 6.9E−08 |
| 3 | hTINA1-H2L2 | 7.1E−08 |
| 4 | hTINA1-H3L3 | 5.8E−08 |
| 5 | cTINA1 | 5.6E−08 |

Binding activity using culture supernatant as antibody sample 8-2) Measurement of Antigen-Binding Affinity Using Purified Antibody Each antibody was assayed for its dissociation constant for an antigen (Recombinant Human TROP-2 Fc chimera) using Biacore 3000 (GE Healthcare Japan Corporation) by the capture method of capturing the antibody as a ligand onto an immobilized anti-human IgG (Fab) antibody and assaying the antigen as an analyte. About 2000 RU of the anti-human IgG (Fab) antibody (Human Fab capture kit, GE Healthcare Japan Corporation) was covalently bonded to a sensor chip CM5 (BIAcore, Inc.) by the amine coupling method. Similarly, this antibody was immobilized onto a reference flow cell. The running buffer used was HBS-EP+ (10 mM HEPES pH 7.4, 0.15 M NaCl, 3 mM EDTA, 0.05% Surfactant P20). The antibody was added for 1 min onto the anti-human IgG (Fab) antibody-immobilized chip, and then, serial dilutions (1 to 1000 nM) of the antigen were each added thereto at a flow rate of 30 µL/min for 300 seconds. Subsequently, the dissociation phase was monitored for 600 seconds. 25 mM NaOH diluted with a running buffer was added twice thereto as a regenerating solution at a flow rate of 100 µl/min for 3 seconds. The data was analyzed in the same manner as above.

TABLE 2

| | Name | KD (M) |
|---|---|---|
| 1 | hTINA1-H1L1 | 2.7E−08 |
| 2 | hTINA1-H2L1 | 3.0E−08 |
| 3 | hTINA1-H2L2 | 2.7E−08 |
| 4 | hTINA1-H3L3 | 1.5E−08 |
| 5 | hRS7 | 3.0E−10 |

Binding activity measurement using purified antibody as antibody sample

Example 9

Production of hTINA1-H1L1 ADC (1)

[Formula 25]

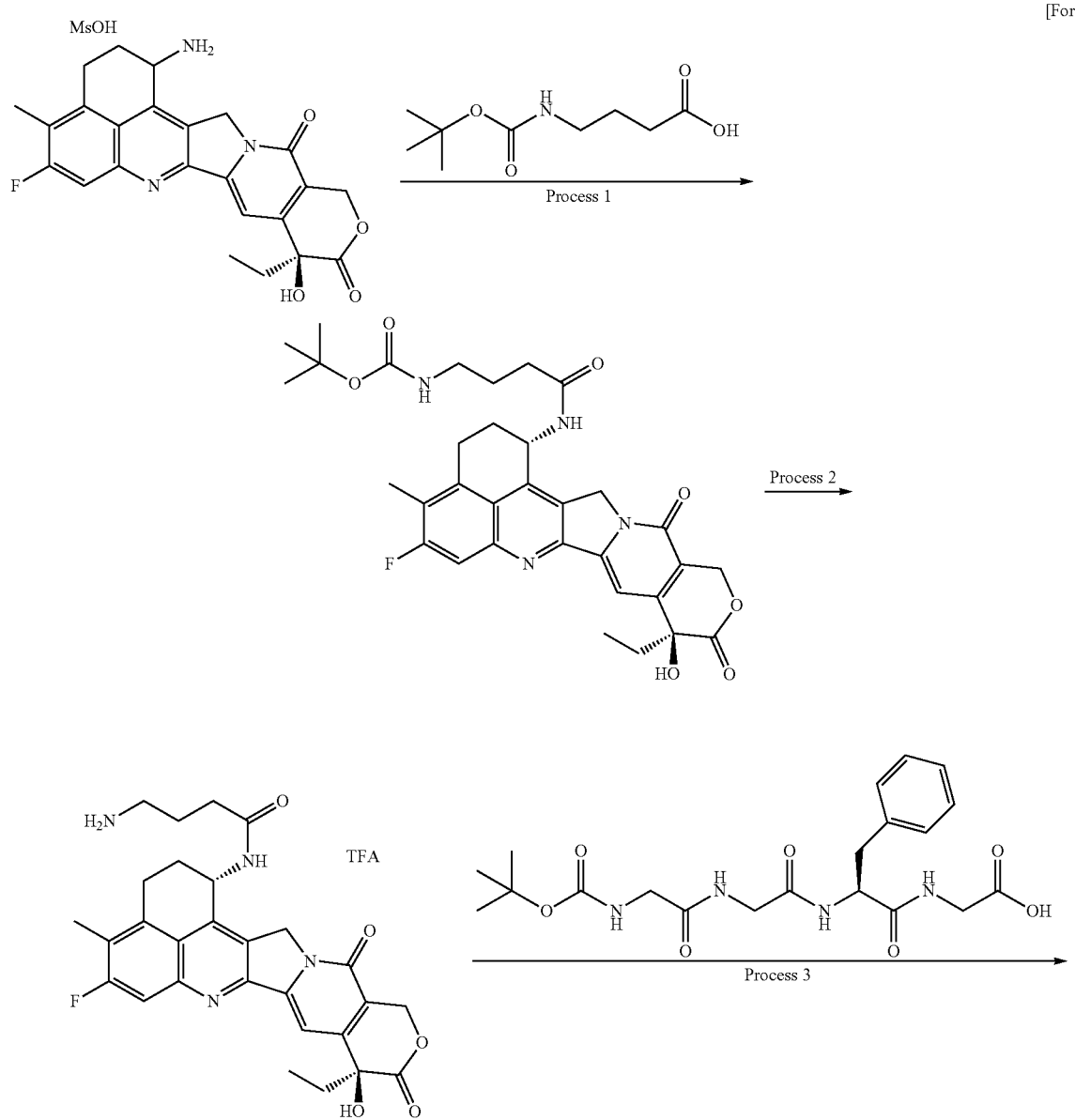

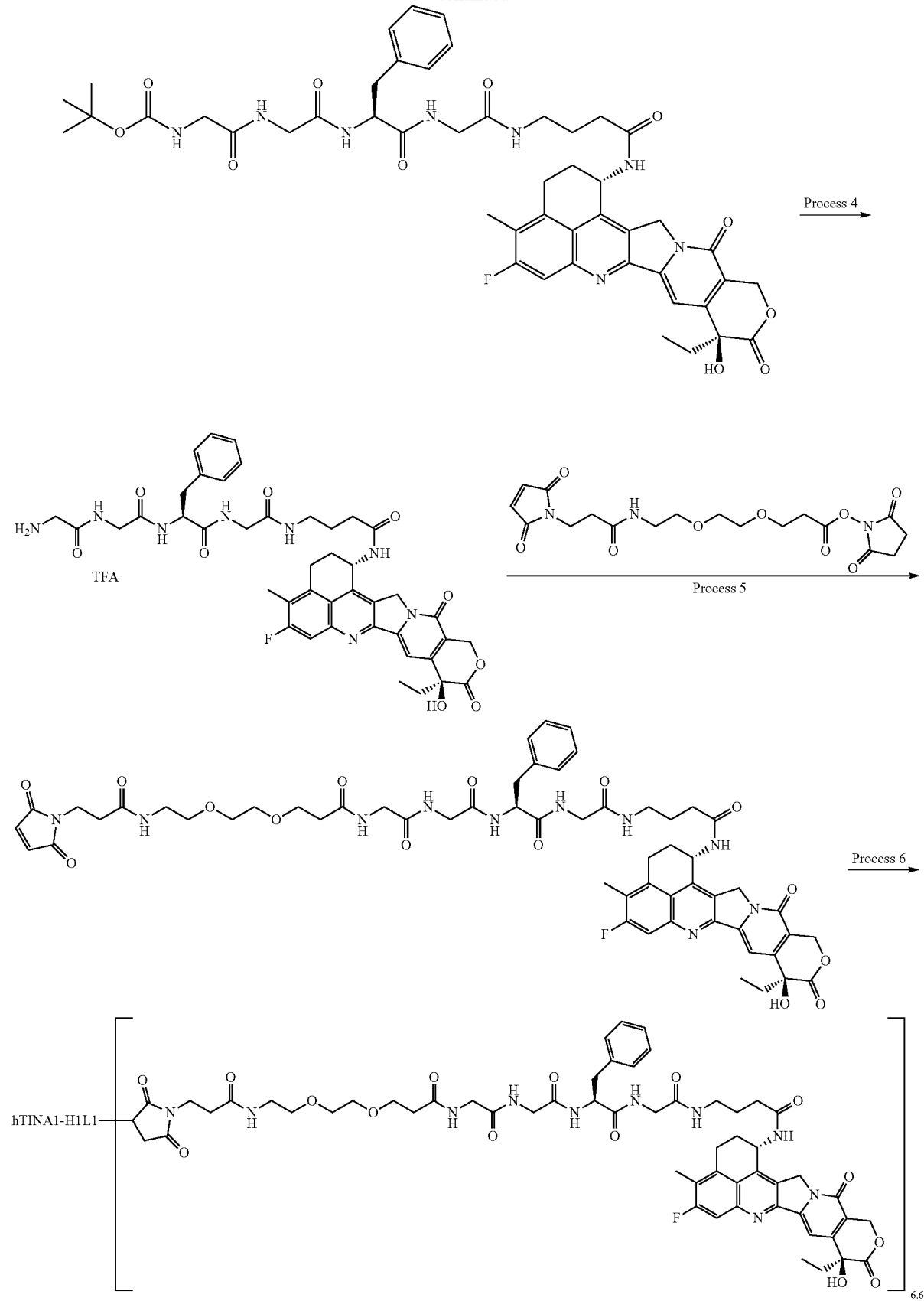

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]aminol-4-oxobutyl) carbamate 4-(tert-Butoxycarbonylamino)butanoic acid (0.237 g, 1.13 mmol) was dissolved in dichloromethane (10 mL), N-hydroxysuccinimide (0.130 g, 1.13 mmol) and 1-ethyl-3-(3-dimethylaminopropyl)carbodiimide hydrochloride (0.216 g, 1.13 mmol) were added, and stirred for 1 hour. The reaction solution was added dropwise to an N,N-dimethylformamide solution (10 mL) charged with exatecan mesylate (0.500 g, 0.94 mmol) and triethylamine (0.157 mL, 1.13 mmol), and stirred at room temperature for 1 day. The solvent was removed under reduced pressure and the residue obtained were purified by silica gel column chromatography [chloroform-chloroform:methanol=8:2 (v/v)] to yield the titled compound (0.595 g, quantitative).
$^1$H-NMR (400 MHz, DMSO-$d_6$) δ: 0.87 (3H, t, J=7.2 Hz), 1.31 (9H, s), 1.58 (1H, t, J=7.2 Hz), 1.66 (2H, t, J=7.2 Hz), 1.89-1.82 (2H, m), 2.12-2.21 (3H, m), 2.39 (3H, s), 2.92 (2H, t, J=6.5 Hz), 3.17 (2H, s), 5.16 (1H, d, J=19.2 Hz), 5.24 (1H, d, J=18.8 Hz), 5.42 (2H, s), 5.59-5.55 (1H, m), 6.53 (1H, s), 6.78 (1H, t, J=6.3 Hz), 7.30 (1H, s), 7.79 (1H, d, J=11.0 Hz), 8.40 (1H, d, J=8.6 Hz).
MS (APCI) m/z: 621 (M+H)$^+$.

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butaneamide trifluoroacetate The compound (0.388 g, 0.61 mmol) obtained in Process 1 above was dissolved in dichloromethane (9 mL). Trifluoroacetic acid (9 mL) was added and it was stirred for 4 hours. The solvent was removed under reduced pressure and the residues obtained were purified by silica gel column chromatography [chloroform-partitioned organic layer of chloroform:methanol:water=7:3:1 (v/v/v)] to yield the titled compound (0.343 g, quantitative).
$^1$H-NMR (400 MHz, DMSO-$d_6$) δ: 0.87 (3H, t, J=7.2 Hz), 1.79-1.92 (4H, m), 2.10-2.17 (2H, m), 2.27 (2H, t, J=7.0 Hz), 2.40 (3H, s), 2.80-2.86 (2H, m), 3.15-3.20 (2H, m), 5.15 (1H, d, J=18.8 Hz), 5.26 (1H, d, J=18.8 Hz), 5.42 (2H, s), 5.54-5.61 (1H, m), 6.55 (1H, s), 7.32 (1H, s), 7.72 (3H, brs), 7.82 (1H, d, J=11.0 Hz), 8.54 (1H, d, J=8.6 Hz).
MS (APCI) m/z: 521 (M+H)$^+$.

Process 3: N-(tert-Butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide N-(tert-Butoxycarbonyl)glycylglycyl-L-phenylalanylglycine (0.081 g, 0.19 mmol) was dissolved in dichloromethane (3 mL), N-hydroxysuccinimide (0.021 g, 0.19 mol) and 1-ethyl-3-(3-dimethylaminopropyl)carbodiimide hydrochloride (0.036 g, 0.19 mmol) were added and then stirred for 3.5 hours. The reaction solution was added dropwise to an N,N-dimethylformamide solution (1.5 mL) charged with the compound (0.080 g, 0.15 mmol) obtained in Process 2 above, and stirred at room temperature for 4 hours. The solvent was removed under reduced pressure and the residues obtained were purified by silica gel column chromatography [chloroform-chloroform:methanol=8:2 (v/v)] to yield the titled compound (0.106 g, 73%).
$^1$H-NMR (400 MHz, DMSO-$d_6$) δ: 0.87 (3H, t, J=7.4 Hz), 1.36 (9H, s), 1.71 (2H, m), 1.86 (2H, t, J=7.8 Hz), 2.15-2.19 (4H, m), 2.40 (3H, s), 2.77 (1H, dd, J=12.7, 8.8 Hz), 3.02 (1H, dd, J=14.1, 4.7 Hz), 3.08-3.11 (2H, m), 3.16-3.19 (2H, m), 3.54 (2H, d, J=5.9 Hz), 3.57-3.77 (4H, m), 4.46-4.48 (1H, m), 5.16 (1H, d, J=19.2 Hz), 5.25 (1H, d, J=18.8 Hz), 5.42 (2H, s), 5.55-5.60 (1H, m), 6.53 (1H, s), 7.00 (1H, t, J=6.3 Hz), 7.17-7.26 (5H, m), 7.31 (1H, s), 7.71 (1H, t, J=5.7 Hz), 7.80 (1H, d, J=11.0 Hz), 7.92 (1H, t, J=5.7 Hz), 8.15 (1H, d, J=8.2 Hz), 8.27 (1H, t, J=5.5 Hz), 8.46 (1H, d, J=8.2 Hz).
MS (APCI) m/z: 939 (M+H)$^+$.

Process 4: Glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide trifluoroacetate The compound (1.97 g, 2.10 mmol) obtained in Process 3 above was dissolved in dichloromethane (7 mL). After adding trifluoroacetic acid (7 mL), it was stirred for 1 hour. The solvent was removed under reduced pressure, and it was charged with toluene for azeotropic distillation. The residues obtained were purified by silica gel column chromatography [chloroform-partitioned organic layer of chloroform:methanol:water=7:3:1 (v/v/v)] to yield the titled compound (1.97 g, 99%).
$^1$H-NMR (400 MHz, DMSO-$d_6$) δ: 0.87 (3H, t, J=7.4 Hz), 1.71-1.73 (2H, m), 1.82-1.90 (2H, m), 2.12-2.20 (4H, m), 2.40 (3H, s), 2.75 (1H, dd, J=13.7, 9.4 Hz), 3.03-3.09 (3H, m), 3.18-3.19 (2H, m), 3.58-3.60 (2H, m), 3.64 (1H, d, J=5.9 Hz), 3.69 (1H, d, J=5.9 Hz), 3.72 (1H, d, J=5.5 Hz), 3.87 (1H, dd, J=16.8, 5.9 Hz), 4.50-4.56 (1H, m), 5.16 (1H, d, J=19.2 Hz), 5.25 (1H, d, J=18.8 Hz), 5.42 (2H, s), 5.55-5.60 (1H, m), 7.17-7.27 (5H, m), 7.32 (1H, s), 7.78-7.81 (2H, m), 7.95-7.97 (3H, m), 8.33-8.35 (2H, m), 8.48-8.51 (2H, m).
MS (APCI) m/z: 839 (M+H)$^+$.

Process 5: N-{3-[2-(2-{[3-(2,5-Dioxo-2,5-dihydro-1H-pyrrol-1-yl)propanoyl]amino}ethoxy)ethoxy]propanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To an N,N-dimethylformamide (1.20 mL) solution of the compound (100 mg, 0.119 mmol) obtained in Process 4 above, diisopropylethylamine (20.8 μL, 0.119 mmol) and N-succinimidyl 3-(2-(2-(3-maleinimidepropanamide) ethoxy)ethoxy)propanoate (50.7 mg, 0.119 mmol) were added and stirred at room temperature for 1 hour. The solvent was removed under reduced pressure and the residues obtained were purified by silica gel column chromatography [chloroform-chloroform:methanol=5:1 (v/v)] to yield the titled compound as a pale yellow solid (66.5 mg, 48%).
$^1$H-NMR (400 MHz, DMSO-$d_6$) δ: 0.85 (3H, t, J=7.4 Hz), 1.65-1.74 (2H, m), 1.77-1.90 (2H, m), 2.07-2.19 (4H, m), 2.30 (2H, t, J=7.2 Hz), 2.33-2.36 (2H, m), 2.38 (3H, s), 2.76 (1H, dd, J=13.7, 9.8 Hz), 2.96-3.18 (9H, m), 3.42-3.44 (4H, m), 3.53-3.76 (10H, m), 4.43 (1H, td, J=8.6, 4.7 Hz), 5.14 (1H, d, J=18.8 Hz), 5.23 (1H, d, J=18.8 Hz), 5.38 (1H, d, J=17.2 Hz), 5.42 (1H, d, J=17.2 Hz), 5.52-5.58 (1H, m), 6.52 (1H, s), 6.98 (2H, s), 7.12-7.17 (1H, m), 7.18-7.25 (4H, m), 7.29 (1H, s), 7.69 (1H, t, J=5.5 Hz), 7.78 (1H, d, J=11.3 Hz), 7.98-8.03 (2H, m), 8.11 (1H, d, J=7.8 Hz), 8.16 (1H, t, J=5.7 Hz), 8.23 (1H, t, J=5.9 Hz), 8.44 (1H, d, J=9.0 Hz).

MS (APCI) m/z: 1149 (M+H)$^+$.

Process 6: Antibody-Drug Conjugate (1)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (10.0 mL) was collected into a 50 mL tube and charged with an aqueous solution of 10 mM TCEP (Tokyo Chemical Industry Co., Ltd.) (0.317 mL; 4.6 equivalents per antibody molecule) and an aqueous solution of 1 M dipotassium hydrogen phosphate (Nacalai Tesque, Inc.; 0.500 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes in a water bath of room temperature, a dimethyl sulfoxide (0.567 mL) was added thereto. Subsequently, a dimethyl sulfoxide solution containing 10 mM of the compound obtained in above Process 5 (0.635 mL; 9.2 equivalents per antibody molecule) was added thereto and stirred by using a tube rotator (MTR-103, manufactured by AS ONE Corporation) for conjugating the drug linker to the antibody at room temperature for 40 minutes. Next, an aqueous solution (0.127 mL; 18.4 equivalents per antibody molecule) of 100 mM NAC (Sigma-Aldrich Co. LLC) was added thereto and stirred to terminate the reaction of drug linker at room temperature for another 20 minutes. Purification: The above solution was subjected to purification using the Common procedure D described in Production method 1 to yield 35.0 mL of a solution containing the titled antibody-drug conjugate. Physicochemical characterization: By using the Common procedure E described in Production method 1 ($\varepsilon_{D,280}$=4964 (measured average value), and $\varepsilon_{D,370}$=18982 (measured average value) were used), the following characteristic values were obtained.

Antibody concentration: 2.70 mg/mL, antibody yield: 94.5 mg (95%), and average number of conjugated drug molecules (n) per antibody molecule measured by Common procedure E: 6.6.

Example 10

Production of hTINA1-H1L1 ADC (2)

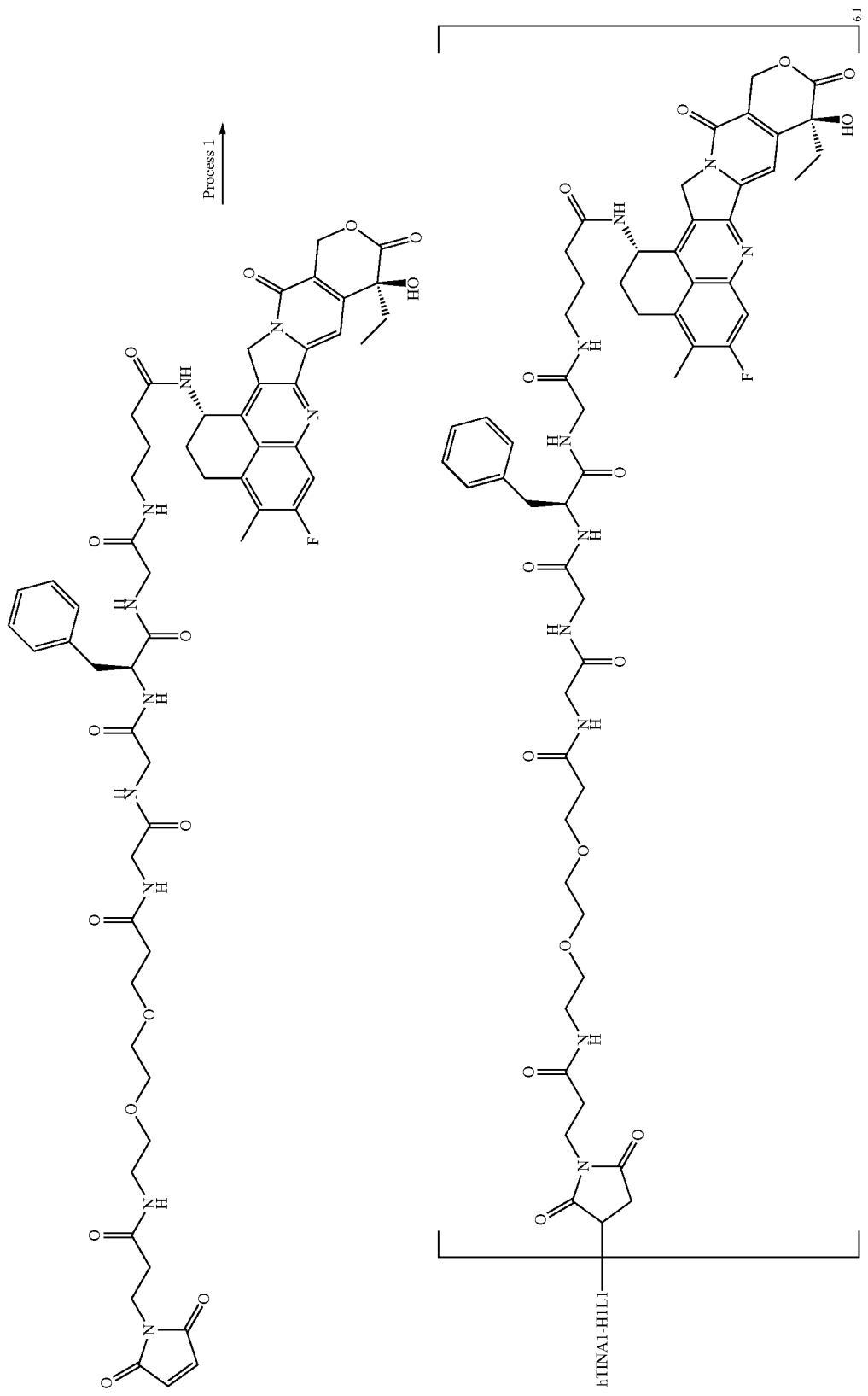

Process 1: Antibody-Drug Conjugate (2)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (2.00 mL) was collected into a 4 mL tube and charged with an aqueous solution of 10 mM TCEP (Tokyo Chemical Industry Co., Ltd.) (0.0690 mL; 5.0 equivalents per antibody molecule) and an aqueous solution of 1 M dipotassium hydrogen phosphate (Nacalai Tesque, Inc.; 0.100 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes in a water bath of 15° C., a dimethyl sulfoxide solution (0.127 mL; 9.2 equivalents per antibody molecule) containing 10 mM of the compound obtained in Process 5 of Example 9 was added thereto and incubated for conjugating the drug linker to the antibody in a water bath of 15° C. for 1 hour. Next, an aqueous solution (0.0190 mL; 13.8 equivalents per antibody molecule) of 100 mM NAC (Sigma-Aldrich Co. LLC) was added thereto and stirred by using a tube rotator to terminate the reaction of drug linker at room temperature for 20 minutes. Purification: The above solution was subjected to purification using the Common procedure D described in Production method 1 to yield 9.00 mL of a solution containing the titled antibody-drug conjugate. Physicochemical characterization: By using the Common procedure E described in Production method 1 ($\varepsilon_{D,280}$=4964 (measured average value), and $\varepsilon_{D,370}$=18982 (measured average value) were used), the following characteristic values were obtained.

Antibody concentration: 2.08 mg/mL, antibody yield: 18.7 mg (94%), and average number of conjugated drug molecules (n) per antibody molecule measured by Common procedure E: 6.1.

Example 11

Production of hTINA1-H1L1 ADC (3)

[Formula 27]
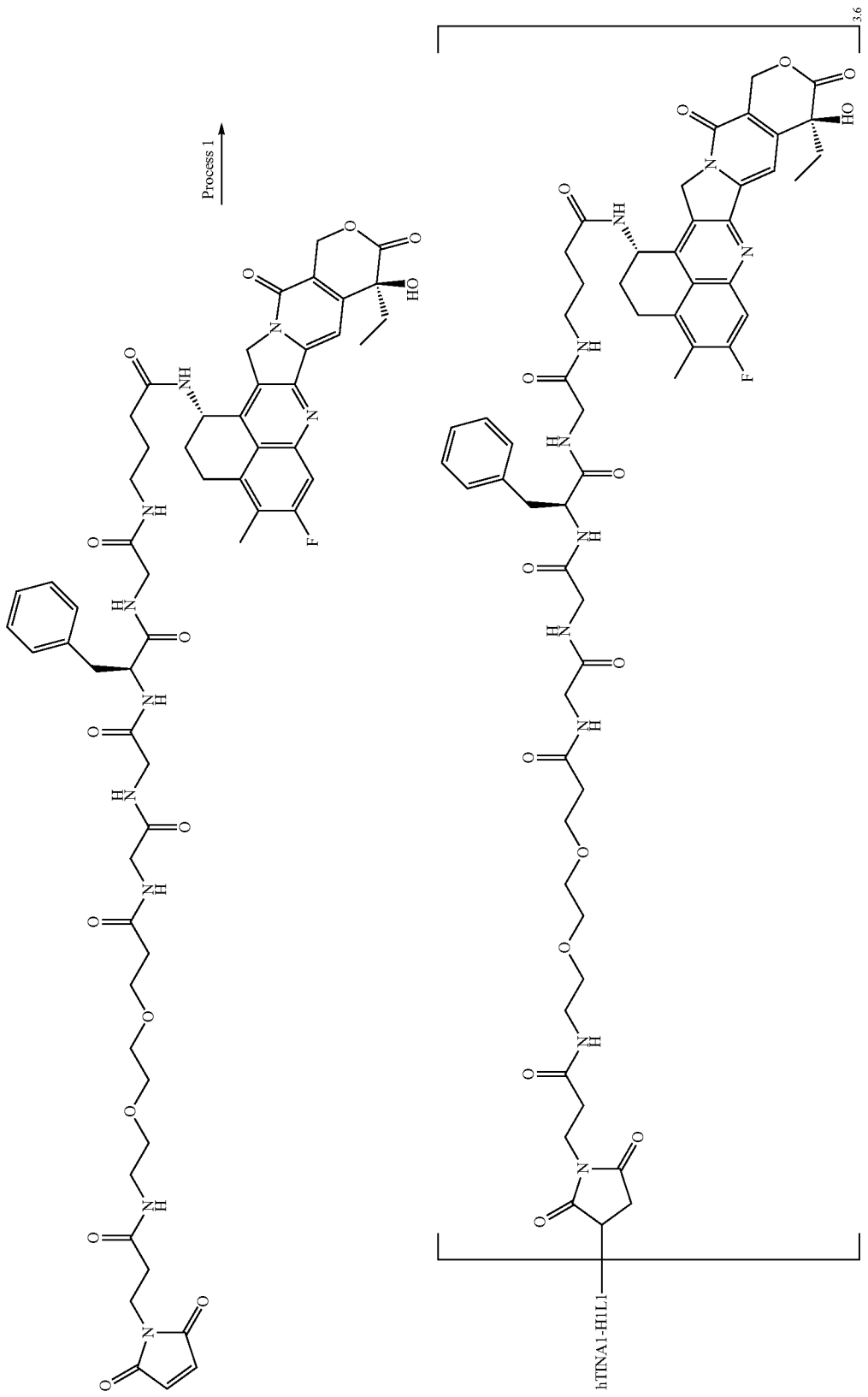

Process 1: Antibody-Drug Conjugate (3)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (5.0 mL) was collected into a 15 mL container, charged with an aqueous solution of 1 M dipotassium hydrogen phosphate (Nacalai Tesque, Inc.; 0.0813 mL) with stirring, and then stirred at 37° C. for 10 minutes. After adding thereto an aqueous solution of 10 mM TCEP (Tokyo Chemical Industry Co., Ltd.) (0.0745 mL; 2.3 equivalents per antibody molecule) with stirring and then confirming that the solution had pH of 7.0±0.1, the disulfide bond at hinge part in the antibody was reduced by stirring at 37° C. for 1 hour. Conjugation between antibody and drug linker: After stirring the above solution for 10 minutes in a water bath of 15° C., a dimethyl sulfoxide solution (0.162 mL; 5.0 equivalents per antibody molecule) containing 10 mM of the compound obtained in Process 5 of Example 9 was gradually added dropwise thereto and stirred for conjugating the drug linker to the antibody in a water bath of 15° C. for 1 hour. Next, an aqueous solution (0.0418 mL; 12.9 equivalents per antibody molecule) of 100 mM NAC (Sigma-Aldrich Co. LLC) was added thereto and stirred to terminate the reaction of drug linker at room temperature for 20 minutes.

Purification: The above solution was subjected to purification using the Common procedure D described in Production method 1 to yield 21.0 mL of a solution containing the titled antibody-drug conjugate.

Physicochemical characterization: By using the Common procedures E and F described in Production method 1 ($\varepsilon_{D,280}$=4964 (measured average value), and $\varepsilon_{D,370}$=18982 (measured average value) were used), the following characteristic values were obtained.

Antibody concentration: 2.19 mg/mL, antibody yield: 46.0 mg (92%), average number of conjugated drug molecules (n) per antibody molecule measured by Common procedure E: 3.6, and average number of conjugated drug molecules (n) per antibody molecule measured by Common procedure F: 3.6.

Example 12

Production of hTINA1-H1L1 ADC (4)

[Formula 28]
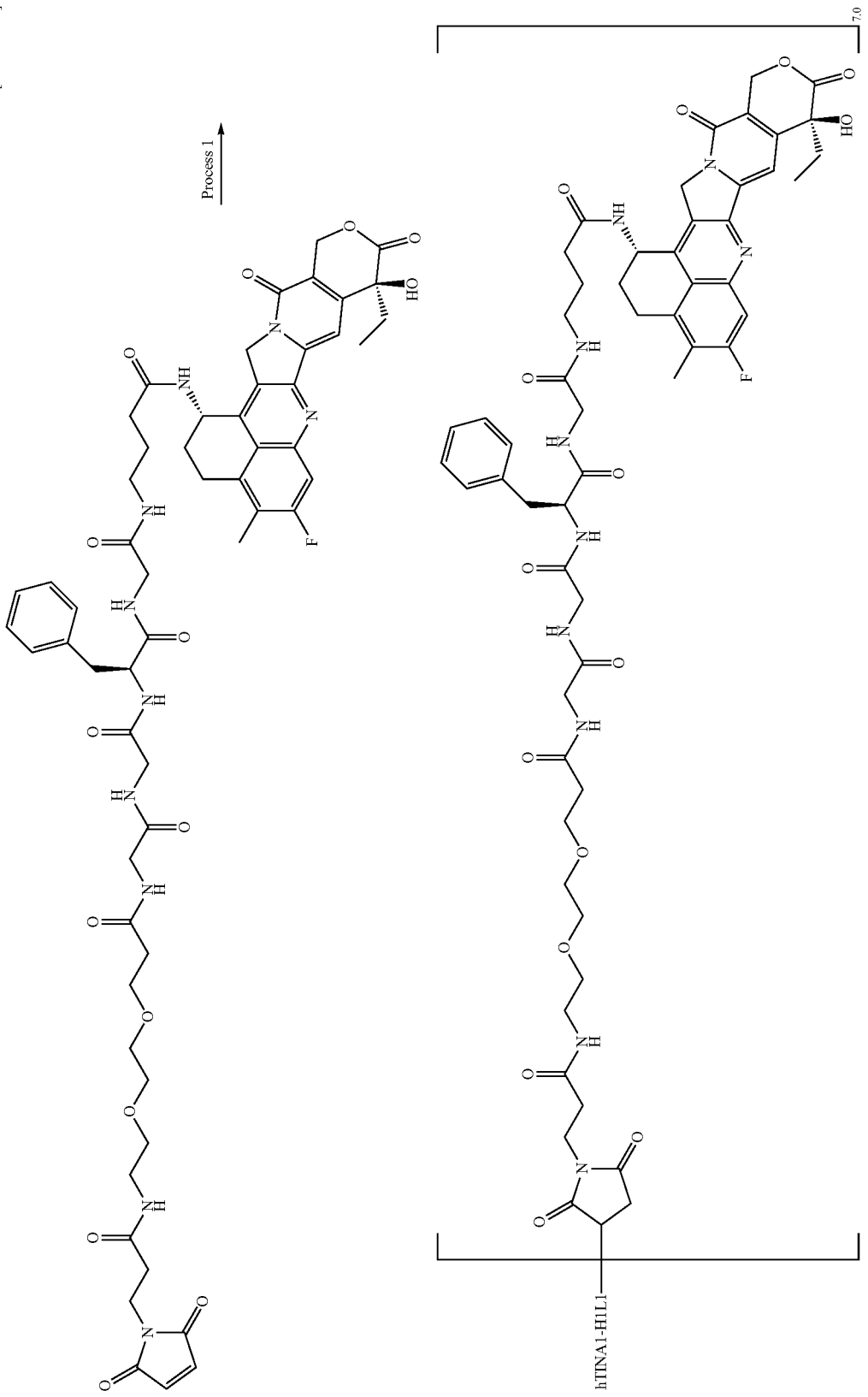

Process 1: Antibody-Drug Conjugate (4)

Reduction of the antibody: The hTINA1-H1L1 produced in Example 7 was prepared to have antibody concentration of 10.0 mg/mL with PBS6.0/EDTA by using the Common procedure B (as absorption coefficient at 280 nm, 1.54 was used) and Common procedure C described in Production method 1. The solution (5.00 mL) was collected into a 15 mL container, charged with an aqueous solution of 1 M dipotassium hydrogen phosphate (Nacalai Tesque, Inc.; 0.0813 mL) with stirring, and then stirred at 37° C. for 10 minutes. After adding thereto an aqueous solution of 10 mM TCEP (Tokyo Chemical Industry Co., Ltd.) (0.162 mL; 5.0 equivalents per antibody molecule) with stirring and then confirming that the solution had pH of 7.0±0.1, the disulfide bond at hinge part in the antibody was reduced by stirring at 37° C. for 1 hour.

Conjugation between antibody and drug linker: After stirring the above solution for 10 minutes in a water bath of 15° C., a dimethyl sulfoxide solution (0.389 mL; 12.0 equivalents per antibody molecule) containing 10 mM of the compound obtained in Process 5 of Example 9 was gradually added dropwise thereto and stirred for conjugating the drug linker to the antibody in a water bath of 15° C. for 1 hour. Next, an aqueous solution (0.0418 mL; 12.9 equivalents per antibody molecule) of 100 mM NAC (Sigma-Aldrich Co. LLC) was added thereto and stirred to terminate the reaction of drug linker at room temperature for 20 minutes.

Purification: The above solution was subjected to purification using the Common procedure D described in Production method 1 to yield 21.0 mL of a solution containing the titled antibody-drug conjugate.

Physicochemical characterization: By using the Common procedures E and F described in Production method 1 ($\varepsilon_{D,280}$=4964 (measured average value), and $\varepsilon_{D,370}$=18982 (measured average value) were used), the following characteristic values were obtained.

Antibody concentration: 2.19 mg/mL, antibody yield: 46.0 mg (92%), average number of conjugated drug molecules (n) per antibody molecule measured by Common procedure E: 7.0, and average number of conjugated drug molecules (n) per antibody molecule measured by Common procedure F: 7.0.

Reference Example 13

Production of hRS7 ADC (5)

[Formula 29]

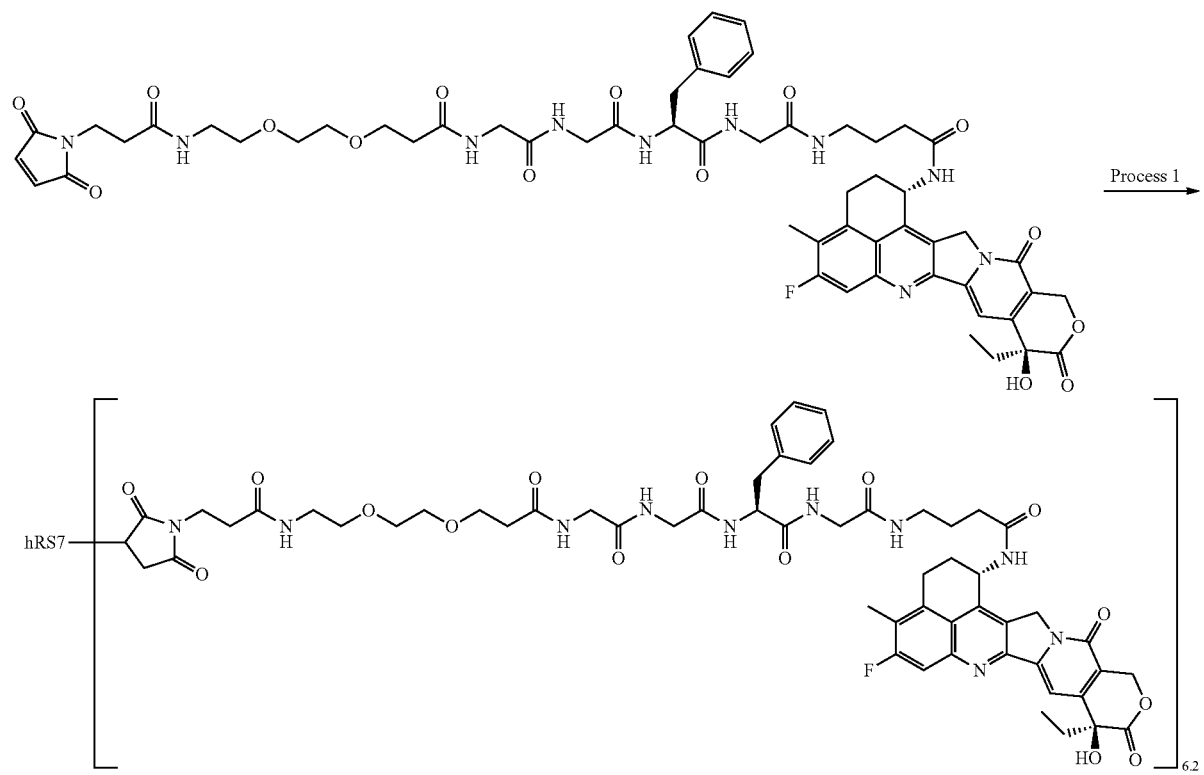

Process 1: Antibody-Drug Conjugate (5)

Reduction of the antibody: The hRS7 produced in Reference Example 1 was prepared to have antibody concentration of 10 mg/mL with PBS6.0/EDTA by using the Common procedure B (as absorption coefficient at 280 nm, 1.56 was used) and Common procedure C described in Production method 1. The solution (2.0 mL) was collected into a 4 mL tube and charged with an aqueous solution of 10 mM TCEP (Tokyo Chemical Industry Co., Ltd.) (0.0690 mL; 5.0 equivalents per antibody molecule) and an aqueous solution of 1 M dipotassium hydrogen phosphate (Nacalai Tesque, Inc.; 0.100 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes in a water bath of 15° C., a dimethyl sulfoxide solution (0.127 mL; 9.2 equivalents per antibody molecule) containing 10 mM of the compound obtained in Process 5 of Example 9 was added thereto and incubated for conjugating the drug linker to the antibody in a water bath of 15° C. for 1 hour. Next, an aqueous solution (0.0190 mL; 13.8 equivalents per antibody molecule) of 100 mM NAC (Sigma-Aldrich Co. LLC) was added thereto and stirred by using a tube rotator to terminate the reaction of drug linker at room temperature for 20 minutes.

Purification: The above solution was subjected to purification using the Common procedure D described in Production method 1 to yield 9.00 mL of a solution containing the titled antibody-drug conjugate.

Physicochemical characterization: By using the Common procedure E described in Production method 1 ($\varepsilon_{D,280}$=4964 (measured average value), and $\varepsilon_{D,370}$=18982 (measured average value) were used), the following characteristic values were obtained.

Antibody concentration: 2.04 mg/mL, antibody yield: 18.4 mg (92%), and average number of conjugated drug molecules (n) per antibody molecule measured by Common procedure E: 6.2.

Example 14

Production of hTINA1-H1L1 ADC (6)

[Formula 30]

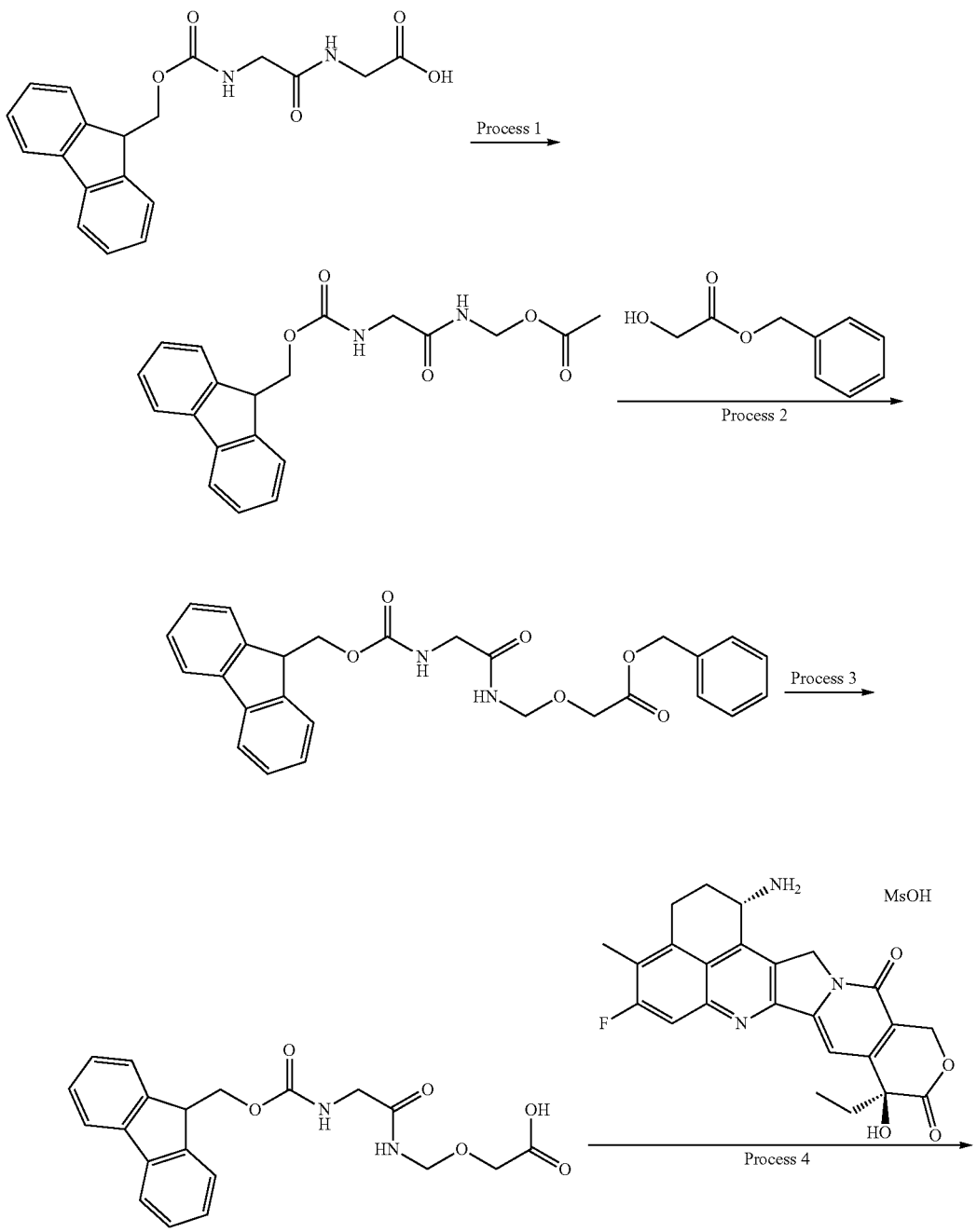

-continued
101
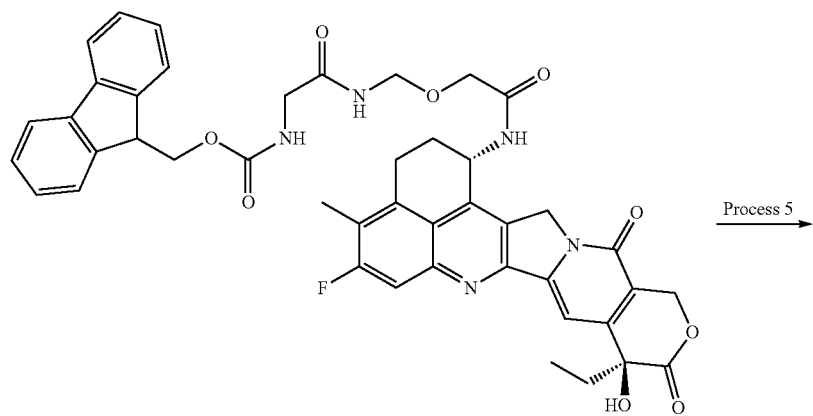
Process 5 →
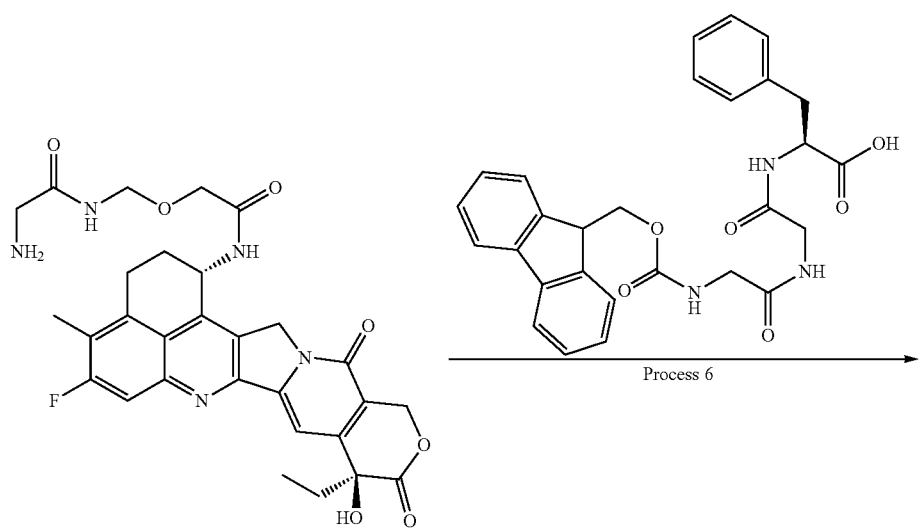
Process 6 →
102
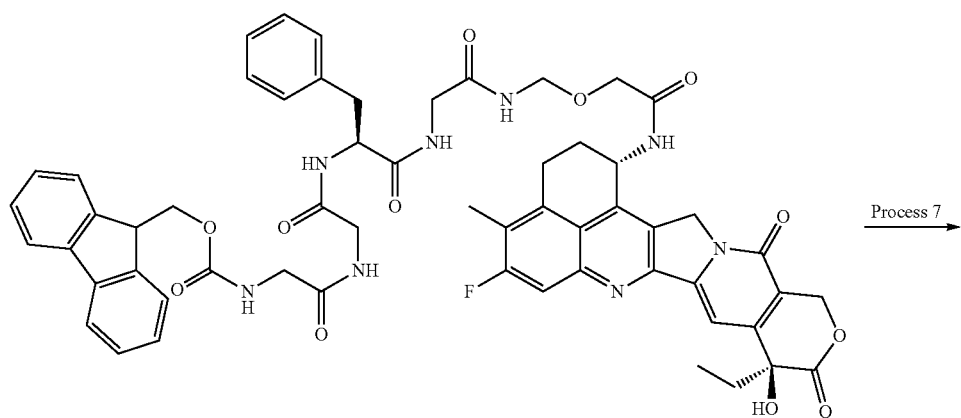
Process 7 →

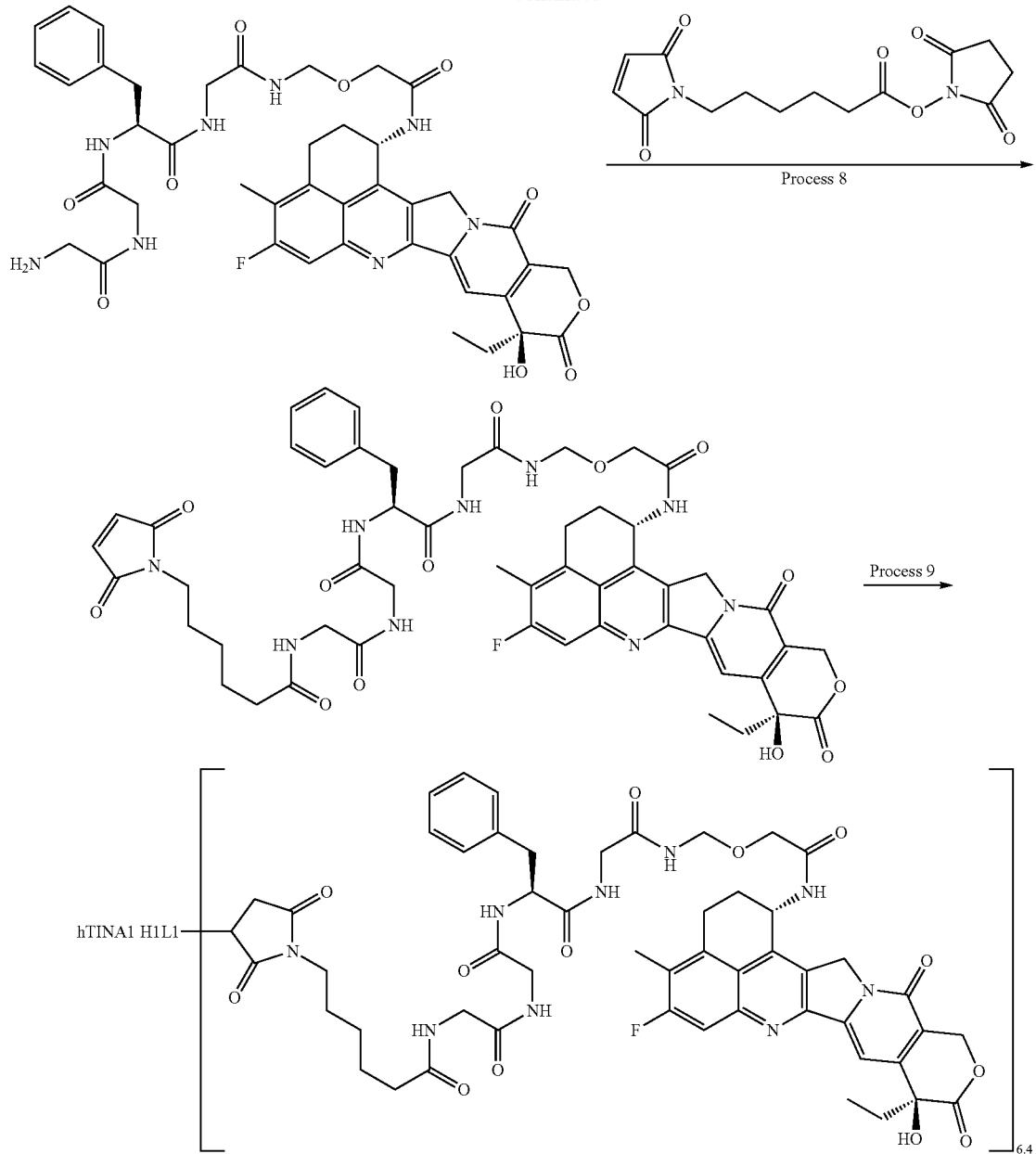

-continued

Process 1: ({N-[(9H-Fluoren-9-ylmethoxy)carbonyl]glycyl}amino)methyl acetate

To a mixture containing N-9-fluorenylmethoxycarbonylglycylglycine (4.33 g, 12.2 mmol), tetrahydrofuran (120 ml), and toluene (40.0 ml), pyridine (1.16 ml, 14.7 mmol) and lead tetraacetate (6.84 g, 14.7 mmol) were added and heated under reflux for 5 hours. After the reaction solution was cooled to room temperature, the insolubles were removed by filtration through Celite, and concentrated under reduced pressure. The residues obtained were dissolved in ethyl acetate and washed with water and saturated brine, and then the organic layer was dried over anhydrous magnesium sulfate. After the solvent was removed under reduced pressure, the residues obtained were purified by silica gel column chromatography [hexane:ethyl acetate=9:1 (v/v)-ethyl acetate] to yield the titled compound as a colorless solid (3.00 g, 67%).

$^1$H-NMR (400 MHz, CDCl$_3$) δ: 2.07 (3H, s), 3.90 (2H, d, J=5.1 Hz), 4.23 (1H, t, J=7.0 Hz), 4.46 (2H, d, J=6.6 Hz), 5.26 (2H, d, J=7.0 Hz), 5.32 (1H, brs), 6.96 (1H, brs), 7.32 (2H, t, J=7.3 Hz), 7.41 (2H, t, J=7.3 Hz), 7.59 (2H, d, J=7.3 Hz), 7.77 (2H, d, J=7.3 Hz).

Process 2: Benzyl [({N-[(9H-Fluoren-9-ylmethoxy)carbonyl]glycyl}amino)methoxy]acetate To a tetrahydrofuran (40.0 mL) solution of the compound (3.68 g, 10.0 mmol) obtained in Process 1 above and benzyl glycolate (4.99 g, 30.0 mmol), potassium tert-butoxide (2.24 g, 20.0 mmol) was added at 0° C. and stirred at room temperature for 15 minutes. The reaction solution was charged with ethyl acetate and water at 0° C. and extracted with ethyl acetate and chloroform. The obtained organic layer was dried over sodium sulfate and filtered. The solvent was removed under reduced pressure. The residues obtained were dissolved in dioxane (40.0 mL) and water (10.0 mL), charged with sodium hydrogen carbonate (1.01 g, 12.0 mmol) and 9-fluorenylmethyl chloroformate (2.59 g, 10.0 mmol), and stirred at room temperature for 2 hours. The reaction solution was charged with water and extracted with ethyl acetate. The obtained organic layer was dried over sodium sulfate and filtered. The solvent was removed under reduced pressure and the residues obtained were purified by silica gel column chromatography [hexane:ethyl acetate=100:0 (v/v)-0:100] to yield the titled compound in colorless oily substance (1.88 g, 40%).

$^1$H-NMR (400 MHz, CDCl$_3$) δ: 3.84 (2H, d, J=5.5 Hz), 4.24 (3H, t, J=6.5 Hz), 4.49 (2H, d, J=6.7 Hz), 4.88 (2H, d, J=6.7 Hz), 5.15-5.27 (1H, m), 5.19 (2H, s), 6.74 (1H, brs), 7.31-7.39 (7H, m), 7.43 (2H, t, J=7.4 Hz), 7.61 (2H, d, J=7.4 Hz), 7.79 (2H, d, J=7.4 Hz).

Process 3: [({N-[(9H-Fluoren-9-ylmethoxy)carbonyl]glycyl}amino)methoxy]acetic acid The compound (1.88 g, 3.96 mmol) obtained in Process 2 above was dissolved in ethanol (40.0 mL) and ethyl acetate (20.0 ml). After adding palladium carbon catalyst (376 mg), it was stirred under hydrogen atmosphere at room temperature for 2 hours. The insolubles were removed by filtration through Celite, and the solvent was removed under reduced pressure to yield the titled compound as a colorless solid (1.52 g, quantitative).

$^1$H-NMR (400 MHz, DMSO-d$_6$) δ: 3.62 (2H, d, J=6.3 Hz), 3.97 (2H, s), 4.18-4.32 (3H, m), 4.60 (2H, d, J=6.7 Hz), 7.29-7.46 (4H, m), 7.58 (1H, t, J=5.9 Hz), 7.72 (2H, d, J=7.4 Hz), 7.90 (2H, d, J=7.4 Hz), 8.71 (1H, t, J=6.5 Hz).

Process 4: 9H-Fluoren-9-ylmethyl(2-{[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]amino}-2-oxoethyl)carbamate Under ice cooling, to an N,N-dimethylformamide (10.0 mL) solution of exatecan mesylate (0.283 g, 0.533 mmol), N-hydroxysuccinimide (61.4 mg, 0.533 mmol), and the compound (0.205 g, 0.533 mmol) obtained in Process 3 above, N,N-diisopropylethylamine (92.9 µL, 0.533 mmol) and N,N'-dicyclohexylcarbodiimide (0.143 g, 0.693 mmol) were added and stirred at room temperature for 3 days. The solvent was removed under reduced pressure and the residues obtained were purified by silica gel column chromatography [chloroform-partitioned organic layer of chloroform:methanol:water=7:3:1 (v/v/v)] to yield the titled compound as a pale brown solid (0.352 g, 82%).

$^1$H-NMR (400 MHz, DMSO-d$_6$) δ: 0.81 (3H, t, J=7.4 Hz), 1.73-1.87 (2H, m), 2.06-2.20 (2H, m), 2.34 (3H, s), 3.01-3.23 (2H, m), 3.58 (2H, d, J=6.7 Hz), 3.98 (2H, s), 4.13-4.25 (3H, m), 4.60 (2H, d, J=6.7 Hz), 5.09-5.22 (2H, m), 5.32-5.42 (2H, m), 5.50-5.59 (1H, m), 6.49 (1H, s), 7.24-7.30 (3H, m), 7.36 (2H, t, J=7.4 Hz), 7.53 (1H, t, J=6.3 Hz), 7.66 (2H, d, J=7.4 Hz), 7.75 (1H, t, J=11.0 Hz), 7.84 (2H, d, J=7.4 Hz), 8.47 (1H, d, J=8.6 Hz), 8.77 (1H, d, J=6.7 Hz). MS (ESI) m/z: 802 (M+H)$^+$.

Process 5: N-[(2-{[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (11.0 mL) solution of the compound (0.881 g, 1.10 mmol) obtained in Process 4 above, piperidine (1.1 mL) was added and stirred at room temperature for 2 hours. The solvent was removed under reduced pressure to yield a mixture containing the titled compound. The mixture was used for the next reaction without further purification.

Process 6: N-[(9H-Fluoren-9-ylmethoxy)carbonyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide Under ice cooling, to an N,N-dimethylformamide (50.0 mL) solution of the mixture (0.439 mmol) obtained in Process 5 above, N-hydroxysuccinimide (0.101 g, 0.878 mmol), and N-[(9H-Fluoren-9-ylmethoxy)carbonyl]glycylglycyl-L-phenylalanine (Japanese Patent Laid-Open No. 2002-60351; 0.440 g, 0.878 mmol), N,N'-dicyclohexylcarbodiimide (0.181 g, 0.878 mmol) was added and stirred at room temperature for 4 days. The solvent was removed under reduced pressure and the residues obtained were purified by silica gel column chromatography [chloroform-chloroform:methanol=9:1 (v/v)] to yield the titled compound as a pale orange solid (0.269 g, 58%).

MS (ESI) m/z: 1063 (M+H)$^+$.

Process 7: Glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (4.00 mL) solution of the compound (0.269 g, 0.253 mmol) obtained in Process 6 above, piperidine (0.251 mL, 2.53 mmol) was added and stirred at room temperature for 2 hours. The solvent was removed under reduced pressure to yield a mixture containing the titled compound. The mixture was used for the next reaction without further purification.

Process 8: N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (10.0 mL) solution of the compound (0.253 mmol) obtained in Process 7 above, N-succinimidyl 6-maleimide hexanoate (0.156 g, 0.506 mmol) was added and stirred at room temperature for 3 days. The solvent was removed under reduced pressure and the residues obtained were purified by silica gel column chromatography [chloroform-chloroform:methanol=9:1 (v/v)] to yield the titled compound as a pale yellow solid (0.100 g, 38%).

$^1$H-NMR (400 MHz, DMSO-d$_6$) δ: 0.83 (3H, t, J=7.2 Hz), 1.09-1.21 (2H, m), 1.33-1.47 (4H, m), 1.75-1.90 (2H, m), 2.00-2.23 (4H, m), 2.36 (3H, s), 2.69-2.81 (1H, m), 2.94-3.03 (1H, m), 3.06-3.22 (2H, m), 3.23-3.74 (8H, m), 3.98 (2H, s), 4.39-4.50 (1H, m), 4.60 (2H, d, J=6.7 Hz), 5.17 (2H, s), 5.39 (2H, s), 5.53-5.61 (1H, m), 6.50 (1H, s), 6.96 (2H, s), 7.11-7.24 (5H, m), 7.28 (1H, s), 7.75 (1H, d, J=11.0 Hz), 7.97 (1H, t, J=5.7 Hz), 8.03 (1H, t, J=5.9 Hz), 8.09 (1H, d, J=7.8 Hz), 8.27 (1H, t, J=6.5 Hz), 8.48 (1H, d, J=9.0 Hz), 8.60 (1H, t, J=6.5 Hz).

MS (ESI) m/z: 1034 (M+H)$^+$.

Process 9: Antibody-Drug Conjugate (6)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (10.0 mL) was collected into a 50 mL tube and charged with an aqueous solution of 10 mM TCEP (Tokyo Chemical Industry Co., Ltd.) (0.317 mL; 4.6 equivalents per antibody molecule) and an aqueous solution of 1 M dipotassium hydrogen phosphate (Nacalai Tesque, Inc.; 0.500 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes in a water bath of ordinary temperature, a dimethyl sulfoxide (0.567 mL) was added thereto. Subsequently, a dimethyl sulfoxide solution containing 10 mM of the compound obtained in above Process 8 (0.635 mL; 9.2 equivalents per antibody molecule) was added thereto and stirred by using a tube rotator for conjugating the drug linker to the antibody at room temperature for 40 minutes. Next, an aqueous solution (0.127 mL; 18.4 equivalents per antibody molecule) of 100 mM NAC (Sigma-Aldrich Co. LLC) was added thereto and stirred to terminate the reaction of drug linker at room temperature for another 20 minutes.

Purification: The above solution was subjected to purification using the Common procedure D described in Production method 1 to yield 35.0 mL of a solution containing the titled antibody-drug conjugate.

Physicochemical characterization: By using the Common procedure E described in Production method 1 ($\varepsilon_{D,280}$=5178 (measured average value), and $\varepsilon_{D,370}$=20217 (measured average value) were used), the following characteristic values were obtained.

Antibody concentration: 2.70 mg/mL, antibody yield: 94.5 mg (95%), and average number of conjugated drug molecules (n) per antibody molecule measured by Common procedure E: 6.4.

Example 15

Production of hTINA1-H1L1 ADC (7)

[Formula 31]

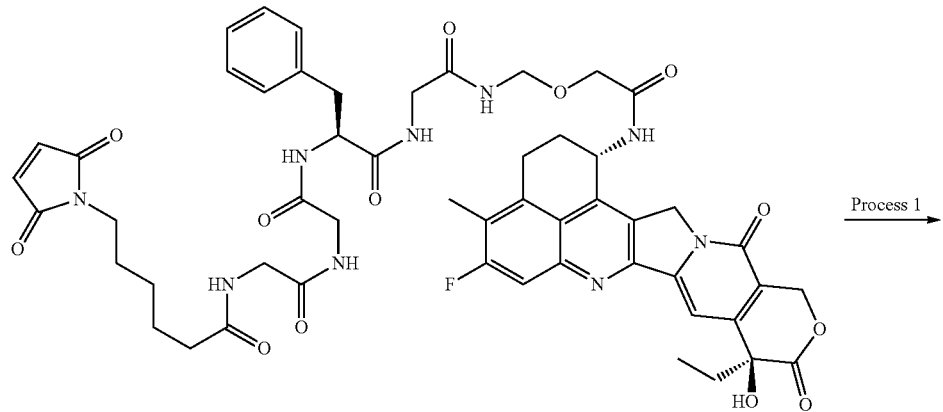

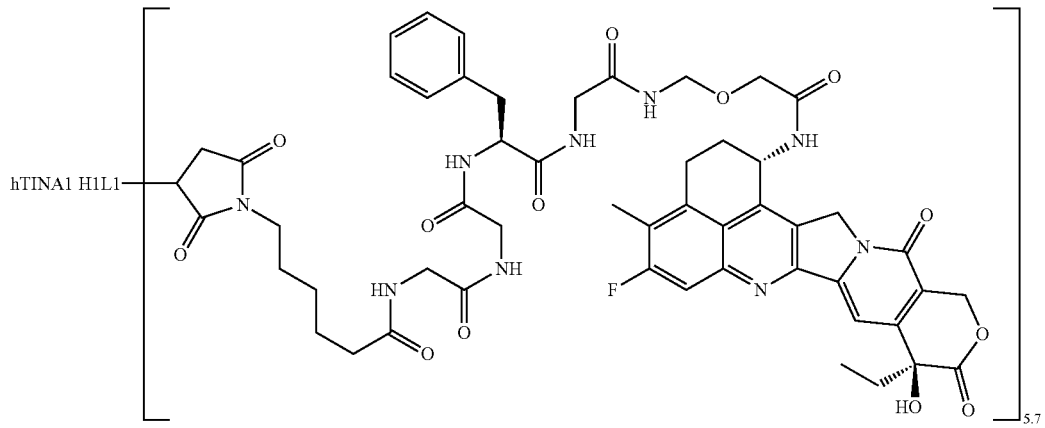

Process 1: Antibody-Drug Conjugate (7)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (2.0 mL) was collected into a 4 mL tube and charged with an aqueous solution of 10 mM TCEP (Tokyo Chemical Industry Co., Ltd.) (0.0690 mL; 5.0 equivalents per antibody molecule) and an aqueous solution of 1 M dipotassium hydrogen phosphate (Nacalai Tesque, Inc.; 0.0299 mL). After confirming that the solution had pH of 7.0±0.1, the disulfide bond at hinge part in the antibody was reduced by incubating at 37° C. for 1 hour.

Physicochemical characterization: By using the Common procedure E described in Production method 1 ($\varepsilon_{D,280}$=5178 (measured average value), and $\varepsilon_{D,370}$=20217 (measured average value) were used), the following characteristic values were obtained.

Antibody concentration: 2.04 mg/mL, antibody yield: 18.4 mg (92%), and average number of conjugated drug molecules (n) per antibody molecule measured by Common procedure E: 5.7.

Example 16

Production of hTINA1-H1L1 ADC (8)

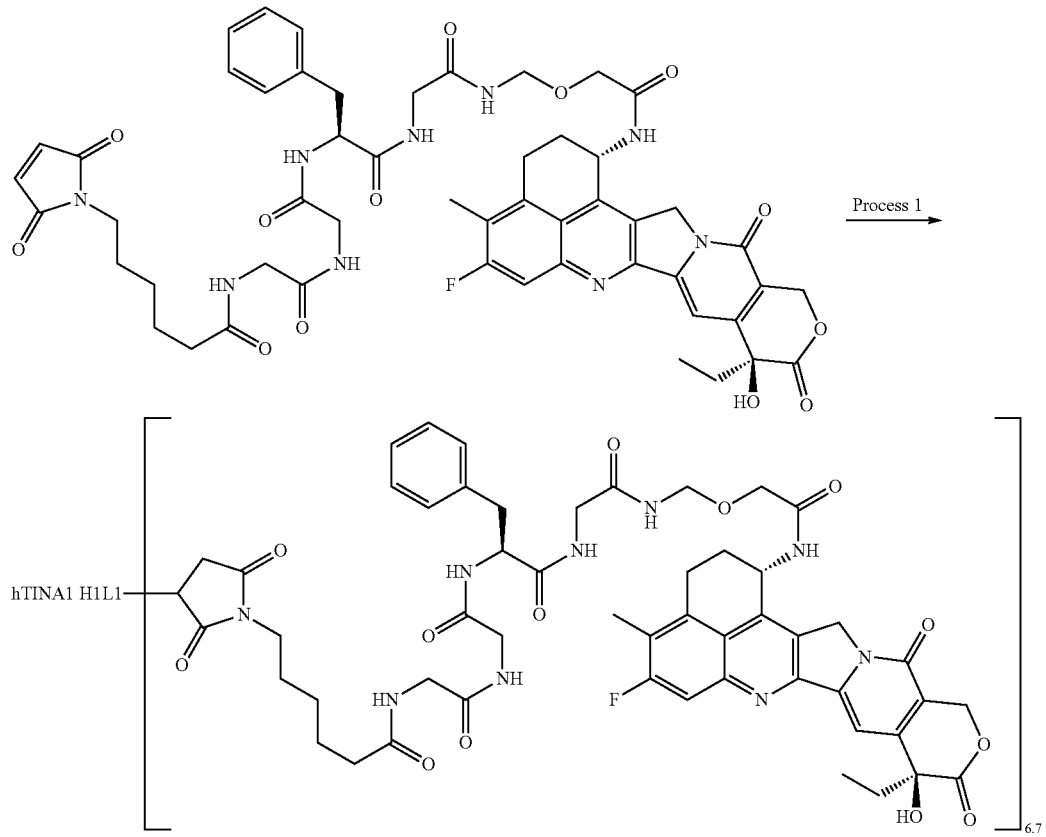

[Formula 32]

Conjugation between antibody and drug linker: After incubating the above solution for 10 minutes in a water bath of 15° C., a dimethyl sulfoxide solution (0.127 mL; 9.2 equivalents per antibody molecule) containing 10 mM of the compound obtained in Process 8 of Example 14 was added thereto and incubated for conjugating the drug linker to the antibody in a water bath of 15° C. for 1 hour. Next, an aqueous solution (0.0190 mL; 13.8 equivalents per antibody molecule) of 100 mM NAC (Sigma-Aldrich Co. LLC) was added thereto and stirred by using a tube rotator to terminate the reaction of drug linker at room temperature for 20 minutes.

Purification: The above solution was subjected to purification using the Common procedure D described in Production method 1 to yield 9.00 mL of a solution containing the titled antibody-drug conjugate.

Process 1: Antibody-Drug Conjugate (8)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (30.0 mL) was collected into a 100 mL container, charged with an aqueous solution of 1 M dipotassium hydrogen phosphate (Nacalai Tesque, Inc.; 0.4875 mL) with stirring, and then stirred at 37° C. for 10 minutes. After adding thereto an aqueous solution of 10 mM TCEP (Tokyo Chemical Industry Co., Ltd.) (0.9721 mL; 5.0 equivalents per antibody molecule) with stirring and then confirming that the solution had pH of 7.0±0.1, the disulfide bond at hinge part in the antibody was reduced by stirring at 37° C. for 1 hour.

Conjugation between antibody and drug linker: After stirring the above solution for 10 minutes in a water bath of 15° C., a dimethyl sulfoxide solution (2.33 mL; 12.0 equivalents per antibody molecule) containing 10 mM of the compound obtained in Process 8 of Example 14 was gradually added dropwise thereto and stirred for conjugating the drug linker to the antibody in a water bath of 15° C. for 1 hour. Next, an aqueous solution (0.251 mL; 12.9 equivalents per antibody molecule) of 100 mM NAC (Sigma-Aldrich Co. LLC) was added thereto and stirred to terminate the reaction of drug linker at room temperature for 20 minutes.

Purification: The above solution was subjected to purification using the Common procedure D described in Production method 1 to yield 98.0 mL of a solution containing the titled antibody-drug conjugate. Then, the solution was concentrated according to the Common procedure A described in Production method 1 to yield 17.5 mL of a solution containing the titled antibody-drug conjugate.

Physicochemical characterization: By using the Common procedures E and F described in Production method 1 ($\varepsilon_{D,280}$=5178 (measured average value), and $\varepsilon_{D,370}$=20217 (measured average value) were used), the following characteristic values were obtained.

Antibody concentration: 14.6 mg/mL, antibody yield: 256 mg (85%), average number of conjugated drug molecules (n) per antibody molecule measured by Common procedure E: 6.7, and average number of conjugated drug molecules (n) per antibody molecule measured by Common procedure F: 7.0.

Example 17: Production of hTINA1-H1L1 ADC (9)

Process 1: Antibody-Drug Conjugate (9)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (5.0 mL) was collected into a 15 mL container, charged with an aqueous solution of 1 M dipotassium hydrogen phosphate (Nacalai Tesque, Inc.; 0.0813 mL) with stirring, and then stirred at 37° C. for 10 minutes. After adding thereto an aqueous solution of 10 mM TCEP (Tokyo Chemical Industry Co., Ltd.) (0.0778 mL; 2.4 equivalents per antibody molecule) with stirring and then confirming that the solution had pH of 7.0±0.1, the disulfide bond at hinge part in the antibody was reduced by stirring at 37° C. for 1 hour. Conjugation between antibody and drug linker: After stirring the above solution for 10 minutes in a water bath of 15° C., a dimethyl sulfoxide solution (0.162 mL; 5.0 equivalents per antibody molecule) containing 10 mM of the compound obtained in Process 8 of Example 14 was gradually added dropwise thereto and stirred for conjugating the drug linker to the antibody in a water bath of 15° C. for 1 hour. Next, an aqueous solution (0.0418 mL; 12.9 equivalents per antibody molecule) of 100 mM NAC (Sigma-Aldrich Co. LLC) was added thereto and stirred to terminate the reaction of drug linker at room temperature for 20 minutes.

Purification: The above solution was subjected to purification using the Common procedure D described in Production method 1 to yield 21.0 mL of a solution containing the titled antibody-drug conjugate.

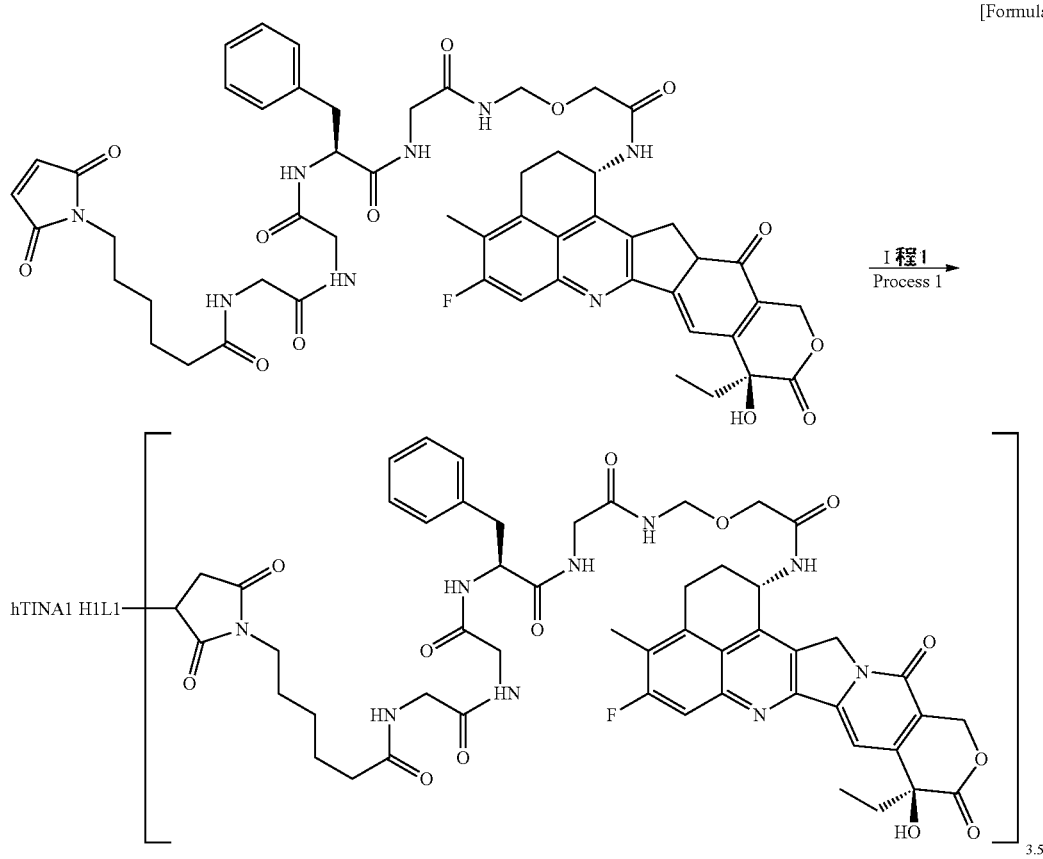

[Formula 33]

Process 1

Physicochemical characterization: By using the Common procedures E and F described in Production method 1 ($\varepsilon_{D,280}$=5178 (measured average value), and $\varepsilon_{D,370}$=20217 (measured average value) were used), the following characteristic values were obtained.

Antibody concentration: 2.26 mg/mL, antibody yield: 47.5 mg (95%), average number of conjugated drug molecules (n) per antibody molecule measured by Common procedure E: 3.5, and average number of conjugated drug molecules (n) per antibody molecule measured by Common procedure F: 3.6.

Reference Example 18

Production of hRS7 ADC (10)

Process 1: Antibody-Drug Conjugate (10)

Reduction of the antibody: The hRS7 produced in Reference Example 1 was prepared to have antibody concentration of 10 mg/mL with PBS6.0/EDTA by using the Common procedure B (as absorption coefficient at 280 nm, 1.56 was used) and Common procedure C described in Production method 1. The solution (2.0 mL) was collected into a 4 mL tube and charged with an aqueous solution of 10 mM TCEP (Tokyo Chemical Industry Co., Ltd.) (0.0690 mL; 5.0 equivalents per antibody molecule) and an aqueous solution of 1 M dipotassium hydrogen phosphate (Nacalai Tesque, Inc.; 0.0299 mL). After confirming that the solution had pH of 7.0±0.1, the disulfide bond at hinge part in the antibody was reduced by incubating at 37° C. for 1 hour.

Conjugation between antibody and drug linker: After incubating the above solution for 10 minutes in a water bath of 15° C., a dimethyl sulfoxide solution (0.1269 mL; 9.2 equivalents per antibody molecule) containing 10 mM of the compound obtained in Process 8 of Example 14 was added thereto and incubated for conjugating the drug linker to the antibody in a water bath of 15° C. for 1 hour. Next, an aqueous solution (0.0190 mL; 13.8 equivalents per antibody molecule) of 100 mM NAC (Sigma-Aldrich Co. LLC) was added thereto and stirred by using a tube rotator to terminate the reaction of drug linker at room temperature for 20 minutes.

[Formula 34]

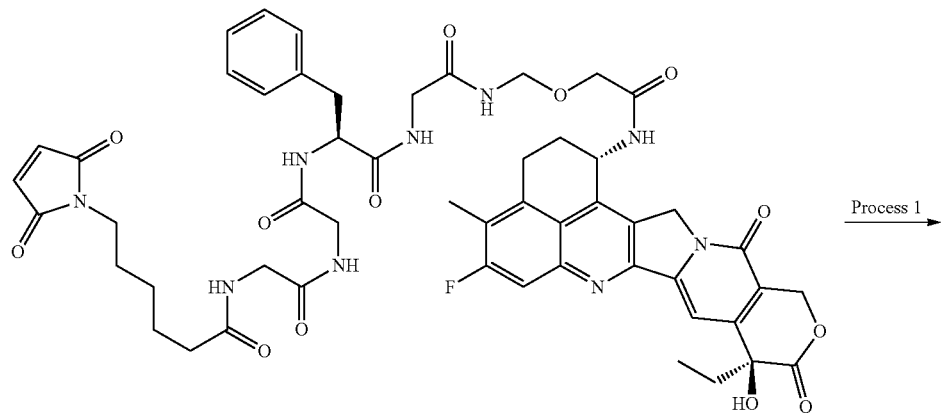

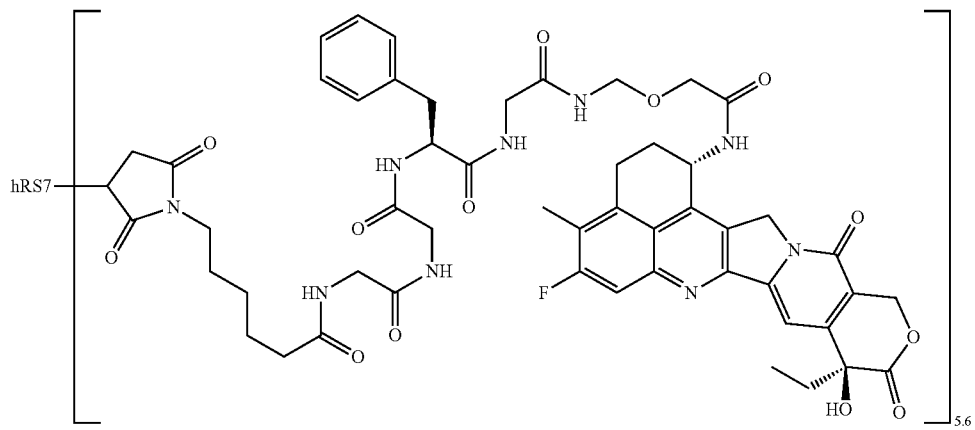

Purification: The above solution was subjected to purification using the Common procedure D described in Production method 1 to yield 9.00 mL of a solution containing the titled antibody-drug conjugate.

Physicochemical characterization: By using the Common procedure E described in Production method 1 ($\varepsilon_{D,280}$=5178 (measured average value), and $\varepsilon_{D,370}$=20217 (measured average value) were used), the following characteristic values were obtained.

Antibody concentration: 2.07 mg/mL, antibody yield: 18.6 mg (93%), and average number of conjugated drug molecules (n) per antibody molecule measured by Common procedure E: 5.6.

Example 19
Production of hTINA1-H1L1 ADC (11)
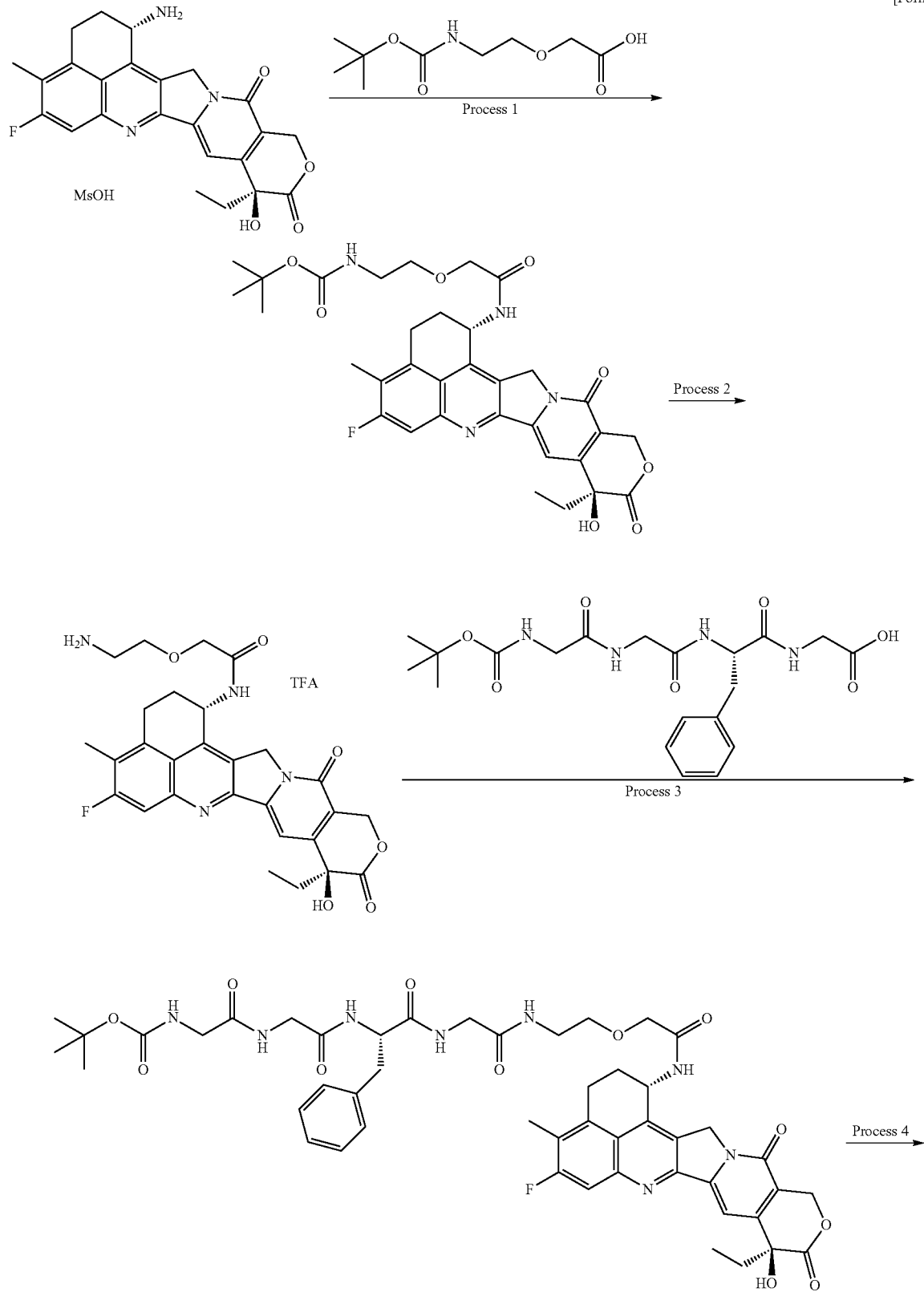

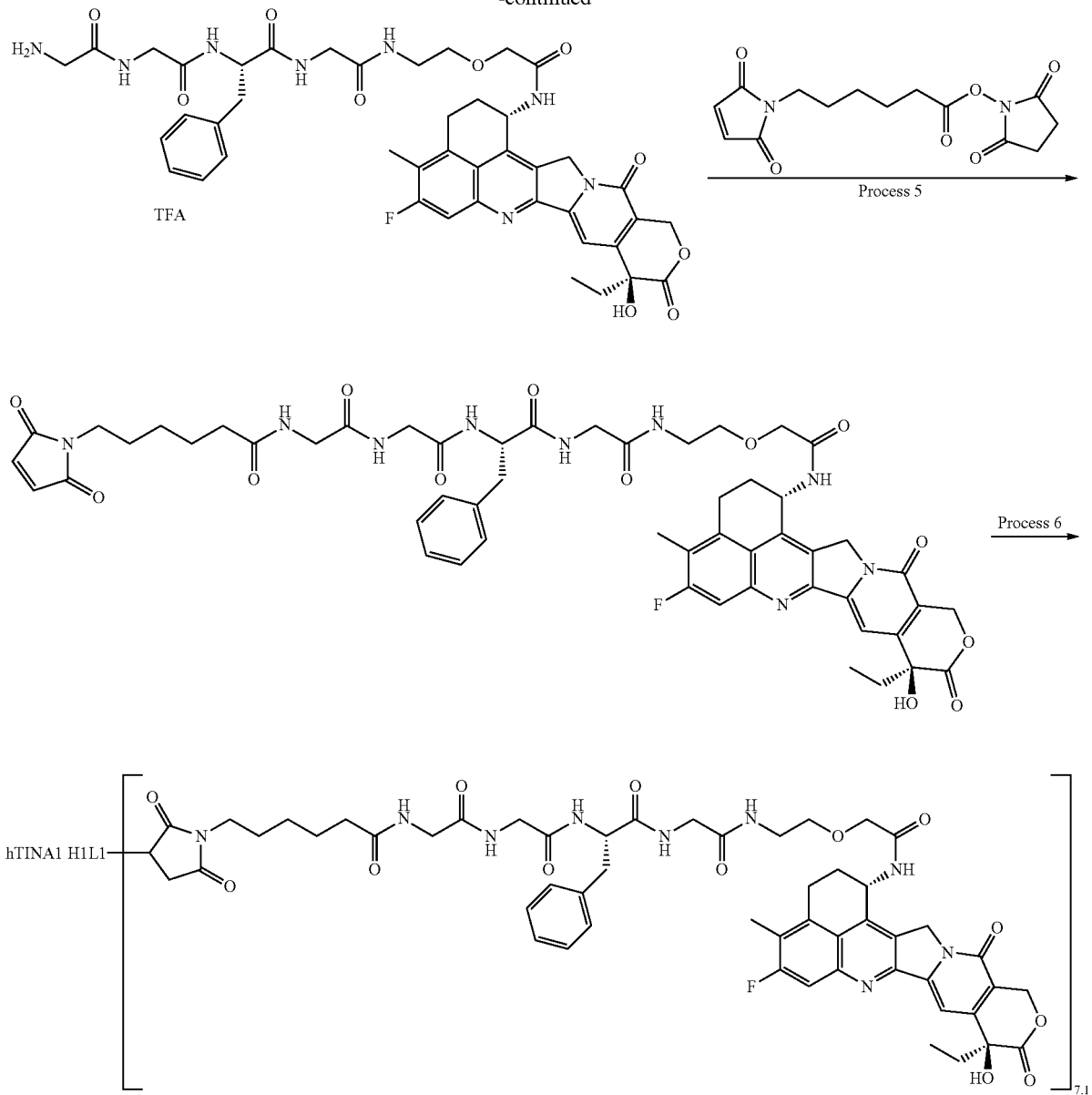

Process 1: tert-Butyl [2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]carbamate Exatecan mesylate (3.10 g, 5.47 mol) was reacted in the same manner as Process 1 of Example 1 by using {2-[(tert-Butoxycarbonyl)amino]ethoxy}acetic acid (J. Med. Chem., 1992, Vol. 35, p. 2928; 1.55 g, 6.01 mmol) instead of 4-(tert-Butoxycarbonylamino)butanoic acid to yield the titled compound as a pale yellow solid (2.56 g, 73%).

$^1$H-NMR (400 MHz, DMSO-d$_6$) δ: 0.87 (3H, t, J=7.3 Hz), 1.26 (9H, s), 1.81-1.91 (2H, m), 2.13-2.22 (2H, m), 2.40 (3H, s), 3.08-3.26 (4H, m), 3.43-3.53 (2H, m), 4.00 (1H, d, J=15.1 Hz), 4.05 (1H, d, J=15.1 Hz), 5.14 (1H, d, J=18.7 Hz), 5.22 (1H, d, J=18.7 Hz), 5.40 (1H, d, J=16.6 Hz), 5.44 (1H, d, J=16.6 Hz), 5.59-5.66 (1H, m), 6.53 (1H, s), 6.86 (1H, t, J=5.4 Hz), 7.31 (1H, s), 7.79 (1H, d, J=10.9 Hz), 8.49 (1H, d, J=9.1 Hz).

MS (APCI) m/z: 637 (M+H)$^+$.

Process 2: 2-(2-Aminoethoxy)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide trifluoroacetate The compound (1.50 g, 2.36 mol) obtained in Process 1 above was reacted in the same manner as Process 2 of Example 1 to yield the titled compound as a pale yellow solid (1.50 g, quantitative).

$^1$H-NMR (400 MHz, DMSO-d$_6$) δ: 0.87 (3H, t, J=7.5 Hz), 1.81-1.92 (2H, m), 2.15-2.23 (2H, m), 2.41 (3H, s), 3.05 (2H, t, J=5.1 Hz), 3.15-3.23 (2H, m), 3.71 (2H, t, J=5.1 Hz), 4.10 (2H, s), 5.19 (1H, d, J=18.7 Hz), 5.24 (1H, d, J=18.7 Hz), 5.43 (2H, s), 5.58-5.66 (1H, m), 6.55 (1H, s), 7.33 (1H, s), 7.73-7.84 (4H, m), 8.55 (1H, d, J=9.1 Hz).

MS (APCI) m/z: 537 (M+H)$^+$.

Process 3: N-(tert-Butoxycarbonyl)glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]glycinamide The compound (554 mg, 0.85 mmol) obtained in Process 2 above was reacted in the same manner as Process 3 of Example 1 to yield the titled compound (775 mg, 95%).

$^1$H-NMR (400 MHz, DMSO-d$_6$) δ: 0.85 (3H, t, J=7.3 Hz), 1.36 (9H, s), 1.78-1.89 (2H, m), 2.13-2.22 (2H, m), 2.39 (3H, s), 2.71 (1H, dd, J=13.4, 9.8 Hz), 2.95 (1H, dd, J=13.4, 4.3 Hz), 3.09-3.23 (1H, m), 3.23-3.32 (2H, m), 3.40-3.62 (8H, m), 3.73 (1H, dd, J=16.5, 5.5 Hz), 4.03 (2H, s), 4.39-4.47 (1H, m), 5.17 (1H, d, J=18.9 Hz), 5.25 (1H, d, J=18.9 Hz), 5.41 (1H, d, J=16.8 Hz), 5.45 (1H, d, J=16.8 Hz), 5.57-5.64 (1H, m), 6.54 (1H, s), 6.99 (1H, t, J=5.8 Hz), 7.13-7.26 (5H, m), 7.31 (1H, s), 7.76-7.82 (2H, m), 7.90 (1H, t, J=5.2 Hz), 8.13 (1H, d, J=7.9 Hz), 8.27 (1H, t, J=5.8 Hz), 8.49 (1H, d, J=8.5 Hz).

MS (APCI) m/z: 955 (M+H)$^+$.

Process 4: Glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]glycinamide trifluoroacetate The compound (630 mg, 0.659 mmol) obtained in Process 3 above was reacted in the same manner as Process 4 of Example 1 to yield the titled compound (588 mg, 92%).

$^1$H-NMR (400 MHz, DMSO-d$_6$) δ: 0.86 (3H, t, J=7.3 Hz), 1.79-1.90 (2H, m), 2.13-2.22 (2H, m), 2.39 (3H, s), 2.71 (1H, dd, J=13.4, 10.1 Hz), 2.99 (1H, dd, J=13.4, 4.3 Hz), 3.09-3.23 (1H, m), 3.24-3.32 (3H, m), 3.41-3.71 (7H, m), 3.86 (1H, dd, J=16.8, 5.8 Hz), 4.04 (2H, s), 4.52 (1H, td, J=9.0, 4.1 Hz), 5.17 (1H, d, J=18.9 Hz), 5.25 (1H, d, J=18.9 Hz), 5.41 (1H, d, J=16.5 Hz), 5.45 (1H, d, J=16.5 Hz), 5.56-5.65 (1H, m), 6.55 (1H, s), 7.13-7.26 (5H, m), 7.32 (1H, s), 7.80 (1H, d, J=11.0 Hz), 7.87-8.01 (4H, m), 8.29-8.36 (2H, m), 8.46-8.55 (2H, m).

MS (APCI) m/z: 855 (M+H)$^+$.

Process 5: N-[6-(2,5-Dioxo-2,5-dihydro-1H-pyrrol-1-yl)hexanoyl]glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]glycinamide The compound (240 mg, 0.247 mmol) obtained in Process 4 above was reacted in the same manner as Process 5 of Example 1 by using triethylamine (31.4 μL, 0.22 mmol) instead of diisopropylethylamine and N-succinimidyl 6-maleimide hexanoate (95.3 mg, 0.31 mmol) instead of N-succinimidyl 3-(2-(2-(3-maleinimidepropanamide)ethoxy)ethoxy)propanoate to yield the titled compound (162 mg, 62%).

$^1$H-NMR (400 MHz, DMSO-d$_6$) δ: 0.86 (3H, t, J=7.6 Hz), 1.13-1.22 (2H, m), 1.40-1.51 (4H, m), 1.78-1.90 (2H, m), 2.09 (2H, t, J=7.6 Hz), 2.14-2.21 (2H, m), 2.39 (3H, s), 2.74 (1H, dd, J=13.6, 9.7 Hz), 2.96 (1H, dd, J=13.6, 4.5 Hz), 3.08-3.24 (1H, m), 3.24-3.30 (1H, m), 3.33-3.40 (4H, m), 3.47-3.68 (7H, m), 3.72 (1H, dd, J=16.6, 5.7 Hz), 4.03 (2H, s), 4.42 (1H, td, J=8.6, 4.2 Hz), 5.17 (1H, d, J=18.7 Hz), 5.25 (1H, d, J=18.7 Hz), 5.40 (1H, d, J=17.2 Hz), 5.44 (1H, d, J=17.2 Hz), 5.57-5.64 (1H, m), 6.52 (1H, s), 6.99 (2H, s), 7.13-7.25 (5H, m), 7.31 (1H, s), 7.74-7.81 (2H, m), 7.99 (1H, t, J=5.7 Hz), 8.03-8.11 (2H, m), 8.22 (1H, t, J=5.7 Hz), 8.47 (1H, d, J=9.1 Hz).

MS (APCI) m/z: 1048 (M+H)$^+$.

Process 6: Antibody-Drug Conjugate (11)

Reduction of the antibody: The hTINA1-H1L1 produced in Example 7 was prepared to have antibody concentration of 10 mg/mL with PBS6.0/EDTA by using the Common procedure B (as absorption coefficient at 280 nm, 1.54 was used) and Common procedure C described in Production method 1. The solution (3.0 mL) was collected into a 15 mL container, charged with an aqueous solution of 1 M dipotassium hydrogen phosphate (Nacalai Tesque, Inc.; 0.0488 mL) with stirring, and then stirred at 37° C. for 10 minutes. After adding thereto an aqueous solution of 10 mM TCEP (Tokyo Chemical Industry Co., Ltd.) (0.0972 mL; 5.0 equivalents per antibody molecule) with stirring and then confirming that the solution had pH of 7.0±0.1, the disulfide bond at hinge part in the antibody was reduced by stirring at 37° C. for 1 hour. Conjugation between antibody and drug linker: After stirring the above solution for 10 minutes in a water bath of 15° C., a dimethyl sulfoxide solution (0.2333 mL; 12.0 equivalents per antibody molecule) containing 10 mM of the compound obtained in Process 8 of Example 11 was gradually added dropwise thereto and stirred for conjugating the drug linker to the antibody in a water bath of 15° C. for 1 hour. Next, an aqueous solution (0.0251 mL; 12.9 equivalents per antibody molecule) of 100 mM NAC (Sigma-Aldrich Co. LLC) was added thereto and stirred to terminate the reaction of drug linker at room temperature for 20 minutes.

Purification: The above solution was subjected to purification using the Common procedure D described in Production method 1 to yield 14 mL of a solution containing the titled antibody-drug conjugate.

Physicochemical characterization: By using the Common procedures E and F described in Production method 1 ($\varepsilon_{D,280}$=5193 (measured average value), and $\varepsilon_{D,370}$=20347 (measured average value) were used), the following characteristic values were obtained.

Antibody concentration: 1.93 mg/mL, antibody yield: 27.0 mg (90%), average number of conjugated drug molecules (n) per antibody molecule measured by Common procedure E: 7.1, and average number of conjugated drug molecules (n) per antibody molecule measured by Common procedure F: 7.0.

Reference Example 2

Production of hRS7-CL2A-SN38 (12)

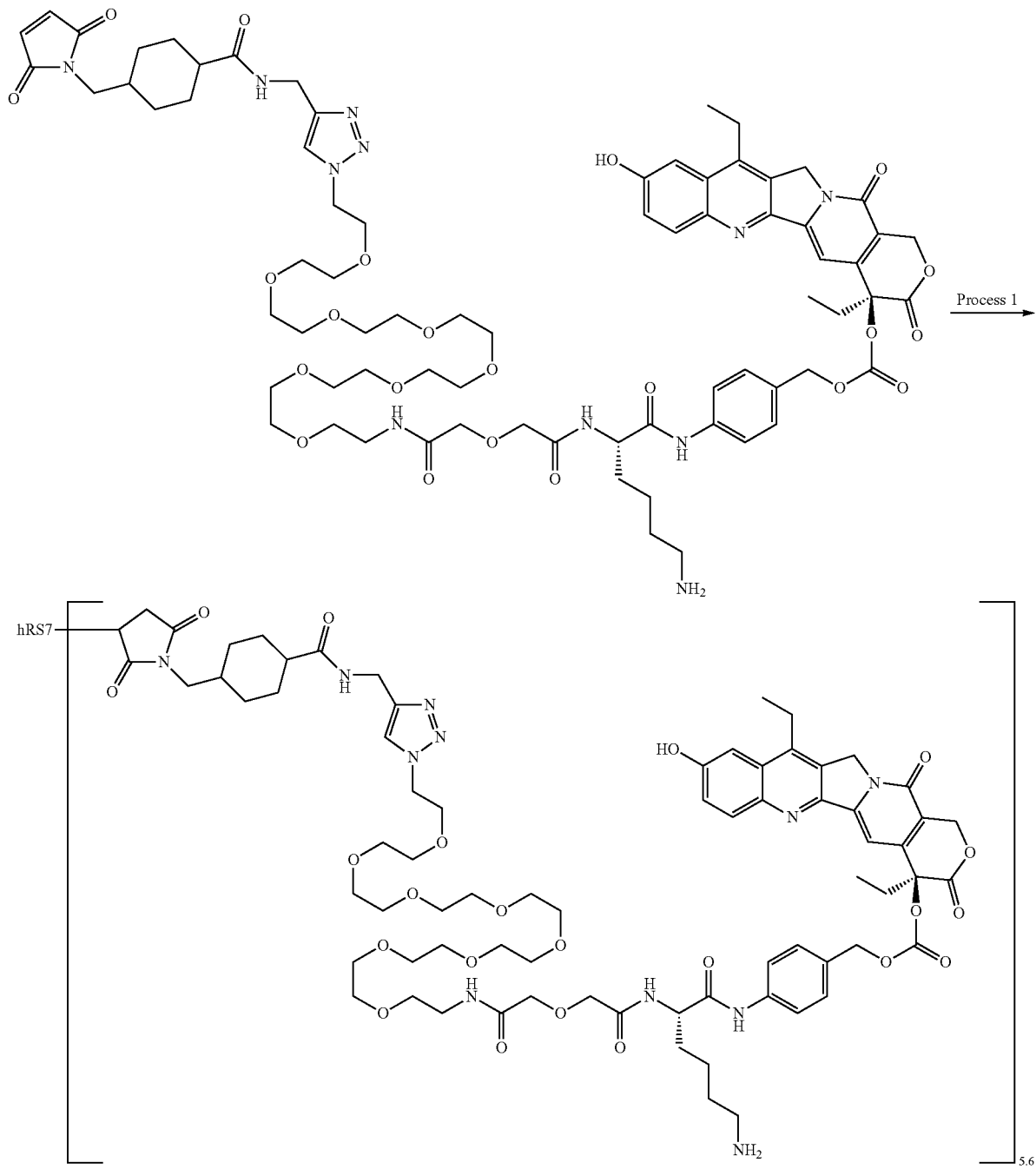

[Formula 36]

Process 1: Antibody-Drug Conjugate (12)

Reduction of the antibody: The hRS7 produced in Reference Example 1 was prepared to have antibody concentration of 10 mg/mL with PBS6.0/EDTA by using the Common procedure B (as absorption coefficient at 280 nm, 1.54 was used) and Common procedure C described in Production method 1. The solution (10.0 mL) was collected into a 50 mL tube and charged with an aqueous solution of 10 mM TCEP (Tokyo Chemical Industry Co., Ltd.) (0.317 mL; 4.6 equivalents per antibody molecule) and an aqueous solution of 1 M dipotassium hydrogen phosphate (Nacalai Tesque, Inc.; 0.500 mL). After confirming that the solution had pH of 7.4±0.1, the disulfide bond at hinge part in the antibody was reduced by incubating at 37° C. for 1 hour. Conjugation between antibody and drug linker: After incubating the above solution for 10 minutes in a water bath of ordinary temperature, a dimethyl sulfoxide (0.567 mL) was added thereto. Subsequently, a dimethyl sulfoxide solution containing 10 mM of CL2A-SN38 synthesized according to U.S. Patent Publication No. 2011/0293513 (0.635 mL; 9.2 equivalents per antibody molecule) was added thereto and stirred by using a tube rotator for conjugating the drug linker to the antibody at room temperature for 40 minutes. Next, an aqueous solution (0.127 mL; 18.4 equivalents per antibody molecule) of 100 mM NAC (Sigma-Aldrich Co. LLC) was added thereto and stirred to terminate the reaction of drug linker at room temperature for another 20 minutes.

Purification: The above reaction solution was subjected repetitively twice to gel filtration and purification described in the Common procedure D of Production method and subsequently subjected similarly to gel filtration purification with the NAP-25 column using 25 mM trehalose solution containing polysorbate 80 (0.01%). Then, the obtained eluate (35 mL) was freeze-dried.

Physicochemical characterization: By using the Common procedure E described in Production method 1 for the eluate before freeze drying, the following characteristic values were obtained.

Antibody concentration: 2.78 mg/mL, antibody yield: 97.3 mg (97%), and average number of conjugated drug molecules (n) per antibody molecule: 5.6.

Example 20

Production of hTINA1-H1L1 ADC (13)

of 10 mg/mL by replacing the medium with PBS6.0/EDTA by using the Common procedure B (as absorption coefficient at 280 nm, 1.54 was used) and Common procedure C described in Production method 1. The solution (100 mL) was placed in a 250 mL polycarbonate Erlenmeyer flask, charged with an aqueous solution of 1 M dipotassium hydrogen phosphate (1.4 mL) at room temperature with stirring using a magnetic stirrer, and then charged with an aqueous solution of 10 mM TCEP (1.62 mL; 2.5 equivalents per antibody molecule). After confirming that the solution had pH of 7.0±0.1, the stirring was terminated, and the disulfide bond at hinge part in the antibody was reduced by incubating at 37° C. for 2 hours.

Conjugation between antibody and drug linker: After cooling the above solution to 15° C., DMSO (3.24 mL) was gradually added dropwise thereto with stirring. Subsequently, a DMSO solution containing 10 mM of the compound obtained in Process 8 of Example 14 (1.76 mL; 5.0 equivalents per antibody molecule) was gradually added dropwise thereto. This solution was stirred for conjugating the drug linker to the antibody at 15° C. for 1 hour. Next, an aqueous solution (0.324 mL; 5.0 equivalents per antibody molecule) of 100 mM NAC was added thereto with stirring and incubated to terminate the reaction of unreacted drug linker at room temperature for another 20 minutes.

Purification: 20% aqueous acetic acid solution (about 0.52 mL) and ABS (100 mL) were gradually added to the above

[Formula 37]

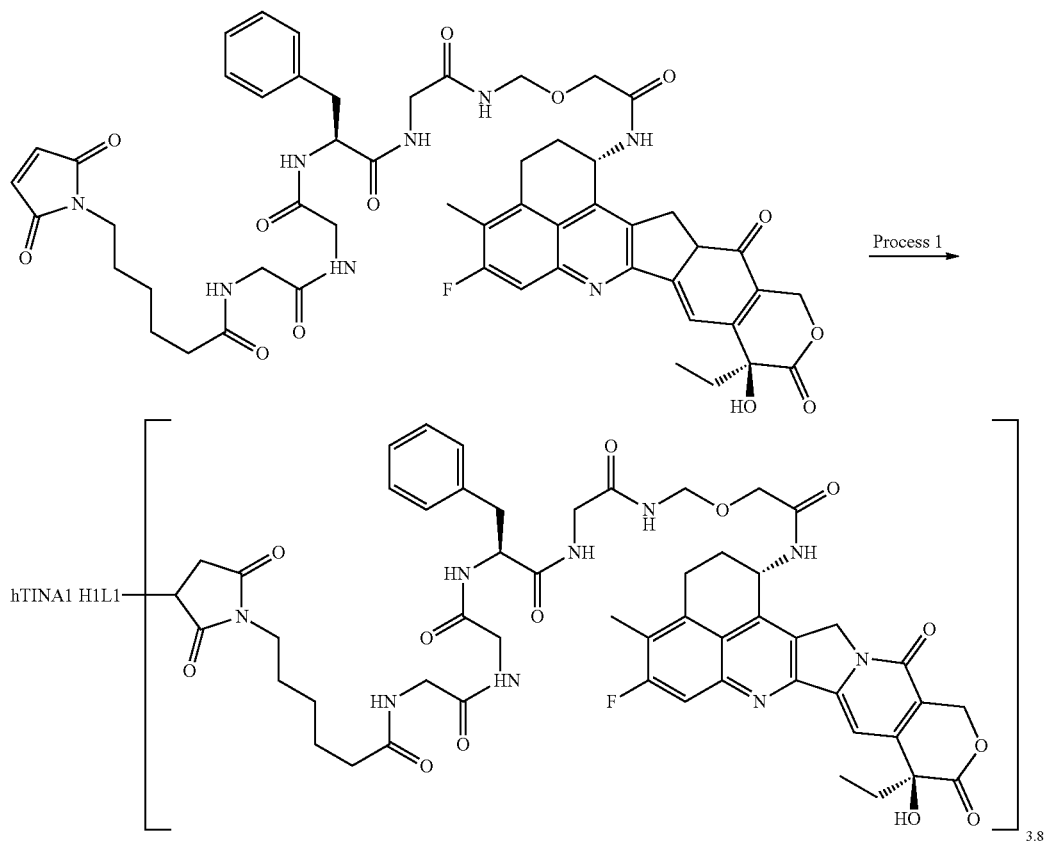

Process 1: Antibody-Drug Conjugate (13)

Reduction of the antibody: The hTINA1-H1L1 produced in Example 7 was prepared to have antibody concentration solution with stirring to adjust the pH of the solution to 5.5±0.1. This solution was subjected to microfiltration (0.45 µm, PVDF membrane) for removing white turbidity and yielding about 200 mL of a filtrate. This filtrate was subjected to ultrafiltration purification using an ultrafiltration apparatus composed of an ultrafiltration membrane (Merck Japan, Pellicon XL Cassette, Ultracell 30 KDa), a tube pump (Cole-Parmer International, MasterFlex Pump model 77521-40, Pump Head model 7518-00), and a tube (Cole-Parmer International, MasterFlex Tube L/S16).

Specifically, while ABS was added dropwise (a total of 1600 mL) as a buffer solution for purification to the reaction solution, ultrafiltration purification was performed for removing unconjugated drug linkers and other low-molecular-weight reagents, also replacing the buffer solution with ABS, and further concentrating the solution. The obtained purified solution was subjected to microfiltration (0.22 μm, PVDF membrane) to yield 88 mL of a solution containing the titled antibody-drug conjugate.

Physicochemical characterization: By using the Common procedure E and Common procedure F ($\varepsilon_{D,280}$=5178, and $\varepsilon_{D,370}$=20217 were used), the following characteristic values were obtained.

Antibody concentration: 9.96 mg/mL, antibody yield: 876 mg (88%), average number of conjugated drug molecules (n) per antibody molecule measured by Common procedure E: 3.8, and average number of conjugated drug molecules (n) per antibody molecule measured by Common procedure F: 3.8.

Example 21

Evaluation of Antitumor Effect of ADC 21-a) Antitumor Effect of ADC—(1)

Mouse: 5- to 6-week-old female BALB/c-nu/nu mice (Charles River Laboratories Japan, Inc.) were acclimatized for 4 to 7 days under SPF conditions before use in the experiment. The mice were fed with sterilized solid feed (FR-2, Funabashi Farms Co., Ltd) and given sterilized tap water (prepared by the addition of 5 to 15 ppm sodium hypochlorite solution).

Assay and calculation expression: In all studies, the major axis and minor axis of tumor were measured twice a week by using an electronic digital caliper (CD-15C, Mitutoyo Corp.), and the tumor volume (mm$^3$) was calculated. The calculation expression is as shown below.

$$\text{Tumor volume } (mm^3) = \frac{1}{2} \times \text{Major axis } (mm) \times [\text{Minor axis } (mm)]^2$$

Figure 13:
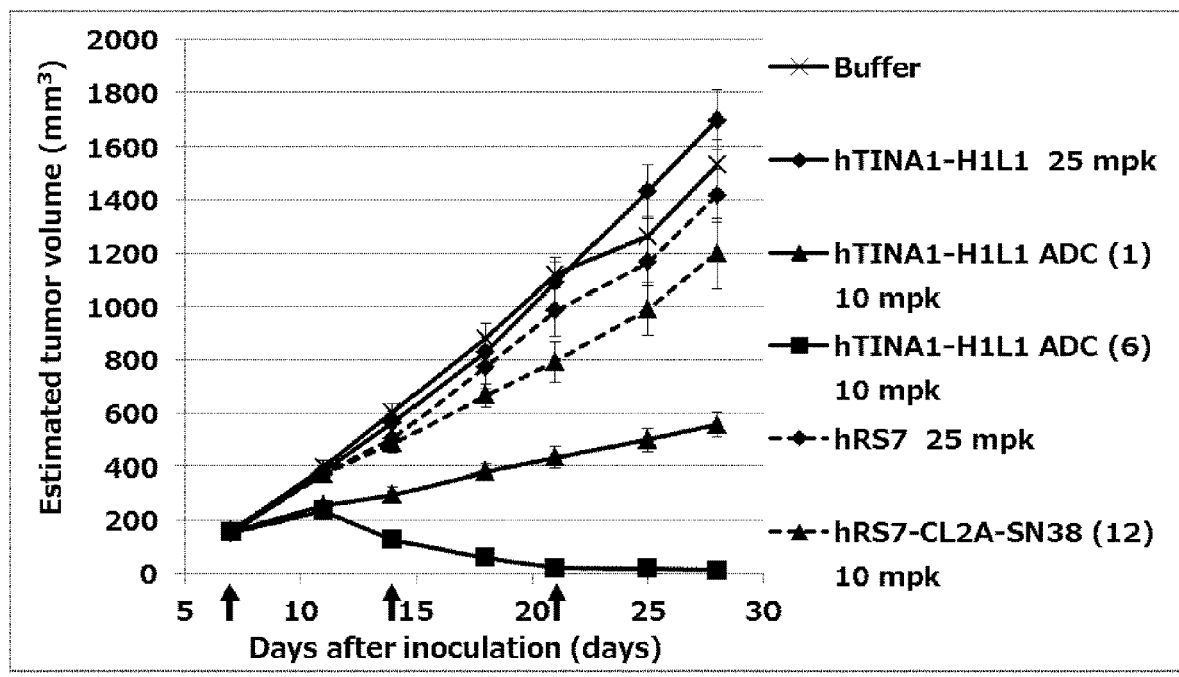
FIG. 13 shows the antitumor effect of an antibody-drug conjugate (1), (6), or (12) on a human colorectal cancer cell line COLO205 subcutaneously transplanted in BALB/c-nu/nu mice.

All of the antibody-drug conjugates were diluted with physiological saline (Otsuka Pharmaceutical Factory, Inc.) and used at a volume of 10 mL/kg for intravenous administration to the tail of each mouse. A human colorectal cancer cell line COLO205 was purchased from ATCC and suspended in physiological saline. 2×10$^6$ cells of the suspension were subcutaneously transplanted to the right abdomen of each female BALB/c-nu/nu mouse (Day 0), and the mice were randomly grouped at Day 7. The antibody-drug conjugate (1), (6), or (12) was intravenously administered at a dose of 10 mg/kg to the tail of each mouse at Days 7, 14, and 21. The non-conjugated hTINA1-H1L1 antibody and hRS7 antibody were each administered as a negative control at a dose of 25 mg/kg through the same route as above. The administration of the antibody-drug conjugate (1) or (6) remarkably decreased the tumor volume compared to the administration of the antibody-drug conjugate (12), and both of the antibody-drug conjugates exerted a tumor growth inhibitory effect (FIG. 13). In the drawing, the abscissa depicts the number of days, and the ordinate depicts the tumor volume.

21-b) Antitumor effect of ADC—(2)

Figure 14:
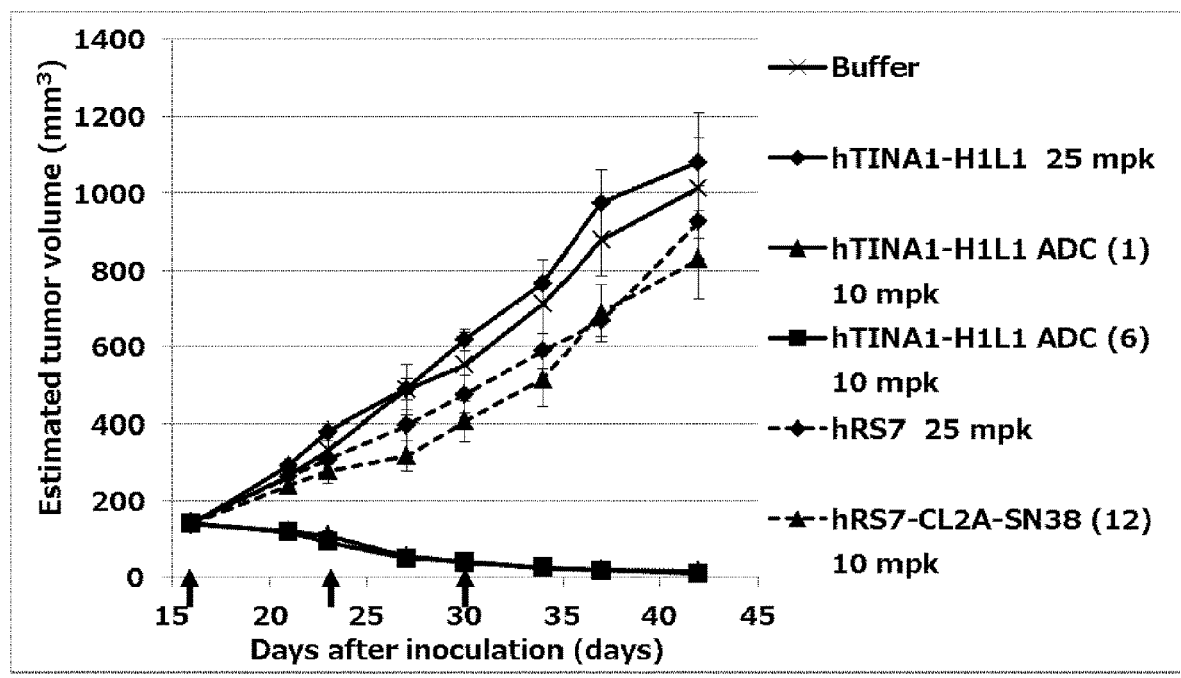
FIG. 14 shows the antitumor effect of the antibody-drug conjugate (1), (6), or (12) on a human pancreatic adenocarcinoma cell line BxPC-3 subcutaneously transplanted in BALB/c-nu/nu mice.

A human pancreatic adenocarcinoma cell line Bx-PC3 purchased from ATCC was transplanted to each female BALB/c-nu/nu mouse and further passaged as a solid tumor graft. This tumor graft was subcutaneously transplanted to the right abdomen of each female BALB/c-nu/nu mouse (Day 0), and the mice were randomly grouped at Day 16. The antibody-drug conjugate (1), (6), or (12) was intravenously administered at a dose of 10 mg/kg to the tail of each mouse at Days 16, 23, and 30. The non-conjugated hTINA1-H1L1 antibody and hRS7 antibody were each administered as a negative control at a dose of 25 mg/kg through the same route as above. The administration of the antibody-drug conjugate (1) or (6) remarkably decreased the tumor volume compared to the administration of the antibody-drug conjugate (12), and both of the antibody-drug conjugates exerted a tumor growth inhibitory effect (FIG. 14).

21-c) Antitumor Effect of ADC—(3)

Figure 15:
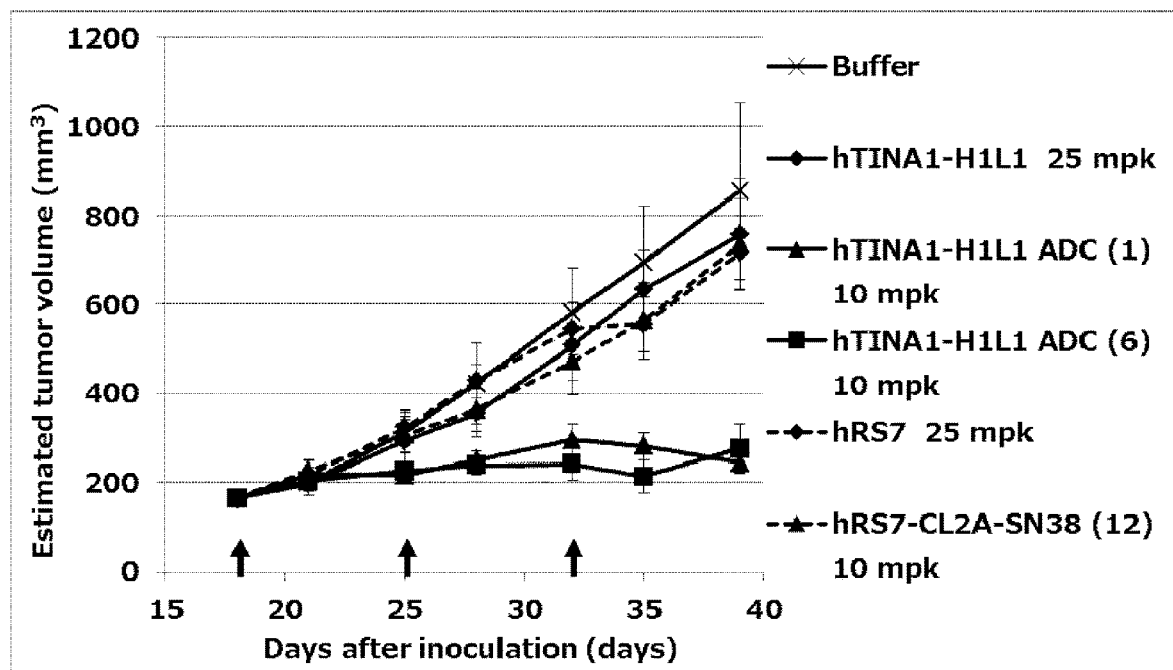
FIG. 15 shows the antitumor effect of the antibody-drug conjugate (1), (6), or (12) on a human pancreatic adenocarcinoma cell line Capan-1 subcutaneously transplanted in BALB/c-nu/nu mice.

A human pancreatic adenocarcinoma cell line Capan-1 purchased from ATCC was transplanted to each female BALB/c-nu/nu mouse and further passaged as a solid tumor graft. This tumor graft was subcutaneously transplanted to the right abdomen of each female BALB/c-nu/nu mouse (Day 0), and the mice were randomly grouped at Day 18. The antibody-drug conjugate (1), (6), or (12) was intravenously administered at a dose of 10 mg/kg to the tail of each mouse at Days 18, 25, and 32. The non-conjugated hTINA1-H1L1 antibody and hRS7 antibody were each administered as a negative control at a dose of 25 mg/kg through the same route as above. The administration of the antibody-drug conjugate (1) or (6) remarkably decreased the tumor volume compared to the administration of the antibody-drug conjugate (12), and both of the antibody-drug conjugates exerted a tumor growth inhibitory effect (FIG. 15).

21-d) Antitumor Effect of ADC—(4)

Figure 16:
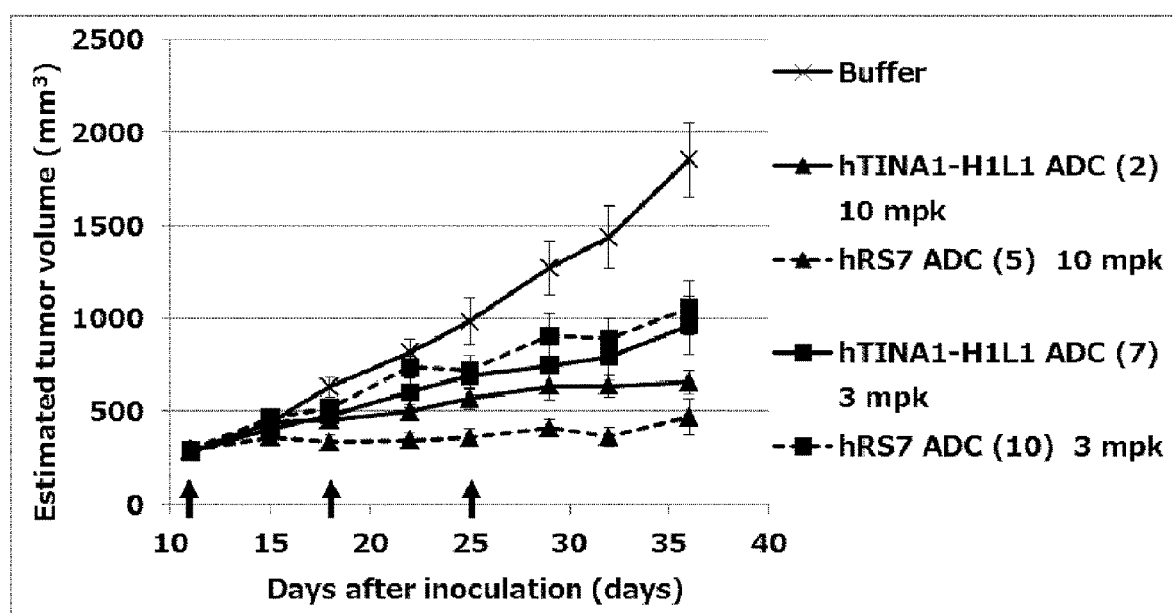
FIG. 16 shows the antitumor effect of the antibody-drug conjugate (2), (5), (7), or (10) on a human colorectal cancer cell line COLO205 subcutaneously transplanted in BALB/c-nu/nu mice.

COLO205 was subcutaneously transplanted to each female BALB/c-nu/nu mouse in the same manner as in Example 21-a) (Day 0), and the mice were randomly grouped at Day 11. The antibody-drug conjugate (2) or (5) at a dose of 10 mg/kg and the antibody-drug conjugate (7) or (10) at a dose of 3 mg/kg were intravenously administered, respectively, to the tail of each mouse at Days 11, 18, and 25. All of the antibody-drug conjugates (2), (5), (7), and (10) administered exerted a tumor growth inhibitory effect (FIG. 16).

21-e) Antitumor Effect of ADC—(5)

Figure 17:
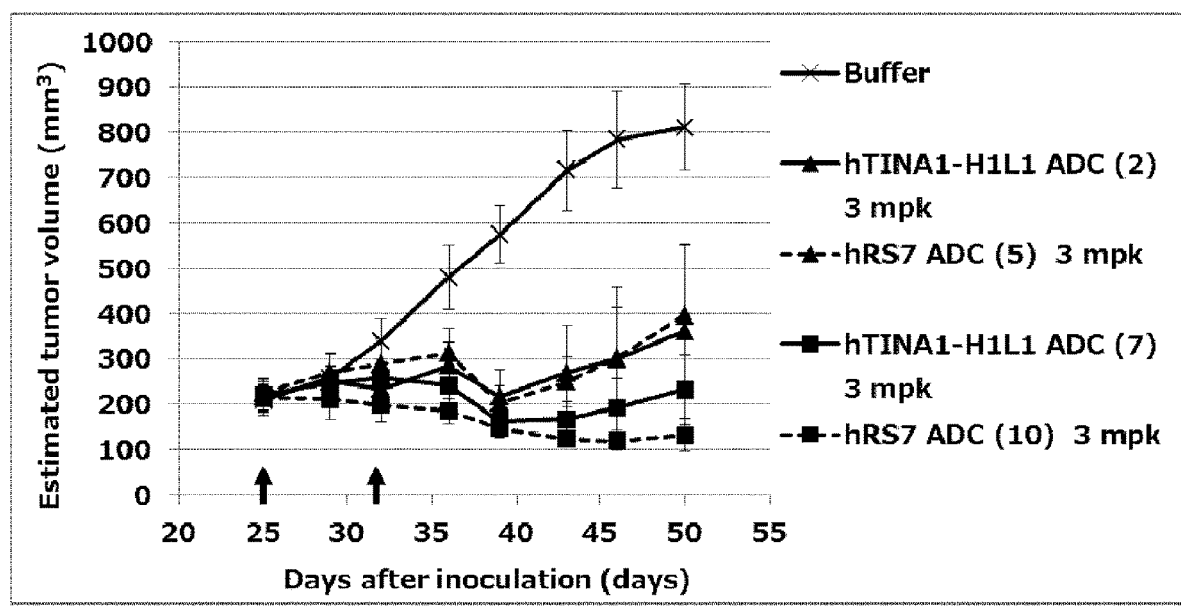
FIG. 17 shows the antitumor effect of the antibody-drug conjugate (2), (5), (7), or (10) on a human pancreatic adenocarcinoma cell line BxPC-3 subcutaneously transplanted in BALB/c-nu/nu mice.

Bx-PC3 was subcutaneously transplanted to each female BALB/c-nu/nu mouse in the same manner as in Example 21-b) (Day 0), and the mice were randomly grouped at Day 25. The antibody-drug conjugate (2), (5), (7), or (10) was intravenously administered at a dose of 3 mg/kg to the tail of each mouse at Days 25 and 32. All of the antibody-drug conjugates (2), (5), (7), and (10) administered exerted a tumor growth inhibitory effect (FIG. 17).

21-f) Antitumor Effect of ADC—(6)

Figure 18:
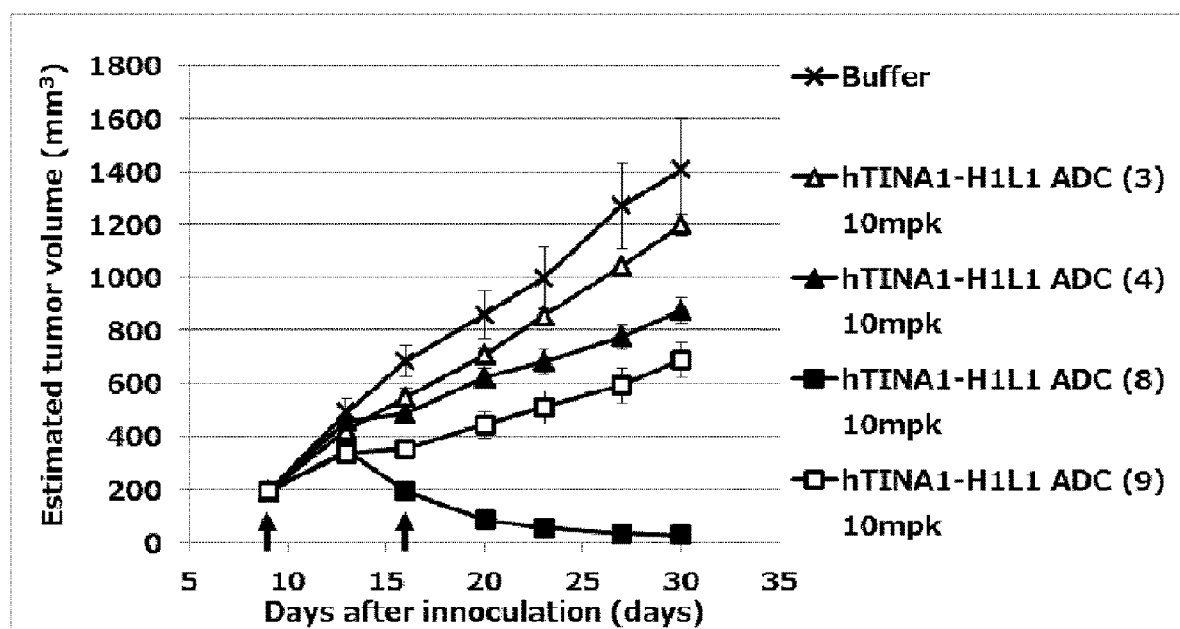
FIG. 18 shows the antitumor effect of the antibody-drug conjugate (3), (4), (8), or (9) on a human colorectal cancer cell line COLO205 subcutaneously transplanted in BALB/c-nu/nu mice.

COLO205 was subcutaneously transplanted to each female BALB/c-nu/nu mouse in the same manner as in Example 21-a) (Day 0), and the mice were randomly grouped at Day 9. The antibody-drug conjugate (3), (4), (8), or (9) was intravenously administered at a dose of 10 mg/kg to the tail of each mouse at Days 9 and 16. All of the antibody-drug conjugates (3), (4), (8), and (9) administered exerted a tumor growth inhibitory effect (FIG. 18).

21-g) Antitumor Effect of ADC—(7)

Figure 19:
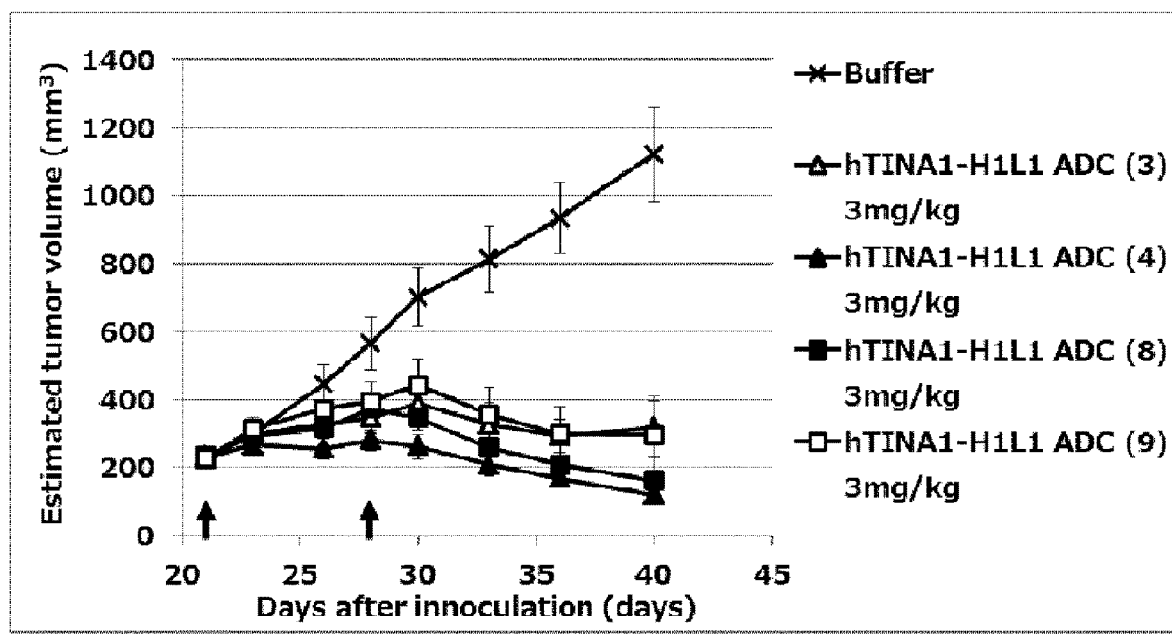
FIG. 19 shows the antitumor effect of the antibody-drug conjugate (3), (4), (8), or (9) on a human pancreatic adenocarcinoma cell line BxPC-3 subcutaneously transplanted in BALB/c-nu/nu mice.

Bx-PC3 was subcutaneously transplanted to each female BALB/c-nu/nu mouse in the same manner as in Example 21-b) (Day 0), and the mice were randomly grouped at Day 21. The antibody-drug conjugate (3), (4), (8), or (9) was intravenously administered at a dose of 3 mg/kg to the tail of each mouse at Days 21 and 28. All of the antibody-drug conjugates (3), (4), (8), and (9) administered exerted a tumor growth inhibitory effect (FIG. 19).

21-h) Antitumor Effect of ADC—(8)

Figure 20:
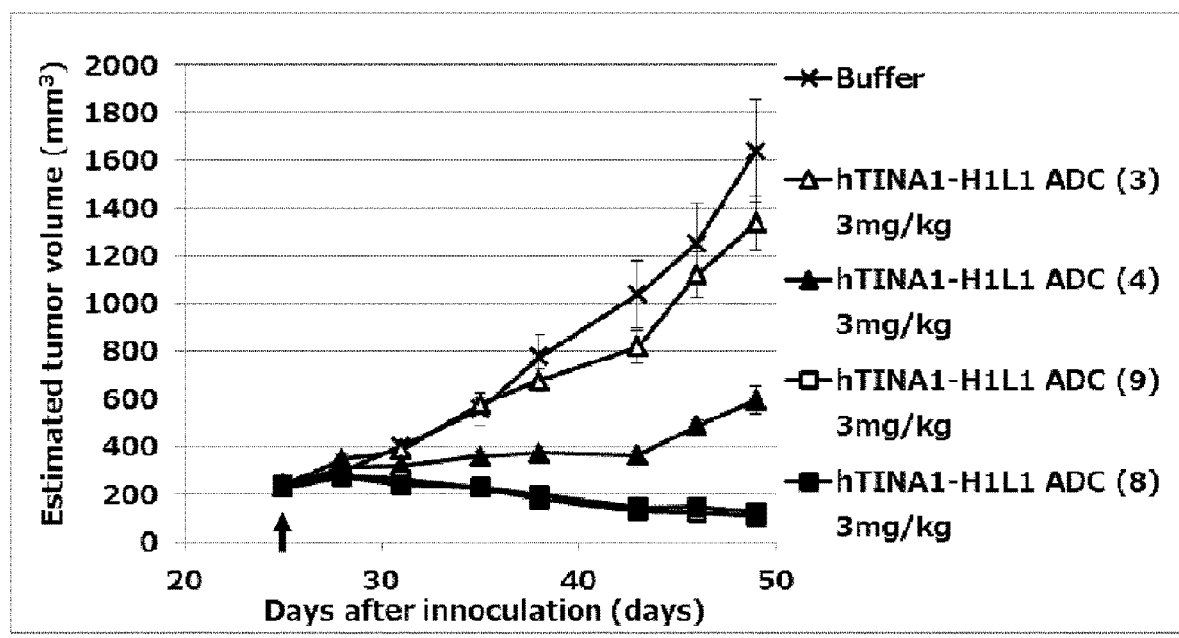
FIG. 20 shows the antitumor effect of the antibody-drug conjugate (3), (4), (8), or (9) on a human ovarian cancer cell line NIH:OVCAR-3 subcutaneously transplanted in BALB/c-nu/nu mice.

$8 \times 10^6$ cells of a human ovarian cancer cell line NIH:OVCAR-3 purchased from ATCC were suspended in Matrigel (Becton, Dickinson and Company) and subcutaneously transplanted to each female BALB/c-nu/nu mouse (Day 0), and the mice were randomly grouped at Day 25. The antibody-drug conjugate (3), (4), (8), or (9) was intravenously administered at a dose of 3 mg/kg to the tail of each mouse at Day 25. All of the antibody-drug conjugates (3), (4), (8), and (9) administered exerted a tumor growth inhibitory effect (FIG. 20).

21-i) Antitumor Effect of ADC—(9)

Figure 21:
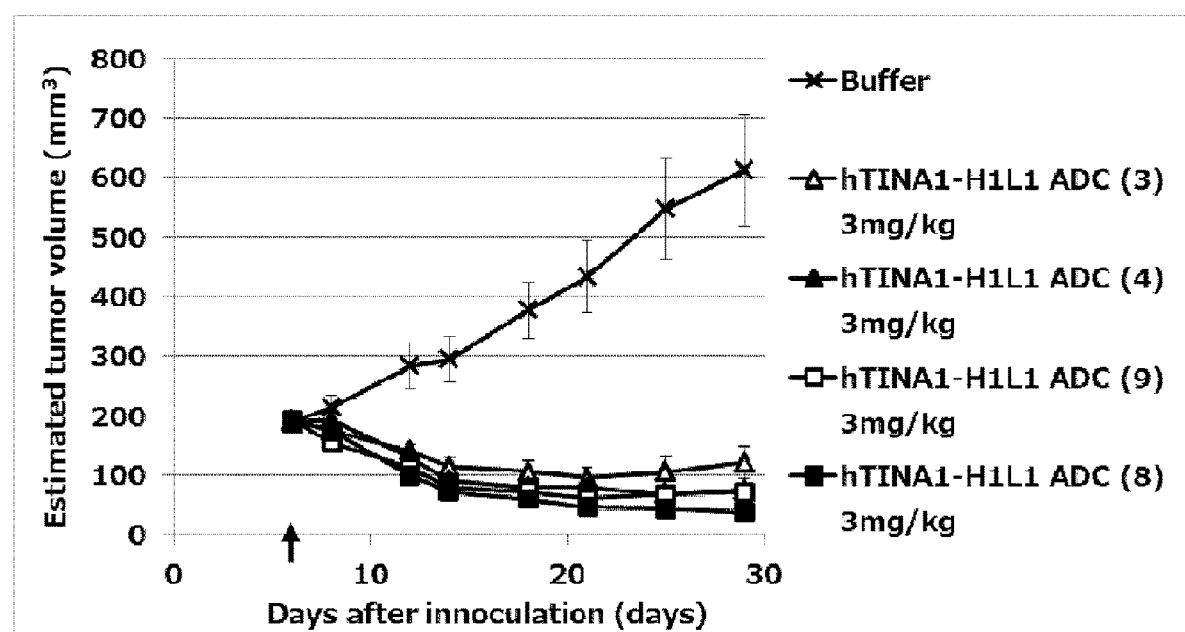
FIG. 21 shows the antitumor effect of the antibody-drug conjugate (3), (4), (8), or (9) on a human gastric cancer cell line NCI-N87 subcutaneously transplanted in BALB/c-nu/nu mice.

$1 \times 10^7$ cells of a human gastric cancer cell line NCI-N87 purchased from ATCC were suspended in physiological saline and subcutaneously transplanted to each female BALB/c-nu/nu mouse (Day 0), and the mice were randomly grouped at Day 6. The antibody-drug conjugate (3), (4), (8), or (9) was intravenously administered at a dose of 3 mg/kg to the tail of each mouse at Day 6. All of the antibody-drug conjugates (3), (4), (8), and (9) administered exerted a tumor growth inhibitory effect (FIG. 21).

21-j) Antitumor Effect of ADC—(10)

Figure 22:
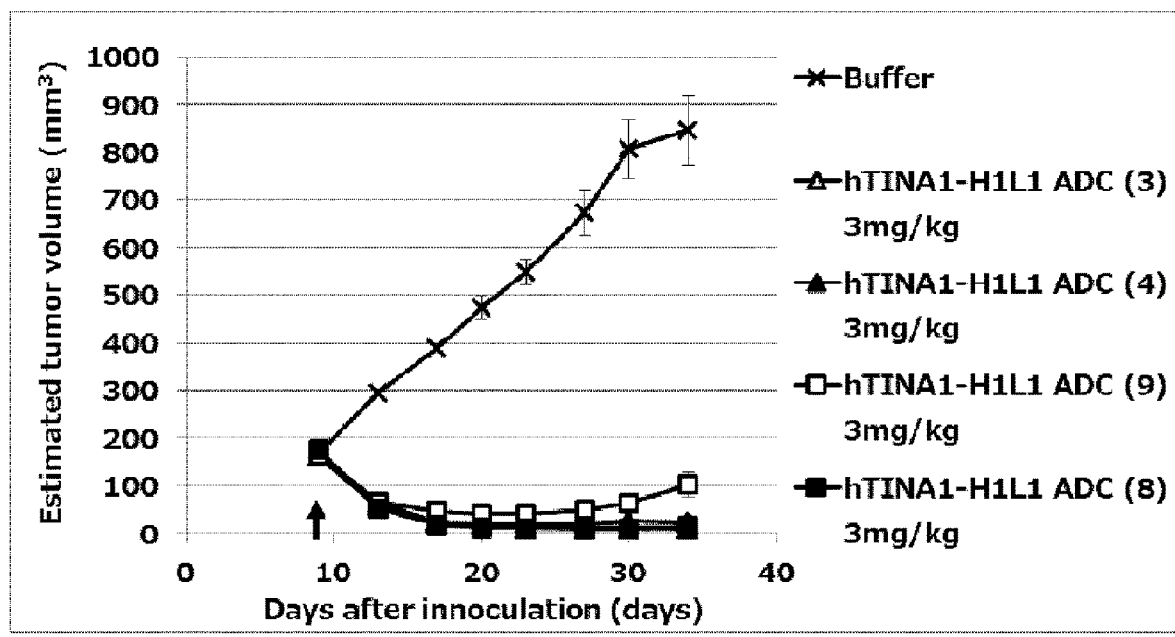
FIG. 22 shows the antitumor effect of the antibody-drug conjugate (3), (4), (8), or (9) on a human lung cancer cell line NCI-H292 subcutaneously transplanted in BALB/c-nu/nu mice.

$5 \times 10^6$ cells of a human lung cancer cell line NCI-H292 purchased from ATCC were suspended in physiological saline and subcutaneously transplanted to each female BALB/c-nu/nu mouse (Day 0), and the mice were randomly grouped at Day 9. The antibody-drug conjugate (3), (4), (8), or (9) was intravenously administered at a dose of 3 mg/kg to the tail of each mouse at Day 9. All of the antibody-drug conjugates (3), (4), (8), and (9) administered exerted a tumor growth inhibitory effect (FIG. 22).

21-k) Antitumor Effect of ADC—(11)

Figure 23:
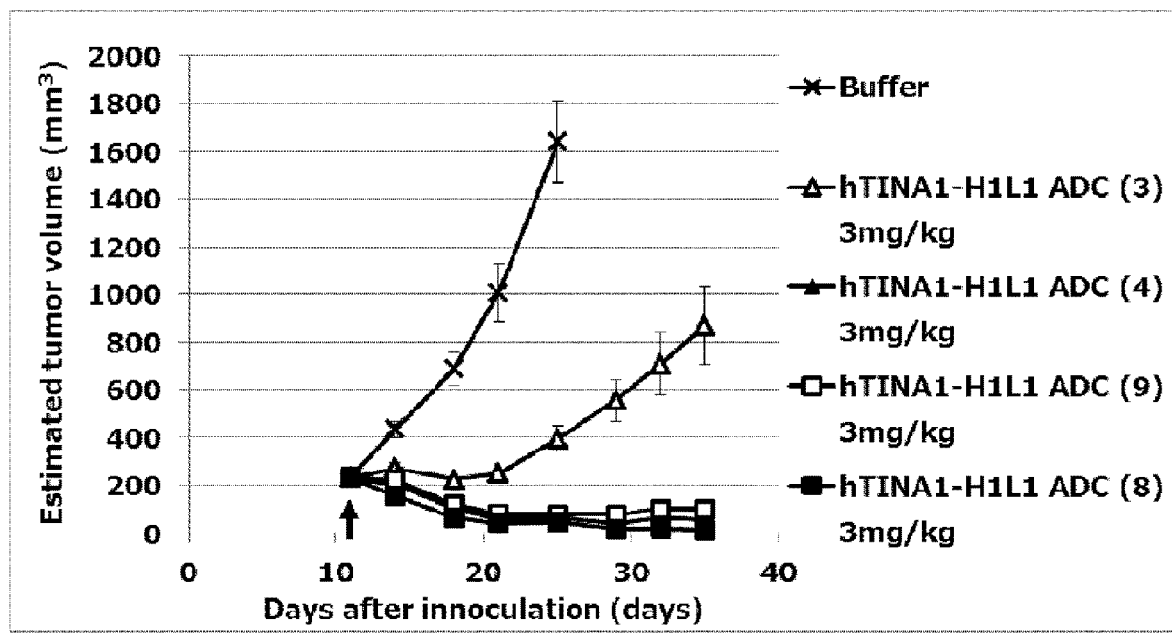
FIG. 23 shows the antitumor effect of the antibody-drug conjugate (3), (4), (8), or (9) on a human throat cancer cell line FaDu subcutaneously transplanted in BALB/c-nu/nu mice.

$3 \times 10^6$ cells of a human throat cancer cell line FaDu purchased from ATCC were suspended in physiological saline and subcutaneously transplanted to each female BALB/c-nu/nu mouse (Day 0), and the mice were randomly grouped at Day 11. The antibody-drug conjugate (3), (4), (8), or (9) was intravenously administered at a dose of 3 mg/kg to the tail of each mouse at Day 11. All of the antibody-drug conjugates (3), (4), (8), and (9) administered exerted a tumor growth inhibitory effect (FIG. 23).

21-l) Antitumor Effect of ADC—(12)

Figure 24:
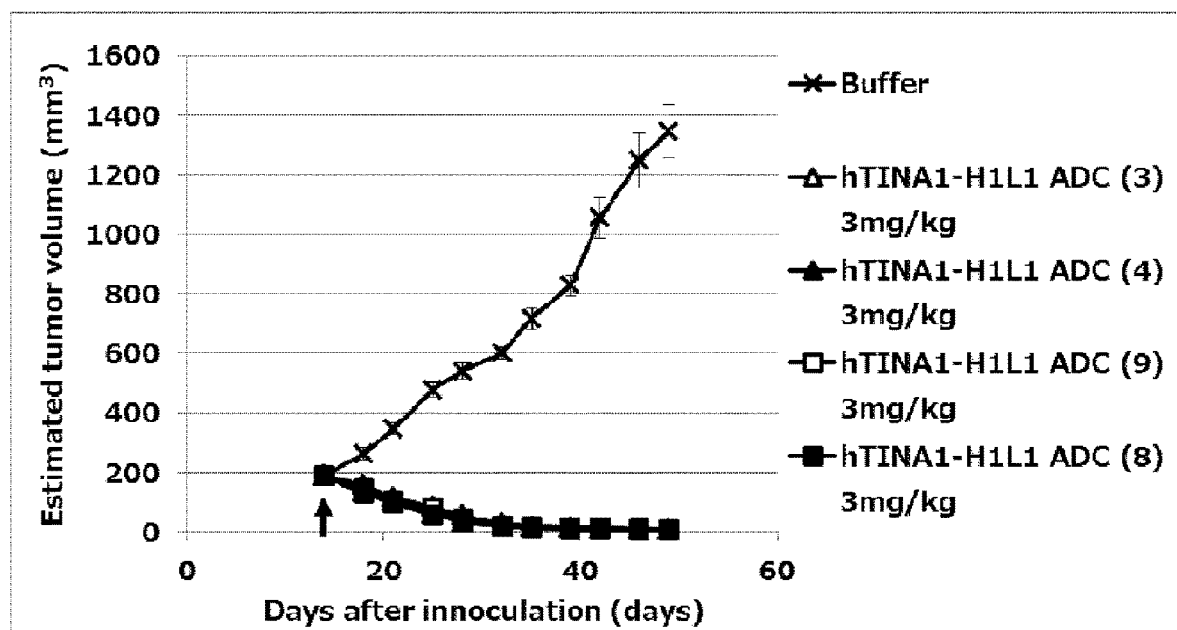
FIG. 24 shows the antitumor effect of the antibody-drug conjugate (3), (4), (8), or (9) on a human pancreatic adenocarcinoma cell line CFPAC-1 subcutaneously transplanted in BALB/c-nu/nu mice.

$4 \times 10^6$ cells of a human pancreatic adenocarcinoma cell line CFPAC-1 purchased from ATCC were suspended in physiological saline and subcutaneously transplanted to each female BALB/c-nu/nu mouse (Day 0), and the mice were randomly grouped at Day 14. The antibody-drug conjugate (3), (4), (8), or (9) was intravenously administered at a dose of 3 mg/kg to the tail of each mouse at Day 14. All of the antibody-drug conjugates (3), (4), (8), and (9) administered exerted a tumor growth inhibitory effect (FIG. 24).

21-m) Antitumor Effect of ADC—(13)

Figure 25:
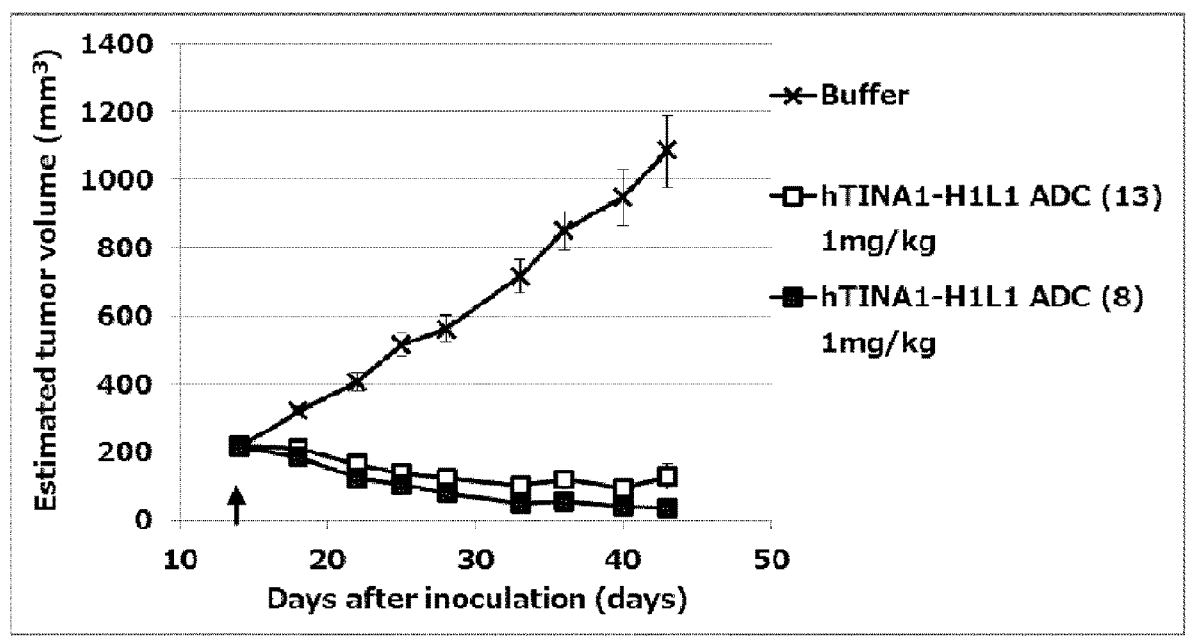
FIG. 25 shows the antitumor effect of the antibody-drug conjugate (8) or (13) on a human pancreatic adenocarcinoma cell line CFPAC-1 subcutaneously transplanted in BALB/c-nu/nu mice.

CFPAC-1 was subcutaneously transplanted to each female BALB/c-nu/nu mouse in the same manner as in Example 21-l) (Day 0), and the mice were randomly grouped at Day 14. The antibody-drug conjugate (8) or (13) was intravenously administered at a dose of 1 mg/kg to the tail of each mouse at Day 14. All of the antibody-drug conjugates (8) or (13) administered exerted a tumor growth inhibitory effect (FIG. 25).

21-n) Antitumor Effect of ADC—(14)

Figure 26:
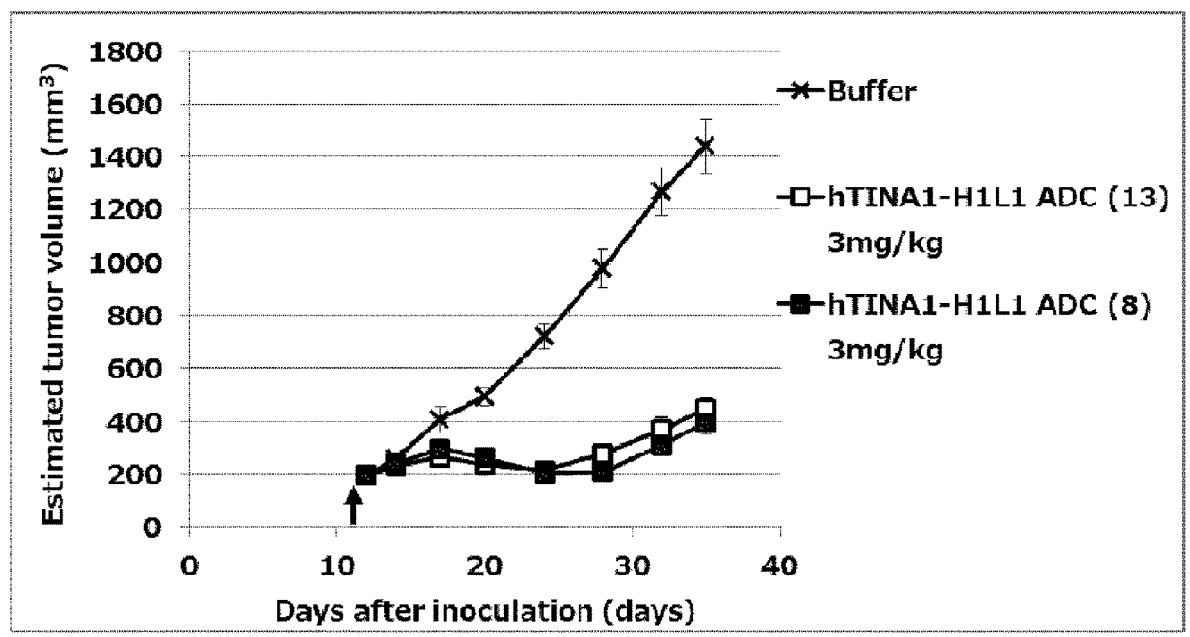
FIG. 26 shows the antitumor effect of the antibody-drug conjugate (8) or (13) on a human pancreatic adenocarcinoma cell line HPAC subcutaneously transplanted in BALB/c-nu/nu mice.

$3 \times 10^6$ cells of a human pancreatic adenocarcinoma cell line HPAC purchased from ATCC were suspended in physiological saline and subcutaneously transplanted to each female BALB/c-nu/nu mouse (Day 0), and the mice were randomly grouped at Day 12. The antibody-drug conjugate (8) or (13) was intravenously administered at a dose of 3 mg/kg to the tail of each mouse at Day 12. All of the antibody-drug conjugates (8) or (13) administered exerted a tumor growth inhibitory effect (FIG. 26).

21-o) Antitumor Effect of ADC—(15)

Figure 27:
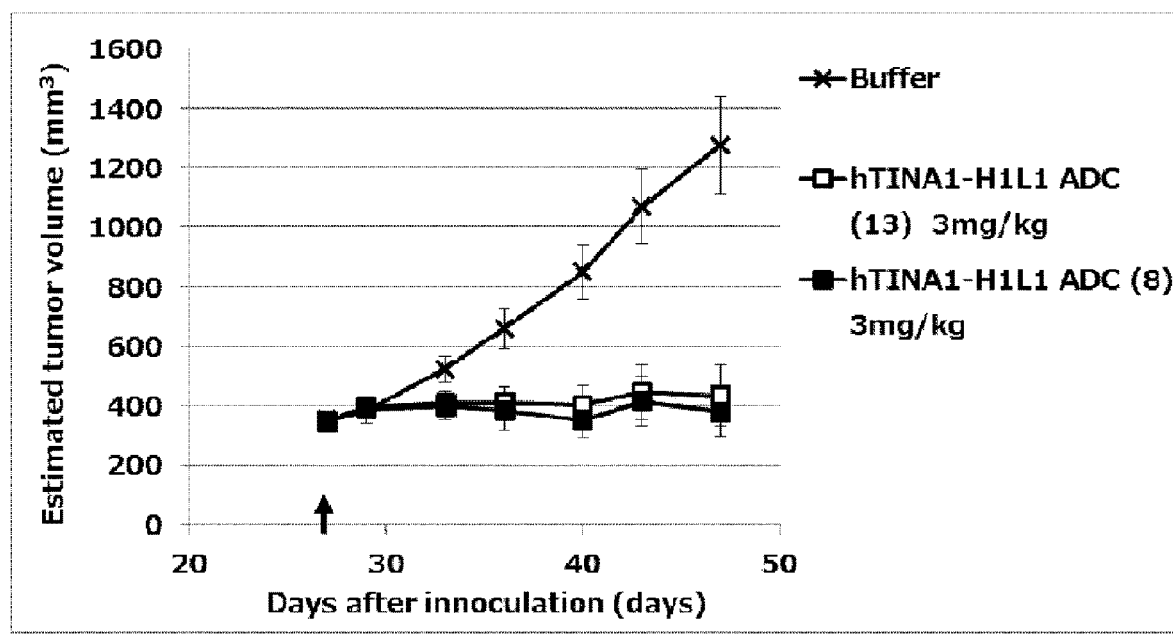
FIG. 27 shows the antitumor effect of the antibody-drug conjugate (8) or (13) on human esophageal cancer tissues subcutaneously transplanted on NOD-scid mice.

Human esophageal cancer tissues obtained from Japan Health Sciences Foundation were subcutaneously transplanted to each NOG mouse (Central Institute for Experimental Animals) and allowed to grow. The obtained tumor graft was further subcutaneously transplanted to each female NOD-scid mouse (Charles River Laboratories Japan, Inc.) (Day 0), and the mice were randomly grouped at Day 27. The antibody-drug conjugate (8) or (13) was intravenously administered at a dose of 3 mg/kg to the tail of each mouse at Day 27. Both of the antibody-drug conjugates (8) and (13) administered exerted a tumor growth inhibitory effect (FIG. 27).

Example 22

Evaluation of Cell Growth Inhibitory Effect of ADC

BxPC3, NCI-H292, NIH:OVCAR-3, CFPAC-1, FaDu, a human lung adenocarcinoma cell line Calu-3 (ATCC), and a human ovarian cancer cell line CaOV3 (ATCC) as TROP2 antigen-positive cell lines, and a human lung cancer cell line Calu-6 (ATCC) and a human cutaneous melanoma cell line A375 (ATCC) as TROP2 antigen-negative cell lines were used in the evaluation of the cell growth inhibitory effect of each ADC. BxPC3 and NCI-H292 were prepared with RPMI1640 Medium (Gibco) containing 10% fetal bovine serum (Moregate Biotech), NIH:OVCAR-3 was prepared with RPMI1640 Medium containing 20% fetal bovine serum and 0.01 mg/mL insulin (Invitrogen Corp.), CFPAC-1 was prepared with Iscove's Modified Dulbecco's Medium (Gibco) containing 10% fetal bovine serum, FaDu, Calu-3, and Calu-6 were prepared with Eagle's Minimum Essential Medium (ATCC) containing 10% fetal bovine serum, and CaOV3 and A375 were prepared with Dulbecco's Modified Eagle Medium (Gibco) containing 10% fetal bovine serum, to each have $2.2 \times 10^6$ cells/mL. Each cell suspension was seeded at 90 μL/well to a 96-well microplate for cell culture. The antibody-drug conjugate (4) or (8) diluted with RPMI1640 Medium to 100 nM, 20 nM, 4 nM, 0.8 nM, 0.16 nM, 0.032 nM, or 0.0064 nM, or RPMI1640 Medium for comparison was added thereto at 10 μL/well, and the cells were cultured under 5% $CO_2$ at 37° C. for 6 days. After the culture, the microplate was taken out of the incubator and left standing at room temperature for 30 minutes. The culture solution was charged with an equal amount of CellTiter-Glo Luminescent Cell Viability Assay (Promega) and stirred for 10 minutes by using a plate mixer. After cell lysis, luminescence intensity was measured by using a plate reader The rate of cell growth inhibition after the culture for 6 days was calculated according to the following equation:

Rate of cell growth inhibition (%)=$a/b \times 100$ a: Average value from the sample-supplemented wells after the culture for 6 days—Average value from the sample—unsupplemented wells at the start of the culture
b: Average value from the medium-supplemented wells after the culture for 6 days—Average value from the medium—unsupplemented wells at the start of the culture The $GI_{50}$ value was calculated according to the following equation:

$$GI_{50}(nM) = \text{antilog}((50-f) \times (LOG_{10}(d) - LOG_{10}(c))/(f-e) + LOG_{10}(d))$$

c: Sample concentration c
d: Sample concentration d
e: Rate of cell growth inhibition at the sample concentration c
f: Rate of cell growth inhibition at the sample concentration d The concentrations c and d establish the relation c>d crossing 50% rate of cell growth inhibition.

The antibody-drug conjugates (4) and (8) exhibited a cell growth inhibitory effect of $GI_{50}<1$ (nM) on the TROP2 antigen-positive cell lines BxPC3, NCI-H292, NIH:OVCAR-3, CFPAC-1, FaDu, Calu-3, and CaOV3. On the other hand, these antibody-drug conjugates exhibit no cell growth inhibitory effect (>100 (nM)) on the TROP2 antigen-negative cell lines Calu-6 and A375.

Free Text of Sequence Listing
SEQ ID NO: 1: Nucleotide sequence of cDNA encoding a heavy chain variable region of the TINA1 antibody
SEQ ID NO: 2: Amino acid sequence of the heavy chain variable region of the TINA1 antibody
SEQ ID NO: 3: Nucleotide sequence of cDNA encoding a light chain variable region of the TINA1 antibody
SEQ ID NO: 4: Amino acid sequence of the light chain variable region of the TINA1 antibody
SEQ ID NO: 5: Nucleotide sequence encoding a human κ chain secretion signal and a human κ chain constant region
SEQ ID NO: 6: Nucleotide sequence encoding a human heavy chain secretion signal and a human IgG1 constant region
SEQ ID NO: 7: Nucleotide sequence of a heavy chain of the cTINA1 antibody
SEQ ID NO: 8: Amino acid sequence of the heavy chain of the cTINA1 antibody
SEQ ID NO: 9: Nucleotide sequence of a light chain of the cTINA1 antibody
SEQ ID NO: 10: Amino acid sequence of the light chain of the cTINA1 antibody
SEQ ID NO: 11: Nucleotide sequence of hTINA1-H1
SEQ ID NO: 12: Amino acid sequence of hTINA1-H1
SEQ ID NO: 13: Nucleotide sequence of hTINA1-H2
SEQ ID NO: 14: Amino acid sequence of hTINA1-H2
SEQ ID NO: 15: Nucleotide sequence of hTINA1-H3
SEQ ID NO: 16: Amino acid sequence of hTINA1-H3
SEQ ID NO: 17: Nucleotide sequence of hTINA1-L1
SEQ ID NO: 18: Amino acid sequence of hTINA1-L1
SEQ ID NO: 19: Nucleotide sequence of hTINA1-L2
SEQ ID NO: 20: Amino acid sequence of hTINA1-L2
SEQ ID NO: 21: Nucleotide sequence of hTINA1-L3
SEQ ID NO: 22: Amino acid sequence of hTINA1-L3
SEQ ID NO: 23: Amino acid sequence of CDRH1 of the TINA1 antibody
SEQ ID NO: 24: Amino acid sequence of CDRH2 of the TINA1 antibody
SEQ ID NO: 25: Amino acid sequence of CDRH3 of the TINA1 antibody
SEQ ID NO: 26: Amino acid sequence of CDRL1 of the TINA1 antibody
SEQ ID NO: 27: Amino acid sequence of CDRL2 of the TINA1 antibody
SEQ ID NO: 28: Amino acid sequence of CDRL3 of the TINA1 antibody
SEQ ID NO: 29: Nucleotide sequence of a heavy chain of the hRS7 antibody
SEQ ID NO: 30: Amino acid sequence of the heavy chain of the hRS7 antibody
SEQ ID NO: 31: Nucleotide sequence of a light chain of the hRS7 antibody
SEQ ID NO: 32: Amino acid sequence of the light chain of the hRS7 antibody
SEQ ID NO: 33: Primer mG2aVR2
SEQ ID NO: 34: Primer mKVR2
SEQ ID NO: 35: Primer 3.3-F1
SEQ ID NO: 36: Primer 3.3-R1
SEQ ID NO: 37: Primer TINA1H-F
SEQ ID NO: 38: Primer TINA1H-R
SEQ ID NO: 39: Primer TINA1L-F
SEQ ID NO: 40: Primer TINA1L-R
SEQ ID NO: 41: Primer EG-Inf-F
SEQ ID NO: 42: Primer EG1-Inf-R
SEQ ID NO: 43: Primer CM-LKF
SEQ ID NO: 44: Primer KCL-Inf-R

The invention claimed is:

1. An antibody-drug conjugate, comprising an anti-TROP2 antibody and an antitumor compound connected by a linker, the anti-TROP2 antibody comprising a heavy chain variable region comprising a CDRH1 consisting of SEQ ID NO: 23, a CDRH2 consisting of SEQ ID NO: 24, and a CDRH3 consisting of SEQ ID NO: 25, and a light chain variable region comprising a CDRL1 consisting of SEQ ID NO: 26, a CDRL2 consisting of SEQ ID NO: 27, and a CDRL3 consisting of SEQ ID NO: 28; wherein the linker and the antitumor compound are represented by any one of the following:

-(Succinimid-3-yl-N)—CH$_2$CH$_2$—C(=O)-GGFG-NH-CH$_2$CH$_2$—C(=O)-(NH-DX),

-(Succinimid-3-yl-N)—CH$_2$CH$_2$—C(=O)-GGFG-NH—CH$_2$CH$_2$CH$_2$—C(=O)-(NH-DX), -(Succinimid-3-yl-N)—CH$_2$CH$_2$CH$_2$CH$_2$CH$_2$—C(=O)-GGFG-NH-CH$_2$CH$_2$—C(=O)-(NH-DX), -(Succinimid-3-yl-N)—CH$_2$CH$_2$CH$_2$CH$_2$CH$_2$—C(=O)-GGFG-NH-CH$_2$CH$_2$CH$_2$—C(=O)-(NH-DX), -(Succinimid-3-yl-N)—CH$_2$CH$_2$CH$_2$CH$_2$CH$_2$—C(=O)-GGFG-NH-CH$_2$CH$_2$CH$_2$CH$_2$CH$_2$-C(=O)-(NH-DX), -(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG-NH—CH$_2$CH$_2$—C(=O)-(NH-DX), -(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$-O—CH$_2$CH$_2$—C(=O)-GGFG-NH-CH$_2$CH$_2$—C(=O)-(NH-DX), or -(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$-O—CH$_2$CH$_2$—C(=O)-GGFG-NH—CH$_2$CH$_2$CH$_2$—C(=O)-(NH-DX)

wherein
-(Succinimid-3-yl-N)- has a structure of:

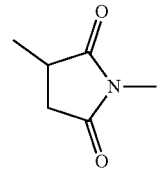

which is connected to the antibody at position 3 thereof and is connected to a methylene group in the linker structure containing this structure on the nitrogen atom at position 1, and (NH-DX) represents:

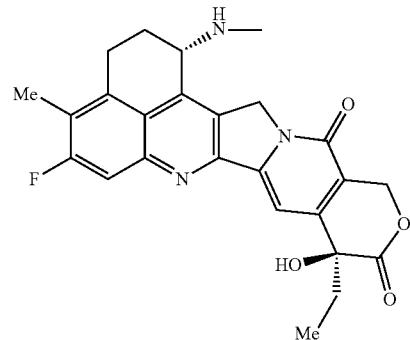 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position.

2. The antibody-drug conjugate according to claim 1, wherein an average number of units of the selected one drug-linker structure conjugated per antibody is in a range of from 2 to 8.

3. The antibody-drug conjugate according to claim 1, wherein an average number of units of the selected one drug-linker structure conjugated per antibody is in a range of from 3 to 8.

4. A drug containing the antibody-drug conjugate according to claim 1 or a salt thereof.

5. An antitumor drug and/or anticancer drug containing the antibody-drug conjugate according to claim 1 or a salt thereof.

6. A method of treating cancer in an individual comprising administering to an individual with cancer the drug according to claim 5, wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, cervical cancer, head and neck cancer, or esophageal cancer.

7. A pharmaceutical composition containing the antibody-drug conjugate according to claim 1 or a salt thereof as an active component, and a pharmaceutically acceptable formulation component.

8. A method of treating cancer in an individual comprising administering to an individual with cancer the pharmaceutical composition according to claim 7, wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, cervical cancer, head and neck cancer, or esophageal cancer.

* * * * *

```
                              SEQUENCE LISTING

<160> NUMBER OF SEQ ID NOS: 44

<210> SEQ ID NO 1
<211> LENGTH: 363
<212> TYPE: DNA
<213> ORGANISM: Mus musculus

<400> SEQUENCE: 1
cagatccagt tggtgcagtc tggacctgag ctgaagaagc ctggagagac agtcaggatc      60
tcctgcaagg cttctgggta taccttcaca actgctggaa tgcagtgggt gcaaaagatg     120
ccaggaaagg gtttgaagtg gattggctgg ataaacaccc actctggagt gccaaaatat     180
gcagaagact tcaagggacg gtttgccttc tctttggaaa cctctgccag cactgcatat     240
ttacagataa gcaacctcaa aaatgaggac acgactacgt atttctgtgc gagatcgggg     300
```

```
ttcggtagta gctactggta cttcgatgtc tggggcgcag ggaccgcggt caccgtctcc    360
tca                                                                  363
```

<210> SEQ ID NO 2
<211> LENGTH: 121
<212> TYPE: PRT
<213> ORGANISM: Mus musculus

<400> SEQUENCE: 2

```
Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ala
            20                  25                  30

Gly Met Gln Trp Val Gln Lys Met Pro Gly Lys Gly Leu Lys Trp Ile
        35                  40                  45

Gly Trp Ile Asn Thr His Ser Gly Val Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Thr Thr Tyr Phe Cys
                85                  90                  95

Ala Arg Ser Gly Phe Gly Ser Ser Tyr Trp Tyr Phe Asp Val Trp Gly
            100                 105                 110

Ala Gly Thr Ala Val Thr Val Ser Ser
        115                 120
```

<210> SEQ ID NO 3
<211> LENGTH: 327
<212> TYPE: DNA
<213> ORGANISM: Mus musculus

<400> SEQUENCE: 3

```
gacattgtga tgacccagtc tcacaaattc atgtccacat cagtaggaga cagggtcagc     60
atcacctgca aggccagtca ggatgtgagt actgctgtag cctggtatca acagaaacca    120
ggacaatctc ctaaactgct gatttactcg gcatcctacc gctacactgg agtccctgat    180
cgcttcactg gcagtggatc tgggacggct ttcactttca ccatcagcag tgtgcaggct    240
gaagacctgg cagtttatta ctgtcagcaa cattatatta ctccgctcac gttcggtgct    300
gggaccaagc tggagctgaa acgggct                                        327
```

<210> SEQ ID NO 4
<211> LENGTH: 109
<212> TYPE: PRT
<213> ORGANISM: Mus musculus

<400> SEQUENCE: 4

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Ala Phe Thr Phe Thr Ile Ser Ser Val Gln Ala
65                  70                  75                  80
```

| Glu | Asp | Leu | Ala | Val | Tyr | Tyr | Cys | Gln | Gln | His | Tyr | Ile | Thr | Pro | Leu |
| | 85 | | | | | 90 | | | | | 95 | | | | |

| Thr | Phe | Gly | Ala | Gly | Thr | Lys | Leu | Glu | Leu | Lys | Arg | Ala |
| | | | 100 | | | | | 105 | | | | |

<210> SEQ ID NO 5
<211> LENGTH: 449
<212> TYPE: DNA
<213> ORGANISM: Homo sapiens

<400> SEQUENCE: 5

```
gcctccggac tctagagcca ccatggtgct gcagacccag gtgttcatct ccctgctgct     60
gtggatctcc ggcgcgtacg gcgatatcgt gatgattaaa cgtacggtgg ccgccccctc    120
cgtgttcatc ttcccccccct ccgacgagca gctgaagtcc ggcaccgcct ccgtggtgtg   180
cctgctgaat aacttctacc ccagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca gggggggagtg   420
ttagggggccc gtttaaacgg gggaggcta                                     449
```

<210> SEQ ID NO 6
<211> LENGTH: 1132
<212> TYPE: DNA
<213> ORGANISM: Homo sapiens

<400> SEQUENCE: 6

```
gcctccggac tctagagcca ccatgaaaca cctgtggttc ttcctcctgc tggtggcagc     60
tcccagatgg gtgctgagcc aggtgcaatt gtgcaggcgg ttagctcagc ctccaccaag   120
ggcccaagcg tcttcccccct ggcaccctcc tccaagagca cctctggcgg cacagccgcc   180
ctgggctgcc tggtcaagga ctacttcccc gaacccgtga ccgtgagctg gaactcaggc   240
gccctgacca gcggcgtgca caccttcccc gctgtcctgc agtcctcagg actctactcc   300
ctcagcagcg tggtgaccgt gccctccagc agcttgggca cccagaccta catctgcaac   360
gtgaatcaca agcccagcaa caccaaggtg gacaagagag ttgagcccaa atcttgtgac   420
aaaactcaca catgcccacc ctgcccagca cctgaactcc tggggggacc ctcagtcttc   480
ctcttccccc caaaacccaa ggacaccctc atgatctccc ggacccctga ggtcacatgc   540
gtggtggtgg acgtgagcca cgaagaccct gaggtcaagt tcaactggta cgtggacggc   600
gtggaggtgc ataatgccaa gacaaagccc cgggaggagc agtacaacag cacgtaccgg   660
gtggtcagcg tcctcaccgt cctgcaccag gactggctga atggcaagga gtacaagtgc   720
aaggtctcca acaaagccct cccagccccc atcgagaaaa ccatctccaa agccaaaggc   780
cagccccggg aaccacaggt gtacaccctg cccccatccc gggaggagat gaccaagaac   840
caggtcagcc tgacctgcct ggtcaaaggc ttctatccca gcgacatcgc cgtggagtgg   900
gagagcaatg gccagcccga gaacaactac aagaccaccc ctcccgtgct ggactccgac   960
ggctccttct tcctctacag caagctcacc gtggacaaga gcaggtggca gcagggcaac  1020
gtcttctcat gctccgtgat gcatgaggct ctgcacaacc actacaccca gaagagcctc  1080
tccctgtctc ccggcaaatg agatatcggg cccgtttaaa cggggggaggc ta          1132
```

<210> SEQ ID NO 7
<211> LENGTH: 1410

<212> TYPE: DNA
<213> ORGANISM: Artificial Sequence
<220> FEATURE:
<223> OTHER INFORMATION: nucleotide sequence of heavy chain of chimeric murine-human TINA1 antibody

<400> SEQUENCE: 7

```
atgaaacacc tgtggttctt cctcctgctg gtggcagctc ccagatgggt gctgagccag      60
atccagttgg tgcagtctgg acctgagctg aagaagcctg agagacagt caggatctcc     120
tgcaaggctt ctgggtatac cttcacaact gctggaatgc agtgggtgca aaagatgcca     180
ggaaagggtt tgaagtggat tgctggata acacccact ctggagtgcc aaaatatgca      240
gaagacttca agggacggtt tgccttctct ttggaaacct ctgccagcac tgcatattta     300
cagataagca acctcaaaaa tgaggacacg actacgtatt tctgtgcgag atcggggttc     360
ggtagtagct actggtactt cgatgtctgg ggcgcaggga ccgcggtcac cgtcagctca     420
gcctccacca agggcccaag cgtcttcccc ctggcaccct cctccaagag cacctctggc     480
ggcacagccg ccctgggctg cctggtcaag gactacttcc ccgaacccgt gaccgtgagc     540
tggaactcag gcgccctgac cagcggcgtg cacaccttcc cgctgtcct gcagtcctca     600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca cctgcccag cacctgaact cctgggggga     780
cctcagtct cctcttccc cccaaaaccc aaggacaccc tcatgatctc ccggaccccct     840
gaggtcacat gcgtggtggt ggacgtgagc cacgaagacc ctgaggtcaa gttcaactgg     900
tacgtggacg gcgtggaggt gcataatgcc aagacaaagc ccgggaagg gcagtacaac     960
agcacgtacc gggtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gccagccccg ggaaccacag gtgtacaccc tgccccatc ccgggaggag    1140
atgaccaaga accaggtcag cctgacctgc ctggtcaaag gcttctatcc cagcgacatc    1200
gccgtggagt gggagagcaa tggccagccc gagaacaact acaagaccac ccctcccgtg    1260
ctggactccg acggctcctt cttcctctac agcaagctca ccgtggacaa gagcaggtgg    1320
cagcagggca acgtcttctc atgctccgtg atgcatgagg ctctgcacaa ccactacacc    1380
cagaagagcc tctccctgtc tccgggcaaa                                     1410
```

<210> SEQ ID NO 8
<211> LENGTH: 470
<212> TYPE: PRT
<213> ORGANISM: Artificial Sequence
<220> FEATURE:
<223> OTHER INFORMATION: amino acid sequence of heavy chain of chimeric murine-human TINA1 antibody

<400> SEQUENCE: 8

```
Met Lys His Leu Trp Phe Phe Leu Leu Leu Val Ala Ala Pro Arg Trp
1               5                   10                  15

Val Leu Ser Gln Ile Gln Leu Val Gln Ser Gly Pro Glu Leu Lys Lys
            20                  25                  30

Pro Gly Glu Thr Val Arg Ile Ser Cys Lys Ala Ser Gly Tyr Thr Phe
        35                  40                  45

Thr Thr Ala Gly Met Gln Trp Val Gln Lys Met Pro Gly Lys Gly Leu
    50                  55                  60
```

```
Lys Trp Ile Gly Trp Ile Asn Thr His Ser Gly Val Pro Lys Tyr Ala
 65                  70                  75                  80

Glu Asp Phe Lys Gly Arg Phe Ala Phe Ser Leu Glu Thr Ser Ala Ser
                 85                  90                  95

Thr Ala Tyr Leu Gln Ile Ser Asn Leu Lys Asn Glu Asp Thr Thr Thr
            100                 105                 110

Tyr Phe Cys Ala Arg Ser Gly Phe Gly Ser Ser Tyr Trp Tyr Phe Asp
        115                 120                 125

Val Trp Gly Ala Gly Thr Ala Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 9
<211> LENGTH: 702
<212> TYPE: DNA
<213> ORGANISM: Artificial Sequence
<220> FEATURE:
<223> OTHER INFORMATION: nucleotide sequence of light chain of chimeric murine-human TINA1 antibody

<400> SEQUENCE: 9

```
atggtgctgc agacccaggt gttcatctcc ctgctgctgt ggatctccgg cgcgtacggc      60
gacattgtga tgacccagtc tcacaaattc atgtccacat cagtaggaga cagggtcagc     120
atcacctgca aggccagtca ggatgtgagt actgctgtag cctggtatca acagaaacca     180
ggacaatctc ctaaactgct gatttactcg gcatcctacc gctacactgg agtccctgat     240
cgcttcactg gcagtggatc tgggacggct ttcactttca ccatcagcag tgtgcaggct     300
gaagacctgg cagtttatta ctgtcagcaa cattatatta ctccgctcac gttcggtgct     360
gggaccaagc tggagctgaa acgggctgtg gccgcccccct ccgtgttcat cttccccccc     420
tccgacgagc agctgaagtc cggcaccgcc tccgtgtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac aggggggagt gt                       702
```

<210> SEQ ID NO 10
<211> LENGTH: 234
<212> TYPE: PRT
<213> ORGANISM: Artificial Sequence
<220> FEATURE:
<223> OTHER INFORMATION: amino acid sequence of light chain of chimeric murine-human TINA1 antibody

<400> SEQUENCE: 10

Met Val Leu Gln Thr Gln Val Phe Ile Ser Leu Leu Leu Trp Ile Ser
1               5                   10                  15

Gly Ala Tyr Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Ala Phe Thr Phe Thr Ile Ser
                85                  90                  95

Ser Val Gln Ala Glu Asp Leu Ala Val Tyr Tyr Cys Gln Gln His Tyr
            100                 105                 110

Ile Thr Pro Leu Thr Phe Gly Ala Gly Thr Lys Leu Glu Leu Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr 180                185                190
Tyr Ser Leu Ser Ser Thr Leu Thr Leu Ser Lys Ala Asp Tyr Glu Lys
        195                200                205

His Lys Val Tyr Ala Cys Glu Val Thr His Gln Gly Leu Ser Ser Pro
    210                215                220

Val Thr Lys Ser Phe Asn Arg Gly Glu Cys
225                230

<210> SEQ ID NO 11
<211> LENGTH: 1410
<212> TYPE: DNA
<213> ORGANISM: Artificial Sequence
<220> FEATURE:
<223> OTHER INFORMATION: nucleotide sequence of heavy chain of humanized
      TINA1 antibody, type H1

<400> SEQUENCE: 11

| | | | | | | |
|---|---|---|---|---|---|---|
| atgaaacacc | tgtggttctt | cctcctgctg | gtggcagctc | ccagatgggt | gctgagccag | 60 |
| gtgcagctgg | tgcagtctgg | cgccgaagtg | aagaaaccag | gcgccagcgt | gaaggtgtcc | 120 |
| tgcaaggcca | gcggctacac | ctttaccacc | gccggcatgc | agtgggtgcg | ccaggctcct | 180 |
| ggacagggcc | tggaatggat | gggctggatc | aacacccaca | gcggcgtgcc | caaatacgcc | 240 |
| gaggacttca | agggcagagt | gaccatcagc | gccgacacca | gcacctccac | agcctacctg | 300 |
| cagctgagca | gcctgaagtc | cgaggacacc | gccgtgtact | actgcgccag | aagcggcttc | 360 |
| ggcagcagct | actggtactt | cgacgtgtgg | ggccagggca | ccctcgtgac | cgtcagctca | 420 |
| gcctccacca | agggcccaag | cgtcttcccc | ctggcaccct | cctccaagag | cacctctggc | 480 |
| ggcacagccg | ccctgggctg | cctggtcaag | gactacttcc | ccgaacccgt | gaccgtgagc | 540 |
| tggaactcag | gcgccctgac | cagcggcgtg | cacaccttcc | ccgctgtcct | gcagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagag | agttgagccc | 720 |
| aaatcttgtg | acaaaactca | cacatgccca | ccctgcccag | cacctgaact | cctgggggga | 780 |
| ccctcagtct | tcctcttccc | cccaaaaccc | aaggacaccc | tcatgatctc | ccggaccct | 840 |
| gaggtcacat | gcgtggtggt | ggacgtgagc | cacgaagacc | ctgaggtcaa | gttcaactgg | 900 |
| tacgtggacg | gcgtggaggt | gcataatgcc | aagacaaagc | cccgggagga | gcagtacaac | 960 |
| agcacgtacc | gggtggtcag | cgtcctcacc | gtcctgcacc | aggactggct | gaatggcaag | 1020 |
| gagtacaagt | gcaaggtctc | caacaaagcc | ctcccagccc | ccatcgagaa | aaccatctcc | 1080 |
| aaagccaaag | gccagccccg | ggaaccacag | gtgtacaccc | tgcccccatc | ccgggaggag | 1140 |
| atgaccaaga | accaggtcag | cctgacctgc | ctggtcaaag | gcttctatcc | cagcgacatc | 1200 |
| gccgtggagt | gggagagcaa | tggccagccc | gagaacaact | acaagaccac | ccctcccgtg | 1260 |
| ctggactccg | acggctcctt | cttcctctac | agcaagctca | ccgtggacaa | gagcaggtgg | 1320 |
| cagcagggca | acgtcttctc | atgctccgtg | atgcatgagg | ctctgcacaa | ccactacacc | 1380 |
| cagaagagcc | tctccctgtc | tccgggcaaa | | | | 1410 |

<210> SEQ ID NO 12
<211> LENGTH: 470
<212> TYPE: PRT
<213> ORGANISM: Artificial Sequence
<220> FEATURE:
<223> OTHER INFORMATION: amino acid sequence of heavy chain of humanized
      TINA1 antibody, type H1

```
<400> SEQUENCE: 12

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Ala Gly Met Gln Trp Val Arg Gln Ala Pro Gly Gln Gly Leu
    50                  55                  60

Glu Trp Met Gly Trp Ile Asn Thr His Ser Gly Val Pro Lys Tyr Ala
65                  70                  75                  80

Glu Asp Phe Lys Gly Arg Val Thr Ile Ser Ala Asp Thr Ser Thr Ser
                85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 13
<211> LENGTH: 1410
<212> TYPE: DNA
<213> ORGANISM: Artificial Sequence
<220> FEATURE:
<223> OTHER INFORMATION: nucleotide sequence of heavy chain of humanized
      TINA1 antibody, type H2

<400> SEQUENCE: 13

```
atgaaacacc tgtggttctt cctcctgctg gtggcagctc ccagatgggt gctgagccag      60
gtgcagctgg tgcagtctgg cgccgaagtg aagaaaccag cgccagcgt gaaggtgtcc      120 tgcaaggcca gcggctacac ctttaccacc gccggcatgc agtgggtgcg ccaggctcct      180
ggacagggcc tggaatggat gggctggatc aacacccaca gcggcgtgcc caaatacgcc      240
gaggacttca agggcagagt gaccatcagc ctggacacca gcacctccac cgcctacctg      300
cagctgagca gcctgaagtc cgaggacacc gccgtgtact actgcgccag aagcggcttc      360
ggcagcagct actggtactt cgacgtgtgg ggccagggca ccctcgtgac cgtcagctca      420
gcctccacca agggcccaag cgtcttcccc ctggcaccct cctccaagag cacctctggc      480
ggcacagccg ccctgggctg cctggtcaag gactacttcc ccgaacccgt gaccgtgagc      540
tggaactcag gcgccctgac cagcggcgtg cacaccttcc ccgctgtcct gcagtcctca      600
ggactctact ccctcagcag cgtggtgacc gtgccctcca gcagcttggg cacccagacc      660
tacatctgca acgtgaatca caagcccagc aacaccaagg tggacaagag agttgagccc      720
aaatcttgtg acaaaactca cacatgccca cctgcccag cacctgaact cctgggggga      780
ccctcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cccgggagga gcagtacaac      960
agcacgtacc gggtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag gcagccccg gaaccacag gtgtacaccc tgcccccatc ccgggaggag     1140
atgaccaaga accaggtcag cctgacctgc ctggtcaaag gcttctatcc cagcgacatc     1200
gccgtggagt gggagagcaa tggccagccc gagaacaact acaagaccac ccctcccgtg     1260
ctggactccg acggctcctt cttcctctac agcaagctca ccgtggacaa gagcaggtgg     1320
cagcagggca acgtcttctc atgctccgtg atgcatgagg ctctgcacaa ccactacacc     1380
cagaagagcc tctccctgtc tccgggcaaa                                    1410
```

<210> SEQ ID NO 14
<211> LENGTH: 470
<212> TYPE: PRT
<213> ORGANISM: Artificial Sequence
<220> FEATURE:
<223> OTHER INFORMATION: amino acid sequence of heavy chain of humanized TINA1 antibody, type H2

<400> SEQUENCE: 14

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Ala Gly Met Gln Trp Val Arg Gln Ala Pro Gly Gln Gly Leu
    50                  55                  60

Glu Trp Met Gly Trp Ile Asn Thr His Ser Gly Val Pro Lys Tyr Ala
65                  70                  75                  80

Glu Asp Phe Lys Gly Arg Val Thr Ile Ser Leu Asp Thr Ser Thr Ser
                85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
        115                 120                 125

Val Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 15
<211> LENGTH: 1410
<212> TYPE: DNA
<213> ORGANISM: Artificial Sequence
<220> FEATURE:
<223> OTHER INFORMATION: nucleotide sequence of heavy chain of humanized
      TINA1 antibody, type H3

<400> SEQUENCE: 15
atgaaacacc tgtggttctt cctcctgctg gtggcagctc ccagatgggt gctgagccag      60
atccagctgg tgcagtctgg cgccgaagtg aagaaacccg cgagagcgt gaaggtgtcc     120
tgcaaggcca gcggctacac ctttaccacc gccggcatgc agtgggtgca gcagatgcct     180
ggcaagggcc tggaatggat gggctggatc aacacccaca cgcgcgtgcc caaatacgcc     240
gaggacttca agggcagagt gaccttcagc ctggacacca gcacctccac cgcctacctg     300
cagctgagca gcctgaagtc cgaggacacc gccgtgtact actgcgccag aagcggcttc     360
ggcagcagct actggtactt cgacgtgtgg ggccagggca ccctcgtgac cgtcagctca     420
gcctccacca agggcccaag cgtcttcccc ctggcaccct cctccaagag cacctctggc     480
ggcacagccg ccctgggctg cctggtcaag gactacttcc ccgaaccgt gaccgtgagc     540
tggaactcag gcgccctgac cagcggcgtg cacaccttcc ccgctgtcct gcagtcctca     600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca ccctgcccag cacctgaact cctgggggga     780
ccctcagtct tcctcttccc cccaaaaccc aaggacaccc tcatgatctc ccggaccct     840
gaggtcacat gcgtggtggt ggacgtgagc cacgaagacc ctgaggtcaa gttcaactgg     900
tacgtggacg gcgtggaggt gcataatgcc aagacaaagc cccgggagga gcagtacaac     960
agcacgtacc gggtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gccagccccg ggaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tggccagccc gagaacaact acaagaccac ccctcccgtg    1260
ctggactccg acggctcctt cttcctctac agcaagctca ccgtggacaa gagcaggtgg    1320
cagcagggca acgtcttctc atgctccgtg atgcatgagg ctctgcacaa ccactacacc    1380
cagaagagcc tctccctgtc tccgggcaaa                                     1410

<210> SEQ ID NO 16
<211> LENGTH: 470
<212> TYPE: PRT
<213> ORGANISM: Artificial Sequence
<220> FEATURE:
<223> OTHER INFORMATION: amino acid sequence of heavy chain of humanized
      TINA1 antibody, type H3

<400> SEQUENCE: 16

```
Met Lys His Leu Trp Phe Phe Leu Leu Leu Val Ala Ala Pro Arg Trp
1               5                   10                  15

Val Leu Ser Gln Ile Gln Leu Val Gln Ser Gly Ala Glu Val Lys Lys
            20                  25                  30

Pro Gly Glu Ser Val Lys Val Ser Cys Lys Ala Ser Gly Tyr Thr Phe
        35                  40                  45

Thr Thr Ala Gly Met Gln Trp Val Gln Gln Met Pro Gly Lys Gly Leu
    50                  55                  60

Glu Trp Met Gly Trp Ile Asn Thr His Ser Gly Val Pro Lys Tyr Ala
65                  70                  75                  80

Glu Asp Phe Lys Gly Arg Val Thr Phe Ser Leu Asp Thr Ser Thr Ser
                85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
```

```
                385               390              395              400

Ala Val Glu Trp Glu Ser Asn Gly Gln Pro Glu Asn Asn Tyr Lys Thr
                    405              410              415

Thr Pro Pro Val Leu Asp Ser Asp Gly Ser Phe Phe Leu Tyr Ser Lys
                420              425              430

Leu Thr Val Asp Lys Ser Arg Trp Gln Gln Gly Asn Val Phe Ser Cys
            435              440              445

Ser Val Met His Glu Ala Leu His Asn His Tyr Thr Gln Lys Ser Leu
        450              455              460

Ser Leu Ser Pro Gly Lys
465             470

<210> SEQ ID NO 17
<211> LENGTH: 702
<212> TYPE: DNA
<213> ORGANISM: Artificial Sequence
<220> FEATURE:
<223> OTHER INFORMATION: nucleotide sequence of light chain of humanized
      TINA1 antibody, type L1

<400> SEQUENCE: 17
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
atcacatgca aggccagcca ggacgtgtcc acagccgtgg cctggtatca gcagaagcct     180
ggcaaggccc ccaagctgct gatctacagc gccagctacc ggtacaccgg cgtgcccagc     240 agatttctg gcagcggctc cggcaccgac ttcaccctga caatcagcag cctgcagccc     300
gaggacttcg ccgtgtacta ctgccagcag cactacatca ccccctgac ctttggccag     360 ggcaccaagc tggaaatcaa gcgtacggtg gccgccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggagt gt     702

<210> SEQ ID NO 18
<211> LENGTH: 234
<212> TYPE: PRT
<213> ORGANISM: Artificial Sequence
<220> FEATURE:
<223> OTHER INFORMATION: amino acid sequence of light chain of humanized
      TINA1 antibody, type L1

<400> SEQUENCE: 18

Met Val Leu Gln Thr Gln Val Phe Ile Ser Leu Leu Leu Trp Ile Ser
1               5                  10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
```

```
                    85                  90                  95
Ser Leu Gln Pro Glu Asp Phe Ala Val Tyr Tyr Cys Gln Gln His Tyr
                100                 105                 110

Ile Thr Pro Leu Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 19
<211> LENGTH: 702
<212> TYPE: DNA
<213> ORGANISM: Artificial Sequence
<220> FEATURE:
<223> OTHER INFORMATION: nucleotide sequence of light chain of humanized
      TINA1 antibody, type L2

<400> SEQUENCE: 19

```
atggtgctgc agacccaggt gttcatctcc ctgctgctgt ggatctccgg cgcgtacggc      60
gacatcgtga tgacccagag ccctagcagc ctgagcgcca gcgtgggcga cagagtgacc     120
atcacatgca aggccagcca ggacgtgtcc acagccgtgg cctggtatca gcagaagcct     180
ggcaaggccc ccaagctgct gatctacagc gccagctacc ggtacaccgg cgtgcccagc     240
agattttctg gcagcggctc cggcaccgac ttcaccctga caatcagcag cctgcagccc     300
gaggacttcg ccgtgtacta ctgccagcag cactacatca ccccccctga cttttggccag    360
ggcaccaagc tggaaatcaa gcgtacggtg gccgccccct ccgtgttcat cttcccccccc    420
tccgacgagc agctgaagtc cggcaccgcc tccgtggtgt gcctgctgaa taacttctac     480
cccagagagg ccaaggtgca gtggaaggtg gacaacgccc tgcagtccgg aactcccag     540
agagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggagt gt                         702
```

<210> SEQ ID NO 20
<211> LENGTH: 234
<212> TYPE: PRT
<213> ORGANISM: Artificial Sequence
<220> FEATURE:
<223> OTHER INFORMATION: amino acid sequence of light chain of humanized
      TINA1 antibody, type L2

<400> SEQUENCE: 20

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Ser Ser Leu Ser
```

```
                    20                  25                  30
Ala Ser Val Gly Asp Arg Val Thr Ile Thr Cys Lys Ala Ser Gln Asp
                35                  40                  45

Val Ser Thr Ala Val Ala Trp Tyr Gln Gln Lys Pro Gly Lys Ala Pro
            50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
                100                 105                 110

Ile Thr Pro Leu Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

<210> SEQ ID NO 21
<211> LENGTH: 702
<212> TYPE: DNA
<213> ORGANISM: Artificial Sequence
<220> FEATURE:
<223> OTHER INFORMATION: nucleotide sequence of light chain of humanized
      TINA1 antibody, type L3

<400> SEQUENCE: 21

```
atggtgctgc agacccaggt gttcatctcc ctgctgctgt ggatctccgg cgcgtacggc    60
gacatcgtga tgacccagag ccctagcagc ctgagcgcca gcgtgggcga cagagtgacc   120
atcacatgca aggccagcca ggacgtgtcc acagccgtgg cctggtatca gcagaagccc   180
ggcaagcagc ccaagctgct gatctacagc gccagctacc ggtacaccgg cgtgcccagc   240
agatttctg gcagcggctc cggcaccgac ttcaccctga caatcagcag cctgcagccc    300
gaggacttcg ccgtgtacta ctgccagcag cactacatca cccccctgac ctttggccag   360
ggcaccaagc tggaaatcaa gcgtacggtg gccgccccct ccgtgttcat cttcccccc    420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag caccctgacc   600
ctgagcaaag ccgactacga gaagcacaag gtgtacgcct gcgaggtgac ccaccagggc   660
ctgagctccc ccgtcaccaa gagcttcaac agggggagt gt                       702
```

<210> SEQ ID NO 22
<211> LENGTH: 234

<212> TYPE: PRT
<213> ORGANISM: Artificial Sequence
<220> FEATURE:
<223> OTHER INFORMATION: amino acid sequence of light chain of humanized
      TINA1 antibody, type L3

<400> SEQUENCE: 22

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Gln Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
            100                 105                 110

Ile Thr Pro Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 23
<211> LENGTH: 5
<212> TYPE: PRT
<213> ORGANISM: Mus musculus

<400> SEQUENCE: 23

Thr Ala Gly Met Gln
1               5

<210> SEQ ID NO 24
<211> LENGTH: 17
<212> TYPE: PRT
<213> ORGANISM: Mus musculus

<400> SEQUENCE: 24

Trp Ile Asn Thr His Ser Gly Val Pro Lys Tyr Ala Glu Asp Phe Lys
1               5                   10                  15

Gly

<210> SEQ ID NO 25

```
<211> LENGTH: 12
<212> TYPE: PRT
<213> ORGANISM: Mus musculus

<400> SEQUENCE: 25

Ser Gly Phe Gly Ser Ser Tyr Trp Tyr Phe Asp Val
1               5                   10

<210> SEQ ID NO 26
<211> LENGTH: 11
<212> TYPE: PRT
<213> ORGANISM: Mus musculus

<400> SEQUENCE: 26

Lys Ala Ser Gln Asp Val Ser Thr Ala Val Ala
1               5                   10

<210> SEQ ID NO 27
<211> LENGTH: 7
<212> TYPE: PRT
<213> ORGANISM: Mus musculus

<400> SEQUENCE: 27

Ser Ala Ser Tyr Arg Tyr Thr
1               5

<210> SEQ ID NO 28
<211> LENGTH: 9
<212> TYPE: PRT
<213> ORGANISM: Mus musculus

<400> SEQUENCE: 28

Gln Gln His Tyr Ile Thr Pro Leu Thr
1               5

<210> SEQ ID NO 29
<211> LENGTH: 1410
<212> TYPE: DNA
<213> ORGANISM: Homo sapiens

<400> SEQUENCE: 29
```

| | | |
|---|---|---|
| atgaaacacc tgtggttctt cctcctgctg gtggcagctc ccagatgggt gctgagccag | 60 |
| gtgcagctgc agcagagcgg cagcgagctg aagaagcctg cgccagcgt caaggtgtcc | 120 |
| tgcaaggcca gcggctacac cttcaccaac tacggcatga actgggtgaa gcaggcccca | 180 |
| ggccagggcc tgaagtggat gggctggatc aacacctaca ccggcgagcc cacctacacc | 240 |
| gacgacttca agggccggtt cgccttcagc ctggacacca gcgtgagcac cgcctacctg | 300 |
| cagatcagca gcctgaaggc cgacgatacc gccgtgtact ctgcgccag aggcggcttc | 360 |
| ggcagcagct actggtactt cgacgtgtgg ggccagggca gctggtgac cgtgagctca | 420 |
| gcctccacca agggcccaag cgtcttcccc ctggcaccct cctccaagag cacctctggc | 480 |
| ggcacagccg ccctgggctg cctggtcaag gactacttcc ccgaacccgt gaccgtgagc | 540 |
| tggaactcag gcgccctgac cagcggcgtg cacaccttcc cgctgtcct gcagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagag agttgagccc | 720 |
| aaatcttgtg acaaaactca cacatgccca ccctgcccag cacctgaact cctgggggga | 780 |
| ccctcagtct tcctcttccc cccaaaaccc aaggacaccc tcatgatctc ccggacccct | 840 |
| gaggtcacat gcgtggtggt ggacgtgagc cacgaagacc ctgaggtcaa gttcaactgg | 900 |

-continued

```
tacgtggacg gcgtggaggt gcataatgcc aagacaaagc cccgggagga gcagtacaac    960
agcacgtacc gggtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gccagccccg ggaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tggccagccc gagaacaact acaagaccac ccctcccgtg   1260
ctggactccg acggctcctt cttcctctac agcaagctca ccgtggacaa gagcaggtgg   1320
cagcagggca acgtcttctc atgctccgtg atgcatgagg ctctgcacaa ccactacacc   1380
cagaagagcc tctccctgtc tcccggcaaa                                     1410
```

<210> SEQ ID NO 30
<211> LENGTH: 470
<212> TYPE: PRT
<213> ORGANISM: Homo sapiens

<400> SEQUENCE: 30

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Tyr Thr Gly Glu Pro Thr Tyr Thr
65                  70                  75                  80

Asp Asp Phe Lys Gly Arg Phe Ala Phe Ser Leu Asp Thr Ser Val Ser
                85                  90                  95

Thr Ala Tyr Leu Gln Ile Ser Ser Leu Lys Ala Asp Asp Thr Ala Val
            100                 105                 110

Tyr Phe Cys Ala Arg Gly Gly Phe Gly Ser Ser Tyr Trp Tyr Phe Asp
        115                 120                 125

Val Trp Gly Gln Gly Ser Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

```
                275                 280                 285
Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 31
<211> LENGTH: 702
<212> TYPE: DNA
<213> ORGANISM: Homo sapiens

<400> SEQUENCE: 31
atggtgctgc agacccaggt gttcatctcc ctgctgctgt ggatctccgg cgcgtacggc      60
gatatccagc tgacccagag ccccagcagc ctgagcgcca gcgtgggcga cagagtgtcc     120
atcacatgca aggccagcca ggacgtgtcc attgccgtgg cctggtatca gcagaagccc     180
ggcaaggccc ccaagctgct gatctacagc gccagctacc ggtacaccgg cgtgcccgac     240
agattcagcg gcagcggctc cggcaccgac ttcaccctga ccatcagcag cctgcagccc     300
gaggacttcg ccgtgtacta ctgccagcag cactacatca ccccctgac cttcggagcc      360 ggcaccaagg tggaaatcaa agctacggtg gccgcccccc tcgtgttcat cttcccccc      420 tccgacgagc agctgaagtc cggcaccgcc tccgtggtgt gcctgctgaa taacttctac     480
cccagagagg ccaaggtgca gtggaaggtg gacaacgccc tgcagtccgg aactcccag      540 gagagcgtga ccgagcagga cagcaaggac agcacctaca gcctgagcag cacctgacc      600 ctgagcaaag ccgactacga aagcacaag gtgtacgcct gcgaggtgac ccaccagggc      660
ctgagctccc ccgtcaccaa gagcttcaac agggggagt gt                         702

<210> SEQ ID NO 32
<211> LENGTH: 234
<212> TYPE: PRT
<213> ORGANISM: Homo sapiens

<400> SEQUENCE: 32

Met Val Leu Gln Thr Gln Val Phe Ile Ser Leu Leu Leu Trp Ile Ser
```

```
            1               5                  10                 15
Gly Ala Tyr Gly Asp Ile Gln Leu Thr Gln Ser Pro Ser Ser Leu Ser
                20                  25                  30

Ala Ser Val Gly Asp Arg Val Ser Ile Thr Cys Lys Ala Ser Gln Asp
            35                  40                  45

Val Ser Ile Ala Val Ala Trp Tyr Gln Gln Lys Pro Gly Lys Ala Pro
50                  55                  60

Lys Leu Leu Ile Tyr Ser Ala Ser Tyr Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
                100                 105                 110

Ile Thr Pro Leu Thr Phe Gly Ala Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 33
<211> LENGTH: 30
<212> TYPE: DNA
<213> ORGANISM: Artificial Sequence
<220> FEATURE:
<223> OTHER INFORMATION: nucleotide sequence of primer mG2aVR2

<400> SEQUENCE: 33
agagttccag gtcaaggtca ctggctcagg                                    30

<210> SEQ ID NO 34
<211> LENGTH: 30
<212> TYPE: DNA
<213> ORGANISM: Artificial Sequence
<220> FEATURE:
<223> OTHER INFORMATION: nucleotide sequence of primer mKVR2

<400> SEQUENCE: 34
agtccaactg ttcaggacgc cattttgtcg                                    30

<210> SEQ ID NO 35
<211> LENGTH: 30
<212> TYPE: DNA
<213> ORGANISM: Artificial Sequence
<220> FEATURE:
<223> OTHER INFORMATION: nucleotide sequence of primer 3.3-F1

<400> SEQUENCE: 35
tataccgtcg acctctagct agagcttggc                                    30
```

<210> SEQ ID NO 36
<211> LENGTH: 30
<212> TYPE: DNA
<213> ORGANISM: Artificial Sequence
<220> FEATURE:
<223> OTHER INFORMATION: nucleotide sequence of primer 3.3-R1

<400> SEQUENCE: 36
gctatggcag ggcctgccgc cccgacgttg                              30

<210> SEQ ID NO 37
<211> LENGTH: 47
<212> TYPE: DNA
<213> ORGANISM: Artificial Sequence
<220> FEATURE:
<223> OTHER INFORMATION: nucleotide sequence of primer TINA1H-F

<400> SEQUENCE: 37
ccagatgggt gctgagccag atccagttgg tgcagtctgg acctgag           47

<210> SEQ ID NO 38
<211> LENGTH: 48
<212> TYPE: DNA
<213> ORGANISM: Artificial Sequence
<220> FEATURE:
<223> OTHER INFORMATION: nucleotide sequence of primer TINA1H-R

<400> SEQUENCE: 38
cttggtggag gctgagctga cggtgaccgc ggtccctgcg ccccagac          48

<210> SEQ ID NO 39
<211> LENGTH: 48
<212> TYPE: DNA
<213> ORGANISM: Artificial Sequence
<220> FEATURE:
<223> OTHER INFORMATION: nucleotide sequence of primer TINA1L-F

<400> SEQUENCE: 39
atctccggcg cgtacggcga cattgtgatg acccagtctc acaaattc          48

<210> SEQ ID NO 40
<211> LENGTH: 45
<212> TYPE: DNA
<213> ORGANISM: Artificial Sequence
<220> FEATURE:
<223> OTHER INFORMATION: nucleotide sequence of primer TINA1L-R

<400> SEQUENCE: 40 ggaggggcg gccacagccc gtttcagctc cagcttggtc ccagc              45

<210> SEQ ID NO 41
<211> LENGTH: 22
<212> TYPE: DNA
<213> ORGANISM: Artificial Sequence
<220> FEATURE:
<223> OTHER INFORMATION: nucleotide sequence of primer EG-Inf-F

<400> SEQUENCE: 41
agctcccaga tgggtgctga gc                                      22

<210> SEQ ID NO 42
<211> LENGTH: 22
<212> TYPE: DNA
<213> ORGANISM: Artificial Sequence
<220> FEATURE:

```
<223> OTHER INFORMATION: nucleotide sequence of primer EG1-Inf-R

<400> SEQUENCE: 42
gggcccttgg tggaggctga gc                                              22

<210> SEQ ID NO 43
<211> LENGTH: 24
<212> TYPE: DNA
<213> ORGANISM: Artificial Sequence
<220> FEATURE:
<223> OTHER INFORMATION: nucleotide sequence of primer CM-LKF

<400> SEQUENCE: 43
ctgtggatct ccggcgcgta cggc                                            24

<210> SEQ ID NO 44
<211> LENGTH: 21
<212> TYPE: DNA
<213> ORGANISM: Artificial Sequence
<220> FEATURE:
<223> OTHER INFORMATION: nucleotide sequence of primer KCL-Inf-R

<400> SEQUENCE: 44 ggaggggcg gccaccgtac g                                                21
```